(12) United States Patent
Miwatashi et al.

(10) Patent No.: US 9,181,186 B2
(45) Date of Patent: Nov. 10, 2015

(54) AROMATIC RING COMPOUND

(71) Applicant: TAKEDA PHARMACEUTICAL COMPANY LIMITED, Osaka (JP)

(72) Inventors: Seiji Miwatashi, Tokyo (JP); Hideo Suzuki, Kanagawa (JP); Tomohiro Okawa, Kanagawa (JP); Yasufumi Miyamoto, Kanagawa (JP); Takeshi Yamasaki, Kanagawa (JP); Yuko Hitomi, Kanagawa (JP); Yasuhiro Hirata, Kanagawa (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

(21) Appl. No.: 14/377,951

(22) PCT Filed: Feb. 12, 2013

(86) PCT No.: PCT/JP2013/053197
§ 371 (c)(1),
(2) Date: Aug. 11, 2014

(87) PCT Pub. No.: WO2013/122029
PCT Pub. Date: Aug. 22, 2013

(65) Prior Publication Data
US 2015/0045378 A1   Feb. 12, 2015

(30) Foreign Application Priority Data
Feb. 13, 2012  (JP) .................. 2012-028943

(51) Int. Cl.
C07D 213/64 (2006.01)
C07D 405/14 (2006.01)
C07D 401/12 (2006.01)
C07D 239/34 (2006.01)
C07D 213/30 (2006.01)
C07D 213/68 (2006.01)
C07D 213/69 (2006.01)
C07D 213/55 (2006.01)
C07D 403/12 (2006.01)

(52) U.S. Cl.
CPC ............ *C07D 213/64* (2013.01); *C07D 213/30* (2013.01); *C07D 213/55* (2013.01); *C07D 213/68* (2013.01); *C07D 213/69* (2013.01); *C07D 239/34* (2013.01); *C07D 401/12* (2013.01); *C07D 403/12* (2013.01); *C07D 405/14* (2013.01)

(58) Field of Classification Search
CPC .. C07D 213/64; C07D 213/30; C07D 213/55; C07D 213/68; C07D 213/69; C07D 239/34; C07D 401/12; C07D 403/12; C07D 405/14
See application file for complete search history.

(56) References Cited

U.S. PATENT DOCUMENTS

| | | |
|---|---|---|
| 7,205,302 B2 | 4/2007 | Asaki et al. |
| 2006/0258722 A1 | 11/2006 | Yasuma et al. |
| 2007/0149608 A1 | 6/2007 | Yasuma et al. |
| 2007/0213364 A1 | 9/2007 | Yasuma et al. |
| 2009/0012093 A1 | 1/2009 | Fukatsu et al. |
| 2010/0004312 A1 | 1/2010 | Yasuma et al. |
| 2010/0144806 A1 | 6/2010 | Yasuma et al. |
| 2011/0195993 A1 | 8/2011 | Masson et al. |
| 2013/0296276 A2 * | 11/2013 | Ujikawa et al. ................. 514/89 |
| 2015/0018422 A1 * | 1/2015 | Miwatashi et al. ........... 514/571 |
| 2015/0119412 A1 * | 4/2015 | Kasai et al. .................... 514/269 |

FOREIGN PATENT DOCUMENTS

| | | |
|---|---|---|
| EP | 0434034 | 6/1991 |
| JP | 08-333287 | 12/1996 |
| WO | 2005/049573 | 6/2005 |
| WO | WO 2005049573 A1 * | 6/2005 |
| WO | 2007/056497 | 5/2007 |
| WO | 2009/048527 | 4/2009 |

OTHER PUBLICATIONS

International Search Report issued Mar. 12, 2013 in International (PCT) Application No. PCT/JP2013/053197.
Epple et al., "Novel Bisaryl Substituted Thiazoles and Oxazoles as Highly Potent and Selective Peroxisome Proliferator-Activated Receptor δ Agonists", J. Med. Chem., vol. 53(1), Nov. 2009, pp. 77-105.
Meanwell et al., "Nonprostanoid Prostacyclin Mimetics. 2. 4,5-Diphenyloxazole Derivatives", J. Med. Chem., vol. 35(19), 1992, pp. 3483-3497.
Asaki et al., "Structure-activity studies on diphenylpyrazine derivatives: A novel class of prostacyclin receptor agonists", Bioorganic & Medicinal Chemistry, vol. 15(21), Aug. 2007, pp. 6692-6704.
CAS Registry No. 1026431-77-5, Jun. 8, 2008.

* cited by examiner

*Primary Examiner* — Alexander R Pagano
(74) *Attorney, Agent, or Firm* — Wenderoth, Lind & Ponack, L.L.P.

(57) ABSTRACT

Provided is an aromatic ring compound having a GPR40 agonist activity. A compound represented by the formula (I):

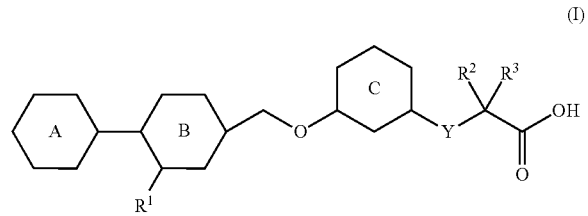

wherein each symbol is as described in the DESCRIPTION, or a salt thereof has a GPR40 agonist activity, and is useful as an agent for the prophylaxis or treatment of diabetes and the like.

12 Claims, No Drawings

AROMATIC RING COMPOUND

TECHNICAL FIELD

The present invention relates to a novel aromatic ring compound having a GPR40 agonist activity.

BACKGROUND OF THE INVENTION

Patent document 1 describes the following compound.

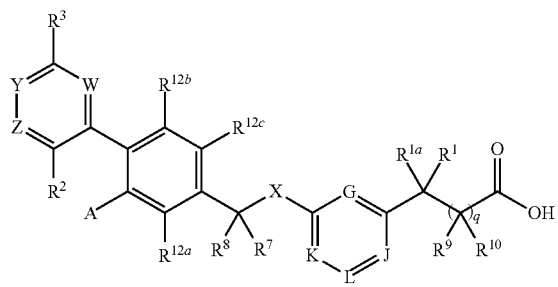

wherein each symbol is as described in patent document 1.

Patent document 2 describes the following compound.

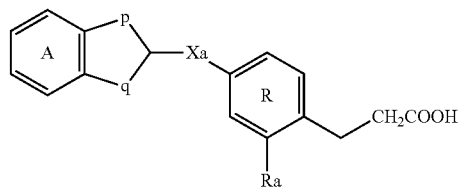

(I-1)

wherein each symbol is as described in patent document 2.

Patent document 3 describes the following compound.

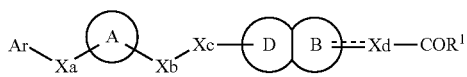

(1)

wherein each symbol is as described in patent document 3.

Patent document 4 describes the following compound.

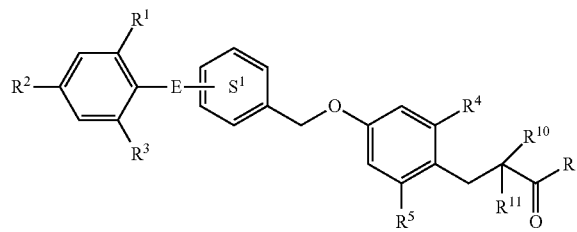

wherein each symbol is as described in patent document 4.

Patent document 5 describes the following compound.

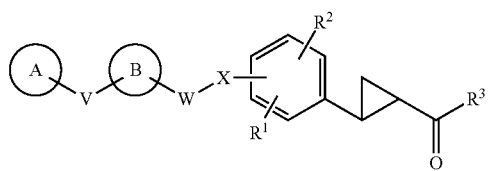

[I]

wherein each symbol is as described in patent document 5.

Non-patent document 1 describes the following compound.

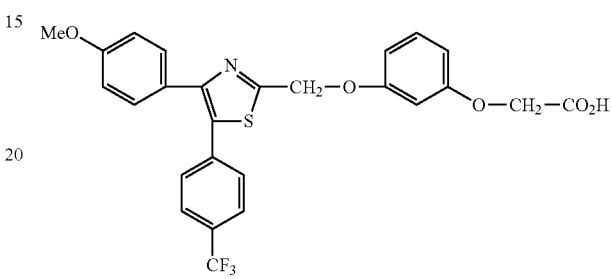

Patent document 6 describes the following compound.

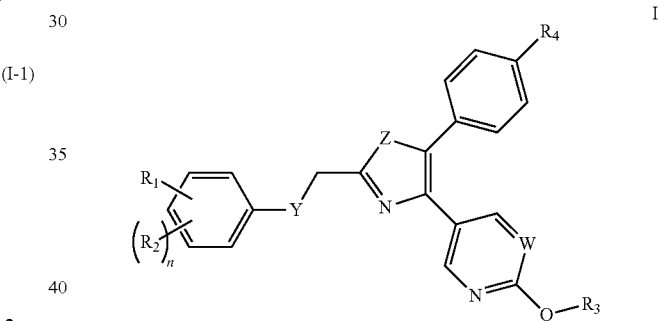

I wherein each symbol is as described in patent document 6.

Non-patent document 2 describes the following compound.

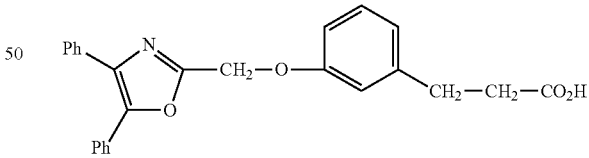

Patent document 7 describes the following compound.

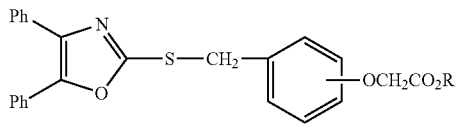

wherein each symbol is as described in patent document 7.

Non-patent document 3 describes the following compound.

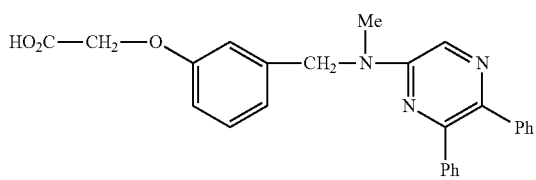 [SMILES: CN(Cc1cccc(OCC(=O)O)c1)c1cnc(-c2ccccc2)c(-c2ccccc2)n1]

Patent document 8 describes the following compound.

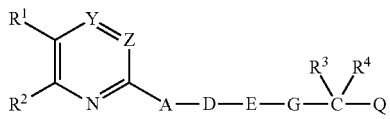

wherein each symbol is as described in patent document 8.

Patent document 9 describes the following compound.

wherein each symbol is as described in patent document 9.

Non-patent document 4 describes the following compound.

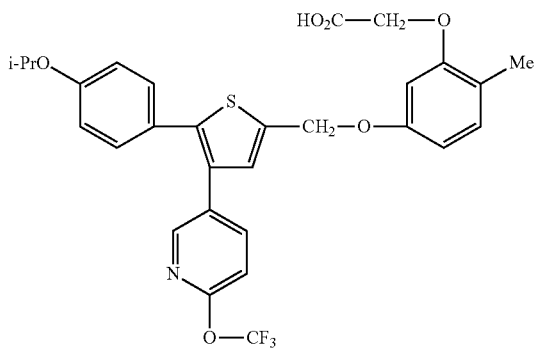

However, no documents specifically disclose the compound of the present application.

Document List

Patent Documents patent document 1: WO2009/048527
patent document 2: WO2004/041266
patent document 3: WO2004/106276
patent document 4: WO2005/063729
patent document 5: WO2007/013689
patent document 6: WO2007/056497
patent document 7: EP434034
patent document 8: WO2002/088084
patent document 9: JP08-333287

Non-Patent Documents non-patent document 1: Journal of Medicinal Chemistry 2010, 53(1), p. 77-105 non-patent document 2: Journal of Medicinal Chemistry 1992, 35(19), p. 3483-3497
non-patent document 3: Bioorganic & Medicinal Chemistry 2007, 15(21), p. 6692-6704
non-patent document 4: CAS Registry No. 1026431-77-5

SUMMARY OF THE INVENTION

Problems to be Solved by the Invention

The present invention aims to provide a novel aromatic ring compound having a GPR40 agonist activity, and useful as an agent for the prophylaxis or treatment of diabetes and the like.

Means of Solving the Problems

The present inventors have conducted various intensive studies and found that the compound represented by the following formula (I) unexpectedly has a superior GPR40 agonist activity, is superior in the property as a pharmaceutical product such as stability and the like, and particularly shows high solubility, low toxicity, good pharmacokinetics such as sustainability in blood and the like, and therefore, provides a safe and useful medicament to be an agent for the prophylaxis or treatment of mammalian GPR40 receptor-related pathology or disease. Based on these findings, they have completed the present invention.

Accordingly, the present invention relates to

[1] a compound represented by the formula (I):

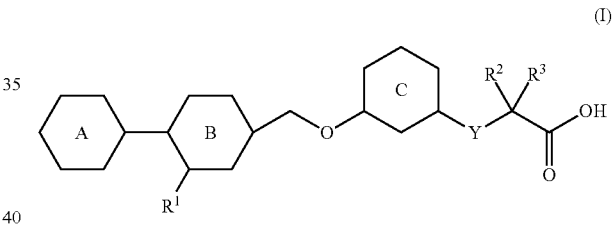

wherein ring A is an optionally further substituted 6-membered aromatic ring;
ring B is an optionally further substituted 6-membered aromatic heterocycle;
ring C is an optionally further substituted 6-membered aromatic ring;
Y is $-NR^{4A}-$, $-CR^{4B}R^{4C}-$ or $-O-$;
$R^1$ is a substituent;
$R^2$ and $R^3$ are each independently a hydrogen atom or a substituent; and
$R^{4A}$, $R^{4B}$ and $R^{4C}$ are each independently a hydrogen atom, an optionally substituted $C_{1-6}$ alkyl group, an optionally substituted $C_{2-6}$ alkenyl group, an optionally substituted $C_{2-6}$ alkynyl group, or an optionally substituted $C_{3-7}$ cycloalkyl group,
or a salt thereof (hereinafter sometimes to be abbreviated as compound (I));

[2] the compound of [1], wherein ring A is a benzene ring further substituted by one halogen atom and one $C_{1-6}$ alkoxy group, or a salt thereof;

[3] the compound of [1] or [2], wherein ring B is (1) a pyridine ring optionally further substituted by 1 to 3 $C_{1-6}$ alkoxy groups, or (2) a pyrimidine ring, or a salt thereof;

[4] the compound of [1], [2] or [3], wherein ring C is (1) a benzene ring optionally further substituted by 1 to 3 substituents selected from a halogen atom, a $C_{1-6}$ alkyl group and a $C_{1-6}$ alkoxy group, (2) a pyridine ring, or (3) a pyrimidine ring optionally further substituted by 1 to 3 substituents selected from a halogen atom, a $C_{1-6}$ alkyl group and a $C_{1-6}$ alkoxy group, or a salt thereof;

[5] the compound of [1], [2], [3] or [4], wherein Y is —N(ethyl)-, —CH$_2$— or —CH(cyclopropyl)-, or a salt thereof;

[6] the compound of [1], [2], [3], [4] or [5], wherein $R^1$ is (1) a $C_{1-8}$ alkyl group optionally substituted by 1 to 3 substituents selected from (i) a $C_{3-7}$ cycloalkyl group and cyano, or (2) a $C_{1-6}$ alkoxy group optionally substituted by 1 to 3 substituents selected from (i) a halogen atom and (ii) a non-aromatic heterocyclic group optionally substituted by 1 or 2 $C_{1-6}$ alkyl groups, or a salt thereof;

[7] the compound of [1], [2], [3], [4], [5] or [6], wherein both $R^2$ and $R^3$ are hydrogen atoms, or a salt thereof;

[8] 3-cyclopropyl-3-(6-((5-(2,2-dimethylpropyl)-6-(2-fluoro-5-methoxyphenyl)pyridin-3-yl)methoxy)pyrimidin-4-yl)propanoic acid or a salt thereof;

[9] 3-cyclopropyl-3-(6-((6-(2,2-dimethylpropyl)-5-(2-fluoro-5-methoxyphenyl)pyridin-2-yl)methoxy)pyrimidin-4-yl)propanoic acid or a salt thereof;

[10] 3-cyclopropyl-3-(3-((5-(2,2-dimethylpropyl)-6-(2-fluoro-5-methoxyphenyl)pyridin-3-yl)methoxy)phenyl)propanoic acid or a salt thereof;

[11] a medicament comprising the compound of [1] or a salt thereof;

[12] the medicament of [11], which is a GPR40 receptor function modulator;

[13] the medicament of [11], which is a prophylactic or therapeutic agent for diabetes;

[14] a method for the prophylaxis or treatment of diabetes in a mammal, comprising administering an effective amount of the compound of [1] or a salt thereof to the mammal;

[15] a method of modulating a GPR40 receptor function in a mammal, comprising administering an effective amount of the compound of [1] or a salt thereof to the mammal;

[16] use of the compound of [1] or a salt thereof in the production of an agent for the prophylaxis or treatment of diabetes;

[17] the compound of [1] or a salt thereof for use in the prophylaxis or treatment of diabetes; and the like.

Effect of the Invention

Since compound (I) has a superior GPR40 agonist activity, is superior in the property as a pharmaceutical product such as stability and the like, and particularly shows high solubility, low toxicity, good kinetics such as sustainability in blood and the like, it can provide a safe and useful agent for the prophylaxis or treatment of mammalian GPR40 receptor-related pathology or disease.

DETAILED DESCRIPTION OF THE INVENTION

The present invention is explained in detail in the following.

Unless otherwise specified, examples of the "halogen atom" in the present specification include a fluorine atom, a chlorine atom, a bromine atom, and an iodine atom.

Unless otherwise specified, examples of the "optionally substituted hydrocarbon group" in the present specification include "optionally substituted $C_{1-6}$ alkyl group", "optionally substituted $C_{2-6}$ alkenyl group", "optionally substituted $C_{2-6}$ alkynyl group", "optionally substituted $C_{3-7}$ cycloalkyl group", "optionally substituted $C_{6-14}$ aryl group", "optionally substituted $C_{7-16}$ aralkyl group" and the like.

Unless otherwise specified, examples of the "$C_{1-8}$ alkyl group" in the present specification include methyl, ethyl, propyl, isopropyl, butyl, isobutyl, sec-butyl, tert-butyl, pentyl, isopentyl, neopentyl, hexyl, neohexyl, 2,2-dimethylbutyl, 2,2,3-trimethylpropyl, heptyl, 2,2-dimethylpentyl, 3,3-dimethylpentyl, 4,4-dimethylpentyl, 3,3-diethylbutyl, octyl and the like. Unless otherwise specified, as the "$C_{1-6}$ alkyl group" in the present specification, $C_{1-6}$ alkyl group from the above-mentioned "$C_{1-8}$ alkyl group" can be mentioned.

Unless otherwise specified, examples of the "$C_{2-6}$ alkenyl group" in the present specification include vinyl, propenyl, isopropenyl, 2-buten-1-yl, 4-penten-1-yl, 5-hexen-1-yl and the like.

Unless otherwise specified, examples of the "$C_{2-6}$ alkynyl group" in the present specification include 2-butyn-1-yl, 4-pentyn-1-yl, 5-hexyn-1-yl and the like.

Unless otherwise specified, examples of the "$C_{3-7}$ cycloalkyl group" in the present specification include cyclopropyl, cyclobutyl, cyclopentyl, cyclohexyl, cycloheptyl and the like.

Unless otherwise specified, examples of the "$C_{6-14}$ aryl group" in the present specification include phenyl, 1-naphthyl, 2-naphthyl, 2-biphenylyl, 3-biphenylyl, 4-biphenylyl, 2-anthryl and the like. The $C_{6-14}$ aryl group may be partially saturated, and examples of the partially saturated $C_{6-14}$ aryl group include tetrahydronaphthyl and the like.

Unless otherwise specified, examples of the "$C_{7-16}$ aralkyl group" in the present specification include benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylylmethyl, 3-biphenylylmethyl, 4-biphenylylmethyl and the like.

Unless otherwise specified, examples of the "optionally substituted hydroxy" in the present specification include "hydroxy", "optionally substituted $C_{1-6}$ alkoxy group", "optionally substituted heterocyclyl-oxy group", "optionally substituted $C_{6-14}$ aryloxy group", "optionally substituted $C_{7-16}$ aralkyloxy group" and the like.

Unless otherwise specified, examples of the "$C_{1-6}$ alkoxy group" in the present specification include methoxy, ethoxy, propoxy, isopropoxy, butoxy, isobutoxy, tert-butoxy, pentyloxy, neopentyloxy, hexyloxy and the like.

Unless otherwise specified, examples of the "$C_{1-6}$ alkoxy-$C_{1-6}$ alkoxy group" in the present specification include methoxymethoxy, methoxyethoxy, ethoxymethoxy, ethoxyethoxy and the like.

Unless otherwise specified, examples of the "heterocyclyl-oxy group" in the present specification include hydroxy substituted by a "heterocyclic group" to be mentioned below. Preferable examples of the heterocyclyl-oxy group include tetrahydropyranyloxy, thiazolyloxy, pyridyloxy, pyrazolyloxy, oxazolyloxy, thienyloxy, furyloxy and the like.

Unless otherwise specified, examples of the "$C_{6-14}$ aryloxy group" in the present specification include phenoxy, 1-naphthyloxy, 2-naphthyloxy and the like.

Unless otherwise specified, examples of the "$C_{7-16}$ aralkyloxy group" in the present specification include benzyloxy, phenethyloxy and the like.

Unless otherwise specified, examples of the "optionally substituted mercapto" in the present specification include "mercapto", "optionally substituted $C_{1-6}$ alkylthio group", "optionally substituted heterocyclyl-thio group", "optionally substituted $C_{6-14}$ arylthio group", "optionally substituted $C_{7-16}$ aralkylthio group" and the like.

Unless otherwise specified, examples of the "$C_{1-6}$ alkylthio group" in the present specification include methylthio, ethylthio, propylthio, isopropylthio, butylthio, sec-butylthio, tert-butylthio and the like.

Unless otherwise specified, examples of the "heterocyclylthio group" in the present specification include mercapto substituted by a "heterocyclic group" to be mentioned below. Preferable examples of the heterocyclyl-thio group include tetrahydropyranylthio, thiazolylthio, pyridylthio, pyrazolylthio, oxazolylthio, thienylthio, furylthio and the like.

Unless otherwise specified, examples of the "$C_{6-14}$ arylthio group" in the present specification include phenylthio, 1-naphthylthio, 2-naphthylthio and the like.

Unless otherwise specified, examples of the "$C_{7-16}$ aralkylthio group" in the present specification include benzylthio, phenethylthio and the like.

Unless otherwise specified, examples of the "heterocyclic group" in the present specification include a 5- to 14-membered (monocyclic, bicyclic or tricyclic) heterocyclic group containing, as a ring-constituting atom besides carbon atom, one or two kinds of 1 to 4 hetero atoms selected from a nitrogen atom, a sulfur atom and an oxygen atom, preferably (i) a 5- to 14-membered (preferably 5- to 10-membered) aromatic heterocyclic group, (ii) a 5- to 10-membered non-aromatic heterocyclic group and the like. Among these, a 5- or 6-membered aromatic heterocyclic group is preferable. Specific examples thereof include aromatic heterocyclic groups such as thienyl (e.g., 2-thienyl, 3-thienyl), furyl (e.g., 2-furyl, 3-furyl), pyridyl (e.g., 2-pyridyl, 3-pyridyl, 4-pyridyl), thiazolyl (e.g., 2-thiazolyl, 4-thiazolyl, 5-thiazolyl), oxazolyl (e.g., 2-oxazolyl, 4-oxazolyl, 5-oxazolyl), pyrazinyl, pyrimidinyl (e.g., 2-pyrimidinyl, 4-pyrimidinyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), triazolyl (e.g., 1-triazolyl, 2-triazolyl), tetrazolyl, pyridazinyl (e.g., 3-pyridazinyl, 4-pyridazinyl), isothiazolyl (e.g., 3-isothiazolyl, 4-isothiazolyl, 5-isothiazolyl), isoxazolyl (e.g., 3-isoxazolyl, 4-isoxazolyl, 5-isoxazolyl), indolyl (e.g., 1-indolyl, 2-indolyl, 3-indolyl), 2-benzothiazolyl, 2-benzoxazolyl, benzimidazolyl (e.g., 1-benzimidazolyl, 2-benzimidazolyl), benzo[b]thienyl (e.g., 2-benzo[b]thienyl, 3-benzo[b]thienyl), benzo[b]furanyl (e.g., 2-benzo[b]furanyl, 3-benzo[b]furanyl), quinolyl (e.g., 2-quinolyl, 3-quinolyl, 4-quinolyl, 5-quinolyl, 8-quinolyl), isoquinolyl (e.g., 1-isoquinolyl, 3-isoquinolyl, 4-isoquinolyl, 5-isoquinolyl) and the like; non-aromatic heterocyclic groups such as pyrrolidinyl (e.g., 1-pyrrolidinyl, 2-pyrrolidinyl, 3-pyrrolidinyl), oxazolidinyl (e.g., 2-oxazolidinyl), imidazolinyl (e.g., 1-imidazolinyl, 2-imidazolinyl, 4-imidazolinyl), piperidinyl (e.g., piperidino, 2-piperidinyl, 3-piperidinyl, 4-piperidinyl), piperazinyl (e.g., 1-piperazinyl, 2-piperazinyl), morpholinyl (e.g., 2-morpholinyl, 3-morpholinyl, morpholino), thiomorpholinyl (e.g., 2-thiomorpholinyl, 3-thiomorpholinyl, thiomorpholino), tetrahydrofuranyl, tetrahydropyranyl, and the like, and the like.

Unless otherwise specified, as the "non-aromatic heterocyclic group" in the present specification, the above-mentioned 5- to 10-membered non-aromatic heterocyclic group can be mentioned.

Unless otherwise specified, examples of the "6-membered aromatic heterocycle" in the present specification include a 6-membered aromatic heterocycle constituting a 6-membered aromatic heterocyclic group in the above-mentioned "5- to 14-membered (preferably 5- to 10-membered) aromatic heterocyclic group" and the like. Specific examples thereof include a pyridine ring, pyrimidine ring, pyrazine ring, pyridazine ring, triazine ring and the like.

Unless otherwise specified, as the "6-membered aromatic ring" in the present specification, for example, a benzene ring and the above-mentioned "6-membered aromatic heterocycle" and the like can be mentioned. Specific examples thereof include a benzene ring, a pyridine ring, a pyrimidine ring, a pyrazine ring, a pyridazine ring, a triazine ring and the like can be mentioned.

Unless otherwise specified, examples of the "$C_{1-6}$ alkylcarbonyl group" in the present specification include acetyl, isobutanoyl, isopentanoyl and the like.

Unless otherwise specified, examples of the "$C_{1-6}$ alkoxy-carbonyl group" in the present specification include methoxycarbonyl, ethoxycarbonyl, propoxycarbonyl, tert-butoxycarbonyl and the like.

Unless otherwise specified, examples of the "$C_{3-7}$ cycloalkyl-carbonyl group" in the present specification include cyclopentylcarbonyl, cyclohexylcarbonyl and the like.

Unless otherwise specified, examples of the "$C_{6-14}$ arylcarbonyl group" in the present specification include benzoyl, 1-naphthoyl, 2-naphthoyl and the like.

Unless otherwise specified, examples of the "$C_{7-16}$ aralkylcarbonyl group" in the present specification include phenylacetyl, 2-phenylpropanoyl and the like.

Unless otherwise specified, examples of the "$C_{6-14}$ aryloxy-carbonyl group" in the present specification include phenoxycarbonyl, naphthyloxycarbonyl and the like.

Unless otherwise specified, examples of the "$C_{7-16}$ aralkyloxy-carbonyl group" in the present specification include benzyloxycarbonyl, phenethyloxycarbonyl and the like.

Unless otherwise specified, examples of the "nitrogen-containing heterocyclyl-carbonyl group" in the present specification include pyrrolidinylcarbonyl, piperidinocarbonyl and the like.

Unless otherwise specified, examples of the "$C_{1-6}$ alkylsulfonyl group" in the present specification include methylsulfonyl, ethylsulfonyl and the like.

Unless otherwise specified, examples of the "$C_{6-14}$ arylsulfonyl group" in the present specification include phenylsulfonyl, 1-naphthylsulfonyl, 2-naphthylsulfonyl and the like.

Unless otherwise specified, examples of the "$C_{1-6}$ alkylsulfinyl group" in the present specification include methylsulfinyl, ethylsulfinyl and the like.

Unless otherwise specified, examples of the "$C_{6-14}$ arylsulfinyl group" in the present specification include phenylsulfinyl, 1-naphthylsulfinyl, 2-naphthylsulfinyl and the like.

Unless otherwise specified, examples of the "optionally esterified carboxyl" in the present specification include carboxyl, $C_{1-6}$ alkoxy-carbonyl group, $C_{6-14}$ aryloxy-carbonyl group, $C_{7-16}$ aralkyloxy-carbonyl group and the like.

Unless otherwise specified, examples of the "$C_{1-6}$ alkyl group optionally substituted by a halogen atom" in the present specification include the above-mentioned "$C_{1-6}$ alkyl group" optionally substituted by the above-mentioned 1 to 5 "halogen atoms". When substituted by plural halogen atoms, respective halogen atoms may be the same or different. For example, methyl, ethyl, propyl, isopropyl, butyl, tert-butyl, isobutyl, trifluoromethyl and the like can be mentioned.

Unless otherwise specified, as the "$C_{1-6}$ alkoxy group optionally substituted a halogen" in the present specification, the above-mentioned "$C_{1-6}$ alkoxy group" optionally substituted by 1 to 5 the above-mentioned "halogen atoms" can be mentioned.

When substituted by plural halogen atoms, respective halogen atoms may be the same or different. For example, methoxy, ethoxy, isopropoxy, tert-butoxy, trifluoromethoxy and the like can be mentioned.

Unless otherwise specified, examples of the "mono- or di-$C_{1-6}$ alkyl-amino group" in the present specification include amino mono- or di-substituted by the above-mentioned "$C_{1-6}$ alkyl group". For example, methylamino, ethylamino, propylamino, dimethylamino, diethylamino and the like can be mentioned.

Unless otherwise specified, examples of the "mono- or di-$C_{6-14}$ aryl-amino group" in the present specification include amino mono- or di-substituted by the above-mentioned "$C_{6-14}$ aryl group". For example, phenylamino, diphenylamino, 1-naphthylamino, 2-naphthylamino and the like can be mentioned.

Unless otherwise specified, examples of the "mono- or di-$C_{7-16}$ aralkyl-amino group" in the present specification include amino mono- or di-substituted by the above-mentioned "$C_{7-16}$ aralkyl group". For example, benzylamino, phenethylamino and the like can be mentioned.

Unless otherwise specified, examples of the "N—$C_{1-6}$ alkyl-N—$C_{6-14}$ aryl-amino group" in the present specification include amino substituted the above-mentioned "$C_{1-6}$ alkyl group" and the above-mentioned "$C_{6-14}$ aryl group". For example, N-methyl-N-phenylamino, N-ethyl-N-phenylamino and the like can be mentioned.

Unless otherwise specified, examples of the "N—$C_{1-6}$ alkyl-N—$C_{7-16}$ aralkyl-amino group" in the present specification include amino substituted by the above-mentioned "$C_{1-6}$ alkyl group" and the above-mentioned "$C_{7-16}$ aralkyl group". For example, N-methyl-N-benzylamino, N-ethyl-N-benzylamino and the like can be mentioned.

Unless otherwise specified, examples of the "mono- or di-$C_{1-6}$ alkyl-carbamoyl group" in the present specification include carbamoyl mono- or di-substituted by the above-mentioned "$C_{1-6}$ alkyl group". For example, methylcarbamoyl, ethylcarbamoyl, dimethylcarbamoyl, diethylcarbamoyl, ethylmethylcarbamoyl and the like can be mentioned.

Unless otherwise specified, examples of the "mono- or di-$C_{6-14}$ aryl-carbamoyl group" in the present specification include carbamoyl mono- or di-substituted by the above-mentioned "$C_{6-14}$ aryl group". For example, phenylcarbamoyl, 1-naphthylcarbamoyl, 2-naphthylcarbamoyl and the like can be mentioned.

Unless otherwise specified, examples of the "mono- or di-$C_{3-7}$ cycloalkyl-carbamoyl group" in the present specification include carbamoyl mono- or di-substituted by the above-mentioned "$C_{3-7}$ cycloalkyl group". For example, cyclopropylcarbamoyl and the like can be mentioned.

Unless otherwise specified, examples of the "mono- or di-$C_{7-16}$ aralkyl-carbamoyl group" in the present specification include carbamoyl mono- or di-substituted by the above-mentioned "$C_{7-16}$ aralkyl group". For example, benzylcarbamoyl and the like can be mentioned.

Unless otherwise specified, examples of the "mono- or di-5- to 7-membered heterocyclyl-carbamoyl group" in the present specification include carbamoyl mono- or di-substituted by a 5- to 7-membered heterocyclic group. Here, as the 5- to 7-membered heterocyclic group, a heterocyclic group containing, as a ring-constituting atom besides carbon atom, one or two kinds of 1 to 4 hetero atoms selected from a nitrogen atom, a sulfur atom and an oxygen atom can be mentioned. Preferable examples of the "mono- or di-5- to 7-membered heterocyclyl-carbamoyl group" include 2-pyridylcarbamoyl, 3-pyridylcarbamoyl, 4-pyridylcarbamoyl, 2-thienylcarbamoyl, 3-thienylcarbamoyl and the like.

Unless otherwise specified, as the "mono- or di-$C_{1-6}$ alkyl-sulfamoyl group" in the present specification, sulfamoyl mono- or di-substituted by the above-mentioned "$C_{1-6}$ alkyl group" is used and, for example, methylsulfamoyl, ethylsulfamoyl, dimethylsulfamoyl, diethylsulfamoyl and the like can be mentioned.

Unless otherwise specified, as the "mono- or di-$C_{6-14}$ aryl-sulfamoyl group" in the present specification, sulfamoyl mono- or di-substituted by the above-mentioned "$C_{6-14}$ aryl group" is used and, for example, phenylsulfamoyl, diphenylsulfamoyl, 1-naphthylsulfamoyl, 2-naphthylsulfamoyl and the like can be mentioned.

Unless otherwise specified, examples of the "mono- or di-$C_{7-16}$ aralkyl-sulfamoyl group" in the present specification include sulfamoyl mono- or di-substituted by the above-mentioned "$C_{7-16}$ aralkyl group". For example, benzylsulfamoyl and the like can be mentioned.

Unless otherwise specified, examples of the "optionally substituted $C_{1-6}$ alkyl group", "optionally substituted $C_{2-6}$ alkenyl group", "optionally substituted $C_{2-6}$ alkynyl group", "optionally substituted $C_{1-6}$ alkoxy group" and "optionally substituted $C_{1-6}$ alkylthio group" in the present specification include "$C_{1-6}$ alkyl group", "$C_{2-6}$ alkenyl group", "$C_{2-6}$ alkynyl group", "$C_{1-6}$ alkoxy group" and "$C_{1-6}$ alkylthio group" optionally having, at each substitutable position, 1 to 5 substituents selected from (1) a halogen atom;
(2) hydroxy;
(3) amino;
(4) nitro;
(5) cyano;
(6) a heterocyclic group (preferably furyl, pyridyl, thienyl, pyrazolyl, thiazolyl, oxazolyl) optionally substituted by 1 to 3 substituents selected from a halogen atom, hydroxy, amino, nitro, cyano, $C_{1-6}$ alkyl optionally substituted by a halogen atom, mono- or di-$C_{1-6}$ alkyl-amino, $C_{6-14}$ aryl, mono- or di-$C_{6-14}$ aryl-amino, $C_{3-7}$ cycloalkyl, $C_{1-6}$ alkoxy, $C_{1-6}$ alkoxy-$C_{1-6}$ alkoxy, $C_{1-6}$ alkylthio, $C_{1-6}$ alkylsulfinyl, $C_{1-6}$ alkylsulfonyl, optionally esterified carboxyl, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;
(7) mono- or di-$C_{1-6}$ alkyl-amino;
(8) mono- or di-$C_{6-14}$ aryl-amino;
(9) mono- or di-$C_{7-16}$ aralkyl-amino;
(10) N—$C_{1-6}$ alkyl-N—$C_{6-14}$ aryl-amino;
(11) N—$C_{1-6}$ alkyl-N—$C_{7-16}$ aralkyl-amino;
(12) $C_{3-7}$ cycloalkyl;
(13) $C_{1-6}$ alkoxy optionally substituted by a halogen atom;
(14) $C_{1-6}$ alkylthio;
(15) $C_{1-6}$ alkylsulfinyl;
(16) $C_{1-6}$ alkylsulfonyl;
(17) optionally esterified carboxyl;
(18) $C_{1-6}$ alkyl-carbonyl;
(19) $C_{3-7}$ cycloalkyl-carbonyl;
(20) $C_{6-14}$ aryl-carbonyl;
(21) carbamoyl;
(22) thiocarbamoyl;
(23) mono- or di-$C_{1-6}$ alkyl-carbamoyl;
(24) mono- or di-$C_{6-14}$ aryl-carbamoyl;
(25) mono- or di-5- to 7-membered heterocyclyl-carbamoyl;
(26) $C_{1-6}$ alkyl-carbonylamino (e.g., acetylamino, propionylamino) optionally substituted by carboxyl;
(27) $C_{6-14}$ aryloxy optionally substituted by 1 to 3 substituents selected from a halogen atom, hydroxy, amino, nitro, cyano, $C_{1-6}$ alkyl optionally substituted by a halogen atom, mono- or di-$C_{1-6}$ alkyl-amino, $C_{6-14}$ aryl, mono- or di-$C_{6-14}$ aryl-amino, $C_{3-7}$ cycloalkyl, $C_{1-6}$ alkoxy, $C_{1-6}$ alkoxy-$C_{1-6}$ alkoxy, $C_{1-6}$ alkylthio, alkylsulfinyl, $C_{1-6}$ alkylsulfonyl, optionally esterified carboxyl, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;

(28) $C_{6-14}$ aryl optionally substituted by 1 to 3 substituents selected from a halogen atom, hydroxy, amino, nitro, cyano, $C_{1-6}$ alkyl optionally substituted by a halogen atom, mono- or di-$C_{1-6}$ alkyl-amino, $C_{6-14}$ aryl, mono- or di-$C_{6-14}$ aryl-amino, $C_{3-7}$ cycloalkyl, $C_{1-6}$ alkoxy, $C_{1-6}$ alkoxy-$C_{1-6}$ alkoxy, $C_{1-6}$ alkylthio, $C_{1-6}$ alkylsulfinyl, $C_{1-6}$ alkylsulfonyl, optionally esterified carboxyl, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;

(29) heterocyclyl-oxy;

(30) sulfamoyl;

(31) mono- or di-$C_{1-6}$ alkyl-sulfamoyl;

(32) mono- or di-$C_{6-14}$ aryl-sulfamoyl;

(33) $C_{7-16}$ aralkyloxy optionally substituted by 1 to 3 substituents selected from a halogen atom, hydroxy, amino, nitro, cyano, $C_{1-6}$ alkyl optionally substituted by a halogen atom, mono- or di-$C_{1-6}$ alkyl-amino, $C_{6-14}$ aryl, mono- or di-$C_{6-14}$ aryl-amino, $C_{3-7}$ cycloalkyl, $C_{1-6}$ alkoxy, $C_{1-6}$ alkoxy-$C_{1-6}$ alkoxy, $C_{1-6}$ alkylthio, $C_{1-6}$ alkylsulfinyl, $C_{1-6}$ alkylsulfonyl, optionally esterified carboxyl, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;

and the like. When plural substituents are present, the respective substituents may be the same or different.

In the present specification, examples of the "optionally substituted $C_{3-7}$ cycloalkyl group", "optionally substituted $C_{6-14}$ aryl group", "optionally substituted $C_{7-16}$ aralkyl group", "optionally substituted heterocyclic group", "optionally substituted heterocyclyl-oxy group", "optionally substituted $C_{6-14}$ aryloxy group", "optionally substituted $C_{7-16}$ aralkyloxy group", "optionally substituted heterocyclyl-thio group", "optionally substituted $C_{6-14}$ arylthio group" and "optionally substituted $C_{7-16}$ aralkylthio group" include "$C_{3-7}$ cycloalkyl group", "$C_{6-14}$ aryl group", "$C_{7-16}$ aralkyl group", "heterocyclic group", "heterocyclyl-oxy group", "$C_{6-14}$ aryloxy group", "$C_{7-16}$ aralkyloxy group", "heterocyclyl-thio group", "$C_{6-14}$ arylthio group" and "$C_{7-16}$ aralkylthio group" optionally having, at each substitutable position, 1 to 5 substituents selected from (1) a halogen atom;

(2) hydroxy;

(3) amino;

(4) nitro;

(5) cyano;

(6) optionally substituted $C_{1-8}$ alkyl (preferably, neopentyl, 2,2-dimethylbutyl, 2,2-dimethylpentyl, 3,3-diethylbutyl, 2,2,3-trimethylpropyl, 3,3-dimethylpentyl);

(7) optionally substituted $C_{2-6}$ alkenyl;

(8) optionally substituted $C_{2-6}$ alkynyl;

(9) $C_{6-14}$ aryl optionally substituted by 1 to 3 substituents selected from a halogen atom, hydroxy, amino, nitro, cyano, $C_{1-6}$ alkyl optionally substituted by a halogen atom, mono- or di-$C_{1-6}$ alkyl-amino, $C_{6-14}$ aryl, mono- or di-$C_{6-14}$ aryl-amino, $C_{3-7}$ cycloalkyl, $C_{1-6}$ alkoxy, $C_{1-6}$ alkoxy-$C_{1-6}$ alkoxy, $C_{1-6}$ alkylthio, $C_{1-6}$ alkylsulfinyl, $C_{1-6}$ alkylsulfonyl, optionally esterified carboxyl, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;

(10) $C_{6-14}$ aryloxy optionally substituted by 1 to 3 substituents selected from a halogen atom, hydroxy, amino, nitro, cyano, $C_{1-6}$ alkyl optionally substituted by a halogen atom, mono- or di-$C_{1-6}$ alkyl-amino, $C_{6-14}$ aryl, mono- or di-$C_{6-14}$ aryl-amino, $C_{3-7}$ cycloalkyl, $C_{1-6}$ alkoxy, $C_{1-6}$ alkoxy-$C_{1-6}$ alkoxy, $C_{1-6}$ alkylthio, $C_{1-6}$ alkylsulfinyl, $C_{1-6}$ alkylsulfonyl, optionally esterified carboxyl, carbamoyl, thiocarbamoyl, mono- or di-$C_{1-6}$ alkyl-carbamoyl, mono- or di-$C_{6-14}$ aryl-carbamoyl, sulfamoyl, mono- or alkyl-sulfamoyl and mono- or di-$C_{6-14}$ aryl-sulfamoyl;

(11) $C_{7-16}$ aralkyloxy optionally substituted by 1 to 3 substituents selected from a halogen atom, hydroxy, amino, nitro, cyano, $C_{1-6}$ alkyl optionally substituted by a halogen atom, mono- or di-$C_{1-6}$ alkyl-amino, $C_{6-14}$ aryl, mono- or di-$C_{6-14}$ aryl-amino, $C_{3-7}$ cycloalkyl, $C_{1-6}$ alkoxy, $C_{1-6}$ alkoxy-$C_{1-6}$ alkoxy, $C_{1-6}$ alkylthio, $C_{1-6}$ alkylsulfinyl, $C_{1-6}$ alkylsulfonyl, optionally esterified carboxyl, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;

(12) a heterocyclic group (preferably, furyl, pyridyl, thienyl, pyrazolyl, thiazolyl, oxazolyl) optionally substituted by 1 to 3 substituents selected from a halogen atom, hydroxy, amino, nitro, cyano, $C_{1-6}$ alkyl optionally substituted by a halogen atom, mono- or di-$C_{1-6}$ alkyl-amino, $C_{6-14}$ aryl, mono- or di-$C_{6-14}$ aryl-amino, $C_{3-7}$ cycloalkyl, $C_{1-6}$ alkoxy, $C_{1-6}$ alkoxy-$C_{1-6}$ alkoxy, $C_{1-6}$ alkylthio, $C_{1-6}$ alkylsulfinyl, $C_{1-6}$ alkylsulfonyl, optionally esterified carboxyl, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;

(13) mono- or di-$C_{1-6}$ alkyl-amino;

(14) mono- or di-$C_{6-14}$ aryl-amino;

(15) mono- or di-$C_{7-16}$ aralkyl-amino;

(16) N—$C_{1-6}$ alkyl-N—$C_{6-14}$ aryl-amino;

(17) N—$C_{1-6}$ alkyl-N—$C_{7-16}$ aralkyl-amino;

(18) $C_{3-7}$ cycloalkyl;

(19) optionally substituted $C_{1-6}$ alkoxy (preferably, methoxy, ethoxy, propoxy, isopropoxy, isobutoxy, neopentyloxy);

(20) optionally substituted $C_{1-6}$ alkylthio;

(21) $C_{1-6}$ alkylsulfinyl;

(22) $C_{1-6}$ alkylsulfonyl;

(23) optionally esterified carboxyl;

(24) $C_{1-6}$ alkyl-carbonyl;

(25) $C_{3-7}$ cycloalkyl-carbonyl;

(26) $C_{6-14}$ aryl-carbonyl;

(27) carbamoyl;

(28) thiocarbamoyl;

(29) mono- or di-$C_{1-6}$ alkyl-carbamoyl;

(30) mono- or di-$C_{6-14}$ aryl-carbamoyl;

(31) mono- or di-5- to 7-membered heterocyclyl-carbamoyl;

(32) sulfamoyl;

(33) mono- or di-$C_{1-6}$ alkyl-sulfamoyl;

(34) mono- or di-$C_{6-14}$ aryl-sulfamoyl;

(35) $C_{1-6}$ alkyl-carbonylamino (e.g., acetylamino, propionylamino) optionally substituted by carboxy;

(36) heterocyclyl-oxy;

and the like. When plural substituents are present, the respective substituents may be the same or different.

Unless otherwise specified, examples of the "optionally substituted amino" in the present specification include amino optionally substituted by 1 or 2 substituents selected from (1) optionally substituted $C_{1-6}$ alkyl;

(2) optionally substituted $C_{2-6}$ alkenyl;

(3) optionally substituted $C_{2-6}$ alkynyl;

(4) optionally substituted $C_{3-7}$ cycloalkyl;

(5) optionally substituted $C_{6-14}$ aryl;

(6) optionally substituted $C_{1-6}$ alkoxy;

(7) optionally substituted acyl;
(8) an optionally substituted heterocyclic group (preferably furyl, pyridyl, thienyl, pyrazolyl, thiazolyl, oxazolyl);
(9) sulfamoyl;
(10) mono- or di-$C_{1-6}$ alkyl-sulfamoyl;
(11) mono- or di-$C_{6-14}$ aryl-sulfamoyl;
and the like. When the "optionally substituted amino" is amino substituted by two substituents, these substituents may be the same or different, or these substituents may form, together with the adjacent nitrogen atom, a nitrogen-containing heterocycle. Examples of the "nitrogen-containing heterocycle" include a 5- to 7-membered nitrogen-containing heterocycle containing, as a ring-constituting atom besides carbon atoms, at least one nitrogen atom and optionally further containing one or two hetero atoms selected from an oxygen atom, a sulfur atom and a nitrogen atom. Preferable examples of the nitrogen-containing heterocycle include pyrrolidine, imidazolidine, pyrazolidine, piperidine, piperazine, morpholine, thiomorpholine, thiazolidine, oxazolidine and the like.

Unless otherwise specified, examples of the "optionally substituted acyl" in the present specification include groups represented by the formulas: —$COR^7$, —CO—$OR^7$, —$SO_2R^7$, —$SOR^7$, —$PO(OR^7)(OR^8)$, —CO—$NR^{7a}R^{8a}$ and —CS—$NR^{7a}R^{8a}$ wherein $R^7$ and $R^8$ are the same or different and each is a hydrogen atom, an optionally substituted hydrocarbon group or an optionally substituted heterocyclic group, $R^{7a}$ and $R^{8a}$ are the same or different and each is a hydrogen atom, an optionally substituted hydrocarbon group or an optionally substituted heterocyclic group, or $R^{7a}$ and $R^{8a}$ may form, together with the adjacent nitrogen atom, an optionally substituted nitrogen-containing heterocycle] and the like.

Examples of the "nitrogen-containing heterocycle" of the "optionally substituted nitrogen-containing heterocycle" formed by $R^{7a}$ and $R^{8a}$ together with the adjacent nitrogen atom include a 5- to 7-membered nitrogen-containing heterocycle containing, as a ring-constituting atom besides carbon atoms, at least one nitrogen atom and optionally further containing one or two hetero atoms selected from an oxygen atom, a sulfur atom and a nitrogen atom. Preferable examples of the nitrogen-containing heterocycle include pyrrolidine, imidazolidine, pyrazolidine, piperidine, piperazine, morpholine, thiomorpholine, thiazolidine, oxazolidine and the like.

The nitrogen-containing heterocycle optionally has 1 or 2 substituents at substitutable position(s). Examples of such substituent include hydroxy, $C_{1-6}$ alkyl optionally substituted by a halogen atom, $C_{6-14}$ aryl, $C_{7-16}$ aralkyl and the like. When the number of the substituents is 2, the respective substituents may be the same or different.

Preferable examples of the "optionally substituted acyl" include
formyl;
carboxyl;
carbamoyl;
$C_{1-6}$ alkyl-carbonyl;
$C_{1-6}$ alkoxy-carbonyl;
$C_{3-7}$ cycloalkyl-carbonyl;
$C_{6-14}$ aryl-carbonyl;
$C_{7-16}$ aralkyl-carbonyl;
$C_{6-14}$ aryloxy-carbonyl;
$C_{7-16}$ aralkyloxy-carbonyl;
mono- or di-$C_{1-6}$ alkyl-carbamoyl;
mono- or di-$C_{6-14}$ aryl-carbamoyl;
mono- or di-$C_{3-7}$ cycloalkyl-carbamoyl;
mono- or di-$C_{7-16}$ aralkyl-carbamoyl;
$C_{1-6}$ alkylsulfonyl;
$C_{6-14}$ arylsulfonyl optionally substituted by nitro;
nitrogen-containing heterocyclyl-carbonyl;
$C_{1-6}$ alkylsulfinyl;
$C_{6-14}$ arylsulfinyl;
thiocarbamoyl;
sulfamoyl;
mono- or di-$C_{1-6}$ alkyl-sulfamoyl;
mono- or di-$C_{6-14}$ aryl-sulfamoyl;
mono- or di-$C_{7-16}$ aralkyl-sulfamoyl;
and the like.

The definition of each symbol in the formula (I) is described in detail in the following.

Ring A is an optionally further substituted 6-membered aromatic ring.

As the "6-membered aromatic ring" of the "optionally further substituted 6-membered aromatic ring" for ring A, a benzene ring, a pyridine ring, a pyrimidine ring, a pyrazine ring, a pyridazine ring, a triazine ring and the like can be mentioned. Preferred is a benzene ring.

The "6-membered aromatic ring" is optionally further substituted by 1-5 (preferably 1-3, more preferably 1 or 2) substituents other than ring B($R^1$)—$CH_2$—O—, at substitutable position(s).

Examples of such substituent include
(1) a $C_{3-10}$ cycloalkyl group (e.g., cyclopropyl, cyclohexyl);
(2) a $C_{6-14}$ aryl group (e.g., phenyl, naphthyl) optionally substituted by 1 to 3 substituents selected from
 (a) a $C_{1-6}$ alkyl group optionally substituted by 1 to 3 halogen atoms,
 (b) a hydroxy group,
 (c) a $C_{1-6}$ alkoxy group optionally substituted by 1 to 3 halogen atoms, and
 (d) a halogen atom;
(3) an aromatic heterocyclic group (e.g., thienyl, furyl, pyridyl, pyrazolyl, imidazolyl, tetrazolyl, oxazolyl, thiazolyl, oxadiazolyl, thiadiazolyl) optionally substituted by 1 to 3 substituents selected from
 (a) a $C_{1-6}$ alkyl group optionally substituted by 1 to 3 halogen atoms,
 (b) a hydroxy group,
 (c) a $C_{1-6}$ alkoxy group optionally substituted by 1 to 3 halogen atoms, and
 (d) a halogen atom;
(4) a non-aromatic heterocyclic group (e.g., tetrahydrofuryl, morpholinyl, thiomorpholinyl, piperidinyl, pyrrolidinyl, piperazinyl) optionally substituted by 1 to 3 substituents selected from
 (a) a $C_{1-6}$ alkyl group optionally substituted by 1 to 3 halogen atoms,
 (b) a hydroxy group,
 (c) a $C_{1-6}$ alkoxy group optionally substituted by 1 to 3 halogen atoms,
 (d) a halogen atom, and
 (e) an oxo group;
(5) an amino group optionally mono- or di-substituted by substituent(s) selected from
 (a) a $C_{1-6}$ alkyl group optionally substituted by 1 to 3 halogen atoms,
 (b) a $C_{1-6}$ alkyl-carbonyl group optionally substituted by 1 to 3 halogen atoms,
 (c) a $C_{1-6}$ alkoxy-carbonyl group optionally substituted by 1 to 3 halogen atoms,
 (d) a $C_{1-6}$ alkylsulfonyl group (e.g., methylsulfonyl) optionally substituted by 1 to 3 halogen atoms,
 (e) a carbamoyl group optionally mono- or di-substituted by a $C_{1-6}$ alkyl group optionally substituted by 1 to 3 halogen atoms, and (f) an aromatic heterocyclic group (e.g., thienyl, furyl, pyridyl, pyrazolyl, imidazolyl, tetrazolyl, oxazolyl, thiazolyl, oxadiazolyl, thiadiazolyl);
(6) a $C_{1-6}$ alkyl-carbonyl group optionally substituted by 1 to 3 halogen atoms;
(7) a $C_{1-6}$ alkoxy-carbonyl group optionally substituted by 1 to 3 substituents selected from
  (a) a halogen atom,
  (b) a $C_{1-6}$ alkoxy group,
  (c) a $C_{6-14}$ aryl group (e.g., phenyl), and
  (d) a heterocyclic group (e.g., tetrahydrofuryl);
(8) a $C_{1-6}$ alkylsulfonyl group (e.g., methylsulfonyl, ethylsulfonyl, isopropylsulfonyl) optionally substituted by 1 to 3 halogen atoms;
(9) a carbamoyl group optionally mono- or di-substituted by a $C_{1-6}$ alkyl group optionally substituted by 1 to 3 halogen atoms;
(10) a thiocarbamoyl group optionally mono- or di-substituted by a $C_{1-6}$ alkyl group optionally substituted by 1 to 3 halogen atoms;
(11) a sulfamoyl group optionally mono- or di-substituted by a $C_{1-6}$ alkyl group optionally substituted by 1 to 3 halogen atoms;
(12) a carboxy group;
(13) a hydroxy group;
(14) a $C_{1-6}$ alkoxy group (e.g., methoxy, ethoxy, propoxy, isopropoxy, isobutoxy, neopentyloxy) optionally substituted by 1 to 3 substituents selected from
  (a) a halogen atom,
  (b) a carboxy group,
  (c) a $C_{1-6}$ alkoxy group,
  (d) a $C_{1-6}$ alkoxy-carbonyl group optionally substituted by 1 to 3 $C_{6-14}$ aryl groups (e.g., phenyl),
  (e) an amino group optionally mono- or di-substituted by substituent(s) selected from a $C_{1-6}$ alkyl group and a $C_{1-6}$ alkoxy-carbonyl group,
  (f) a heterocyclic group (e.g., tetrahydrofuryl), and
  (g) a $C_{3-10}$ cycloalkyl group;
(15) a $C_{2-6}$ alkenyloxy group (e.g., ethenyloxy) optionally substituted by 1 to 3 halogen atoms;
(16) a $C_{7-13}$ aralkyloxy group (e.g., benzyloxy);
(17) a $C_{6-14}$ aryloxy group (e.g., phenyloxy, naphthyloxy);
(18) a $C_{1-6}$ alkyl-carbonyloxy group (e.g., acetyloxy, tert-butylcarbonyloxy);
(19) a $C_{6-14}$ aryl-carbonyl group (e.g., benzoyl) optionally substituted by 1 to 3 substituents selected from
  (a) a halogen atom, and
  (b) a $C_{1-6}$ alkyl group optionally substituted by 1 to 3 halogen atoms;
(20) a non-aromatic heterocyclylcarbonyl group (e.g., pyrrolidinylcarbonyl, morpholinylcarbonyl) optionally substituted by 1 to 3 substituents selected from a $C_{1-6}$ alkyl group optionally substituted by 1 to 3 halogen atoms;
(21) a mercapto group;
(22) a $C_{1-6}$ alkylthio group (e.g., methylthio, ethylthio) optionally substituted by 1 to 3 substituents selected from
  (a) a halogen atom, and
  (b) a $C_{1-6}$ alkoxy-carbonyl group;
(23) a $C_{7-13}$ aralkylthio group (e.g., benzylthio);
(24) a $C_{6-14}$ arylthio group (e.g., phenylthio, naphthylthio);
(25) a cyano group;
(26) a nitro group;
(27) a halogen atom (e.g., fluorine atom);
(28) a $C_{1-3}$ alkylenedioxy group;
(29) a $C_{1-3}$ alkyleneoxy group (e.g., methyleneoxy, ethyleneoxy);
(30) aromatic heterocyclylcarbonyl group (e.g., pyrazolylcarbonyl, pyrazinylcarbonyl, isoxazolylcarbonyl, pyridylcarbonyl, thiazolylcarbonyl) optionally substituted by 1 to 3 substituents selected from a $C_{1-6}$ alkyl group optionally substituted by 1 to 3 halogen atoms;
(31) a $C_{3-10}$ cycloalkoxy group (e.g., cyclopropoxy, cyclopentyloxy) optionally substituted by 1 to 3 substituents selected from
  (a) a halogen atom (e.g., fluorine atom), and
  (b) a $C_{1-6}$ alkoxy group (e.g., methoxy);
(32) a $C_{1-8}$ alkyl group (e.g., methyl, ethyl, propyl, butyl, isobutyl, neopentyl, neohexyl, 2,2-dimethylbutyl, 2,2-dimethylpentyl, 3,3-diethylbutyl, 2,2,3-trimethylpropyl, 3,3-dimethylpentyl) optionally substituted by 1 to 3 substituents selected from
  (a) a halogen atom,
  (b) a carboxy group,
  (c) a hydroxy group,
  (d) a $C_{1-6}$ alkoxy-carbonyl group,
  (e) a $C_{1-6}$ alkoxy group, and
  (f) an amino group optionally mono- or di-substituted by a $C_{1-6}$ alkyl group;
(33) a $C_{2-6}$ alkenyl group (e.g., ethenyl, 1-propenyl) optionally substituted by 1 to 3 substituents selected from
  (a) a halogen atom,
  (b) a carboxy group,
  (c) a hydroxy group,
  (d) a $C_{1-6}$ alkoxy-carbonyl group,
  (e) a $C_{1-6}$ alkoxy group, and
  (f) an amino group optionally mono- or di-substituted by a $C_{1-6}$ alkyl group;
(34) a $C_{7-13}$ aralkyl group (e.g., benzyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group, and
  (d) a halogen atom; and the like. When the number of the substituents is two or more, the respective substituents may be the same or different.

The substituent is preferably a halogen atom (e.g., fluorine atom), a $C_{1-6}$ alkoxy group (e.g., methoxy), a $C_{1-6}$ alkyl group, a $C_{1-5}$ alkylthio group, a alkylamino group (e.g., methylamino), or a cyano group, more preferably a halogen atom (e.g., fluorine atom) or a $C_{1-6}$ alkoxy group (e.g., methoxy).

Ring A is preferably an optionally further substituted benzene ring, more preferably a benzene ring optionally further substituted by 1 to 3 substituents selected from a halogen atom (e.g., fluorine atom) and a $C_{1-6}$ alkoxy group (e.g., methoxy).

Ring A is more preferably a benzene ring further substituted by 1 to 3 substituents selected from a halogen atom (e.g., fluorine atom) and a $C_{1-6}$ alkoxy group (e.g., methoxy), further preferably a benzene ring further substituted by one halogen atom (e.g., fluorine atom) and one $C_{1-6}$ alkoxy group (e.g., methoxy).

Ring B is an optionally further substituted 6-membered aromatic heterocycle.

As the "6-membered aromatic heterocycle" of the "optionally further substituted 6-membered aromatic heterocycle" for ring B, a pyridine ring, a pyrimidine ring, a pyrazine ring, a pyridazine ring, and a triazine ring can be mentioned. Preferred are a pyridine ring, and a pyrimidine ring.

The "6-membered aromatic heterocycle" of the "optionally further substituted 6-membered aromatic heterocycle" for ring B is more preferably a pyridine ring.

The "6-membered aromatic heterocycle" is optionally further substituted by 1 or 2 (preferably 1) substituents other than $R^1$, ring A and $CH_2$—O-ring C—, at substitutable position(s).

Examples of such substituent include those similar to the substituents that the "6-membered aromatic ring" of the "optionally further substituted 6-membered aromatic ring" for ring A optionally has. When the number of the substituents is two, the respective substituents may be the same or different. The substituent is preferably $C_{1-6}$ alkoxy groups (e.g., methoxy).

Ring B is preferably a pyridine ring or pyrimidine ring each of which is optionally further substituted, more preferably a pyridine ring or pyrimidine ring optionally further substituted by 1 to 3 $C_{1-6}$ alkoxy groups (e.g., methoxy), further preferably (1) a pyridine ring optionally further substituted by 1 to 3 (preferably, 1) $C_{1-6}$ alkoxy groups (e.g., methoxy), or (2) a pyrimidine ring.

Ring B is particularly preferably an (unsubstituted) pyridine ring.

Ring C is an optionally further substituted 6-membered aromatic ring.

Examples of the "6-membered aromatic ring" of the "optionally further substituted 6-membered aromatic ring" for ring C include a benzene ring, a pyridine ring, a pyrimidine ring, a pyrazine ring, a pyridazine ring and a triazine ring, preferably a benzene ring, a pyridine ring and a pyrimidine ring.

the "6-membered aromatic ring" of the "optionally further substituted 6-membered aromatic ring" for ring C is more preferably a pyrimidine ring.

The "6-membered aromatic ring" is optionally further substituted by 1-4 (preferably 1-3, more preferably 1 or 2) substituents other than —$CH_2$—O— and —Y—$CR^2R^3$—CO—OH, at substitutable position(s).

Examples of such substituent include those similar to the substituents that the "6-membered aromatic ring" of the "optionally further substituted 6-membered aromatic ring" for ring A optionally has. When the number of the substituents is two or more, the respective substituents may be the same or different. The substituent is preferably a halogen atom (e.g., fluorine atom), a $C_{1-6}$ alkyl group (e.g., methyl) or a $C_{1-6}$ alkoxy group (e.g., methoxy).

Ring C is preferably a benzene ring, a pyridine ring or a pyrimidine ring, each of which is optionally further substituted, more preferably a benzene ring, a pyridine ring or a pyrimidine ring, each of which is optionally further substituted by 1 to 3 substituents selected from a halogen atom (e.g., fluorine atom), a $C_{1-6}$ alkyl group (e.g., methyl) and a $C_{1-6}$ alkoxy group (e.g., methoxy).

Ring C is further more preferably (1) a benzene ring optionally further substituted by 1 to 3 (preferably, 1) substituents selected from a halogen atom (e.g., fluorine atom), a $C_{1-6}$ alkyl group (e.g., methyl) and a $C_{1-6}$ alkoxy group (e.g., methoxy), (2) a pyridine ring, or (3) a pyrimidine ring optionally further substituted by 1 to 3 (preferably, 1) substituents selected from a halogen atom (e.g., fluorine atom), a $C_{1-6}$ alkyl group (e.g., methyl) and a $C_{1-6}$ alkoxy group (e.g., methoxy).

Ring C is particularly preferably an (unsubstituted) pyrimidine ring.

As another embodiment of ring C, an (unsubstituted) benzene ring is preferable.

Another embodiment of ring C is a pyrimidine ring optionally further substituted by 1 to 3 (preferably, 1) substituents selected from a halogen atom (e.g., fluorine atom), a $C_{1-6}$ alkyl group (e.g., methyl) and a $C_{1-6}$ alkoxy group (e.g., methoxy).

Another embodiment of ring C is a pyridine ring optionally further substituted by 1 to 3 (preferably, 1) substituents selected from a halogen atom (e.g., fluorine atom), a $C_{1-6}$ alkyl group (e.g., methyl) and a $C_{1-6}$ alkoxy group (e.g., methoxy).

Y is —$NR^{4A}$—, —$CR^{4B}R^{4C}$—, or —O— wherein $R^{4A}$, $R^{4B}$ and $R^{4C}$ are each independently a hydrogen atom, an optionally substituted $C_{1-6}$ alkyl group, an optionally substituted $C_{2-6}$ alkenyl group, an optionally substituted $C_{2-6}$ alkynyl group, or an optionally substituted $C_{3-7}$ cycloalkyl group.

The "$C_{1-6}$ alkyl group" of the "optionally substituted $C_{1-6}$ alkyl group" for $R^{4A}$, $R^{4B}$ or $R^{4C}$ is preferably methyl, ethyl, propyl, isopropyl or isobutyl, more preferably, methyl or ethyl.

The "$C_{2-6}$ alkenyl group" of the "optionally substituted $C_{2-6}$ alkenyl group" for $R^{4A}$, $R^{4B}$ or $R^{4C}$ is preferably vinyl, allyl, 1-butenyl or 2-methyl-1-propenyl.

The "$C_{2-6}$ alkynyl group" of the "optionally substituted $C_{2-6}$ alkynyl group" for $R^{4A}$, $R^{4B}$ or $R^{4C}$ is preferably ethynyl, propen-2-yl or cyclopropylethynyl, more preferably, ethynyl or propen-2-yl.

The "$C_{3-7}$ cycloalkyl group" of the "optionally substituted $C_{3-7}$ cycloalkyl group" for $R^{4A}$, $R^{4B}$ or $R^{4C}$ is preferably cyclopropyl, cyclobutyl, cyclopentyl or cyclohexyl, more preferably, cyclopropyl or cyclobutyl.

$R^{4A}$ is preferably an optionally substituted $C_{1-6}$ alkyl group (e.g., methyl, ethyl, propyl), more preferably, a $C_{1-6}$ alkyl group (e.g., ethyl).

$R^{4B}$ is preferably a hydrogen atom.

$R^{4C}$ is preferably a hydrogen atom or an optionally substituted $C_{3-7}$ cycloalkyl group (e.g., cyclopropyl, cyclopropylmethyl, cyclobutyl, cyclopentyl), more preferably, a hydrogen atom or a $C_{3-7}$ cycloalkyl group (e.g., cyclopropyl, cyclobutyl).

Y is specifically —N(ethyl)-, —$CH_2$— or —CH(cyclopropyl)-, preferably —CH(cyclopropyl)-.

$R^1$ is a substituent.

Examples of the substituent for $R^1$ include "halogen atom", "nitro", "cyano", "optionally substituted hydrocarbon group", "optionally substituted heterocyclic group", "optionally substituted hydroxy", "optionally substituted amino", "optionally substituted mercapto", "optionally substituted acyl" and the like, preferably, an optionally substituted $C_{1-8}$ alkyl group, and an optionally substituted $C_{1-6}$ alkoxy group.

$R^1$ is more preferably a $C_{1-6}$ alkoxy group (e.g., methoxy, propoxy, isobutoxy, neopentyloxy) optionally substituted by substituent(s) selected from (1) a $C_{1-8}$ alkyl group (e.g., neopentyl), (2) a non-aromatic heterocyclic group (e.g., tetrahydrofuranyl, tetrahydropyranyl) optionally substituted by (i) a halogen atom (e.g., fluorine atom) and (ii) 1 or 2 $C_{1-6}$ alkyl groups (e.g., methyl), more preferably, (1) neopentyl, (2) methoxy, propoxy, isobutoxy or neopentyloxy, each of which is optionally substituted by 1 to 3 substituents selected from (i) a fluorine atom; and (ii) tetrahydrofuranyl and tetrahydropyranyl each optionally substituted by 1 or 2 methyl.

In another embodiment of the present invention, $R^1$ is preferably a (1) $C_{1-8}$ alkyl group (e.g., methyl, neopentyl), optionally substituted by 1 to 3 substituents selected from (i) a $C_{3-7}$ cycloalkyl group (e.g., cyclopentyl) optionally substituted by cyano and (ii) cyano or (2) a $C_{1-6}$ alkoxy group (e.g., methoxy, propoxy, isobutoxy, neopentyloxy) optionally substituted by 1 to 3 substituents selected from (i) a halogen atom (e.g., fluorine atom) and (ii) a non-aromatic heterocyclic group (e.g., tetrahydrofuranyl, tetrahydropyranyl) optionally substituted by 1 or 2 $C_{1-6}$ alkyl groups (e.g., methyl).

In another embodiment of the present invention, $R^1$ is more preferably, (1) a $C_{1-8}$ alkyl group (e.g., methyl, neopentyl)

optionally substituted by 1 to 3 substituents selected from (i) a $C_{3-7}$ cycloalkyl group (e.g., cyclopentyl) and (ii) cyano, or (2) a $C_{1-6}$ alkoxy group (e.g., methoxy, propoxy, isobutoxy, neopentyloxy) optionally substituted by 1 to 3 substituents selected from (i) a halogen atom (e.g., fluorine atom) and (ii) a non-aromatic heterocyclic group (e.g., tetrahydrofuranyl, tetrahydropyranyl) optionally substituted by 1 or 2 $C_{1-6}$ alkyl groups (e.g., methyl).

In another embodiment of the present invention, $R^1$ is more preferably (1) a $C_{1-8}$ alkyl group (e.g., methyl, neopentyl), or (2) a $C_{1-6}$ alkoxy group (e.g., methoxy, propoxy, isobutoxy, neopentyloxy).

$R^2$ and $R^3$ are each independently a hydrogen atom or a substituent.

Examples of the substituent for $R^2$ or $R^3$ include "halogen atom", "nitro", "cyano", "optionally substituted hydrocarbon group", "optionally substituted heterocyclic group", "optionally substituted hydroxy", "optionally substituted amino", "optionally substituted mercapto", "optionally substituted acyl" and the like, preferably, a hydrogen atom and methyl.

Both $R^2$ and $R^3$ are preferably hydrogen atoms.

Preferable examples of compound (I) include the following compounds.

[Compound I-1]
Compound (I) wherein
ring A is an optionally further substituted benzene ring;
ring B is a pyridine ring or a pyrimidine ring each of which is optionally further substituted;
ring C is benzene ring, a pyridine ring or a pyrimidine ring each of which is optionally further substituted;
Y is —$NR^{4A}$— or —$CR^{4B}R^{4C}$— wherein $R^{4A}$, $R^{4B}$ and $R^{4C}$ are each independently a hydrogen atom, an optionally substituted $C_{1-6}$ alkyl group (e.g., methyl, ethyl), an optionally substituted $C_{2-6}$ alkenyl group (e.g., vinyl, allyl, 1-butenyl, 2-methyl-1-propenyl), an optionally substituted $C_{2-6}$ alkynyl group (e.g., ethynyl, propen-2-yl, cyclopropylethynyl) or an optionally substituted $C_{3-7}$ cycloalkyl group (e.g., cyclopropyl, cyclobutyl);
$R^1$ is an optionally substituted $C_{1-8}$ alkyl group, optionally substituted $C_{1-6}$ alkoxy group; and
both $R^2$ and $R^3$ are hydrogen atoms.

[Compound I-2]
Compound (I) wherein
ring A is a benzene ring optionally further substituted by 1 to 3 substituents selected from a halogen atom (e.g., fluorine atom) and a $C_{1-6}$ alkoxy group (e.g., methoxy);
ring B is a pyridine ring or a pyrimidine ring each optionally further substituted by 1 to 3 $C_{1-6}$ alkoxy groups (e.g., methoxy);
ring C is a benzene ring, a pyridine ring or a pyrimidine ring, each optionally further substituted by 1 to 3 substituents selected from a halogen atom (e.g., fluorine atom), a $C_{1-6}$ alkyl group (e.g., methyl) and a $C_{1-6}$ alkoxy group (e.g., methoxy);
Y is —$NR^{4A}$— or —$CR^{4B}R^{4C}$— wherein $R^{4A}$, $R^{4B}$ and $R^{4C}$ are each independently a hydrogen atom, an optionally substituted $C_{1-6}$ alkyl group (e.g., ethyl) or an optionally substituted $C_{3-7}$ cycloalkyl group (e.g., cyclopropyl);
$R^1$ is (1) a $C_{1-8}$ alkyl group (e.g., neopentyl), or (2) a $C_{1-6}$ alkoxy group (e.g., methoxy, ethoxy, propoxy, isobutoxy, neopentyloxy) optionally substituted by substituent(s) selected from (i) a halogen atom (e.g., fluorine atom) and (ii) a non-aromatic heterocyclic group (e.g., tetrahydrofuranyl, tetrahydropyranyl) optionally substituted by 1 or 2 $C_{1-6}$ alkyl groups (e.g., methyl); and
both $R^2$ and $R^3$ are hydrogen atoms.

[Compound I-3]
Compound (I) wherein
ring A is a benzene ring further substituted by 1 to 3 substituents selected from a halogen atom (e.g., fluorine atom) and a $C_{1-6}$ alkoxy group (e.g., methoxy);
ring B is (1) a pyridine ring optionally further substituted by 1 to 3 $C_{1-6}$ alkoxy groups (e.g., methoxy), or (2) a pyrimidine ring;
ring C is (1) a benzene ring optionally further substituted by 1 to 3 substituents selected from a halogen atom (e.g., fluorine atom), a $C_{1-6}$ alkyl group (e.g., methyl) and a $C_{1-6}$ alkoxy group (e.g., methoxy), (2) a pyridine ring, or (3) a pyrimidine ring optionally further substituted by 1 to 3 substituents selected from a halogen atom (e.g., fluorine atom), a $C_{1-6}$ alkyl group (e.g., methyl) and a $C_{1-6}$ alkoxy group (e.g., methoxy);
Y is —N(ethyl)-, —$CH_2$— or —CH(cyclopropyl)-;
$R^1$ is (1) neopentyl, or (2) methoxy, propoxy, isobutoxy or neopentyloxy optionally substituted by substituent(s) selected from (i) a fluorine atom; and (ii) tetrahydrofuranyl and tetrahydropyranyl each optionally substituted by 1 or 2 methyl; and
both $R^2$ and $R^3$ are hydrogen atoms.

[Compound I-4]
Compound (I) wherein
ring A is a benzene ring further substituted by 1 to 3 substituents selected from a halogen atom (e.g., fluorine atom) and a $C_{1-6}$ alkoxy group (e.g., methoxy);
ring B is (1) a pyridine ring optionally further substituted by 1 to 3 $C_{1-6}$ alkoxy groups (e.g., methoxy), or (2) a pyrimidine ring;
ring C is a pyrimidine ring optionally further substituted by 1 to 3 substituents selected from a halogen atom (e.g., fluorine atom), a $C_{1-6}$ alkyl group (e.g., methyl) and a $C_{1-6}$ alkoxy group (e.g., methoxy);
Y is —N(ethyl)-, —$CH_2$— or —CH(cyclopropyl)-;
$R^1$ is (1) neopentyl, or (2) methoxy, propoxy, isobutoxy or neopentyloxy, each optionally substituted by substituent(s) selected from (i) a fluorine atom; and (ii) tetrahydrofuranyl and tetrahydropyranyl optionally substituted by 1 or 2 methyl; and
both $R^2$ and $R^3$ are hydrogen atoms.

[Compound I-5]
Compound (I) wherein
ring A is a benzene ring further substituted by one halogen atom (e.g., fluorine atom) and one $C_{1-6}$ alkoxy group (e.g., methoxy);
ring B is (1) a pyridine ring optionally further substituted by 1 to 3 (preferably, 1) $C_{1-6}$ alkoxy groups (e.g., methoxy), or (2) a pyrimidine ring;
ring C is (1) a benzene ring optionally further substituted by 1 to 3 (preferably, 1) substituents selected from a halogen atom (e.g., fluorine atom), a $C_{1-6}$ alkyl group (e.g., methyl) and a $C_{1-6}$ alkoxy group (e.g., methoxy), (2) a pyridine ring, or (3) a pyrimidine ring optionally further substituted 1 to 3 (preferably, 1) substituent selected from a halogen atom (e.g., fluorine atom), a $C_{1-6}$ alkyl group (e.g., methyl) and a $C_{1-6}$ alkoxy group (e.g., methoxy);
Y is —N(ethyl)-, —$CH_2$— or —CH(cyclopropyl)-;
$R^1$ is (1) a $C_{1-8}$ alkyl group (e.g., methyl, neopentyl) optionally substituted by 1 to 3 substituents selected from (i) a $C_{3-7}$ cycloalkyl group (e.g., cyclopentyl) and cyano, or (2) a $C_{1-6}$ alkoxy group (e.g., methoxy, propoxy, isobutoxy, neopentyloxy) optionally substituted by 1 to 3 substituents selected from (i) a halogen atom (e.g., fluorine atom) and (ii) a non-aromatic heterocyclic group (e.g., tetrahydrofuranyl, tetrahydropyranyl) optionally substituted by 1 or 2 $C_{1-6}$ alkyl groups (e.g., methyl); and both $R^2$ and $R^3$ are hydrogen atoms.

[Compound I-6]

Compound (I) wherein ring A is a benzene ring further substituted by one halogen atom (e.g., fluorine atom) and one $C_{1-6}$ alkoxy group (e.g., methoxy);

ring B is an (unsubstituted) pyridine ring;

ring C is an (unsubstituted) pyrimidine ring;

Y is —CH(cyclopropyl)-;

$R^1$ is (1) a $C_{1-8}$ alkyl group (e.g., methyl, neopentyl), or (2) a $C_{1-6}$ alkoxy group (e.g., methoxy, propoxy, isobutoxy, neopentyloxy); and both $R^2$ and $R^3$ are hydrogen atoms.

[Compound I-7]

Compound (I) wherein ring A is a benzene ring further substituted by one halogen atom (e.g., fluorine atom) and one $C_{1-6}$ alkoxy group (e.g., methoxy);

ring B is an (unsubstituted) pyridine ring;

ring C is an (unsubstituted) benzene ring;

Y is —CH(cyclopropyl)-;

$R^1$ is (1) a $C_{1-8}$ alkyl group (e.g., methyl, neopentyl), or (2) a $C_{1-6}$ alkoxy group (e.g., methoxy, propoxy, isobutoxy, neopentyloxy); and both $R^2$ and $R^3$ are hydrogen atoms.

Specific examples of compound (I) include the compounds of Examples 1-44, of which 3-cyclopropyl-3-(6-((5-(2,2-dimethylpropyl)-6-(2-fluoro-5-methoxyphenyl)pyridin-3-yl)methoxy)pyrimidin-4-yl)propanoic acid or a salt thereof (Example 35);

3-cyclopropyl-3-(6-((6-(2,2-dimethylpropyl)-5-(2-fluoro-5-methoxyphenyl)pyridin-2-yl)methoxy)pyrimidin-4-yl)propanoic acid or a salt thereof (Example 8); or 3-cyclopropyl-3-(3-((5-(2,2-dimethylpropyl)-6-(2-fluoro-5-methoxyphenyl)pyridin-3-yl)methoxy)phenyl)propanoic acid or a salt thereof (Example 34) is preferable.

Examples of salts of compounds represented by the formula (I) include metal salt, ammonium salt, salt with organic base, salt with inorganic acid, salt with organic acid, salt with basic or acidic amino acid and the like.

Preferable examples of the metal salt include alkali metal salts such as sodium salt, potassium salt and the like; alkaline earth metal salts such as calcium salt, magnesium salt, barium salt and the like; aluminum salt and the like.

Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like.

Preferable examples of the salt with inorganic acid include salt with hydrochloric acid, hydrobromic acid, nitric acid, sulfuric acid, phosphoric acid and the like.

Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like, and preferable examples of the salt with acidic amino acid include salts with aspartic acid, glutamic acid and the like.

Among the above-mentioned salts, a pharmaceutically acceptable salt is preferable.

Compound (I) may be used as a prodrug.

A prodrug of the compound (I) means a compound which is converted to the compound (I) with a reaction due to an enzyme, an gastric acid, etc. under the physiological condition in the living body, that is, a compound which is converted to the compound (I) with enzymatic oxidation, reduction, hydrolysis and the like; a compound which is converted to the compound (I) by hydrolysis and the like due to gastric acid and the like.

A prodrug of the compound (I) may be a compound obtained by subjecting amino in the compound (I) to an acylation, alkylation or phosphorylation (e.g., a compound obtained by subjecting amino in the compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation); a compound obtained by subjecting hydroxy in the compound (I) to an acylation, alkylation, phosphorylation or boration (e.g., a compound obtained by subjecting hydroxy in the compound (I) to an acetylation, palmitoylation, propanoylation, pivaloylation, succinylation, fumarylation, alanylation or dimethylaminomethylcarbonylation); a compound obtained by subjecting carboxy in the compound (I) to an esterification or amidation (e.g., a compound obtained by subjecting carboxy in the compound (I) to $C_{1-6}$ alkyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation) and the like. Particularly, a compound (I) wherein carboxy is esterified by $C_{1-6}$ alkyl such as methyl, ethyl, tert-butyl and the like is preferably used. These compounds can be produced from the compound (I) according to a method known per se.

A prodrug of compound (I) may also be one which is converted to compound (I) under a physiological condition, such as those described in IYAKUHIN no KAIHATSU, Development of to Pharmaceuticals, Vol. 7, Design of Molecules, p. 163-198, Published by HIROKAWA SHOTEN, 1990.

In the present specification, a prodrug may be in the form of a salt. Examples of the salt include those exemplified as the salt of the compound represented by the aforementioned formula (I).

The production method of compound (I) is explained below.

While a representative production method of compound (I) is described below as an exemplary production method, the production method is not limited thereto.

Compound (I) can be produced by a method known per se, for example, reaction schemes 1-5 shown below or a method analogous thereto. In each of the following reaction schemes, the starting material compound may be used in the form of a salt. As such salt, those exemplified as the salt of a compound represented by the formula (I) can be used.

When a specific production method is not described, the starting compound may be easily commercially available, or can also be produced according to a method known per se, or a method analogous thereto.

The resultant product obtained by each reaction can be used directly as the reaction mixture or as a crude product for the next reaction, or can be isolated from the reaction mixture according a conventional method, and can be purified according to separation means such as recrystallization, distillation, chromatography and HPLC and the like. When the resultant product is a mixture of stereoisomers, the mixture can be purified by separation means (e.g., diastereomer salt method, chromatography, HPLC or SFC (supercritical fluid chromatography) and the like), for example, the method described in Example or a method analogous thereto and the like.

When the reagents and reactants used in each reaction are commercially available, such commercially available products can also be used directly, or can also be produced by a method known per se or a method analogous thereto, or the method described in the Examples. For example, the reagents and reactants described in the Examples can be used.

Unless otherwise specified, the leaving group used in each reaction is, for example, a halogen atom, —OSO$_2$Me, —OSO$_2$(4-tolyl), —OSO$_2$CF$_3$ and the like.

Unless particularly indicated, the solvent in each reaction is not particularly limited as long as the reaction proceeds, and the reaction can be performed in a solvent inert to the reaction, or without solvent, and two or more kinds thereof may be mixed at an appropriately ratio and used. For example, the solvents described in the Examples can be used.

Unless particularly indicated, the equivalent amount of the reagents and reactants used in each reaction is 0.001 equivalent—100 equivalents relative to the substrate in each reaction. For example, equivalent amounts of the reagents and reactants described in the Examples can be used.

Unless particularly indicated, the reaction time of each reaction is generally 5 min-72 hr. For example, the reaction time described in the Examples can be employed.

Unless particularly indicated, the reaction temperature of each reaction is under ice-cooling to reflux under heating. For example, the reaction temperatures described in the Examples can be employed.

While the solvent used for the reaction in each of the following reaction schemes is not particularly limited as long as it does not inhibit the reaction and dissolves the starting material to a certain degree, for example, aromatic hydrocarbons such as benzene, toluene, xylene and the like; aliphatic hydrocarbons such as hexane, heptane, cyclohexane and the like; ethers such as diethyl ether, diisopropyl ether, tert-butyl methyl ether, tetrahydrofuran, dioxane, 1,2-dimethoxyethane, diphenyl ether and the like; ketones such as acetone, 2-butanone and the like; nitriles such as acetonitrile, propionitrile and the like; esters such as ethyl acetate, isopropyl acetate, tert-butyl acetate and the like; amides such as N,N-dimethylformamide, N,N-dimethylacetamide, 1-methyl-2-pyrrolidinone, hexamethylphosphoric triamide and the like; imides such as 1,3-dimethyl-2-imidazolidinone and the like; alcohols such as methanol, ethanol, isopropanol, tert-butanol and the like; halogenated hydrocarbons such as chloroform, dichloromethane, 1,2-dichloroethane, carbon tetrachloride and the like; sulfoxides such as dimethyl sulfoxide and the like; organic acids such as acetic acid, propionic acid, trifluoroacetic acid and the like; water and the like can be mentioned. These solvents may be mixed at an appropriately ratio and used. The reaction temperature is generally −100° C.-250° C. which is not higher than the boiling point of the aforementioned solvent. In some cases, a pressure-resistant reaction conditions and the like may be used, and the reaction may be performed at a temperature not lower than the boiling point of the solvent. The reaction time is generally 0.5 hr-100 hr. In the following reaction schemes, ring A, ring B, ring C, $R^1$, $R^2$, $R^3$, $R^4$ and Y are as defined above.

[reaction scheme 1]

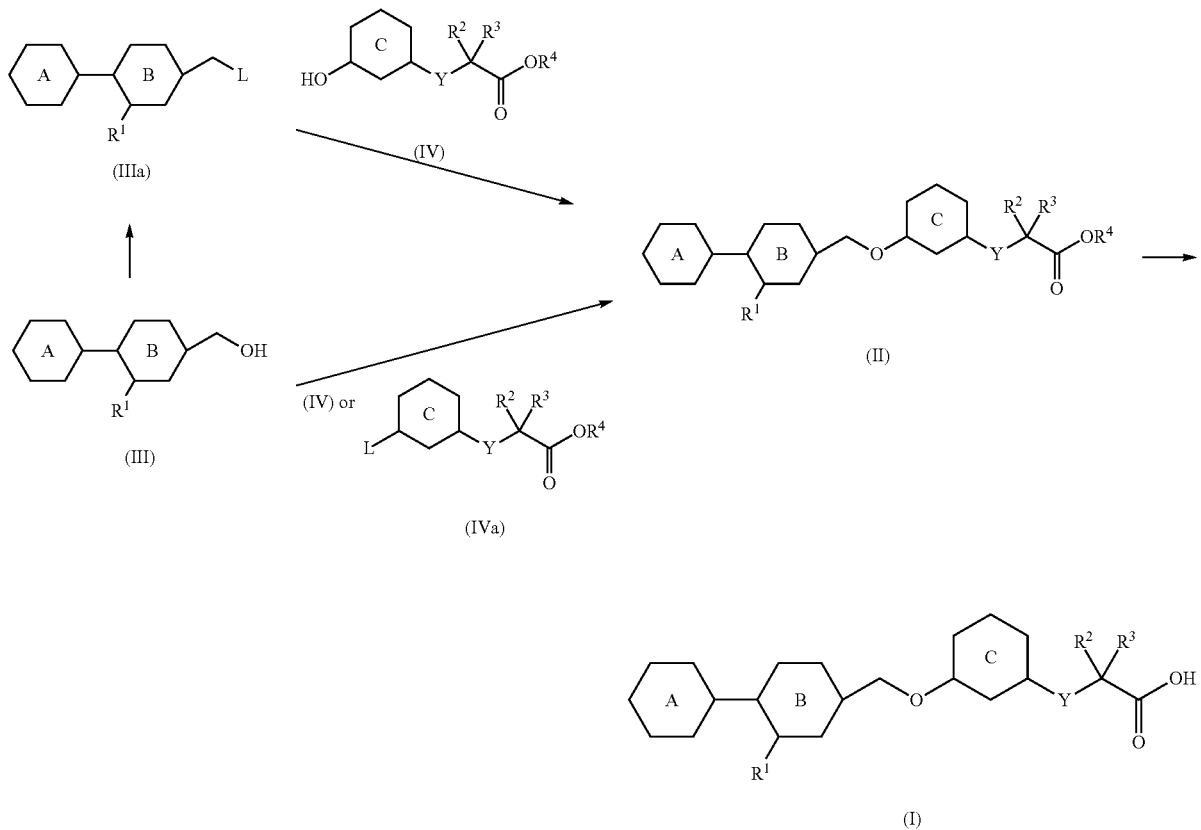

Compound (I) can be produced, for example, according to the method shown in reaction scheme 1, or a method analogous thereto.

Compound (I) can be produced from compound (II) by, for example, a method using hydrolysis in the presence of a base such as sodium hydroxide, lithium hydroxide and the like, or in the presence of an acid such as hydrochloric acid and the like, or a method analogous thereto. Compound (II) can be produced, for example, by a method using the Mitsunobu reaction of compound (III) and compound (IV), or a method analogous thereto. The Mitsunobu reaction is performed, for example, by reacting compound (III) with compound (IV) in the presence of a hydroxy group activator (e.g., cyanomethylene tri-n-butylphosphorane, diisopropyl azodicarboxylate and triphenylphosphine, diethyl azodicarboxylate and triphenylphosphine, ADDP (1,1'-(azodicarbonyl)dipiperidine) and tributylphosphine and the like) in an inert solvent (e.g., toluene, THF and the like). In addition, compound (II) can also be produced, for example, by reacting compound (IIIa) with compound (IV) or compound (III) with compound (IVa) generally in the presence of a base (e.g., pyridine, 2,6-lutidine, 4-dimethylaminopyridine, triethylamine, diisopropylethylamine, sodium hydride, t-butoxy potassium, potassium carbonate, sodium carbonate, potassium phosphate, cesium carbonate and the like). Here, $R^4$ is a $C_{1-6}$ alkyl group, a $C_{7-16}$ aralkyl group and the like, and L is a leaving group (e.g., a halogen atom or —$OSO_2Me$, —$OSO_2(4\text{-tolyl})$, —$OSO_2CF_3$ and the like). Compound (III) can be produced by the method shown in the below-mentioned reaction scheme 4, or a method known per se, or a method analogous thereto. In addition, compound (IV) and compound (IVa) can be produced by the method shown in the below-mentioned reaction scheme 5, or a method known per se, or a method analogous thereto.

[reaction scheme 2]

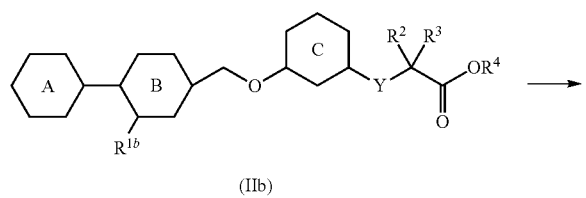

(IIb)

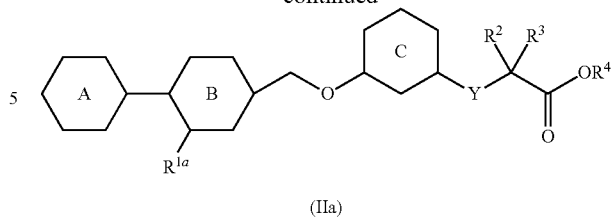

(IIa)

Compounds (IIa) wherein $R^{1a}$ is variously converted can be produced by, for example, the method shown in reaction scheme 2, which is a method including Suzuki reaction using compound (IIb) as a starting material, a method using other coupling reaction, or a method analogous thereto. The Suzuki reaction can be performed, for example, by a method known per se including reacting compound (IIb) with a boronic acid derivative generally in the presence of a base and in the presence of a catalyst (e.g., palladium catalyst, copper catalyst, nickel catalyst and the like) and an appropriate ligand. Here, $R^{1a}$ is a group similar to those exemplified for $R^1$ and $R^{1b}$ is a leaving group and the like.

[reaction scheme 3]

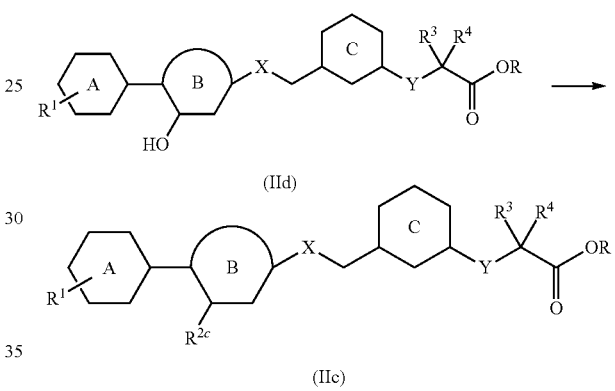

Compounds (IIc) wherein $R^{1c}$ is variously converted can be produced by, for example, the method shown in reaction scheme 3, which is a method including an alkylation reaction or Mitsunobu reaction in the presence of a base, using compound (IId) as a starting material, or a method analogous thereto. Here, $R^{1c}$ is a group similar to those exemplified for $R^1$.

[reaction scheme 4]

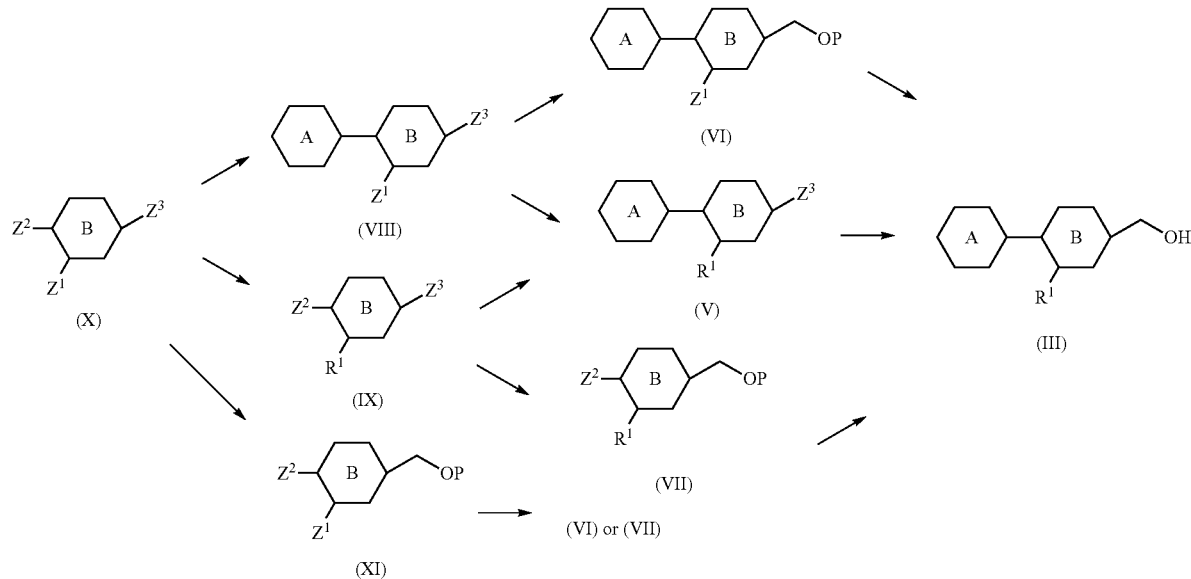

Compound (III) can be produced by, for example, the method shown in reaction scheme 4, or a method analogous thereto. Compound (III) can be produced by hydroxylation reaction when $Z^3$ in compound (V) is a methyl group, or a reduction reaction thereof when $Z^3$ is carboxylic acid or ester group, or an aldehyde group, or a method analogous thereto and the like. Here, $Z^3$ is a carboxylic acid or ester group, an aldehyde group, a cyano group, a methyl group, a hydroxyl group, a leaving group, a substituent having an optionally protected hydroxyl group, or a substituent having a leaving group. Compound (III) can also be produced, for example, by a method known per se including reacting compound (VI) or compound (VII) with halogenated aryl or aryl sulfonate, an organic metal reagent (e.g., lithium reagent or Grignard reagent, zinc reagent and the like), or a boronic acid reagent generally in the presence of a base, and in the presence of a catalyst and an appropriate ligand where necessary. Also, compound (III) can be produced by an alkylation reaction or Mitsunobu reaction in the presence of a base when $Z^1$ of compound (VI) is a substituent containing an optionally protected hydroxyl group, or a method analogous thereto. Here, P is a protecting group or hydrogen, and $Z^1$ and $Z^2$ are each a hydroxyl group, a substituent having an optionally protected hydroxyl group, a leaving group or a substituent of a precursor thereof. Compound (VI) and compound (VII) can be each produced by, as mentioned above, converting $Z^3$ of compound (VIII) or compound (IX) to an optionally protected hydroxymethyl group by a method known per se or a method analogous thereto. In addition, compound (V) can be produced by, as mentioned above, converting $Z^1$ of compound (VIII) to $R^1$ or $Z^2$ of compound (IX) to ring A, by a method known per se or a method analogous thereto. Compound (VIII) and compound (IX) can be each produced by, as mentioned above, converting $Z^1$ of compound (X) to $R^1$ or $Z^2$ of compound (X) to ring A, by a method known per se or a method analogous thereto. Moreover, compound (VI) and compound (VII) can be each produced by, as mentioned above, converting $Z^1$ of compound (XI) to $R^1$ or $Z^2$ of compound (XI) to ring A, by a method known per se or a method analogous thereto. Compound (XI) can be produced by converting $Z^3$ of compound (X) to an optionally protected hydroxymethyl group by a method known per se or a method analogous thereto.

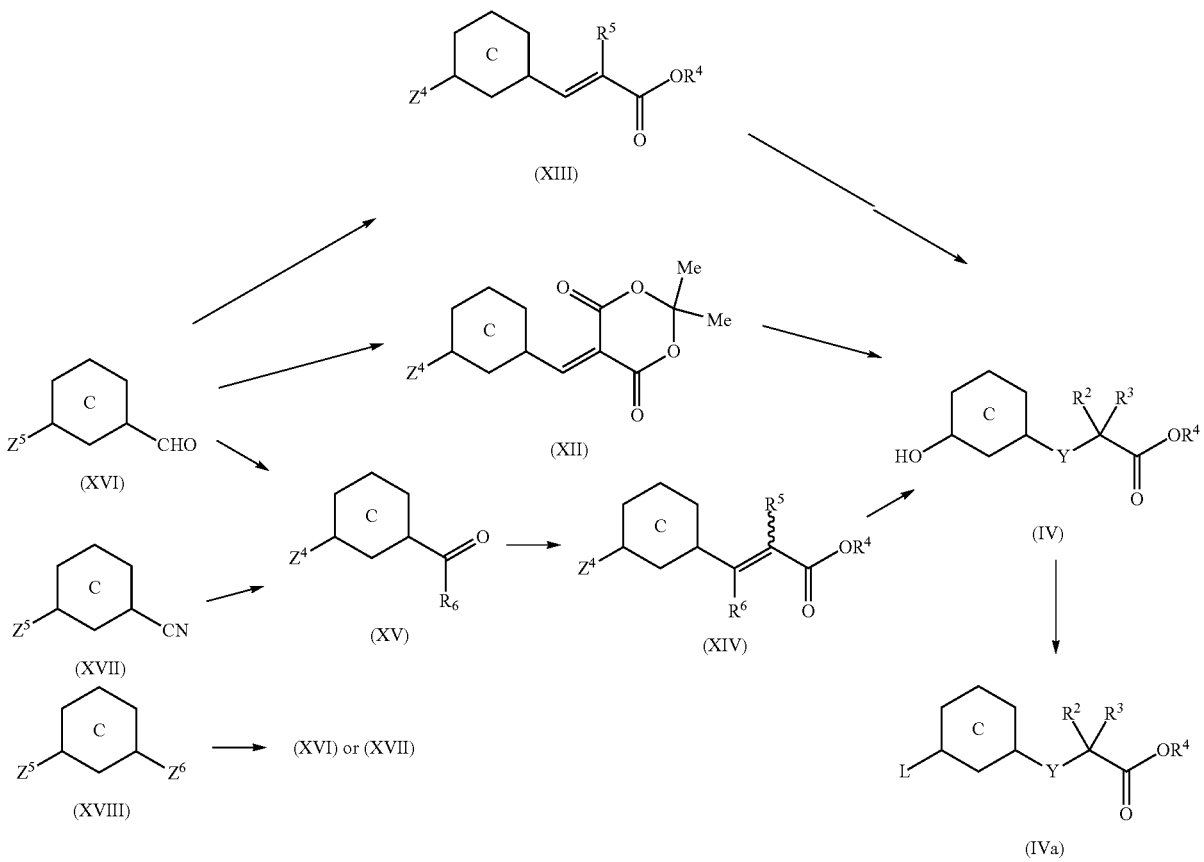

[reaction scheme 5]

Compound (IV) wherein Y is an optionally substituted carbon ($-CR^{4B}R^{4C}-$) can be produced, for example, by the method shown in reaction scheme 5, or a method analogous thereto. Compound (IVa) can be produced, for example, by converting the hydroxyl group of compound (IV) to a leaving group L by a method known per se or a method analogous thereto. Compound (IV) can be produced, for example, by reacting compound (XII) and an organic metal reagent by a method known per se or a method analogous thereto to convert the meldrum's acid moiety to an ester. Compound (IV)

can be produced, for example, by reacting compound (XIII) or compound (XIV) and an organic metal reagent by a method known per se or a method analogous thereto. Here, $R^5$ is a group similar to those exemplified for $R^2$ and $R^3$, $R^6$ is a group similar to those exemplified for $R^{4B}$ or $R^{4C}$, and $Z^4$ is ester, amide, carboxylic acid, a halogen atom or an optionally protected hydroxymethyl group. In addition, compound (IV) can be produced by reacting compound (XV) with a Wittig reagent or phosphonic acid ester according to the Horner-Emmons reaction or a method analogous thereto, and subjecting the resulting compound (XIV) to, for example, catalytic reduction (e.g., hydrogen-palladium/carbon, hydrogen-platinum oxide, hydrogen-palladium hydroxide/carbon, hydrogen-palladium/carbon ethylenediamine complex) or reduction using copper hydride and the like. Furthermore, compound (IV) can be produced by subjecting compound (XIII) to, for example, catalytic reduction and the like. Compound (XII) can be produced, for example, by reacting compound (XVI) and meldrum's acid by a method known per se or a method analogous thereto. Compound (XV) can also be produced, for example, by reacting compound (XVI) and an organic metal reagent by a method known per se or a method analogous thereto, and oxidizing the resulting hydroxyl group. Compound (XV) can be produced, for example, by reacting compound (XVII) with an organic metal reagent by a method known per se or a method analogous thereto. Here, $Z^5$ is ester, amide, carboxylic acid, a halogen atom or an optionally protected hydroxymethyl group. Compound (XVI) and compound (XVII) can be produced by, for example, converting $Z^6$ of compound (XVIII) to a formyl group or a cyano group by a method known per se or a method analogous thereto. Here, $Z^6$ is ester, amide, carboxylic acid, a halogen atom or an optionally protected hydroxymethyl group.

In each of the aforementioned reactions, when the starting compound has an amino group, a carboxy group, a hydroxy group, a carbonyl group or a mercapto group as a substituent, a protecting group generally used in the peptide chemistry and the like may be introduced into these groups, and the object compound can be obtained by eliminating the protecting group as necessary after the reaction.

Examples of the amino-protecting group include a formyl group; a $C_{1-6}$ alkyl-carbonyl group, a $C_{1-6}$ alkoxy-carbonyl group, a benzoyl group, a $C_{7-10}$ aralkyl-carbonyl group (e.g., benzylcarbonyl), a $C_{7-13}$ aralkyloxy-carbonyl group (e.g., benzyloxycarbonyl, 9-fluorenylmethoxycarbonyl), a trityl group, a phthaloyl group, an N,N-dimethylaminomethylene group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkoxy group and a nitro group.

Examples of the carboxyl-protecting group include a $C_{1-6}$ alkyl group, a $C_{7-11}$ aralkyl group (e.g., benzyl), a phenyl group, a trityl, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkoxy group and a nitro group.

Examples of the hydroxy-protecting group include a $C_{1-6}$ alkyl group, a phenyl group, a trityl group, a $C_{7-10}$ aralkyl group (e.g., benzyl), a formyl group, a $C_{1-6}$ alkyl-carbonyl group, a benzoyl group, a $C_{7-10}$ aralkyl-carbonyl group (e.g., benzylcarbonyl), a 2-tetrahydropyranyl group, a 2-tetrahydrofuranyl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl), and the like. These groups are optionally substituted by 1 to 3 substituents selected from a halogen atom, a $C_{1-6}$ alkyl group, a $C_{1-6}$ alkoxy group and a nitro group.

Examples of the carbonyl-protecting group include a cyclic acetal (e.g., 1,3-dioxane), a non-cyclic acetal (e.g., a di-$C_{1-6}$ alkylacetal) and the like.

Examples of the mercapto-protecting group include a $C_{1-6}$ alkyl group, a phenyl group, a trityl group, a $C_{7-10}$ aralkyl group (e.g., benzyl), a $C_{1-6}$ alkyl-carbonyl group, a benzoyl group, a $C_{7-10}$ aralkyl-carbonyl group (e.g., benzylcarbonyl), a $C_{1-6}$ alkoxy-carbonyl group, a $C_{6-14}$ aryloxy-carbonyl group (e.g., phenyloxycarbonyl), a $C_{7-14}$ aralkyloxy-carbonyl group (e.g., benzyloxycarbonyl, 9-fluorenylmethoxycarbonyl), a 2-tetrahydropyranyl group, a $C_{1-6}$ alkylamino-carbonyl group (e.g., methylaminocarbonyl, ethylaminocarbonyl) and the like. These groups are optionally substituted by 1 to 3 substituents selected from a halogen atom, a $C_{1-6}$ alkyl group, a $C_{1-6}$ alkoxy group and a nitro group.

The above-mentioned protecting groups can be removed by a method known per se, for example, the method described in Protective Groups in Organic Synthesis, John Wiley and Sons (1980) and the like. Specifically, a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method and the like can be mentioned.

In compound (I) obtained by each of the above-mentioned production methods, a functional group in a molecule can also be converted to a desired functional group by a combination of chemical reactions known per se. Examples of the chemical reaction include oxidation reaction, reduction reaction, alkylation reaction, acylation reaction, ureation reaction, hydrolysis reaction, amination reaction, esterification reaction, aryl coupling reaction, deprotection reaction and the like.

The compound of the formula (I) obtained by each of the is above-mentioned production methods can be isolated and purified by a known means such as concentration, concentration under reduced pressure, solvent extraction, crystallization, recrystallization, phase transfer, chromatography and the like. In addition, the starting compounds used for each of the above-mentioned production methods can be isolated and purified by a known means similar to the aforementioned methods. These starting compounds may be used in the form of a reaction mixture without isolation, as a starting material for the next step.

When compound (I) contains an isomer such as an optical isomer, a stereoisomer, a regioisomer or a rotamer, any one of them and a mixture thereof are also encompassed in compound (I). For example, when compound (I) contains an optical isomer, an optical isomer resolved from racemate is also encompassed in compound (I). Each of these isomers can be obtained as a single product by a synthesis means, separation means (e.g., concentration, solvent extraction, column chromatography, recrystallization etc.), optical resolution means (e.g., fractional recrystallization method, chiral column method, diastereomer method etc.) and the like, which are known per se.

Compound (I) may be a crystal, and the crystal form may be single or a mixture of crystal forms, both of which are encompassed in compound (I). The crystal can be produced by a crystallization method known per se.

Compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, stability etc.). The cocrystal and cocrystal salt can be produced by cocrystallization method known per se.

In the present specification, the melting point means that measured using, for example, a micromelting point apparatus (Yanako, MP-500D or Buchi, B-545), a DSC (differential scanning calorimetry) device (SEIKO, EXSTAR6000) or the like.

In general, the melting points vary depending on the measurement apparatuses, the measurement conditions and the like. The crystal in the present specification may show different values from the melting point described in the present specification, as long as they are within each of a general error range.

The crystal of the present invention is superior in physicochemical properties (e.g., melting point, solubility, stability) and biological properties (e.g., pharmacokinetics (absorption, distribution, metabolism, excretion), efficacy expression), and thus it is extremely useful as a medicament.

Compound (I) may be a solvate (e.g., hydrate etc.), or a non-solvate (e.g., non-hydrate etc.), and both are encompassed in compound (I).

A compound labeled with an isotope (e.g., $^3$H, $^{13}$C, $^{14}$C, $^{18}$F, $^{35}$S, $^{125}$I etc.) and the like is also encompassed in compound (I).

Compound (I) also encompasses a deuterium conversion form wherein $^1$H is converted to $^2$H(D).

Compound (I) labeled or substituted with an isotope can be used as, for example, a tracer (PET tracer) used for Positron Emission Tomography (PET), and is useful in the fields of medical diagnosis and the like.

Compound (I) and a prodrug thereof (hereinafter, these are collectively abbreviated as the compound of the present invention) have a GPR40 receptor function modulating action, particularly, a GPR40 agonist activity. GPR40 agonist activates GPR40 expressed in pancreatic β cells to promote insulin secretion, and activates GPR40 expressed in the intestine to promote glucagon-like peptide-1 (glucagon-like peptide-1; GLP-1) secretion. That is, the compound of the present invention has a hypoglycemic action, an insulin secretagogue action, a GLP-1 secretagogue action and a pancreatic β cell protecting action. Moreover, the compound of the present invention may have a glucose-dependent insulinotropic polypeptide (GIP) secretagogue action, a food ingestion suppressive action and a glucagon secretion suppressive action.

The compound of the present invention shows low toxicity (e.g., acute toxicity, chronic toxicity, genetic toxicity, reproductive toxicity, cardiotoxicity, carcinogenicity and the like) and can be safely administered a mammal (e.g., mouse, rat, hamster, rabbit, cat, dog, bovine, sheep, monkey, human) directly or as a pharmaceutical composition by mixing same with a pharmacologically acceptable carrier and the like.

The compound of the present invention is useful as modulators of physiological function in which GPR40 receptor is involved or as agents for the prophylaxis or treatment of pathology or disease in which GPR40 receptor is involved.

To be specific, the compound of the present invention is useful as an agent for the prophylaxis or treatment of diabetes (e.g., type 1 diabetes, type 2 diabetes, gestational diabetes, obese diabetes), an insulin secretagogue, a pancreatic β cell protector, a GLP-1 secretion promoter, a GIP secretion promoter, an agent for the prophylaxis or treatment of impaired glucose tolerance (IGT) and an agent for preventing progression of impaired glucose tolerance to diabetes.

Particularly, the compound of the present invention is useful as blood glucose level-dependent insulin secretagogues based on the GPR40 agonist activity thereof. That is different from sulfonylureas, the compound of the present invention is useful as insulin secretagogues that do not cause hypoglycemia.

Furthermore, the compound of the present invention can be used as an agent for the prophylaxis or treatment of obesity, hyperlipidemia (e.g., hypertriglyceridemia, hypercholesterolemia, high LDL-cholesterolemia, hypoHDL-emia, postprandial hyperlipemia), hypertension, cardiac failure, diabetic complications [e.g., neuropathy, nephropathy, retinopathy, diabetic cardiomyopathy, cataract, macroangiopathy, osteopenia, hyperosmolar diabetic coma, infections (e.g., respiratory infection, urinary tract infection, gastrointestinal infection, dermal soft tissue infections, inferior limb infection), diabetic gangrene, xerostomia, hypacusis, cerebrovascular disorder, peripheral blood circulation disorder], metabolic syndrome (according to the diagnostic criteria for Japanese people as reported in 2005 by the Japan Society for the Study of Obesity and the like, the metabolic syndrome refers to males having an abdominal circumference of 85 cm or above and females having an abdominal circumference of 90 cm or above and satisfying two items out of three items of: systolic blood pressure of not less than 130 or diastolic blood pressure of not less than 85 mmHg, neutral triglyceride not less than 150 mg/dl or HDLc less than 40 mg/dl, and fasting blood sugar level (venous plasma glucose concentration) not less than 110 mg/dl) and the like.

For diagnostic criteria of diabetes, Japan Diabetes Society reported diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 h level (glucose concentration of intravenous plasma) of not less than 200 mg/dl, and a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 h level (glucose concentration of intravenous plasma) of less than 140 mg/dl" (normal type) is called a "borderline type".

In addition, ADA (American Diabetes Association) and WHO reported diagnostic criteria of diabetes.

According to these reports, diabetes is a condition showing a fasting blood glucose level (glucose concentration of intravenous plasma) of not less than 126 mg/dl, or a 75 g oral glucose tolerance test 2 h level (glucose concentration of intravenous plasma) of not less than 200 mg/dl.

According to the above-mentioned reports by ADA and WHO, impaired glucose tolerance is a condition showing a 75 g oral glucose tolerance test 2 h level (glucose concentration of intravenous plasma) of not less than 140 mg/dl and less than 200 mg/dl. According to the report of ADA, a condition showing a fasting blood glucose level (glucose concentration of intravenous plasma) of not less than 110 mg/dl and less than 126 mg/dl is called IFG (Impaired Fasting Glucose). According to the report of WHO, among the IFG (Impaired Fasting Glucose), a condition showing a fasting blood glucose level (glucose concentration of intravenous plasma) of not less than 110 mg/dl and less than 126 mg/dl is called IFG (Impaired Fasting Glycemia).

The compound of the present invention can also be used as an agent for the prophylaxis or treatment of diabetes, borderline type, impaired glucose tolerance, IFG (Impaired Fasting Glucose) and IFG (Impaired Fasting Glycemia), as determined according to the above-mentioned diagnostic criteria. Moreover, the compound of the present invention can prevent progress of borderline type, impaired glucose tolerance, IFG (Impaired Fasting Glucose) or IFG (Impaired Fasting Glycemia) into diabetes.

The compound of the present invention is also useful as a therapeutic agent for diabetes with sulfonylurea secondary failure and affords a superior insulin secretion effect and a hypoglycemic effect for diabetic patients for whom sulfonylurea compounds and fast-acting insulin secretagogues fail to provide an insulin secretion effect, and therefore, fail to provide a sufficient hypoglycemic effect.

As the sulfonylurea compound here, a compound having a sulfonylurea skeleton or a derivative thereof (e.g., tolbutamide, glibenclamide, gliclazide, chlorpropamide, tolazamide, acetohexamide, glyclopyramide, glimepiride, glipizide, glybuzole and the like) can be mentioned.

As the fast-acting insulin secretagogue, a compound that promotes insulin secretion from pancreatic B cell in the same manner as a sulfonylurea compound, though it does not have a sulfonylurea skeleton, such as glinide compounds (e.g., repaglinide, senaglinide, nateglinide, mitiglinide or a calcium salt hydrate thereof etc.), and the like, can be mentioned.

The compound of the present invention can also be used as an agent for the prophylaxis or treatment of, for example, cognitive impairment, osteoporosis, cachexia (e.g., cancerous cachexia, tuberculous cachexia, diabetic cachexia, hemopathic cachexia, endocrinopathic cachexia, infectious cachexia or cachexia induced by acquired immunodeficiency syndrome), fatty liver, polycystic ovary syndrome, renal disease (e.g., diabetic nephropathy, glomerulonephritis, glomerulosclerosis, nephrotic syndrome, hypertensive nephrosclerosis, end-stage renal disorder), muscular dystrophy, myocardial infarction, angina pectoris, cerebrovascular disorder (e.g., cerebral infarction, cerebral apoplexy), insulin resistance syndrome, syndrome X, hyperinsulinemia, perception disorder in hyperinsulinemia, tumor (e.g., leukemia, breast cancer, prostate cancer, skin cancer), irritable bowel syndrome, acute or chronic diarrhea, inflammatory disease (e.g., arteriosclerosis (e.g., atherosclerosis), rheumatoid arthritis, spondylitis deformans, osteoarthritis, lumbago, gout, postoperative or post-traumatic inflammation, swelling, neuralgia, pharyngolaryngitis, bladder inflammation, hepatitis (including nonalcoholic steatohepatitis), pneumonia, pancreatitis, inflammatory colitis, ulcerative colitis, chronic obstructive pulmonary diseases (COPD)), visceral fat syndrome, foot ulcer, sepsis, psoriasis and the like.

In addition, the compound of the present invention can also be used for the improvement of the symptoms of abdominal pain, nausea, vomiting, uncomfortable feeling in the upper abdomen and the like, which are associated with peptic ulcer, acute or chronic gastritis, biliary dyskinesia, cholecystitis and the like and the like.

Since the compound of the present invention has a pancreatic β cell protection action, it can be used for the prognosis improvement in pancreatic islet transplantation.

The compound of the present invention can also be used for decreasing the visceral fat, suppressing visceral fat accumulation, improving sugar metabolism, improving lipid metabolism, insulin sensitizing, suppressing oxidized LDL production, improving lipoprotein metabolism, improving coronary metabolism, preventing or treating cardiovascular complication, preventing or treating heart failure complication, decreasing blood remnant, preventing or treating anovulation, preventing or treating hirsutism, preventing or treating hyperandrogenism and the like.

The compound of the present invention can also be used for the secondary prevention and the suppression of progression of the above-mentioned various diseases (e.g., cardiovascular event such as myocardial infarction and the like).

A medicament containing the compound of the present invention can be safely administered solely to a mammal or by mixing with a pharmacologically acceptable carrier according to a method known per se (e.g., the method described in the Japanese Pharmacopoeia etc.) as the production method of a pharmaceutical preparation, and in the form of, for example, tablet (including sugar-coated tablet, film-coated tablet, sublingual tablet, orally disintegrating tablet, buccal tablet and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal and intratumor administrations, administration to the vicinity of tumor, and direct administration to the lesion).

A pharmaceutical composition can be produced by a method conventionally used in the technical field of pharmaceutical preparation, for example, the method described in the Japanese Pharmacopoeia and the like.

During production of an oral preparation, coating may be applied as necessary for the purpose of masking of taste, enteric property or durability.

Examples of the coating base to be used for coating include sugar coating base, aqueous film coating base, enteric film coating base and sustained-release film coating base.

As the sugar coating base, sucrose is used. Moreover, one or more kinds selected from talc, precipitated calcium carbonate, gelatin, gum arabic, pullulan, carnauba wax and the like may be used in combination.

Examples of the aqueous film coating base include cellulose polymers such as hydroxypropyl cellulose, hydroxypropylmethyl cellulose, hydroxyethyl cellulose, methylhydroxyethyl cellulose etc.; synthetic polymers such as polyvinylacetal diethylaminoacetate, aminoalkyl methacrylate copolymer E [Eudragit E (trade name)], polyvinylpyrrolidone etc.; and polysaccharides such as pullulan etc.

Examples of the enteric film coating base include cellulose polymers such as hydroxypropylmethyl cellulose phthalate, hydroxypropylmethyl cellulose acetate succinate, carboxymethylethyl cellulose, cellulose acetate phthalate etc.; acrylic polymers such as methacrylic acid copolymer L [Eudragit L (trade name)], methacrylic acid copolymer LD [Eudragit L-30D55 (trade name)], methacrylic acid copolymer S [Eudragit S (trade name)] etc.; and naturally occurring substances such as shellac etc.

Examples of the sustained-release film coating base include cellulose polymers such as ethyl cellulose etc.; and acrylic polymers such as aminoalkyl methacrylate copolymer RS [Eudragit RS (trade name)], ethyl acrylate-methyl methacrylate copolymer suspension [Eudragit NE (trade name)] etc.

The above-mentioned coating bases may be used after mixing with two or more kinds thereof at appropriate ratios.

For coating, for example, a light shielding agent such as titanium oxide, red ferric oxide and the like can be used.

The content of the compound of the present invention in a pharmaceutical preparation is about 0.01 to about 100% by weight relative to the whole preparation. While the dose varies depending on the administration subject, administration route, diseases, condition and the like, for example, the compound of the present invention (as an active ingredient) can be orally administered to a patient with diabetes (body weight about 60 kg) in about 0.01 to about 30 mg/kg body weight per day, preferably about 0.1 to about 20 mg/kg body weight per day, more preferably about 1 to about 20 mg/kg body weight per day, which may be given at once or in several portions (e.g., 1-3 portions) a day.

As the above-mentioned pharmacologically acceptable carrier, various organic or inorganic carrier substances conventionally used as a preparation material. For example, excipient, lubricant, binder and disintegrant for solid preparations; solvent, solubilizing agents, suspending agent, isotonicity agent, buffer and soothing agent for liquid preparations and the like can be mentioned. Where necessary, conventional additives such as preservatives, antioxidants, colorants, sweetening agents, adsorbing agents, wetting agents and the like can be used.

As the excipient, for example, lactose, sucrose, D-mannitol, starch, corn starch, crystalline cellulose, light anhydrous silicic acid and the like can be mentioned.

As the lubricant, for example, magnesium stearate, calcium stearate, talc, colloidal silica and the like can be mentioned.

As the binder, for example, crystalline cellulose, sucrose, D-mannitol, dextrin, hydroxypropylcellulose, hydroxypropylmethylcellulose, polyvinylpyrrolidone, starch, saccharose, gelatin, methylcellulose, carboxymethylcellulose sodium and the like can be mentioned.

As the disintegrant, for example, starch, carboxymethylcellulose, carboxymethylcellulose calcium, carboxymethylstarch sodium, L-hydroxypropylcellulose and the like can be mentioned.

As the solvent, for example, water for injection, alcohol, propylene glycol, macrogol, sesame oil, corn oil, olive oil and the like can be mentioned.

As the solubilizing agents, for example, polyethylene glycol, propylene glycol, D-mannitol, benzyl benzoate, ethanol, trisaminomethane, cholesterol, triethanolamine, sodium carbonate, sodium citrate and the like can be mentioned.

As the suspending agent, for example, surfactants such as stearyltriethanolamine, sodium lauryl sulfate, lauryl aminopropionate, lecithin, benzalkonium chloride, benzethonium chloride, glycerol monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like, and the like can be mentioned.

As the isotonicity agent, for example, glucose, D-sorbitol, sodium chloride, glycerin, D-mannitol and the like can be mentioned.

As the buffer, for example, buffers such as phosphates, acetates, carbonates, citrates and the like, and the like can be mentioned.

As the soothing agent, for example, benzyl alcohol and the like can be mentioned.

As the preservative, for example, p-hydroxybenzoates, chlorobutanol, benzyl alcohol, phenethyl alcohol, dehydroacetic acid, sorbic acid and the like can be mentioned.

As the antioxidant, for example, sulfites, ascorbic acid, α-tocopherol and the like can be mentioned.

As the colorant, for example, water-soluble edible tar pigments (e.g., foodcolors such as Food Color Red Nos. 2 and 3, Food Color Yellow Nos. 4 and 5, Food Color Blue Nos. 1 and 2 and the like), water insoluble lake pigments (e.g., aluminum salt of the aforementioned water-soluble edible tar pigment and the like), natural pigments (e.g., (β-carotene, chlorophil, ferric oxide red etc.) and the like can be mentioned.

As the sweetening agent, for example, saccharin sodium, dipotassium glycyrrhizinate, aspartame, stevia and the like can be mentioned.

Moreover, the compound of the present invention can be used in combination with drugs other than the compound of the present invention.

As the drugs that can be used in combination with the compound of the present invention (hereinafter sometimes to be abbreviated as a concomitant drug), for example, other therapeutic agents for diabetes, therapeutic agents for diabetic complications, therapeutic agents for hyperlipidemia, antihypertensive agents, antiobesity agents, diuretics, chemotherapeutic agents, immunotherapeutic agents, antiinflammatory agents, antithrombotic agents, therapeutic agents for osteoporosis, vitamins, antidementia agents, erectile dysfunction improving drugs, therapeutic agents for pollakiuria or urinary incontinence, therapeutic agents for dysuria and the like can be mentioned. Specifically, the following agents can be mentioned.

Examples of other therapeutic agents for diabetes include insulin preparations (e.g., animal insulin preparations extracted from pancreas of bovine or swine; human insulin preparations genetically synthesized using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), Metaglidasen, AMG-131, Balaglitazone, MBX-2044, Rivoglitazone, Aleglitazar, Chiglitazar, Lobeglitazone, PLX-204, PN-2034, GFT-505, THR-0921, compounds described in WO2007/013694, WO2007/018314, WO2008/093639 and WO2008/099794), α-glucosidase inhibitors (e.g., voglibose, acarbose, miglitol, emiglitate), biguanides (e.g., metformin, buformin or a salt thereof (e.g., hydrochloride, fumarate, succinate)), insulin secretagogues [sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or calcium salt hydrate thereof], dipeptidyl-peptidase IV inhibitors (e.g., Alogliptin or a salt thereof (preferably benzoate), Vildagliptin, Sitagliptin, Saxagliptin, BI1356, GRC8200, MP-513, PF-00734200, PHX1149, SK-0403, ALS2-0426, TA-6666, TS-021, KRP-104, 2-[[6-[(3R)-3-amino-1-piperidinyl]-3,4-dihydro-3-methyl-2,4-dioxo-1(2H)-pyrimidinyl]methyl]-4-fluorobenzonitrile or a salt thereof), β3 agonists (e.g., N-5984), GPR40 agonists (e.g., compounds described in WO2004/041266, WO2004/106276, WO2005/063729, WO2005/063725, WO2005/087710, WO2005/095338, WO2007/013689 and WO2008/001931), GLP-1 receptor agonists (e.g., GLP-1, GLP-1MR agent, Liraglutide, Exenatide, AVE-0010, BIM-51077, Aib(8,35)hGLP-1(7,37)NH$_2$, CJC-1131, Albiglutide), amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists, FBPase inhibitors), SGLT2 (sodium-glucose cotransporter 2) inhibitors (e.g., Depagliflozin, AVE2268, TS-033, YM543, TA-7284, Remogliflozin, ASP1941), SGLT1 inhibitor, 11β-hydroxysteroid dehydrogenase inhibitors (e.g., BVT-3498, INCB- 13739), adiponectin or agonist thereof, IKK inhibitors (e.g., AS-2868), leptin resistance improving drugs, somatostatin receptor agonists, glucokinase activators (e.g., Piragliatin, AZD1656, AZD6370, TTP-355, compounds described in WO2006/112549, WO2007/028135, WO2008/047821, WO2008/050821, WO2008/136428 and WO2008/156757), GIP (Glucose-dependent insulinotropic peptide), GPR119 agonists (e.g., PSN821, MBX-2982, APD597), FGF21, FGF analogue and the like.

Examples of the therapeutic agents for diabetic complications include aldose reductase inhibitors (e.g., Tolrestat, Epalrestat, Zopolrestat, Fidarestat, CT-112, ranirestat (AS-3201), Lidorestat), neurotrophic factors and increasing drugs thereof (e.g., NGF, NT-3, BDNF, neurotrophin production-secretion promoters described in WO01/14372 (e.g., 4-(4-chlorophenyl)-2-(2-methyl-1-imidazolyl)-5-[3-(2-methylphenoxy) propyl]oxazole), compound described in WO2004/039365), PKC inhibitors (e.g., ruboxistaurin mesylate). AGE inhibitors (e.g., ALT-946, N-phenacylthiazolium bromide (ALT-766), EXO-226, Pyridorin, Pyridoxamine), GABA receptor agonists (e.g., gabapentin, Pregabalin), serotonin-noradrenaline reuptake inhibitors (e.g., duloxetine), sodium channel inhibitors (e.g., Lacosamide), active oxygen scavengers (e.g., thioctic acid), cerebral vasodilators (e.g., tiapuride, mexiletine), somatostatin receptor agonists (BIM23190), apoptosis signal regulating kinase-1 (ASK-1) inhibitors and the like.

Examples of the therapeutic agent for hyperlipidemia include HMG-CoA reductase inhibitors (e.g., pravastatin, simvastatin, lovastatin, atorvastatin, fluvastatin, rosuvastatin, pitavastatin or a salt thereof (e.g., sodium salt, calcium salt)), squalene synthase inhibitors (e.g., compound described in WO97/10224, for example, N—[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid), fibrate compounds (e.g., bezafibrate, clofibrate, simfibrate, clinofibrate), anion exchange resins (e.g., colestyramine), probucol, nicotinic acid drugs (e.g., nicomol, niceritrol, niaspan), ethyl icosapentate, phytosterol (e.g., soysterol, gamma oryzanol), cholesterol absorption inhibitors (e.g., Zetia), CETP inhibitors (e.g., dalcetrapib, anacetrapib), ω-3 fatty acid preparations (e.g., ω-3-acid ethyl esters 90) and the like.

Examples of the antihypertensive agent include angiotensin converting enzyme inhibitors (e.g., captopril, enalapril, delapril and the like), angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, azilsartan medoxomil and the like), calcium antagonists (e.g., manidipine, nifedipine, amlodipine, efonidipine, nicardipine, amlodipine, cilnidipine and the like), β blockers (e.g., metoprolol, atenolol, propranolol, carvedilol, pindolol and the like), clonidine and the like.

Examples of the antiobesity agent include monoamine uptake inhibitors (e.g., phentermine, sibutramine, mazindol, fluoxetine, tesofensine), serotonin 2C receptor agonists (e.g., lorcaserin), serotonin 6 receptor antagonists, histamine H3 receptor modulator, GABA modulator (e.g., topiramate), neuropeptide Y antagonists (e.g., velneperit), cannabinoid receptor antagonists (e.g., rimonabant, taranabant), ghrelin antagonists, ghrelin receptor antagonists, ghrelin acylation enzyme inhibitors, opioid receptor antagonists (e.g., GSK-1521498), orexin receptor antagonists, melanocortin 4 receptor agonists, 11β-hydroxysteroid dehydrogenase inhibitors (e.g., AZD-4017), pancreatic lipase inhibitors (e.g., orlistat, cetilistat), β3 agonists (e.g., N-5984), diacylglycerol acyltransferase 1 (DGAT1) inhibitors, acetylCoA carboxylase (ACC) inhibitors, stearoyl-CoA desaturated enzyme inhibitors, microsomal triglyceride transfer protein inhibitors (e.g., R-256918), Na-glucose cotransporter inhibitors (e.g., JNJ-28431754, remogliflozin), NFK inhibitors (e.g., HE-3286), PPAR agonists (e.g., GFT-505, DRF-11605), phosphotyrosine phosphatase inhibitors (e.g., sodium vanadate, Trodusquemin), GPR119 agonists (e.g., PSN-821, MBX-2982, APD597), glucokinase activators (e.g., AZD-1656), leptin, leptin derivatives (e.g., metreleptin), CNTF (ciliary neurotrophic factor), BDNF (brain-derived neurotrophic factor), cholecystokinin agonists, glucagon-like peptide-1 (GLP-1) preparations (e.g., animal GLP-1 preparations extracted from the pancreas of bovine or swine; human GLP-1 preparations genetically synthesized using *Escherichia coli* or yeast; fragments or derivatives of GLP-1 (e.g., exenatide, liraglutide)), amylin preparations (e.g., pramlintide, AC-2307), neuropeptide γ agonists (e.g., PYY3-36, derivatives of PYY3-36, obineptide, TM-30339, TM-30335), oxyntomodulin preparations; FGF21 preparations (e.g., animal FGF21 preparations extracted from the pancreas of bovine or swine; human FGF21 preparations genetically synthesized using *Escherichia coli* or yeast; fragments or derivatives of FGF21)), anorexigenic agents (e.g., P-57) and the like.

Examples of the diuretics include xanthine derivatives (e.g., sodium salicylate and theobromine, calcium salicylate and theobromine), thiazide preparations (e.g., ethiazide, cyclopenthiazide, trichloromethiazide, hydrochlorothiazide, hydroflumethiazide, benzylhydrochlorothiazide, penflutizide, poly5thiazide, methyclothiazide), antialdosterone preparations (e.g., spironolactone, triamterene), carbonate dehydratase inhibitors (e.g., acetazolamide), chlorobenzenesulfonamide preparations (e.g., chlortalidone, mefruside, indapamide), azosemide, isosorbide, etacrynic acid, piretanide, bumetanide, furosemide and the like.

Examples of the chemotherapeutic agents include alkylating agents (e.g., cyclophosphamide, ifosfamide), metabolic antagonists (e.g., methotrexate, 5-fluorouracil), antitumor antibiotics (e.g., mitomycin, adriamycin), plant-derived antitumor agents (e.g., vincristine, vindesine, Taxol), cisplatin, carboplatin, etoposide and the like. Of these, Furtulon or NeoFurtulon, which are 5-fluorouracil derivatives, and the like are preferable.

Examples of the immunotherapeutic agents include microorganism or bacterial components (e.g., muramyl dipeptide derivatives, Picibanil), polysaccharides having immunity potentiating activity (e.g., lentinan, schizophyllan, krestin), cytokines obtained by genetic engineering techniques (e.g., interferon, interleukin (IL)), colony stimulating factors (e.g., granulocyte colony stimulating factor, erythropoietin) and the like, with preference given to interleukins such as IL-1, IL-2, IL-12 and the like.

Example of the antiinflammatory agents include non-steroidal antiinflammatory agents such as aspirin, acetaminophen, indomethacin and the like.

Examples of the antithrombotic agents include heparin (e.g., heparin sodium, heparin calcium, enoxaparin sodium, dalteparin sodium), warfarins (e.g., warfarin potassium), anti-thrombin drugs (e.g., aragatroban, dabigatran)), FXa inhibitors (e.g., rivaroxaban, apixaban, edoxaban, YM150, compounds described in WO02/06234, WO2004/048363, WO2005/030740, WO2005/058823 and WO2005/113504), thrombolytic agents (e.g., urokinase, tisokinase, alteplase, nateplase, monteplase, pamiteplase), platelet aggregation inhibitors (e.g., ticlopidine hydrochloride, clopidogrel, prasugrel, E5555, SHC530348, cilostazol, ethyl icosapentate, beraprost sodium, sarpogrelate hydrochloride) and the like.

Examples of the therapeutic agents for osteoporosis include alfacalcidol, calcitriol, elcatonin, calcitonin salmon, estriol, ipriflavone, pamidronate disodium, alendronate sodium hydrate, incadronate disodium, risedronate disodium and the like.

Examples of the vitamins include vitamin $B_1$, vitamin $B_{12}$ and the like.

Examples of the antidementia agents include tacrine, donepezil, rivastigmine, galanthamine and the like.

Examples of the erectile dysfunction improving drug include apomorphine, sildenafil citrate and the like.

Examples of the therapeutic agents for pollakiuria or urinary incontinence include flavoxate hydrochloride, oxybutynin hydrochloride, propiverine hydrochloride and the like.

Examples of the therapeutic agents for dysuria include acetylcholine esterase inhibitors (e.g., distigmine) and the like.

Furthermore, drugs having a cachexia-improving action established in animal models and clinical situations, such as cyclooxygenase inhibitors (e.g., indomethacin), progesterone derivatives (e.g., megestrol acetate), glucosteroids (e.g., dexamethasone), metoclopramide agents, tetrahydrocannabinol agents, fat metabolism improving agents (e.g., eicosapentanoic acid), growth hormones, IGF-1, or antibodies to a cachexia-inducing factor such as TNF-α, LIF, IL-6, oncostatin M and the like, can be used in combination with the compound of the present invention.

Furthermore, glycosylation inhibitors (e.g., ALT-711), nerve regeneration promoting drugs (e.g., Y-128, VX853, prosaptide), antidepressants (e.g., desipramine, amitriptyline, imipramine), antiepileptics (e.g., lamotrigine, Trileptal, Keppra, Zonegran, Pregabalin, Harkoseride, carbamazepine), antiarrhythmic agents (e.g., mexiletine), acetylcholine receptor ligands (e.g., ABT-594), endothelin receptor antagonists (e.g., ABT-627), monoamine uptake inhibitors (e.g., tramadol), narcotic analgesics (e.g., morphine), GABA receptor agonists (e.g., gabapentin, gabapentin MR agent), $\alpha_2$ receptor agonists (e.g., clonidine), local analgesics (e.g., capsaicin), antianxiety drugs (e.g., benzothiazepines), phosphodiesterase inhibitors (e.g., sildenafil), dopamine receptor agonists (e.g., apomorphine), midazolam, Ketoconazole and the like can be also used in combination with the compound of the present invention.

The concomitant drug is preferably an insulin preparation, a PPAR function modulator (preferably pioglitazone or its hydrochloride), an α-glucosidase inhibitor (preferably voglibose), a biguanide (preferably metformin or hydrochloride thereof), a sulfonylurea (preferably glibenclamide, glimepiride), mitiglinide or calcium salt hydrate thereof, nateglinide, a dipeptidyl peptidase IV inhibitor (preferably alogliptin or benzoate thereof, 2-[[6-[(3R)-3-amino-1-piperidinyl]-3,4-dihydro-3-methyl-2,4-dioxo-1(2H)-pyrimidinyl]methyl]-4-fluorobenzonitrile or succinate thereof, 2-[2-(3-(R)-amino-piperidin-1-yl)-5-fluoro-6-oxo-6H-pyrimidin-1-ylmethyl]-benzonitrile or tartrate thereof), GLP-1 receptor agonist and the like. For enhancing the food ingestion suppressive action, a combined use with a dipeptidyl peptidase IV inhibitor (preferably, alogliptin or a salt thereof) is more preferable. Two or more kinds of the above-mentioned concomitant drugs may be used in combination at an appropriate ratio.

When the compound of the present invention is used in combination with a concomitant drug, the amounts thereof can be increased or decreased within the safe range in consideration of the side effects thereof. Particularly, the doses of insulin sensitizer, dipeptidyl peptidase IV inhibitor, α-glucosidase inhibitor, biguanide, insulin secretagogue and GLP-1 receptor agonist can be reduced from the general doses. Therefore, the side effects that will be caused by these agents can be prevented safely. In addition, the doses of therapeutic agents for diabetic complications, therapeutic agents for hyperlipidemia, and antihypertensive agents can be reduced and, as a result, the side effects that will be caused by these agents can be prevented effectively.

By combining the compound of the present invention with a concomitant drug, superior effects such as (1) decreased dose of the compound of the present invention or a concomitant drug as compared to single administration of the compound of the present invention or a concomitant drug, (2) possible setting of a long treatment period by selecting a concomitant drug having different action and mechanism from those of the compound of the present invention, (3) possible designing of a sustained treatment effect by selecting a concomitant drug having different action and mechanism from those of the compound of the present invention, (4) a synergistic effect afforded by a combined use of the compound of the present invention and a concomitant drug, and the like can be achieved.

When the compound of the present invention and a concomitant drug are used in combination, the administration time of the compound of the present invention and the concomitant drug is not restricted, and the compound of the present invention and the concomitant drug may be administered simultaneously, or may be administered at staggered times, to an administration subject. The dosage of the concomitant drug may be determined according to the dose clinically used, and can be appropriately selected depending on an administration subject, administration route, disease, combination and the like.

As the administration mode of the compound of the present invention and the concomitant drug, the following methods can be mentioned: (1) The compound of the present invention and the concomitant drug are simultaneously formulated to give a single preparation which is administered. (2) The compound of the present invention and the concomitant drug are separately formulated to give two kinds of preparations which are administered simultaneously by the same administration route. (3) The compound of the present invention and the concomitant drug are separately formulated to give two kinds of preparations which are administered by the same administration route at staggered times. (4) The compound of the present invention and the concomitant drug are separately formulated to give two kinds of preparations which are administered simultaneously by the different administration routes. (5) The compound of the present invention and the concomitant drug are separately formulated to give two kinds of preparations which are administered by the different administration routes at staggered times (e.g., the compound of the present invention and the concomitant drug are administered in this order, or in the reverse order), and the like.

EXAMPLES

The present invention is further explained in detail by referring to the following Reference Examples and Examples and Experimental Example which are not to be construed as limitative and may be changed without departing from the scope of the present invention.

The term "room temperature" in the following Examples indicates the range of generally from about 10° C. to about 35° C. The ratios indicated for mixed solvents are volume mixing ratios, unless otherwise specified. % means wt %, unless otherwise specified.

In silica gel column chromatography, NH means use of aminopropylsilane-bound silica gel. In HPLC (high performance liquid chromatography), C18 means use of octadecyl-bound silica gel. The ratios of elution solvents are volume mixing ratios, unless otherwise specified.

In the following Reference Examples and Examples, the following abbreviations are used.

mp: melting point
THF: tetrahydrofuran
DMF: dimethylformamide
WSC: 1-(3-dimethylaminopropyl)-3-ethylcarbodiimide hydrochloride
HOBt: 1-hydroxybenzotriazole monohydrate
$^1$H NMR (proton nuclear magnetic resonance spectrum) was measured by Fourier-transform type NMR. For the analysis, ACD/SpecManager (trade name) and the like were used. Peaks with very mild protons such as hydroxyl group, amino group and the like are not described.

The other symbols used herein mean the following:
s: singlet
d: doublet
t: triplet
q: quartet
m: multiplet
br: broad
J: coupling constant
Hz: Hertz
CDCl$_3$: deuterated chloroform
DMSO-d$_6$: d$_6$-dimethyl sulfoxide
$^1$H-NMR: proton nuclear magnetic resonance
TFA: trifluoroacetic acid MS (mass spectrum) was measured by LC/MS (liquid chromatography mass spectrometer). As the ionization method, ESI (ElectroSpray Ionization) method, or APCI (Atmospheric Pressure Chemical Ionization) method was used. As the ionization mode, both or either one of the positive mode (ESI+) and negative mode (ESI−) were/was used and either data are described. The data indicates those found. Generally, a molecular ion peak is observed. In the case of a compound having a tert-butoxycarbonyl group (−Boc), a peak after elimination of a tert-butoxycarbonyl group or tert-butyl group may be observed as a fragment ion. Depending on the compound, a peak after addition of a sodium ion (+Na) is sometimes observed as a fragment ion. In the case of a compound having a hydroxyl group (—OH), a peak after elimination of H$_2$O may be observed as a fragment ion. In the case of a salt, a molecular ion peak or fragment ion peak of free form is generally observed.

The unit of reagent concentration (c) in optical rotation ([α]$_D$) is g/100 mL.

The elemental analysis value (Anal.) shows Calculated (Calcd) and Found.

Example 1

3-cyclopropyl-3-(3-((5-(2-fluoro-5-methoxyphenyl)-6-isobutoxypyridin-2-yl)methoxy)phenyl)propanoic acid A) (5-(3-hydroxybenzylidene)-2,2-dimethyl-1,3-dioxane-4,6-dione Under a nitrogen atmosphere, to water (2.10 L) were added m-hydroxybenzaldehyde (70.0 g) and meldrum's acid (82.6 g), and the mixture was stirred at room temperature for 16 hr. Meldrum's acid (20.7 g) was added, and the mixture was further stirred at room temperature for 4 hr. The precipitated crystals were collected by filtration, washed with water, and dried to give the title compound (139 g) as yellow crystals. This compound was used for the next step without further purification.

B) 5-(cyclopropyl(3-hydroxyphenyl)methyl)-2,2-dimethyl-1,3-dioxane-4,6-dione

To a solution of (5-(3-hydroxybenzylidene)-2,2-dimethyl-1,3-dioxane-4,6-dione (65.0 g) in THF (1.30 L) was added dropwise a 10% solution of cyclopropylmagnesium bromide in THF (2.20 kg) at −11° C. to −1° C. over 1.6 hr, and the mixture was stirred at room temperature for 2 hr. 1N Hydrochloric acid was added to the reaction mixture at 2° C. to 17° C. to adjust the solution to pH 3. Water was added to the reaction mixture, and the mixture was extracted with ethyl acetate. The extract was washed with saturated brine and dried over anhydrous sodium sulfate. The solvent was evaporated under reduced pressure and the residue was purified by silica gel column chromatography (ethyl acetate/hexane) to give the title compound (76.0 g) as a yellow oil.

C) 3-cyclopropyl-3-(3-hydroxyphenyl)propanoic acid

To a solution of 5-(cyclopropyl(3-hydroxyphenyl)methyl)-2,2-dimethyl-1,3-dioxane-4,6-dione (164 g) in DMF (1.64 L) was added water (164 mL), and the mixture was stirred at 90° C. for 7 hr. Water and sodium chloride were added to the reaction mixture, and the mixture was extracted with ethyl acetate. The organic layer was back-extracted with saturated aqueous sodium hydrogen carbonate solution, and hydrochloric acid was added until the aqueous layer became pH 4. The reaction mixture was extracted with ethyl acetate, and the extract was washed with saturated brine, and dried over anhydrous sodium sulfate. The solvent was evaporated under reduced pressure to give the title compound (100 g) as a brown oil. This compound was used for the next step without further purification.

D) methyl 3-cyclopropyl-3-(3-hydroxyphenyl)propanoate

To a solution of 3-cyclopropyl-3-(3-hydroxyphenyl)propanoic acid (99.0 g) in methanol (990 mL) was added conc. sulfuric acid (4.71 g), and the mixture was stirred at 64° C. for 2 hr. Water and sodium chloride were added to the reaction mixture, and the mixture was extracted with ethyl acetate. The extract was washed with saturated aqueous sodium hydrogen carbonate solution and then saturated brine, and dried over anhydrous sodium sulfate. The solvent was evaporated under reduced pressure and the residue was purified by silica gel column chromatography (ethyl acetate/hexane) to give the title compound (84.0 g) as a pale-yellow oil.

E) 5-bromo-2-carboxypyridine 1-oxide

To a solution of 5-bromopicolinic acid (25.0 g) and urea. hydrogen peroxide adduct (20.0 g) in acetonitrile (200 mL) was added trifluoroacetic anhydride (50 ml) at 0° C., and the mixture was stirred for 30 min. The reaction mixture was filtered and the filtrate was concentrated under reduced pressure. The crude crystals were recrystallized from diethyl ether to give the title compound (19.6 g) as white crystals.
MS (ESI+): [M+H]$^+$ 217.8

F) 5-bromo-2-(methoxycarbonyl)pyridine 1-oxide

To a solution of 5-bromo-2-carboxypyridine 1-oxide (19.6 g) in methanol (300 mL) was added dropwise thionyl chloride (37.1 g) at 0° C., and the mixture was heated under reflux for 1 hr. The reaction mixture was concentrated under reduced pressure and the residue was washed with ethyl acetate to give the title compound (22.0 g) as white crystals. This compound was used for the next step without further purification.

MS (ESI+): [M+H]$^+$ 231.9

G) methyl 5-bromo-6-chloropicolinate

To 5-bromo-2-(methoxycarbonyl)pyridine 1-oxide (22.0 g) was added phosphoryl chloride (40.0 ml), and the mixture was stirred at 90° C. for 10 min. The reaction mixture was cooled to room temperature and poured into ice water. The reaction mixture was extracted with ethyl acetate, and the extract was washed with saturated aqueous sodium hydrogen carbonate solution and saturated brine, and dried over anhydrous sodium sulfate. The solvent was evaporated under reduced pressure to give the title compound (16.0 g) as a white amorphous solid. This compound was used for the next step without further purification.

MS (ESI+): [M+H]$^+$ 251.8

H) 5-bromo-6-chloropicolinic acid

To a solution of methyl 5-bromo-4-chloropicolinate (1.08 g) in THF (25 mL) and methanol (12.5 mL) was added 1N aqueous sodium hydroxide solution (25 mL), and the mixture was stirred at room temperature for 30 min. 1N Hydrochloric acid was added to the reaction mixture at 0° C., and the mixture was extracted with ethyl acetate. The extract was washed with water and saturated brine, and dried over anhydrous magnesium sulfate. The solvent was evaporated under reduced pressure to give a crude product of the title compound (944 mg) as a pale-yellow solid. This compound was used for the next step without further purification.

$^1$H NMR (300 MHz, DMSO-d$_6$) δ 7.92 (1H, d, J=8.0 Hz), 8.44 (1H, d, J=9.1 Hz), 13.73 (1H, brs).

I) methyl 5-bromo-6-isobutoxypicolinate

2-Methyl-1-propanol (1.48 mL) was added to a suspension of 60% sodium hydride (958 mg) in DMF (30 mL) at room temperature. 5-Bromo-6-chloropicolinic acid (entire amount) obtained in Example 1, step H, was added to the reaction mixture at room temperature. The reaction mixture was stirred under a nitrogen atmosphere at 90° C. for 1 hr. Iodomethane (2.49 mL) was added to the reaction mixture, and the mixture was stirred at 90° C. for 5 min. Water was added to the reaction mixture at room temperature, and the mixture was extracted with ethyl acetate. The extract was washed with water and saturated brine, and dried over anhydrous magnesium sulfate. The solvent was evaporated under reduced pressure and the residue was purified by silica gel column chromatography (ethyl acetate/hexane) to give a crude product of the title compound (698 mg) as a pale-yellow oil. This compound was used for the next step without further purification.

$^1$H NMR (300 MHz, DMSO-d$_6$) δ 1.00 (6H, d, J=6.8 Hz), 2.01-2.18 (1H, m), 3.87 (3H, s), 4.15 (2H, d, J=6.4 Hz), 7.58 (1H, d, J=7.5 Hz), 8.22 (1H, d, J=7.9 Hz).

J) methyl 5-(2-fluoro-5-methoxyphenyl)-6-isobutoxypicolinate

Under an argon atmosphere, to a solution of methyl 5-bromo-6-isobutoxypicolinate (698 mg), 2-fluoro-5-methoxyphenylboronic acid (454 mg), tris(dibenzylideneacetone) dipalladium(0) (65 mg) and 2-dicyclohexylphosphino-2',6'-dimethoxybiphenyl (117 mg) in toluene (10 mL) was added 2.0 M aqueous sodium carbonate solution (2.67 mL), and the mixture was stirred at 100° C. for 30 min. The reaction mixture was filtered through celite, and water was added at room temperature. The reaction mixture was extracted with ethyl acetate, and the extract was washed with water and saturated brine. The organic layer was dried over anhydrous magnesium sulfate, and the solvent was evaporated under reduced pressure. The residue was purified by silica gel column chromatography (ethyl acetate/hexane) to give the title compound (594 mg) as a pale-yellow oil.

$^1$H NMR (300 MHz, DMSO-d$_6$) δ 0.89 (6H, d, J=6.8 Hz), 1.87-1.99 (1H, m), 3.77 (3H, s), 3.89 (3H, s), 4.11 (2H, d, J=6.4 Hz), 6.95-7.07 (2H, m), 7.17-7.28 (1H, m), 7.76 (1H, d, J=7.2 Hz), 7.90 (1H, d, J=7.6 Hz).

K) (5-(2-fluoro-5-methoxyphenyl)-6-isobutoxypyridin-2-yl)methanol

To a suspension of lithium aluminum hydride (250 mg) in diethyl ether (5.0 mL) was added a solution of methyl 5-(2-fluoro-5-methoxyphenyl)-6-isobutoxypicolinate (594 mg) in diethyl ether (2.0 mL) at 0° C., and the mixture was stirred for 1 hr. Water and aqueous sodium hydroxide solution were added to the reaction mixture at 0° C., and the mixture was extracted with ethyl acetate. The extract was washed with water and saturated brine, and dried over anhydrous magnesium sulfate.

The solvent was evaporated under reduced pressure, and the residue was purified by silica gel column chromatography (ethyl acetate/hexane) to give the title compound (486 mg) as a colorless oil.

$^1$H NMR (300 MHz, DMSO-d$_6$) δ 0.87 (6H, d, J=6.8 Hz), 1.80-1.97 (1H, m), 3.76 (3H, s), 4.02 (2H, d, J=6.4 Hz), 4.50 (2H, d, J=6.0 Hz), 5.38 (1H, t, J=5.9 Hz), 6.86-7.00 (2H, m), 7.06-7.25 (2H, m), 7.68 (1H, d, J=7.2 Hz).

L) methyl 3-cyclopropyl-3-(3-((5-(2-fluoro-5-methoxyphenyl)-6-isobutoxypyridin-2-yl)methoxy)phenyl)propanoate Under a nitrogen atmosphere, to a solution of (5-(2-fluoro-5-methoxyphenyl)-6-isobutoxypyridin-2-yl)methanol (100 mg) and methyl 3-cyclopropyl-3-(3-hydroxyphenyl)propanoate (72 mg) in toluene (4.7 mL) were added 1,1'-(azodicarbonyl)dipiperidine (132 mg) and tributylphosphine (131 μL), and the mixture was stirred at room temperature for 14 hr. To the reaction mixture was added hexane/ethyl acetate (1:1), and the resulting precipitate was removed by filtration. The solvent in the filtrate was evaporated under reduced pressure, and the residue was purified by silica gel column chromatography (ethyl acetate/hexane) to give the title compound (131 mg) as a colorless oil.

$^1$H NMR (300 MHz, DMSO-d$_6$) δ 0.03-0.38 (3H, m), 0.42-0.57 (1H, m), 0.88 (6H, d, J=6.8 Hz), 0.95-1.11 (1H, m), 1.83-1.99 (1H, m), 2.18-2.34 (1H, m), 2.74 (2H, dd, J=7.6, 2.6 Hz), 3.50 (3H, s), 3.76 (3H, s), 4.06 (2H, d, J=6.4 Hz), 5.11 (2H, s), 6.80-7.03 (5H, m), 7.11-7.29 (3H, m), 7.73 (1H, d, J=7.6 Hz).

M) 3-cyclopropyl-3-(3-((5-(2-fluoro-5-methoxyphenyl)-6-isobutoxypyridin-2-yl)methoxy)phenyl)propanoic acid To a solution of methyl 3-cyclopropyl-3-(3-((5-(2-fluoro-5-methoxyphenyl)-6-isobutoxypyridin-2-yl)methoxy)phenyl)propanoate (131 mg) in THF (2.0 mL) and methanol (1.0 ml) was added 1N aqueous sodium hydroxide solution (2.0 ml), and the mixture was stirred at room temperature for 14 hr. 1N Hydrochloric acid (2.0 ml) was added to the reaction mixture at 0° C., and the mixture was extracted with ethyl acetate. The extract was washed with water and saturated brine, and dried over anhydrous magnesium sulfate. After silica gel filtration, the solvent was evaporated under reduced pressure to give the title compound (124 mg) as a white amorphous solid.

MS (ESI+): [M+H]$^+$ 494.2

$^1$H NMR (300 MHz, DMSO-$d_6$) δ 0.04-0.16 (1H, m), 0.17-0.36 (2H, m), 0.41-0.57 (1H, m), 0.88 (6H, d, J=6.8 Hz), 0.93-1.05 (1H, m), 1.83-1.98 (1H, m), 2.19-2.36 (1H, m), 2.64 (2H, dd, J=7.5, 3.4 Hz), 3.76 (3H, s), 4.06 (2H, d, J=6.4 Hz), 5.11 (2H, s), 6.77-6.91 (2H, m), 6.92-7.03 (3H, m), 7.13-7.27 (3H, m), 7.73 (1H, d, J=7.5 Hz), 12.00 (1H, brs).

Example 2

3-cyclopropyl-3-(6-((5-(2-fluoro-5-methoxyphenyl)-6-isobutoxypyridin-2-yl)methoxy)pyrimidin-4-yl) propanoic acid A) 4-chloro-6-methoxypyrimidine Under a nitrogen atmosphere, methanol (5.4 mL) was added to a suspension of 60% sodium hydride (8.05 g) in THF (200 mL) at 0° C. To the obtained suspension was added a solution of 4,-dichloropyrimidine (20.0 g) in THF (45 mL) at 0° C., and the mixture was stirred at 0° C. for 1 hr. 1N Hydrochloric acid was added to the reaction mixture at 0° C., and the mixture was extracted with ethyl acetate. The extract was washed with water and saturated brine, and dried over anhydrous magnesium sulfate. The solvent was evaporated under reduced pressure, and the residue was recrystallized (hexane) to give the title compound (10.2 g) as pale-yellow crystals.

$^1$H NMR (300 MHz, DMSO-$d_6$) δ 3.96 (3H, s), 7.19 (1H, s), 8.69 (1H, s).

B) 6-methoxypyrimidine-4-carbonitrile

To a solution of 4-chloro-6-methoxypyrimidine (10.6 g) in acetonitrile (150 mL) was added 1,4-diazabicyclo[2.2.2]octane (8.18 g), and the mixture was stirred at room temperature for 10 min. Tetraethylammonium cyanide (11.5 g) was added to the obtained reaction mixture, and the mixture was stirred at room temperature for 3 hr. Water was added to the reaction mixture at room temperature, and the mixture was extracted with ethyl acetate. The extract was washed with water and saturated brine, and dried over anhydrous magnesium sulfate. The solvent was evaporated under reduced pressure, and the residue was purified by silica gel column chromatography (ethyl acetate/hexane) to give the title compound (6.00 g) as a pale-yellow oil.

$^1$H NMR (300 MHz, DMSO-$d_6$) δ 4.00 (3H, s), 7.75 (1H, s), 8.96 (1H, s).

C) cyclopropyl(6-methoxypyrimidin-4-yl)methanone

Under a nitrogen atmosphere, to a solution of 6-methoxy-pyrimidine-4-carbonitrile (6.00 g) in THF (120 mL) was added dropwise a 0.52 M solution of cyclopropylmagnesium bromide in THF (215 mL) at 0° C., and the mixture was stirred at 0° C. for 1 hr. 6N Hydrochloric acid (60 mL) was added to the reaction mixture at 0° C., and the mixture was stirred at room temperature for 15 min. The reaction mixture was neutralized with sodium hydrogen carbonate (35.0 g), and extracted with ethyl acetate. The extract was washed with water and saturated brine, and dried over anhydrous magnesium sulfate. The solvent was evaporated under reduced pressure to give a crude product of the title compound as a brown oil. This compound was used for the next step without further purification.

$^1$H NMR (300 MHz, DMSO-$d_6$) δ 1.07-1.24 (4H, m), 3.57-3.80 (1H, m), 4.00 (3H, s), 7.25 (1H, s, J=1.1 Hz), 9.02 (1H, d, J=1.1 Hz).

D) ethyl 3-cyclopropyl-3-(6-methoxypyrimidin-4-yl)acrylate

Under a nitrogen atmosphere, to a suspension of 60% sodium hydride (2.13 g) in THF (100 ml) was added ethyl diethylphosphonoacetate (13.2 mL) at 0° C. To the obtained solution was added cyclopropyl(6-methoxypyrimidin-4-yl) methanone (entire amount) obtained in Example 2, step C, and the mixture was stirred at 0° C. for 1 hr. Water was added to the reaction mixture at room temperature, and the mixture was extracted with ethyl acetate. The extract was washed with water and saturated brine, and dried over anhydrous magnesium sulfate. The solvent was evaporated under reduced pressure, and the residue was purified by silica gel column chromatography (ethyl acetate/hexane) to give an isomer mixture of the title compound (E:Z=93:7 or 7:93, 5.57 g) as a yellow oil.

$^1$H NMR (300 MHz, DMSO-$d_6$) δ 0.56-0.66 (2H, m), 0.79-0.91 (2H, m), 1.02 (3H, t, J=7.2 Hz), 1.73-1.91 (1H, m), 3.89 (2H, q, J=7.2 Hz), 3.93 (3H, s), 5.98 (1H, s), 6.79 (1H, s), 8.75 (1H, s).

E) ethyl 3-cyclopropyl-3-(6-methoxypyrimidin-4-yl) propanoate

A zinc powder (11.5 g) was added to a solution of ethyl 3-cyclopropyl-3-(6-methoxypyrimidin-4-yl)acrylate (5.57 g) in acetic acid (60 mL), and the mixture was stirred at room temperature for 10 min. The reaction mixture was filtered, and the solvent in the filtrate was evaporated under reduced pressure to give a crude product of the title compound (5.68 g) as a yellow oil. This compound was used for the next step without further purification.

$^1$H NMR (300 MHz, DMSO-$d_6$) δ 0.18-0.43 (3H, m), 0.52 (1H, td, J =8.3, 2.3 Hz), 0.86-1.04 (1H, m), 1.09 (3H, t, J=7.0 Hz), 2.24-2.41 (1H, m), 2.66-2.79 (1H, m), 2.85-3.00 (1H, m), 3.91 (3H, s), 3.92-4.04 (2H, m), 6.88 (1H, s), 8.70 (1H, s).

F) ethyl 3-cyclopropyl-3-(6-hydroxypyrimidin-4-yl) propanoate

Under a nitrogen atmosphere, to a solution of ethyl 3-cyclopropyl-3-(6-methoxypyrimidin-4-yl)propanoate (entire amount) in DMF (15 mL) was added pyridinium chloride (25.9 g), and the mixture was stirred at 130° C. for 20 min. The reaction mixture was cooled to 0° C. and diluted with acetonitrile (20 mL). Sodium hydrogen carbonate (17.0 g) was added to the reaction mixture, the insoluble material was filtered off, and the solvent in the filtrate was evaporated under reduced pressure. The residue was purified by silica gel column chromatography (ethyl acetate/hexane), and the obtained solid was washed with diisopropyl ether to give the title compound (3.66 g) as a white solid.

$^1$H NMR (300 MHz, DMSO-$d_6$) δ 0.11-0.29 (2H, m), 0.31-0.43 (1H, m), 0.44-0.59 (1H, m), 0.82-1.03 (1H, m), 1.12 (3H, t, J=7.2 Hz), 1.99-2.19 (1H, m), 2.55-2.69 (1H, m), 2.70-2.86 (1H, m), 3.86-4.10 (2H, m), 6.20 (1H, s), 8.12 (1H, s), 12.37 (1H, brs).

G) ethyl 3-(6-chloropyrimidin-4-yl)-3-cyclopropylpropanoate

Under a nitrogen atmosphere, to a solution of ethyl 3-cyclopropyl-3-(6-hydroxypyrimidin-4-yl)propanoate (1.00 g) and DMF (66 μL) in ethyl acetate (11 mL) was added oxalyl dichloride (1.11 mL) at 0° C., and the mixture was stirred at room temperature for 1 hr. A small amount of 1N hydrochloric acid was added to the reaction mixture, and the solvent was evaporated under reduced pressure. The residue was purified by silica gel column chromatography (ethyl acetate/hexane) to give the title compound (929 mg) as a colorless oil.
$^1$H NMR (300 MHz, DMSO-$d_6$) δ 0.20-0.46 (3H, m), 0.48-0.60 (1H, m), 0.80-1.03 (1H, m), 1.08 (3H, t, J=7.0 Hz), 2.44 (1H, d, J=3.8 Hz), 2.68-2.87 (1H, m), 2.90-3.12 (1H, m), 3.72-4.11 (2H, m), 7.75 (1H, d, J=1.1 Hz), 8.96 (1H, d, J=1.1 Hz).

H) ethyl 3-cyclopropyl-3-(6-((5-(2-fluoro-5-methoxyphenyl)-6-isobutoxypyridin-2-yl)methoxy)pyrimidin-4-yl)propanoate 60% Sodium hydride (34 mg) was added to a solution of (5-(2-fluoro-5-methoxyphenyl)-6-isobutoxypyridin-2-yl)methanol (200 mg) and ethyl 3-(6-chloropyrimidin-4-yl)-3-cyclopropylpropanoate (167 mg) in THF (6.0 mL) at 0° C., and the mixture was stirred at room temperature for 30 min and at 50° C. for 4 hr. 1N Hydrochloric acid was added to the reaction mixture at 0° C., and the mixture was extracted with ethyl acetate. The extract was washed with water and saturated brine, and dried over anhydrous magnesium sulfate. The solvent was evaporated under reduced pressure, and the residue was purified by silica gel column chromatography (ethyl acetate/hexane) and silica gel column chromatography (NH, ethyl acetate/hexane) to give the title compound (198 mg) as a colorless oil.
$^1$H NMR (300 MHz, DMSO-$d_6$) δ 0.17-0.45 (3H, m), 0.47-0.61 (1H, m), 0.86 (6H, d, J=6.4 Hz), 0.92-1.04 (1H, m), 1.09 (3H, t, J=7.2 Hz), 1.90 (1H, dt, J=13.2, 6.6 Hz), 2.37 (1H, td, J=9.0, 6.0 Hz), 2.66-2.82 (1H, m), 2.86-3.03 (1H, m), 3.76 (3H, s), 3.90-4.10 (4H, m), 5.46 (2H, s), 6.80-7.00 (2H, m), 7.02 (1H, s), 7.11 (1H, d, J=7.5 Hz), 7.19 (1H, t, J=9.4 Hz), 7.72 (1H, d, J=7.5 Hz), 8.71 (1H, s).

I) 3-cyclopropyl-3-(6-((5-(2-fluoro-5-methoxyphenyl)-6-isobutoxypyridin-2-yl)methoxy)pyrimidin-4-yl)propanoic acid To a solution of ethyl 3-cyclopropyl-3-(6-((5-(2-fluoro-5-methoxyphenyl)-6-isobutoxypyridin-2-yl)methoxy)pyrimidin-4-yl)propanoate (198 mg) in THF (3.0 mL) and methanol (1.5 mL) was added 1N aqueous sodium hydroxide solution (3.0 mL), and the mixture was stirred at room temperature for 30 min. 1N Hydrochloric acid (3.0 ml) was added to the reaction mixture at 0° C., and the mixture was extracted with ethyl acetate. The extract was washed with water and saturated brine, and dried over anhydrous magnesium sulfate. After silica gel filtration, the solvent was evaporated under reduced pressure to give the title compound (180 mg) as a white amorphous solid.
MS (ESI+): [M+H]$^+$ 496.3
$^1$H NMR (300 MHz, DMSO-$d_6$) δ 0.19-0.44 (3H, m), 0.47-0.62 (1H, m), 0.86 (6H, d, J=6.8 Hz), 0.92-1.06 (1H, m), 1.81-2.00 (1H, m), 2.28-2.42 (1H, m), 2.61-2.74 (1H, m), 2.82-2.98 (1H, m), 3.76 (3H, s), 4.01 (2H, d, J=6.4 Hz), 5.45 (2H, s), 6.87-7.05 (3H, m), 7.12 (1H, d, J=7.6 Hz), 7.15-7.25 (1H, m), 7.72 (1H, d, J=7.2 Hz), 8.72 (1H, s), 12.08 (1H, brs).

Example 3

3-cyclopropyl-3-(6-(((5-(2-fluoro-5-methoxyphenyl)-6-isobutoxypyridin-2-yl)methyl)amino)pyrimidin-4-yl)propanoic acid

A) ethyl 3-(6-chloropyrimidin-4-yl)-3-cyclopropylpropanoate

To a solution of ethyl 3-cyclopropyl-3-(6-hydroxypyrimidin-4-yl)propanoate (199 mg) and DMF (13 μL) in ethyl acetate (3.0 ml) was added oxalyl dichloride (220 μL), and the mixture was stirred at room temperature for 1 hr. Water was added, and the reaction mixture was extracted with ethyl acetate. The extract was washed with saturated brine and dried over anhydrous magnesium sulfate. The solvent was evaporated under reduced pressure, and the residue was purified by silica gel column chromatography (ethyl acetate/hexane) to give the title compound (194 mg) as a colorless oil.
$^1$H NMR (300 MHz, CDCl$_3$) δ0.20-0.40 (2H, m), 0.47-0.60 (1H, m), 0.61-0.72 (1H, m), 0.97-1.14 (1H, m), 1.19 (3H, t, J=7.0 Hz), 2.39 (1H, dt, J=9.5, 4.7 Hz), 2.82 (1H, dd, J=16.3, 4.9 Hz), 3.07 (1H, dd, J=16.3, 9.1 Hz), 4.00-4.13 (2H, m), 7.32 (1H, d, J=1.1 Hz), 8.90 (1H, d, J=0.8 Hz).

B) 2-((5-(2-fluoro-5-methoxyphenyl)-6-isobutoxypyridin-2-yl)methyl)-1H-isoindole-1,3(2H)-dione To a solution of (5-(2-fluoro-5-methoxyphenyl)-6-isobutoxypyridin-2-yl)methanol (177 mg) in THF (5.0 mL) was added phthalimide (102 mg), triphenylphosphine (181 mg) and a 40% solution of diethyl azodicarboxylate in toluene (320 μL), and the mixture was stirred at room temperature for 15 hr. Water was added, and the reaction mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (228 mg) as a colorless oil.
$^1$H NMR (300 MHz, DMSO-$d_6$) δ 0.59 (6H, d, J=6.8 Hz), 1.61-1.77 (1H, m), 3.64 (2H, d, J=6.8 Hz), 3.73 (3H, s), 4.92 (2H, s), 6.88-6.98 (2H, m), 7.08 (1H, d, J=7.5 Hz), 7.12-7.21 (1H, m), 7.67 (1H, d, J=7.5 Hz), 7.86-7.92 (2H, m), 7.93-8.00 (2H, m).

C) 1-(5-(2-fluoro-5-methoxyphenyl)-6-isobutoxypyridin-2-yl)methanamine

To a solution of 2-((5-(2-fluoro-5-methoxyphenyl)-6-isobutoxypyridin-2-yl)methyl)-1H-isoindole-1,3(2H)-dione (228 mg) in ethanol (3.0 ml) was added hydrazine monohydrate (3.0 mL), and the mixture was stirred at room temperature for 20 hr. The solvent was evaporated under reduced pressure, and the residue was dissolved in ethyl acetate. The mixture was washed with water and saturated brine, and dried over anhydrous sodium sulfate. The solvent was evaporated under reduced pressure to give the title compound (152 mg) as a pale-yellow oil. This compound was used for the next step without further purification.
$^1$H NMR (300 MHz, DMSO-$d_6$) δ 0.88 (6H, d, J=6.8 Hz), 1.84-1.99 (3H, m), 3.74 (2H, s), 3.76 (3H, s), 4.05 (2H, d, J=6.4 Hz), 6.89-6.98 (2H, m), 7.09 (1H, d, J=7.5 Hz), 7.18 (1H, m), 7.64 (1H, d, J=7.5 Hz).

D) ethyl 3-cyclopropyl-3-(6-(((5-(2-fluoro-5-methoxyphenyl)-6-isobutoxypyridin-2-yl)methyl)amino)pyrimidin-4-yl)propanoate To a solution of 1-(5-(2-fluoro-5-methoxyphenyl)-6-isobutoxypyridin-2-yl)methanamine (56 mg) and ethyl 3-(6-chloropyrimidin-4-yl)-3-cyclopropylpropanoate (137 mg) in acetonitrile (3.0 mL) was added N,N-diisopropylethylamine (96 µL), and the mixture was stirred at 70° C. for 15 hr. Water was added, and the reaction mixture was extracted with ethyl acetate. The extract was washed with saturated brine, and dried over anhydrous sodium sulfate. The solvent was evaporated under reduced pressure, and the residue was purified to by silica gel column chromatography (ethyl acetate/hexane) to give the title compound (52 mg) as a colorless oil.

$^1$H NMR (300 MHz, CDCl$_3$) δ 0.13-0.34 (2H, m), 0.39-0.52 (1H, m), 0.54-0.66 (1H, m), 0.95 (6H, d, J=6.8 Hz), 1.02-1.15 (1H, m), 1.19 (3H, t, J=7.2 Hz), 1.94-2.10 (1H, m), 2.18-2.30 (1H, m), 2.75 (1H, dd, J=15.5, 6.0 Hz), 3.00 (1H, dd, J=15.7, 8.5 Hz), 3.80 (3H, s), 4.02-4.11 (2H, m), 4.13 (2H, d, J=6.4 Hz), 4.60 (2H, d, J=5.3 Hz), 5.88 (1H, brs), 6.34 (1H, d, J=0.8 Hz), 6.80-6.97 (3H, m), 7.04 (1H, t, J=9.1 Hz), 7.57 (1H, dd, J=7.6, 1.1 Hz), 8.58 (1H, s).

E) 3-cyclopropyl-3-(6-(((5-(2-fluoro-5-methoxyphenyl)-6-isobutoxypyridin-2-yl)methyl)amino)pyrimidin-4-yl)propanoic acid To a solution of ethyl 3-cyclopropyl-3-(6-(((5-(2-fluoro-5-methoxyphenyl)-6-isobutoxypyridin-2-yl)methyl)amino)pyrimidin-4-yl)propanoate (65 mg) in methanol (5.0 mL) was added 1N aqueous sodium hydroxide solution (0.37 mL), and the mixture was stirred at 50° C. for 15 hr. 1N Hydrochloric acid was added, and the reaction mixture was extracted with ethyl acetate. The extract was washed with saturated brine, and dried over anhydrous sodium sulfate. The solvent was evaporated under reduced pressure, and the residue was recrystallized from hexane/diethyl ether to give the title compound (51 mg) as a white solid.

$^1$H NMR (300 MHz, DMSO-d$_6$) δ 0.09-0.31 (2H, m), 0.31-0.42 (1H, m), 0.44-0.56 (1H, m), 0.87 (6H, d, J=6.8 Hz), 0.90-1.04 (1H, m), 1.83-1.99 (1H, m), 2.07-2.19 (1H, m), 2.57 (1H, dd, J=15.5, 5.7 Hz), 2.81 (1H, dd, J=15.7, 8.5 Hz), 3.75 (3H, s), 4.04 (2H, d, J=6.4 Hz), 4.54 (2H, m,), 6.48 (1H, s), 6.88-6.99 (3H, m), 7.12-7.23 (1H, m), 7.64 (1H, d, J=7.2 Hz), 7.79-7.89 (1H, m), 8.35 (1H, s), 12.13 (1H, brs).

Example 4

3-cyclopropyl-3-(6-(((5-(2-fluoro-5-methoxyphenyl)-6-isobutoxypyridin-2-yl)methyl)(methyl)amino)pyrimidin-4-yl)propanoic acid A) ethyl 3-cyclopropyl-3-(6-(((5-(2-fluoro-5-methoxyphenyl)-6-isobutoxypyridin-2-yl)methyl)(methyl)amino)pyrimidin-4-yl)propanoate To a solution of ethyl 3-cyclopropyl-3-(6-(((5-(2-fluoro-5-methoxyphenyl)-6-isobutoxypyridin-2-yl)methyl)amino)pyrimidin-4-yl)propanoate (52 mg) in DMF (3.0 mL) were added potassium carbonate (21 mg) and iodomethane (20 µL), and the mixture was stirred at 40° C. for 17 hr. 60% Sodium hydride (10 mg) was added, and the mixture was stirred at room temperature for 1 hr. Saturated aqueous ammonium chloride solution was added, and the reaction mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (30 mg) as a colorless oil.

$^1$H NMR (300 MHz, CDCl$_3$) δ 0.08-0.21 (1H, m), 0.22-0.33 (1H, m), 0.43 (1H, m), 0.51-0.65 (1H, m), 0.91 (6H, d, J=6.8 Hz), 1.00-1.14 (1H, m), 1.18 (3H, t, J=7.2 Hz), 1.98 (1H, m), 2.21 (1H, m), 2.74 (1H, dd, J=15.5, 6.0 Hz), 2.98 (1H, dd, J=15.5, 8.3 Hz), 3.22 (3H, s), 3.78 (3H, s), 3.99-4.11 (4H, m), 4.81 (2H, brs), 6.36-6.42 (1H, m), 6.78 (1H, d, J=7.6 Hz), 6.80-6.86 (1H, m), 6.89 (1H, dd, J=5.9, 3.2 Hz), 6.97-7.08 (1H, m), 7.51 (1H, dd, J=7.4, 0.9 Hz), 8.59 (1H, s).

B) 3-cyclopropyl-3-(6-(((5-(2-fluoro-5-methoxyphenyl)-6-isobutoxypyridin-2-yl)methyl)(methyl)amino)pyrimidin-4-yl)propanoic acid To a solution of ethyl 3-cyclopropyl-3-(6-(((5-(2-fluoro-5-methoxyphenyl)-6-isobutoxypyridin-2-yl)methyl)(methyl)amino)pyrimidin-4-yl)propanoate (30 mg) in methanol (3.0 mL) was added 1N aqueous sodium hydroxide solution (0.17 mL), and the mixture was stirred at 50° C. for 3 hr. 1N Hydrochloric acid was added, and the reaction mixture was extracted with ethyl acetate. The extract was washed with saturated brine, and dried over anhydrous sodium sulfate. The solvent was evaporated under reduced pressure, and the residue was recrystallized from hexane/diethyl ether to give the title compound (20 mg) as a white solid.

$^1$H NMR (300 MHz, DMSO-d$_6$) δ 0.16-0.45 (3H, m), 0.48-0.65 (1H, m), 0.68-0.95 (6H, m), 0.97-1.16 (1H, m), 1.72-1.95 (1H, m), 2.31-2.46 (1H, m), 2.71-2.91 (1H, m), 2.93-3.14 (1H, m), 3.33 (3H, s), 3.75 (3H, s), 3.82-3.98 (2H, m), 4.91-5.12 (2H, m), 6.85-7.28 (5H, m), 7.70 (1H, d, J=7.2 Hz), 8.75 (1H, brs).

Example 5

3-cyclopropyl-3-(3-((5-(2-fluoro-5-methoxyphenyl)-4-isobutoxypyridin-2-yl)methoxy)phenyl)propanoic acid A) 5-bromo-2-methylpyridine 1-oxide To a solution of 5-bromo-2-methylpyridine (5.00 g) in acetonitrile (30 mL) was added 70% m-chloroperbenzoic acid (10.8 g), and the mixture was stirred at room temperature for 30 min. The resulting white precipitate was filtered off, and the solvent in the filtrate was evaporated under reduced pressure. The residue was purified by silica gel column chromatography (NH, methanol/ethyl acetate) and recrystallized (ethyl acetate/hexane) to give the title compound (5.36 g) as a pale-yellow solid.

$^1$H NMR (300 MHz, DMSO-d$_6$) δ 2.30 (3H, s), 7.44 (1H, d, J=8.7 Hz), 7.52 (1H, d, J=9.0 Hz), 8.58 (1H, s).

B) 5-bromo-2-methyl-4-nitropyridine 1-oxide

5-Bromo-2-methylpyridine 1-oxide (5.36 g) was added to a mixture of conc. nitric acid (10.1 mL) and conc. sulfuric acid (8.94 mL), and the mixture was stirred at 90° C. for 20 hr. The reaction mixture was poured into ice water, and the resulting pale-yellow precipitate was collected by filtration. The crude crystals were washed with water to give the title compound (3.83 g) as a pale-yellow solid. The filtrate was neutralized with 8N aqueous sodium hydroxide solution at room temperature, and extracted with a mixed solvent of ethyl acetate and THF. The extract was washed with water and saturated brine, and dried over anhydrous magnesium sulfate. The solvent was evaporated under reduced pressure, and the residue was purified by silica gel column chromatography (NH, ethyl acetate/hexane) to give the title compound (360 mg) as a pale-yellow solid.

$^1$H NMR (300 MHz, DMSO-$d_6$) δ2.36 (3H, s), 8.39 (1H, s), 8.88 (1H, s).

C) 5-bromo-4-isobutoxy-2-methylpyridine 1-oxide

Under a nitrogen atmosphere, to a solution of 5-bromo-2-methyl-4-nitropyridine 1-oxide (4.10 g) in 2-methyl-1-propanol (80 mL) was added 60% sodium hydride (2.69 g) at 0° C., and the mixture was stirred for 2 hr. 6N Hydrochloric acid was added to the reaction mixture, and the resulting brown solid was filtered off. The solvent in the filtrate was evaporated under reduced pressure, and the residue was purified by silica gel column chromatography (NH, methanol/ethyl acetate) to give the title compound (3.40 g) as a pale-yellow solid.

$^1$H NMR (300 MHz, DMSO-$d_6$) δ 1.00 (6H, d, J=6.8 Hz), 1.84-2.17 (1H, m), 2.31 (3H, s), 3.89 (2H, d, J=6.4 Hz), 7.33 (1H, s), 8.49 (1H, s).

D) (5-bromo-4-isobutoxypyridin-2-yl)methanol

A mixture of 5-bromo-4-isobutoxy-2-methylpyridine 1-oxide (3.40 g) and acetic anhydride (50 mL) was stirred at 80° C. for 1 hr. The solvent in the reaction mixture was evaporated under reduced pressure, and the residue was dissolved in THF (50 mL) and methanol (25 mL). 1N Aqueous sodium hydroxide solution (50 mL) was added to the obtained solution, and the reaction mixture was stirred at room temperature for 15 min. 1N Hydrochloric acid (50 mL) was added to the reaction mixture at 0° C., and the mixture was extracted with ethyl acetate. The extract was washed with water and saturated brine, and dried over anhydrous magnesium sulfate. The solvent was evaporated under reduced pressure, and the residue was purified by silica gel column chromatography (ethyl acetate/hexane) to give the title compound (2.20 g) as a pale-yellow oil.

$^1$H NMR (300 MHz, DMSO-$d_6$) δ 1.01 (6H, d, J=6.8 Hz), 1.88-2.21 (1H, m), 3.95 (2H, d, J=6.4 Hz), 4.48 (2H, d, J=5.7 Hz), 5.48 (1H, t, J=5.7 Hz), 7.16 (1H, s), 8.44 (1H, s).

E) (5-(2-fluoro-5-methoxyphenyl)-4-isobutoxypyridin-2-yl)methanol

Under an argon atmosphere, to a solution of (5-bromo-4-isobutoxypyridin-2-yl)methanol (500 mg) in toluene (8.0 mL) were added 2-fluoro-5-methoxyphenylboronic acid (490 mg), tris(dibenzylideneacetone)dipalladium(0) (70 mg), 2-dicyclohexylphosphino-2',6'-dimethoxybiphenyl (126 mg) and 2.0 M aqueous sodium carbonate solution (2.9 mL), and the mixture was stirred at 100° C. for 1 hr. The reaction mixture was filtered through celite, and water was added at room temperature. The reaction mixture was extracted with ethyl acetate, and the extract was washed with water and saturated brine. The organic layer was dried over anhydrous magnesium sulfate, and the solvent was evaporated under reduced pressure. The residue was purified by silica gel column chromatography (NH, ethyl acetate/hexane) to give the title compound (506 mg) as a pale-yellow solid.

$^1$H NMR (300 MHz, DMSO-$d_6$) δ 0.89 (6H, d, J=6.8 Hz), 1.81-1.98 (1H, m), 3.76 (3H, s), 3.86 (2H, d, J=6.4 Hz), 4.56 (2H, d, J=6.0 Hz), 5.45 (1H, t, J=5.8 Hz), 6.87-7.02 (2H, m), 7.12-7.25 (2H, m), 8.21 (1H, s).

F) methyl 3-cyclopropyl-3-(3-((5-(2-fluoro-5-methoxyphenyl)-4-isobutoxypyridin-2-yl)methoxy)phenyl)propanoate Under a nitrogen atmosphere, to a solution of (5-(2-fluoro-5-methoxyphenyl)-4-isobutoxypyridin-2-yl)methanol (214 mg) and methyl 3-cyclopropyl-3-(3-hydroxyphenyl)propanoate (155 mg) in toluene (10 mL) were added 1,1'-(azodicarbonyl)dipiperidine (283 mg) and tributylphosphine (280 μL), and the mixture was stirred at room temperature overnight. Hexane/ethyl acetate (1:1) was added to the reaction mixture, and the resulting precipitate was filtered off. The solvent in the filtrate was evaporated under reduced pressure, and the residue was purified by silica gel column chromatography (ethyl acetate/hexane) to give the title compound (302 mg) as a colorless amorphous solid.

$^1$H NMR (300 MHz, DMSO-$d_6$) δ 0.05-0.39 (3H, m), 0.41-0.58 (1H, m), 0.87 (6H, d, J=6.4 Hz), 0.94-1.11 (1H, m), 1.75-1.97 (1H, m), 2.18-2.35 (1H, m), 2.74 (2H, dd, J=7.3, 3.2 Hz), 3.50 (3H, d, J=0.8 Hz), 3.76 (3H, d, J=0.8 Hz), 3.87 (2H, d, J=6.0 Hz), 5.15 (2H, s), 6.76-7.05 (5H, m), 7.07-7.26 (2H, m), 7.27 (1H, s), 8.32 (1H, s).

G) 3-cyclopropyl-3-(3-((5-(2-fluoro-5-methoxyphenyl)-4-isobutoxypyridin-2-yl)methoxy)phenyl)propanoic acid To a solution of methyl 3-cyclopropyl-3-(3-((5-(2-fluoro-5-methoxyphenyl)-4-isobutoxypyridin-2-yl)methoxy)phenyl)propanoate (128 mg) in THF (2.0 mL) and methanol (1.0 mL) was added 1N aqueous sodium hydroxide solution (2.0 mL), and the mixture was stirred at room temperature for 4 hr. 1N Hydrochloric acid (2.0 mL) was added to the reaction mixture at 0° C., and the mixture was extracted with ethyl acetate. The extract was washed with water and saturated brine, and dried over anhydrous magnesium sulfate. After silica gel filtration, the solvent was evaporated under reduced pressure to give the title compound (121 mg) as a white amorphous solid.

MS (ESI+): [M+H]$^+$ 494.2

$^1$H NMR (300 MHz, DMSO-$d_6$) δ 0.03-0.17 (1H, m), 0.18-0.37 (2H, m), 0.42-0.57 (1H, m), 0.87 (6H, d, J=6.4 Hz), 0.93-1.09 (1H, m), 1.80-1.97 (1H, m), 2.19-2.35 (1H, m), 2.65 (2H, dd, J=7.6, 4.2 Hz), 3.76 (3H, s), 3.87 (2H, d, J=6.4 Hz), 5.15 (2H, s), 6.76-7.06 (5H, m), 7.12-7.25 (2H, m), 7.28 (1H, s), 8.32 (1H, s), 12.01 (1H, brs).

Example 6

3-cyclopropyl-3-(6-((5-(2-fluoro-5-methoxyphenyl)-4-isobutoxypyridin-2-yl)methoxy)pyrimidin-4-yl)propanoic acid

A) ethyl 3-cyclopropyl-3-(6-((5-(2-fluoro-5-methoxyphenyl)-4-isobutoxypyridin-2-yl)methoxy)pyrimidin-4-yl)propanoate Under a nitrogen atmosphere, to a solution of (5-(2-fluoro-5-methoxyphenyl)-4-isobutoxypyridin-2-yl)methanol (200 mg) and ethyl 3-cyclopropyl-3-(6-hydroxypyrimidin-4-yl)propanoate (155 mg) in toluene (9.4 mL) were added 1,1'-(azodicarbonyl)dipiperidine (264 mg) and tributylphosphine (261 μL), and the mixture was stirred at room temperature for 24 hr. Hexane/ethyl acetate (1:1) was added to the reaction mixture, the resulting precipitate was filtered off, and the solvent in the filtrate was evaporated under reduced pressure. The residue was purified by silica gel column chromatography (ethyl acetate/hexane) to give the title compound (78 mg) as a colorless amorphous solid.

$^1$H NMR (300 MHz, DMSO-$d_6$) δ 0.24-0.43 (3H, m), 0.48-0.59 (1H, m), 0.87 (6H, d, J=6.8 Hz), 0.94-1.04 (1H, m), 1.09 (3H, t, J=7.2 Hz), 1.84-1.97 (1H, m), 2.29-2.43 (1H, m), 2.69-2.81 (1H, m), 2.89-3.01 (1H, m), 3.76 (3H, s), 3.86 (2H, d, J=6.4 Hz), 3.97 (2H, qd, J=7.1, 2.8 Hz), 5.47 (2H, s), 6.87-7.01 (2H, m), 7.02 (1H, d, J=1.1 Hz), 7.16-7.27 (2H, m), 8.31 (1H, s), 8.73 (1H, d, J=0.8 Hz).

B) 3-cyclopropyl-3-(6-((5-(2-fluoro-5-methoxyphenyl)-4-isobutoxypyridin-2-yl)methoxy)pyrimidin-4-yl)propanoic acid To a solution of ethyl 3-cyclopropyl-3-(6-((5-(2-fluoro-5-methoxyphenyl)-4-isobutoxypyridin-2-yl)methoxy)pyrimidin-4-yl)propanoate (78 mg) in THF (2.0 mL) and methanol (1.0 mL) was added 1N aqueous sodium hydroxide solution (2.0 mL), and the mixture was stirred at room temperature for 1 hr. 1N Hydrochloric acid (2.0 ml) was added to the reaction mixture at 0° C., and the mixture was extracted with ethyl acetate. The extract was washed with water and saturated brine, and dried over anhydrous magnesium sulfate. After silica gel filtration, the solvent was evaporated under reduced pressure to give the title compound (19 mg) as a pale-yellow amorphous solid.

MS (ESI+): [M+H]$^+$ 496.3

$^1$H NMR (300 MHz, DMSO-$d_6$) δ 0.16-0.61 (4H, m), 0.87 (6H, d, J=6.8 Hz), 0.92-1.11 (1H, m), 1.81-2.01 (1H, m), 2.28-2.44 (1H, m), 2.59-2.70 (1H, m), 2.80-3.00 (1H, m), 3.76 (3H, s), 3.87 (2H, d, J=6.4 Hz), 5.47 (2H, s), 6.85-7.05 (3H, m), 7.11-7.33 (2H, m), 8.31 (1H, s), 8.73 (1H, s), 12.11 (1H, brs).

Example 7

3-cyclopropyl-3-(3-((6-(2,2-dimethylpropyl)-5-(2-fluoro-5-methoxyphenyl)pyridin-2-yl)methoxy)phenyl)propanoic acid

A) methyl 6-chloro-5-(2-fluoro-5-methoxyphenyl)picolinate

Under an argon atmosphere, to a solution of methyl 5-bromo-6-chloropicolinate (12.0 g) in toluene (300 mL) was added a solution of 2-fluoro-5-methoxyphenylboronic acid (9.83 g), [1,1-bis(diphenylphosphino)ferrocene]dichloropalladium(II) dichloromethane adduct (1.00 g) and sodium carbonate (14.8 g) in water (60 mL), and the mixture was stirred at 80° C. for 2 hr. The reaction mixture was concentrated under reduced pressure and diluted with water. The reaction mixture was extracted with ethyl acetate, and the extract was washed with saturated brine, and dried over anhydrous sodium sulfate. The solvent was evaporated under reduced pressure, and the crude crystals were recrystallized from ethyl acetate to give the title compound (13.1 g) as pale-yellow crystals.

MS (ESI+): [M+H]$^+$ 296.0

B) (6-chloro-5-(2-fluoro-5-methoxyphenyl)pyridin-2-yl)methanol

Under a nitrogen atmosphere, to a suspension of calcium chloride (12.3 g) in ethanol (100 mL) and THF (50 ml) was added sodium tetrahydroborate (2.62 g) at 0° C., and the mixture was stirred at 0° C. for 10 min. To the reaction mixture was added a solution of methyl 6-chloro-5-(2-fluoro-5-methoxyphenyl)picolinate (8.30 g) in ethanol (25 ml) and THF (50 ml) at room temperature, and the mixture was stirred for 14 hr. 1N Hydrochloric acid was added to the reaction mixture, and the mixture was neutralized with aqueous sodium hydrogen carbonate solution. The reaction mixture was extracted with ethyl acetate, and the extract was washed with saturated brine, and dried over anhydrous sodium sulfate. The solvent was evaporated under reduced pressure to give the title compound (7.30 g) as a pale-gray amorphous solid. This compound was used for the next step without further purification.

MS (ESI+): [M+H]$^+$ 268.0

C) 6-((tert-butyldiphenylsilyloxy)methyl)-2-chloro-3-(2-fluoro-5-methoxyphenyl)pyridine To a solution of (6-chloro-5-(2-fluoro-5-methoxyphenyl)pyridin-2-yl)methanol (3.00 g) and tert-butylchlorodiphenylsilane (1.53 g) in DMF (7.0 mL) was added imidazole (1.53 g) at room temperature, and the mixture was stirred for 14 hr. Water was added to the reaction mixture, and the mixture was extracted with ethyl acetate. The extract was washed with saturated brine, and dried over anhydrous sodium sulfate. The solvent was evaporated under reduced pressure to give the title compound (7.10 g) as a pale-yellow oil. This compound was used for the next step without further purification.

MS (ESI+): [M+H]$^+$ 506.0

D) 6-((tert-butyldiphenylsilyloxy)methyl)-3-(2-fluoro-5-methoxyphenyl)-2-neopentylpyridine Under an argon atmosphere, to a solution of 6-((tert-butyldiphenylsilyloxy)methyl)-2-chloro-3-(2-fluoro-5-methoxyphenyl)pyridine (10.0 g) and PEPPSIT™-SIPr catalyst (trade name) (1.33 g) in THF (100 mL) was added a 1.5 M solution of 2,2-dimethylpropylmagnesium chloride in diethyl ether (50 mL), and the mixture was stirred at room temperature for 16 hr. 1N Hydrochloric acid was added to the reaction mixture at 0° C., and the mixture was extracted with ethyl acetate. The extract was washed with saturated brine, and dried over anhydrous sodium sulfate. The solvent was evaporated under reduced pressure to give the title compound (10.0 g) as a crude brown oil. This compound was used for the next step without further purification.

MS (ESI+): [M+H]$^+$ 542.3

E) (5-(2-fluoro-5-methoxyphenyl)-6-neopentylpyridin-2-yl)methanol

To a solution of 6-((tert-butyldiphenylsilyloxy)methyl)-3-(2-fluoro-5-methoxyphenyl)-2-neopentylpyridine (10.0 g) in THF (50 mL) was added a 1.0 M solution of tetrabutylammonium fluoride in THF (55.0 ml), and the mixture was stirred at room temperature for 2 hr. Water was added to the reaction mixture, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/petroleum ether) to give the title compound (3.00 g) as a white amorphous solid.

$^1$H NMR (400 MHz, DMSO-$d_6$) δ 0.74 (9H, s), 2.55-2.67 (2H, br), 3.76 (3H, s), 4.59 (2H, d, J=5.6 Hz), 5.40 (1H, t,

J=5.6 Hz), 6.85-6.87 (1H, m), 6.97-7.02 (1H, m), 7.23 (1H, t, J=9.2 Hz), 7.39 (1H, d, J=8.0 Hz), 7.60 (1H, d, J=8.0 Hz).

F) methyl 3-cyclopropyl-3-(3-((5-(2-fluoro-5-methoxyphenyl)-6-neopentylpyridin-2-yl)methoxy)phenyl)propanoate Under a nitrogen atmosphere, to a solution of (5-(2-fluoro-5-methoxyphenyl)-6-neopentylpyridin-2-yl)methanol (100 mg) and methyl 3-cyclopropyl-3-(3-hydroxyphenyl)propanoate (72 mg) in toluene (4.7 mL) were added 1,1'-(azodicarbonyl)dipiperidine (133 mg) and tributylphosphine (131 μL), and the mixture was stirred at room temperature for 14 hr. Hexane/ethyl acetate (1:1) was added to the reaction mixture, and the resulting precipitate was filtered off. The solvent in the filtrate was evaporated under reduced pressure, and the residue was purified by silica gel column chromatography (ethyl acetate/hexane) to give the title compound (90 mg) as a colorless oil.

$^1$H NMR (300 MHz, DMSO-d$_6$) δ 0.04-0.38 (3H, m), 0.41-0.59 (1H, m), 0.75 (9H, s), 0.91-1.09 (1H, m), 2.14-2.33 (1H, m), 2.58-2.82 (4H, m), 3.51 (3H, s), 3.76 (3H, s), 5.20 (2H, s), 6.70-6.95 (4H, m), 7.01 (1H, dt, J=9.1, 3.6 Hz), 7.14-7.29 (2H, m), 7.43 (1H, d, J=7.6 Hz), 7.65 (1H, d, J=8.0 Hz).

G) 3-cyclopropyl-3-(3-((6-(2,2-dimethylpropyl)-5-(2-fluoro-5-methoxyphenyl)pyridin-2-yl)methoxy)phenyl)propanoic acid To a solution of methyl 3-cyclopropyl-3-(3-((5-(2-fluoro-5-methoxyphenyl)-6-neopentylpyridin-2-yl)methoxy)phenyl)propanoate (90 mg) in THF (2.0 mL) and methanol (1.0 mL) was added 1N aqueous sodium hydroxide solution (2.0 mL), and the mixture was stirred at room temperature for 4 hr. 1N Hydrochloric acid (2.0 mL) was added to the reaction mixture at 0° C., and the mixture was extracted with ethyl acetate. The extract was washed with water and saturated brine, and dried over anhydrous magnesium sulfate.

After silica gel filtration, the solvent was evaporated under reduced pressure to give the title compound (81 mg) as a white amorphous solid.

MS (ESI+): [M+H]$^+$ 492.2

$^1$H NMR (300 MHz, DMSO-d$_6$) δ 0.04-0.16 (1H, m), 0.17-0.37 (2H, m), 0.41-0.59 (1H, m), 0.76 (9H, s), 0.88-1.06 (1H, m), 2.13-2.34 (1H, m), 2.57-2.81 (4H, m), 3.76 (3H, s), 5.19 (2H, s), 6.69-6.95 (4H, m), 6.97-7.07 (1H, m), 7.13-7.30 (2H, m), 7.44 (1H, d, J=7.6 Hz), 7.65 (1H, d, J=8.0 Hz), 11.98 (1H, brs).

Example 8

3-cyclopropyl-3-(6-((6-(2,2-dimethylpropyl)-5-(2-fluoro-5-methoxyphenyl)pyridin-2-yl)methoxy)pyrimidin-4-yl)propanoic acid A) ethyl 3-cyclopropyl-3-(6-((5-(2-fluoro-5-methoxyphenyl)-6-neopentylpyridin-2-yl)methoxy)pyrimidin-4-yl)propanoate To a solution of (5-(2-fluoro-5-methoxyphenyl)-6-neopentylpyridin-2-yl)methanol (504 mg) and ethyl 3-(6-chloropyrimidin-4-yl)-3-cyclopropylpropanoate (465 mg) in THF (5.0 mL) was added 60% sodium hydride (86 mg) at 0° C., and the mixture was stirred at room temperature for 14 hr. The reaction mixture was diluted with ethyl acetate, and water was added at room temperature. The reaction mixture was extracted with ethyl acetate, and the extract was washed with water and saturated brine. The organic layer was dried over anhydrous magnesium sulfate, and the solvent was evaporated under reduced pressure. The residue was purified by silica gel column chromatography (ethyl acetate/hexane) to give the title compound (672 mg) as a pale-yellow oil.

$^1$H NMR (300 MHz, DMSO-d$_6$) δ 0.19-0.44 (3H, m), 0.46-0.57 (1H, m), 0.69 (9H, s), 0.89-1.05 (1H, m), 1.09 (3H, t, J=7.0 Hz), 2.37 (1H, td, J=9.2, 6.0 Hz), 2.62 (2H, brs), 2.69-2.79 (1H, m), 2.84-3.02 (1H, m), 3.76 (3H, s), 3.90-4.01 (2H, m), 5.54 (2H, s), 6.88 (1H, dd, J=6.0, 3.4 Hz), 6.95-7.06 (2H, m), 7.24 (1H, t, J=9.0 Hz), 7.38 (1H, d, J=7.9 Hz), 7.64 (1H, d, J=7.9 Hz), 8.69 (1H, d, J=1.1 Hz).

B) 3-cyclopropyl-3-(6-((6-(2,2-dimethylpropyl)-5-(2-fluoro-5-methoxyphenyl)pyridin-2-yl)methoxy)pyrimidin-4-yl)propanoic acid To a solution of ethyl 3-cyclopropyl-3-(6-((5-(2-fluoro-5-methoxyphenyl)-6-neopentylpyridin-2-yl)methoxy)pyrimidin-4-yl)propanoate (672 mg) in THF (6.0 mL) and methanol (3.0 mL) was added 1N aqueous sodium hydroxide solution (6.0 mL), and the mixture was stirred at room temperature for 1 hr. 1N Hydrochloric acid (6.0 mL) was added to the reaction mixture at room temperature, and the mixture was extracted with ethyl acetate. The extract was washed with water and saturated brine, and dried over anhydrous magnesium sulfate. After silica gel filtration, the solvent was evaporated under reduced pressure to give the title compound (549 mg) as a white amorphous solid.

MS (ESI+): [M+H]$^+$ 492.2

$^1$H NMR (300 MHz, DMSO-d$_6$) δ 0.22-0.41 (3H, m), 0.45-0.58 (1H, m), 0.70 (9H, s), 0.88-1.05 (1H, m), 2.28-2.41 (1H, m), 2.56-2.74 (3H, m), 2.83-2.95 (1H, m), 3.76 (3H, s), 5.53 (2H, s), 6.89 (1H, dd, J=6.0, 3.0 Hz), 6.95-7.05 (2H, m), 7.24 (1H, t, J=8.7 Hz), 7.38 (1H, d, J=7.9 Hz), 7.64 (1H, d, J=7.9 Hz), 8.69 (1H, d, J=1.1 Hz), 12.04 (1H, brs).

Example 9

3-cyclopropyl-3-(6-((6-(2,2-dimethylpropyl)-5-(2-fluoro-5-methoxyphenyl)pyridin-2-yl)methoxy)pyrimidin-4-yl)propanoic acid A) 3-cyclopropyl-3-(3-hydroxyphenyl)propanoic acid The racemate (11.1 g) of 3-cyclopropyl-3-(3-hydroxyphenyl)propanoic acid was fractionated by SFC (column: CHIRALCEL AD-H (KG010), 20 mmID×250 mL, manufactured by DAICEL CHEMICAL INDUSTRIES, LTD., mobile phase: carbon dioxide/ethanol=900/100), whereby the title compound (4.75 g) with a shorter retention time and the title compound (4.76 g) with a longer retention time were obtained.

B) methyl 3-cyclopropyl-3-(3-hydroxyphenyl)propanoate

To a solution of 3-cyclopropyl-3-(3-hydroxyphenyl)propanoic acid (longer retention time: 2.47 g) in methanol (60 mL) was added conc. sulfuric acid (64 μL), and the mixture was heated under reflux for 12 hr. The reaction mixture was cooled to room temperature, and the solvent was evaporated under reduced pressure. The residue was diluted with ethyl acetate (30 mL), and washed with saturated aqueous sodium hydrogen carbonate solution and saturated brine. The organic layer was dried over anhydrous magnesium sulfate. The solvent was evaporated under reduced pressure to give a crude product of the title compound (2.53 g) as a colorless oil. This compound was used for the next step without further purification.

$^1$H NMR (300 MHz, DMSO-d$_6$) δ 0.04-0.13 (1H, m), 0.14-0.24 (1H, m), 0.26-0.40 (1H, m), 0.42-0.55 (1H, m), 0.89-1.05 (1H, m), 2.18 (1H, dt, J=9.4, 7.6 Hz), 2.65 (1H, dd, J=14.7, 7.9 Hz), 2.71 (1H, dd, J=14.3, 7.2 Hz), 3.51 (3H, s), 6.58 (1H, ddd, J=8.0, 2.3, 1.0 Hz), 6.61-6.69 (2H, m), 7.06 (1H, t, J=7.7 Hz), 9.23 (1H, s).

C) methyl 3-cyclopropyl-3-(3-((5-(2-fluoro-5-methoxyphenyl)-6-neopentylpyridin-2-yl)methoxy)phenyl)propanoate Under a nitrogen atmosphere, to a solution of (5-(2-fluoro-5-methoxyphenyl)-6-neopentylpyridin-2-yl)methanol (207 mg) and methyl 3-cyclopropyl-3-(3-hydroxyphenyl)propanoate (150 mg) in toluene (9.7 ml) were added 1,1'-(azodicarbonyl)dipiperidine (275 mg) and tributylphosphine (271 μL), and the mixture was stirred at room temperature for 14 hr. Hexane/ethyl acetate (1:1) was added to the reaction mixture, and the resulting precipitate was filtered off. The solvent in the filtrate was evaporated under reduced pressure, and the residue was purified by silica gel column chromatography (ethyl acetate/hexane) to give the title compound (224 mg) as a colorless oil.

$^1$H NMR (300 MHz, DMSO-d$_6$) δ 0.03-0.37 (3H, m), 0.42-0.57 (1H, m), 0.75 (9H, s), 0.91-1.09 (1H, m), 2.15-2.32 (1H, m), 2.57-2.81 (4H, m), 3.51 (3H, s), 3.76 (3H, s), 5.20 (2H, s), 6.80-6.91 (3H, m), 6.93 (1H, d, J=1.5 Hz), 7.01 (1H, dt, J=9.0, 3.6 Hz), 7.14-7.29 (2H, m), 7.44 (1H, d, J=7.9 Hz), 7.65 (1H, d, J=7.9 Hz).

D) 3-cyclopropyl-3-(6-((6-(2,2-dimethylpropyl)-5-(2-fluoro-5-methoxyphenyl)pyridin-2-yl)methoxy)pyrimidin-4-yl)propanoic acid To a solution of ethyl 3-cyclopropyl-3-(6-((5-(2-fluoro-5-methoxyphenyl)-6-neopentylpyridin-2-yl)methoxy)pyrimidin-4-yl)propanoate (224 mg) in THF (4.0 mL) and methanol (2.0 ml) was added 1N aqueous sodium hydroxide solution (4.0 mL), and the mixture was stirred at room temperature for 4 hr. 1N Hydrochloric acid (4.0 mL) was added to the reaction mixture at room temperature, and the mixture was extracted with ethyl acetate. The extract was washed with water and saturated brine, and dried over anhydrous magnesium sulfate. After silica gel filtration, the solvent was evaporated under reduced pressure to give the title compound (549 mg) as a white amorphous solid.

MS (ESI+): [M+H]$^+$ 492.2
$^1$H NMR (300 MHz, DMSO-d$_6$) δ 0.02-0.15 (1H, m), 0.17-0.38 (2H, m), 0.41-0.57 (1H, m), 0.76 (9H, s), 0.90-1.10 (1H, m), 2.17-2.32 (1H, m), 2.55-2.80 (4H, m), 3.76 (3H, s), 5.19 (2H, s), 6.78-6.96 (4H, m), 7.01 (1H, dt, J=8.9, 3.7 Hz), 7.12-7.30 (2H, m), 7.44 (1H, d, J=7.9 Hz), 7.65 (1H, d, J=7.6 Hz), 11.98 (1H, brs).

Example 10

N-(3-((6-(2,2-dimethylpropyl)-5-(2-fluoro-5-methoxyphenyl)pyridin-2-yl)methoxy)phenyl)-N-ethylglycine A) ethyl 2-((3-(benzyloxy)phenyl)amino)acetate To a solution of 3-(benzyloxy)aniline (5.00 g) in DMF (50% mL) were added sodium acetate (2.10 g) and ethyl bromoacetate (4.20 g), and the mixture was stirred at room temperature for 12 hr. Water was added, and the reaction mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (4.80 g) as orange crystals.

$^1$H NMR (300 MHz, DMSO-d$_6$) δ 1.15-1.22 (3H, m), 3.85 (2H, d, J=6.4 Hz), 4.10 (2H, q, J=6.9 Hz), 5.00 (2H, s), 5.98 (1H, t, J=6.4 Hz), 6.12-6.28 (3H, m), 6.96 (1H, t, J=8.1 Hz), 7.26-7.50 (4H, m).

B) ethyl 2-((3-(benzyloxy)phenyl)(ethyl)amino)acetate

To a solution of ethyl 2-((3-(benzyloxy)phenyl)amino)acetate (1.00 g) in DMF (10 mL) were added potassium carbonate (970 mg) and iodoethane (2.20 g), and the mixture was stirred at 120° C. for 4 hr. The mixture was allowed to cool to room temperature, and water was added. The reaction mixture was extracted with ethyl acetate, and the extract was washed with saturated brine. The organic layer was dried over anhydrous sodium sulfate, and the solvent was evaporated under reduced pressure. The residue was purified by silica gel column chromatography (ethyl acetate/hexane) to give the title compound (960 mg) as a colorless oil.

C) ethyl 2-(ethyl(3-hydroxyphenyl)amino)acetate

To a solution of ethyl 2-((3-(benzyloxy)phenyl)(ethyl)amino)acetate (960 mg) in methanol (30 mL) was added 10% palladium-activated carbon (300 mg) and, under a hydrogen atmosphere, the mixture was stirred at room temperature for 12 hr. The reaction mixture was filtered, and the filtrate was evaporated under reduced pressure. The residue was purified by silica gel column chromatography (ethyl acetate/hexane) to give the title compound (360 mg) as a colorless oil.

MS (ESI+): [M+H]$^+$ 314.2

D) 6-(bromomethyl)-3-(2-fluoro-5-methoxyphenyl)-2-neopentylpyridine

Phosphorus tribromide (112 μL) was added to DMF (3.0 mL) at 0° C., and the mixture was stirred at 0° C. for 20 min. To the obtained white suspension was added a solution of (5-(2-fluoro-5-methoxyphenyl)-6-neopentylpyridin-2-yl)methanol (300 mg) in DMF (1.0 mL), and the mixture was stirred at room temperature for 1 hr. Saturated aqueous sodium hydrogen carbonate solution was added to the reaction mixture at 0° C., and the mixture was extracted with ethyl acetate. The extract was washed with water and saturated brine, and dried over anhydrous magnesium sulfate. The solvent was evaporated under reduced pressure, and the residue was purified by silica gel column chromatography (ethyl acetate/hexane) to give the title compound (255 mg) as a pale-yellow oil.

$^1$H NMR (300 MHz, DMSO-d$_6$) δ 0.75 (9H, s), 2.64 (2H, brs), 3.76 (3H, s), 4.72 (2H, s), 6.90 (1H, dd, J=6.0, 3.0 Hz), 7.01 (1H, dt, J=9.0, 3.6 Hz), 7.24 (1H, t, J=9.2 Hz), 7.47 (1H, d, J=7.5 Hz), 7.63 (1H, d, J=7.9 Hz).

E) ethyl 2-(ethyl(3-((5-(2-fluoro-5-methoxyphenyl)-6-neopentylpyridin-2-yl)methoxy)phenyl)amino)acetate To a solution of ethyl 2-(ethyl(3-hydroxyphenyl)amino) acetate (122 mg) in DMF (5.0 mL) were added potassium carbonate (75 mg) and 6-(bromomethyl)-3-(2-fluoro-5-methoxyphenyl)-2-neopentylpyridine (100 mg), and the mixture was stirred at 80° C. for 1 hr. The mixture was allowed to cool to room temperature, and water was added. The reaction mixture was extracted with ethyl acetate, and the extract was washed with saturated brine. The organic layer was dried over anhydrous sodium sulfate, and the solvent was evaporated under reduced pressure. The residue was purified by silica gel column chromatography (NH, ethyl acetate/hexane) to give the title compound (107 mg) as a colorless oil.

MS (ESI+): [M+H]+ 509.2

F) N-(3-((6-(2,2-dimethylpropyl)-5-(2-fluoro-5-methoxyphenyl)pyridin-2-yl)methoxy)phenyl)-N-ethylglycine To a solution of ethyl 2-(ethyl(3-((5-(2-fluoro-5-methoxyphenyl)-6-neopentylpyridin-2-yl)methoxy)phenyl)amino)acetate (entire amount) in ethanol (3.0 mL) was added 1N aqueous sodium hydroxide solution (2.0 mL), and the mixture was stirred at 50° C. for 1 hr. 1N Hydrochloric acid was added, and the reaction mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (90 mg) as pale-yellow crystals.

MS (ESI+): [M+H]+ 481.3

$^1$H NMR (300 MHz, DMSO-$d_6$) δ 0.76 (9H, s), 1.03-1.15 (3H, m), 2.67 (2H, brs), 3.17-3.48 (2H, m), 3.76 (3H, s), 3.98 (2H, s), 5.15 (2H, s), 6.15-6.25 (2H, m), 6.30 (1H, d, J=7.2 Hz), 6.85-6.95 (1H, m), 6.97-7.10 (2H, m), 7.24 (1H, t, J=9.1 Hz), 7.41 (1H, d, J=7.6 Hz), 7.64 (1H, d, J=8.0 Hz), 12.08-13.08 (1H, m).

Example 11

3-cyclopropyl-3-(6-((6-(2,2-dimethylpropyl)-5-(2-fluoro-5-methoxyphenyl)pyridin-2-yl)methoxy)pyrimidin-4-yl)propanoic acid B) methyl 3-cyclopropyl-3-(3-hydroxyphenyl)propanoate To a solution of 3-cyclopropyl-3-(3-hydroxyphenyl)propanoic acid (1.45 g) in methanol (20 mL) was added conc. sulfuric acid (75 μL), and the mixture was heated under reflux for 14 hr. Saturated aqueous sodium hydrogen carbonate solution was added to the reaction mixture at room temperature, and the mixture was extracted with ethyl acetate. The extract was washed with water and saturated brine, and dried over anhydrous magnesium sulfate. The solvent was evaporated under reduced pressure to give a crude product of the title compound (1.43 g) as a pale-brown oil. This compound was used for the next step without further purification.

$^1$H NMR (300 MHz, DMSO-$d_6$) δ 0.03-0.23 (2H, m), 0.26-0.38 (1H, m), 0.42-0.55 (1H, m), 0.88-1.05 (1H, m), 2.10-2.25 (1H, m), 2.68 (2H, dd, J=7.5, 5.3 Hz), 3.51 (3H, s), 6.52-6.61 (1H, m), 6.61-6.70 (2H, m), 7.06 (1H, t, J=7.7 Hz), 9.23 (1H, s).

C) methyl 3-cyclopropyl-3-(3-((5-(2-fluoro-5-methoxyphenyl)-6-neopentylpyridin-2-yl)methoxy)phenyl)propanoate Under a nitrogen atmosphere, to a solution of (5-(2-fluoro-5-methoxyphenyl)-6-neopentylpyridin-2-yl)methanol (100 mg) and methyl 3-cyclopropyl-3-(3-hydroxyphenyl)propanoate (73 mg) in toluene (4.7 mL) were added 1,1'-(azodicarbonyl)dipiperidine (133 mg) and tributylphosphine (131 μL) at room temperature, and the mixture was stirred at room temperature for 14 hr. Hexane/ethyl acetate (1:1) was added to the reaction mixture, and the resulting precipitate was filtered off. The solvent in the filtrate was evaporated under reduced pressure, and the residue was purified by silica gel column chromatography (ethyl acetate/hexane) to give the title compound (112 mg) as a colorless oil.

$^1$H NMR (300 MHz, DMSO-$d_6$) δ 0.03-0.38 (3H, m), 0.40-0.58 (1H, m), 0.75 (9H, s), 0.91-1.11 (1H, m), 2.17-2.33 (1H, m), 2.57-2.83 (4H, m), 3.51 (3H, s), 3.76 (3H, s), 5.20 (2H, s), 6.80-6.96 (4H, m), 7.01 (1H, dt, J=8.9, 3.7 Hz), 7.13-7.30 (2H, m), 7.43 (1H, d, J=8.0 Hz), 7.65 (1H, d, J=7.6 Hz).

D) 3-cyclopropyl-3-(6-((6-(2,2-dimethylpropyl)-5-(2-fluoro-5-methoxyphenyl)pyridin-2-yl)methoxy)pyrimidin-4-yl)propanoic acid To a solution of methyl 3-cyclopropyl-3-(6-((5-(2-fluoro-5-methoxyphenyl)-6-neopentylpyridin-2-yl)methoxy)pyrimidin-4-yl)propanoate (112 mg) in THF (2.0 mL) and methanol (1.0 ml) was added 1N aqueous sodium hydroxide solution (2.0 mL), and the mixture was stirred at 50° C. for 30 min. 1N Hydrochloric acid (2.0 mL) was added to the reaction mixture at room temperature, and the mixture was extracted with ethyl acetate. The extract was washed with water and saturated brine, and dried over anhydrous magnesium sulfate. After silica gel filtration, the solvent was evaporated under reduced pressure to give the title compound (96 mg) as a white amorphous solid.

MS (ESI+): [M+H]+ 492.2

$^1$H NMR (300 MHz, DMSO-$d_6$) δ 0.04-0.15 (1H, m), 0.18-0.36 (2H, m), 0.41-0.57 (1H, m), 0.76 (9H, s), 0.91-1.06 (1H, m), 2.18-2.32 (1H, m), 2.55-2.80 (4H, m), 3.76 (3H, s), 5.19 (2H, s), 6.78-6.96 (4H, m), 6.97-7.05 (1H, m), 7.14-7.30 (2H, m), 7.44 (1H, d, J=7.9 Hz), 7.65 (1H, d, J=7.9 Hz), 11.98 (1H, brs).

Example 12

3-cyclopropyl-3-(3-((6-(2,2-dimethylpropyl)-5-(2-fluoro-5-methoxyphenyl)pyridin-2-yl)methoxy)-4-methoxyphenyl)propanoic acid A) 5-(3-hydroxy-4-methoxybenzylidene)-2,2-dimethyl-1,3-dioxane-4,6-dione To a solution of titanium (IV) chloride (11.1 g) in THF (50 mL) was added dropwise a solution of 2,2-dimethyl-1,3-dioxane-4,6-dione (4.26 g) and 3-hydroxy-4-methoxybenzaldehyde (3.00 g) in THF (50 mL) at 0° C., and then a solution of pyridine (4.00 g) in THF (20 mL) was added dropwise. The reaction mixture was stirred for 1 hr, and water was added to the reaction mixture. The reaction mixture was extracted with ethyl acetate, and the extract was washed with 1N hydrochloric acid and saturated brine. The organic layer was dried over anhydrous sodium sulfate. The solvent was evaporated under reduced pressure to give the title compound (3.50 g) as a yellow solid. This compound was used for the next step without further purification.

$^1$H NMR (400 MHz, CDCl$_3$) δ 1.80 (6H, s), 4.01 (3H, s), 5.78 (1H, s), 6.95 (1H, dd, J=2.0 Hz, 8.4 Hz), 7.73 (1H, d, J=8.4 Hz), 7.93 (1H, s), 8.33 (1H, d, J=2.0 Hz).

B) 5-(cyclopropyl(3-hydroxy-4-methoxyphenyl)methyl)-2,2-dimethyl-1,3-dioxane-4,6-dione To a solution of 5-(3-hydroxy-4-methoxybenzylidene)-2,2-dimethyl-1,3-dioxane-4,6-dione (556 mg) in THF (10 mL) was added a 1.0 M solution of cyclopropylmagnesium bromide in THF (6.0 mL) at 0° C., and the mixture was stirred for 1 hr. 3N Hydrochloric acid (10 mL) was added to the reaction mixture, and the mixture was stirred for 15 min. The reaction mixture was neutralized with saturated aqueous sodium hydrogen carbonate solution, and the mixture was extracted with ethyl acetate. The extract was washed with saturated brine, and dried over anhydrous sodium sulfate. The solvent was evaporated under reduced pressure to give the title compound (300 mg) as a yellow solid. This compound was used for the next step without further purification.
MS (ESI+): [M+H]$^+$ 321.0

C) 3-cyclopropyl-3-(3-hydroxy-4-methoxyphenyl)propanoic acid

To a solution of 5-(cyclopropyl(3-hydroxy-4-methoxyphenyl)methyl)-2,2-dimethyl-1,3-dioxane-4,6-dione (2.70 g) in DMF (20 mL) was added water (2.0 mL), and the mixture was stirred at 90° C. for 15 hr. The reaction mixture was cooled to room temperature, and extracted with ethyl acetate. The extract was washed with 1N hydrochloric acid and saturated brine, and dried over anhydrous sodium sulfate. The solvent was evaporated under reduced pressure, and the residue was purified by silica gel column chromatography (ethyl acetate/hexane) to give the title compound (1.50 g) as a yellow oil.
MS (ESI+): [M+H]$^+$ 237.1

D) methyl 3-cyclopropyl-3-(3-hydroxy-4-methoxyphenyl)propanoate

To a solution of 3-cyclopropyl-3-(3-hydroxy-4-methoxyphenyl)propanoic acid (1.40 g) in methanol (50 mL) was added dropwise thionyl chloride (2.0 mL) at room temperature, and the mixture was stirred at room temperature for 1 hr. Water was added to the reaction mixture, and the mixture was extracted with ethyl acetate. The extract was washed with saturated brine, and dried over anhydrous sodium sulfate. The solvent was evaporated under reduced pressure to give the title compound (4.30 g) as a colorless oil. Ethyl acetate (250 mL) was added to the reaction mixture, and the insoluble material was filtered off. The filtrate was washed with saturated brine, and dried over anhydrous sodium sulfate. The solvent was evaporated under reduced pressure, and the residue was purified by silica gel column chromatography (ethyl acetate/hexane) to give the title compound (1.00 g) as a yellow oil.
MS (ESI+): [M+H]$^+$ 251.1

E) methyl 3-cyclopropyl-3-(3-((6-(2,2-dimethylpropyl)-5-(2-fluoro-5-methoxyphenyl)pyridin-2-yl)methoxy)-4-methoxyphenyl)propanoate Under a nitrogen atmosphere, to a solution of methyl 3-cyclopropyl-3-(3-hydroxy-4-methoxyphenyl)propanoate (168 mg) and (6-(2,2-dimethylpropyl)-5-(2-fluoro-5-methoxyphenyl)pyridin-2-yl)methanol (202 mg) in toluene (15 mL) were added 1,1'-(azodicarbonyl)dipiperidine (268 mg) and tributylphosphine (262 and the mixture was stirred at room temperature for 15 hr. Hexane and ethyl acetate were added to the reaction mixture, and the insoluble material was filtered off. The filtrate was concentrated under reduced pressure, and the residue was purified by silica gel column chromatography (ethyl acetate/hexane) to give the title compound (190 mg) as a colorless oil.
MS (ESI+): [M+H]$^+$ 536.2

F) 3-cyclopropyl-3-(3-((6-(2,2-dimethylpropyl)-5-(2-fluoro-5-methoxyphenyl)pyridin-2-yl)methoxy)-4-methoxyphenyl)propanoic acid To a solution of methyl 3-cyclopropyl-3-(3-((6-(2,2-dimethylpropyl)-5-(2-fluoro-5-methoxyphenyl)pyridin-2-yl)methoxy)-4-methoxyphenyl)propanoate (190 mg) in methanol (2.0 mL) and THF (4.0 mL) was added 1N aqueous sodium hydroxide solution (4.5 mL), and the mixture was stirred at room temperature for 3 hr. The reaction mixture was concentrated under reduced pressure, and 1N hydrochloric acid was added to the residue to adjust to pH<4. The reaction mixture was extracted with ethyl acetate, and the extract was washed with saturated brine. The organic layer was dried over anhydrous sodium sulfate. The solvent was evaporated under reduced pressure to give the title compound (144 mg) as a white solid.
MS (ESI+): [M+H]$^+$ 522.2
$^1$H NMR (400 MHz, DMSO-d$_6$) δ 0.01-0.05 (1H, m), 0.18-0.25 (2H, m), 0.43-0.47 (1H, m), 0.75 (9H, s), 0.92-0.95 (1H, m), 2.18-0.23 (1H, m), 2.53-2.66 (4H, m), 3.76 (6H, s), 5.19 (2H, s), 6.76-6.79 (1H, m), 6.86-6.93 (3H, m), 7.00-7.03 (1H, m), 7.25 (1H, t, J=7.2 Hz), 7.45 (1H, d, J=8.0 Hz), 7.67 (1H, d, J=8.0 Hz), 12.03 (1H, brs).

Example 13

3-(3-((6-(2,2-dimethylpropyl)-5-(2-fluoro-5-methoxyphenyl)pyridin-2-yl)methoxy)-4-methylphenyl)propanoic acid

A) benzyl 3-(benzyloxy)-4-methylbenzoate

To a mixture of 3-hydroxy-4-methylbenzoic acid (2.00 g) and potassium carbonate (5.40 g) in DMF (20 mL) was added dropwise benzyl bromide (4.50 g) at room temperature, and the mixture was stirred for 3 hr. Water was added to the reaction mixture, and the mixture was extracted with ethyl acetate. The extract was washed with saturated brine, and dried over anhydrous sodium sulfate. The solvent was evaporated under reduced pressure to give the title compound (4.30 g) as a colorless oil. This compound was used for the next step without further purification.
MS (ESI+): [M+H]$^+$ 333.1

B) 3-(benzyloxy)-4-methylbenzoic acid

To a solution of benzyl 3-(benzyloxy)-4-methylbenzoate (4.30 g) in methanol (40 mL) and THF (40 mL) was added a solution of sodium hydroxide (2.60 g) in water (40 mL), and the mixture was stirred at 70° C. for 2 hr. The reaction mixture was allowed to cool to room temperature, and evaporated under reduced pressure. Water (20 mL) was added to the residue, and the mixture was adjusted with 1N hydrochloric acid to pH<4. The precipitated crystals were collected by filtration, and dried to give the title compound (2.80 g) as white crystals.
MS (ESI+): [M+H]$^+$ 243.1

C) (3-(benzyloxy)-4-methylphenyl)methanol

To a solution of 3-(benzyloxy)-4-methylbenzoic acid (2.80 g) in THF (10 mL) was added dropwise a 1.0 M solution of borane-THF complex in THF (23 mL) at room temperature over 30 min, and the mixture was stirred for 2 hr. Methanol (20 mL) was added dropwise to the reaction mixture over 20 min, and water was further added. The reaction mixture was extracted with ethyl acetate, and the extract was washed with saturated brine. The organic layer was dried over anhydrous sodium sulfate. The solvent was evaporated under reduced pressure to give the title compound (2.60 g) as a yellow oil. This compound was used for the next step without further purification.

D) 3-(benzyloxy)-4-methylbenzaldehyde

To a solution of (3-(benzyloxy)-4-methylphenyl)methanol (entire amount) in DMSO (15 mL) was added 2-iodoxybenzoic acid (3.20 g), and the mixture was stirred at room temperature for 2 hr. Ethyl acetate (250 mL) was added to the reaction mixture, and the insoluble material was filtered off. The filtrate was washed with saturated brine, and dried over anhydrous sodium sulfate. The solvent was evaporated under reduced pressure, and the residue was purified by silica gel column chromatography (ethyl acetate/hexane) to give the title compound (2.50 g) as a yellow oil.
MS (ESI+): [M+H]$^+$ 270.0

E) ethyl 3-(3-(benzyloxy)-4-methylphenyl)acrylate

Under a nitrogen atmosphere, to a solution of 3-(benzyloxy)-4-methylbenzaldehyde (2.50 g) in toluene (50 mL) was added ethyl (triphenylphosphoranylidene)acetate (4.20 g), and the mixture was stirred at 70° C. for 15 hr. The reaction mixture was concentrated, diethyl ether (100 mL) was added, and the insoluble material was filtered off. The filtrate was concentrated under reduced pressure. The residue was purified by silica gel column chromatography (ethyl acetate/hexane) to give the title compound (2.50 g) as a colorless oil. This compound was used for the next step without further purification.
$^1$H NMR (400 MHz, CDCl$_3$) δ 1.37 (3H, t, J=7.6 Hz), 2.33 (3H, s), 4.29 (2H, q, J=7.6 Hz), 5.13 (2H, s), 6.40 (1H, d, J=16.0 Hz), 7.06-7.10 (2H, m), 7.18-7.21 (1H, m), 7.34-7.50 (5H, m), 7.67 (1H, d, J=16.0 Hz).

F) ethyl 3-(3-hydroxy-4-methylphenyl)propanoate

To a solution of ethyl 3-(3-(benzyloxy)-4-methylphenyl)acrylate (2.50 g) in ethanol (50 mL) was added 10% palladium-activated carbon (250 mg) and, under a hydrogen atmosphere, the mixture was stirred at room temperature for 15 hr. The reaction mixture was filtered, and the filtrate was concentrated under reduced pressure. The residue was purified by silica gel column chromatography (ethyl acetate/hexane) to give the title compound (1.50 g) as a colorless oil.
MS (ESI+): [M+H]$^+$ 209.1

G) 6-(chloromethyl)-2-(2,2-dimethylpropyl)-3-(2-fluoro-5-methoxyphenyl)pyridine

To a solution of (6-(2,2-dimethylpropyl)-5-(2-fluoro-5-methoxyphenyl)pyridin-2-yl)methanol (4.00 g) and triethylamine (4.00 g) in dichloromethane (20 mL) was added dropwise methanesulfonyl chloride (3.00 g) at 0° C., and the mixture was stirred at room temperature for 15 hr. Dichloromethane (150 ml) was added to the reaction mixture, and the mixture was washed with saturated brine. The organic layer was dried over anhydrous sodium sulfate, and the solvent was evaporated under reduced pressure. The residue was purified by silica gel column chromatography (ethyl acetate/hexane) to give the title compound (2.75 g) as a colorless oil.
MS (ESI+): [M+H]$^+$ 322.1

H) ethyl 3-(3-((5-(2-fluoro-5-methoxyphenyl)-6-neopentylpyridin-2-yl)methoxy)-4-methylphenyl)propanoate To a solution of 6-(chloromethyl)-2-(2,2-dimethylpropyl)-3-(2-fluoro-5-methoxyphenyl)pyridine (350 mg) in acetonitrile (30 ml) were added ethyl 3-(3-hydroxy-4-methylphenyl)propanoate (191 mg) and cesium carbonate (597 mg), and the mixture was heated under reflux for 15 hr. The reaction mixture was concentrated, and water was added to the residue. The reaction mixture was extracted with ethyl acetate, and the extract was washed with saturated brine. The organic layer was dried over anhydrous sodium sulfate, and the solvent was evaporated under reduced pressure. The residue was purified by silica gel column chromatography (ethyl acetate/hexane) to give the title compound (400 mg) as a yellow oil.
MS (ESI+): [M+H]$^+$ 494.1

I) 3-(3-((6-(2,2-dimethylpropyl)-5-(2-fluoro-5-methoxyphenyl)pyridin-2-yl)methoxy)-4-methylphenyl)propanoic acid To a solution of ethyl 3-(3-((5-(2-fluoro-5-methoxyphenyl)-6-neopentylpyridin-2-yl)methoxy)-4-methylphenyl)propanoate (400 mg) in methanol (5.0 mL) and THF (10 mL) was added a solution of sodium hydroxide (333 mg) in water (10 mL), and the mixture was stirred at room temperature for 15 hr. The reaction mixture was concentrated under reduced pressure, and 1N hydrochloric acid was added to the residue to adjust to pH<4. The reaction mixture was extracted with ethyl acetate, and the extract was washed with saturated brine. The organic layer was dried over anhydrous sodium sulfate, and the solvent was evaporated under reduced pressure. The residue was purified by silica gel column chromatography (ethyl acetate/hexane) to give the title compound (350 mg) as a yellow solid.
MS (ESI+): [M+H]$^+$466.1
$^1$H NMR (400 MHz, CDCl$_3$) δ 0.82 (9H, s), 2.34 (3H, s), 2.68 (2H, t, J=7.6 Hz), 2.72-2.91 (2H, m), 2.95 (2H, t, J=7.6 Hz), 3.83 (3H, s), 5.29 (2H, s), 6.76-6.82 (3H, m), 6.89-6.93 (1H, m), 7.07-7.13 (2H, m), 7.52 (1H, d, J=8.0 Hz), 7.60 (1H, d, J=8.0 Hz).

Example 14

3-cyclopropyl-3-(3-((6-(2,2-dimethylpropyl)-5-(2-fluoro-5-methoxyphenyl)pyridin-2-yl)methoxy)-4-fluorophenyl)propanoic acid A) (5-(4-fluoro-3-methoxybenzylidene)-2,2-dimethyl-1,3-dioxane-4,6-dione To a solution of titanium (IV) chloride (11.1 g) in THF (50 mL) was added dropwise a solution of 2,2-dimethyl-1,3-dioxane-4,6-dione (4.26 g) and 4-fluoro-3-methoxybenzaldehyde (3.08 g) in THF (50 mL) at 0° C., and then a solution of pyridine (4.00 g) in THF (20 mL) was added dropwise. The reaction mixture was stirred for 1 hr, and water was added. The reaction mixture was extracted with ethyl acetate, and the extract was washed with 1N hydrochloric acid and saturated brine. The organic layer was dried over anhydrous sodium sulfate. The solvent was evaporated under reduced pressure to give the title compound (3.20 g) as a yellow solid. This compound was used for the next step without further purification.

$^1$H NMR (400 MHz, CDCl$_3$) δ 1.81 (6H, s), 3.98 (3H, s), 7.17-7.21 (1H, m), 7.55-7.59 (1H, m), 8.25-8.28 (1H, m), 8.38 (1H, s).

B) 5-(cyclopropyl(4-fluoro-3-methoxyphenyl)methyl)-2,2-dimethyl-1,3-dioxane-4,6-dione Under an argon atmosphere, to a solution of (5-(4-fluoro-3-methoxybenzylidene)-2,2-dimethyl-1,3-dioxane-4,6-dione (3.00 g) in THF (20 mL) was added dropwise a 1.0 M solution of cyclopropylmagnesium bromide in THF (53.5 mL) at 0° C., and the mixture was stirred for 1 hr. 3N Hydrochloric acid (30 mL) was added to the reaction mixture, and the mixture was stirred for 15 min. The reaction mixture was neutralized with saturated aqueous sodium hydrogen carbonate solution, and extracted with ethyl acetate. The extract was washed with saturated brine, and dried over anhydrous sodium sulfate. The solvent was evaporated under reduced pressure to give the title compound (2.40 g) as a yellow solid. This compound was used for the next step without further purification.

MS (ESI+): [M+H]$^+$ 323.0

C) 3-cyclopropyl-3-(4-fluoro-3-methoxyphenyl)propanoic acid

To a solution of 5-(cyclopropyl(4-fluoro-3-methoxyphenyl)methyl)-2,2-dimethyl-1,3-dioxane-4,6-dione (2.00 g) in DMF (20 mL) was added water (2.0 mL), and the mixture was stirred at 90° C. for 15 hr. The reaction mixture was allowed to cool to room temperature, and extracted with ethyl acetate. The extract was washed with 1N hydrochloric acid and saturated brine, and dried over anhydrous sodium sulfate. The solvent was evaporated under reduced pressure, and the obtained residue was purified by silica gel column chromatography (ethyl acetate/hexane) to give the title compound (1.10 g) as a yellow oil.

$^1$H NMR (400 MHz, CDCl$_3$) δ 0.15-0.19 (1H, m), 0.28-0.32 (1H, m), 0.44-0.49 (1H, m), 0.59-0.64 (1H, m), 1.00-1.05 (1H, m), 2.32-2.38 (1H, m), 2.71-2.84 (2H, m), 3.92 (3H, s), 6.75-6.79 (1H, m), 6.83-6.85 (1H, m), 6.99-7.04 (1H, m).

D) methyl 3-cyclopropyl-3-(4-fluoro-3-methoxyphenyl)propanoate

To a solution of 3-cyclopropyl-3-(4-fluoro-3-methoxyphenyl)propanoic acid (1.00 g) in methanol (50 mL) was added dropwise at room temperature thionyl chloride (2.0 mL), and the mixture was stirred at room temperature for 1 hr. Water was added to the reaction mixture, and the mixture was extracted with ethyl acetate. The extract was washed with saturated brine, and dried over anhydrous sodium sulfate. The solvent was evaporated under reduced pressure, and the obtained residue was purified by silica gel column chromatography (ethyl acetate/hexane) to give the title compound (900 mg) as a yellow oil.

MS (ESI+): [M+H]$^+$ 253.1

E) methyl 3-cyclopropyl-3-(4-fluoro-3-hydroxyphenyl)propanoate

To a solution of methyl 3-cyclopropyl-3-(4-fluoro-3-methoxyphenyl)propanoate (800 mg) in dichloromethane (20 mL) was added dropwise a 1.0 M solution of boron tribromide in dichloromethane (3.8 mL) at −5° C. over 20 min, and thereafter the mixture was stirred for 2 hr. Water (20 mL) was added dropwise to the reaction mixture, and the mixture was extracted with dichloromethane. The extract was washed with saturated brine, and dried over anhydrous sodium sulfate. The solvent was evaporated under reduced pressure and the obtained residue was purified by silica gel column chromatography (ethyl acetate/hexane) to give the title compound (400 mg) as a yellow oil.

MS (ESI+): [M+H]$^+$ 239.1

F) methyl 3-cyclopropyl-3-(3-((6-(2,2-dimethylpropyl)-5-(2-fluoro-5-methoxyphenyl)pyridin-2-yl)methoxy)-4-fluorophenyl)propanoate To a solution of 6-(chloromethyl)-2-(2,2-dimethylpropyl)-3-(2-fluoro-5-methoxyphenyl)pyridine (320 mg) in acetonitrile (30 mL) were added methyl 3-cyclopropyl-3-(4-fluoro-3-hydroxyphenyl)propanoate (220 mg) and cesium carbonate (550 mg), and the mixture was heated under reflux for 15 hr. The reaction mixture was concentrated, and water was added to the residue. The mixture was extracted with ethyl acetate, and the extract was washed with saturated brine. The organic layer was dried over anhydrous sodium sulfate, and the solvent was evaporated under reduced pressure. The residue was purified by silica gel column chromatography (ethyl acetate/hexane) to give the title compound (400 mg) as a yellow oil.

$^1$H NMR (400 MHz, CDCl$_3$) δ 0.06-0.09 (1H, m), 0.21-0.27 (1H, m), 0.36-0.43 (1H, m), 0.54-0.60 (1H, m), 0.82 (9H, s), 0.87-0.98 (1H, m), 2.28-2.35 (1H, m), 2.64-2.87 (4H, m), 3.60 (3H, s), 3.82 (2H, s), 5.33 (2H, s), 6.76-6.80 (2H, m), 6.88-6.94 (2H, m), 7.02-7.10 (2H, m), 7.49-7.58 (2H, m).

G) 3-cyclopropyl-3-(3-((6-(2,2-dimethylpropyl)-5-(2-fluoro-5-methoxyphenyl)pyridin-2-yl)methoxy)-4-fluorophenyl)propanoic acid To a solution of methyl 3-cyclopropyl-3-(3-((6-(2,2-dimethylpropyl)-5-(2-fluoro-5-methoxyphenyl)pyridin-2-yl)methoxy)-4-fluorophenyl)propanoate (400 mg) in methanol (5.0 mL) and THF (10 mL) was added a solution of sodium hydroxide (305 mg) in water (10 mL), and the mixture was stirred at room temperature for 15 hr. The reaction mixture was concentrated under reduced pressure, and 1N hydrochloric acid was added to the residue to adjust to pH<4. The reaction mixture was extracted with ethyl acetate, and the extract was washed with saturated brine. The organic layer was dried over anhydrous sodium sulfate, and the solvent was evaporated under reduced pressure. The residue was purified by silica gel column chromatography (ethyl acetate/hexane) to give the title compound (350 mg) as a yellow solid.

MS (ESI+): [M+H]$^+$ 510.2

$^1$H NMR (400 MHz, CDCl$_3$) δ 0.08-0.11 (1H, m), 0.26-0.30 (1H, m), 0.38-0.40 (1H, m), 0.57-0.60 (1H, m), 0.80 (9H, s), 0.95-0.98 (1H, m), 2.33-2.35 (1H, m), 2.68-2.82 (4H, m), 3.82 (3H, s), 5.33 (2H, s), 6.76-6.81 (2H, m), 6.88-6.95 (2H, m), 7.02-7.07 (2H, m), 7.50-7.59 (2H, m).

Example 15

3-(3-((6-(2,2-dimethylpropyl)-5-(2-fluoro-5-methoxyphenyl)pyridin-2-yl)methoxy)-5-methoxyphenyl)propanoic acid

A) methyl 3,5-dihydroxybenzoate

To a solution of 3,5-dihydroxybenzoic acid (30.0 g) in methanol (300 mL) was added dropwise thionyl chloride (20 mL) at 0° C., and the mixture was heated under reflux for 2 hr. The reaction mixture was concentrated, and the obtained crystals were washed with diethyl ether to give the title compound (30.0 g) as a white solid.

$^1$H NMR (400 MHz, DMSO-$d_6$) δ 3.79 (3H, s), 6.44 (1H, s), 6.81 (2H, s), 9.60 (2H, s).

B) methyl 3-hydroxy-5-methoxybenzoate

To a solution of methyl 3,5-dihydroxybenzoate (28.0 g) in DMF (300 mL) was added 60% sodium hydride (4.70 g) at 0° C., and the mixture was stirred for 30 min. Iodomethane (23.7 g) was added dropwise, and the mixture was stirred at 0° C. for 1 hr. 1N Hydrochloric acid (300 mL) was added to the reaction mixture, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (10.1 g) as a white solid.

MS (ESI+): [M+H]$^+$ 183.1

C) methyl 3-(benzyloxy)-5-methoxybenzoate

To a solution of methyl 3-hydroxy-5-methoxybenzoate (6.00 g) in DMF (50 mL) were added benzyl bromide (6.20 g) and potassium carbonate (5.50 g), and the mixture was stirred at room temperature for 15 hr. Water was added to the reaction mixture, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (8.90 g) as a white solid.

MS (ESI+): [M+H]$^+$ 273.1

D) (3-(benzyloxy)-5-methoxyphenyl)methanol

To a solution of methyl 3-(benzyloxy)-5-methoxybenzoate (8.90 g) in THF (100 mL) was added lithium aluminum hydride (1.30 g) at 0° C., and the mixture was stirred at room temperature for 1 hr. Water was added to the reaction mixture, and the mixture was extracted with ethyl acetate. The extract was washed with saturated brine, and dried over anhydrous sodium sulfate. The solvent was evaporated under reduced pressure to give the title compound (7.50 g) as an oil. This compound was used for the next step without further purification.

MS (ESI+): [M+H]$^+$ 245.1

E) 3-(benzyloxy)-5-methoxybenzaldehyde

To a solution of (3-(benzyloxy)-5-methoxyphenyl)methanol (6.50 g) in DMSO (100 mL) was added 2-iodoxybenzoic acid (9.00 g), and the mixture was stirred at room temperature for 3 hr. Water was added to the reaction mixture, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (5.50 g) as an oil.

MS (ESI+): [M+H]$^+$ 243.1

F) ethyl 3-(3-(benzyloxy)-5-methoxyphenyl)acrylate

To a solution of 3-(benzyloxy)-5-methoxybenzaldehyde (5.50 g) in toluene (50 mL) was added ethyl (triphenylphosphoranylidene)acetate (7.90 g), and the mixture was heated under reflux for 4 hr. The reaction mixture was concentrated, and the residue was purified by silica gel column chromatography (ethyl acetate/hexane) to give the title compound (6.00 g) as a colorless oil.

MS (ESI+): [M+H]$^+$ 313.1

G) ethyl 3-(3-hydroxy-5-methoxyphenyl)propanoate

To a solution of ethyl 3-(3-(benzyloxy)-5-methoxyphenyl)acrylate (6.00 g) in methanol (100 mL) was added 10% palladium-activated carbon (500 mg) was added, and the mixture was stirred for 15 hr under a hydrogen atmosphere. The reaction mixture was filtered, and the filtrate was concentrated under reduced pressure. The residue was purified by silica gel column chromatography (ethyl acetate/hexane) to give the title compound (4.00 g) as a colorless oil.

MS (ESI+): [M+H]$^+$ 225.1

H) ethyl 3-(3-((6-(2,2-dimethylpropyl)-5-(2-fluoro-5-methoxyphenyl)pyridin-2-yl)methoxy)-5-methoxyphenyl)propanoate To a solution of 6-(chloromethyl)-2-(2,2-dimethylpropyl)-3-(2-fluoro-5-methoxyphenyl)pyridine (300 mg) in acetonitrile (10 mL) were added ethyl 3-(3-hydroxy-5-methoxyphenyl)propanoate (270 mg) and cesium carbonate (510 mg), and the mixture was heated under reflux for 15 hr. Ethyl acetate was added to the reaction mixture, and the insoluble material was filtered off. The solvent in the filtrate was evaporated under reduced pressure, and the residue was purified by silica gel column chromatography (ethyl acetate/hexane) to give the title compound (450 mg) as a colorless oil.

MS (ESI+): [M+H]$^+$ 510.0

I) 3-(3-((6-(2,2-dimethylpropyl)-5-(2-fluoro-5-methoxyphenyl)pyridin-2-yl)methoxy)-5-methoxyphenyl)propanoic acid To a solution of ethyl 3-(3-((6-(2,2-dimethylpropyl)-5-(2-fluoro-5-methoxyphenyl)pyridin-2-yl)methoxy)-5-methoxyphenyl)propanoate (450 mg) in methanol (4.0 mL) and THF (8.0 mL) was added 1N aqueous sodium hydroxide solution (8.0 mL), and the mixture was stirred at room temperature for 15 hr. The reaction mixture was concentrated under reduced pressure, and 1N hydrochloric acid was added to the residue to adjust to pH<4. The reaction mixture was extracted with ethyl acetate, and the extract was washed with saturated brine. The organic layer was dried over anhydrous sodium sulfate. The solvent was evaporated under reduced pressure to give the title compound (319 mg) as a yellow solid.

$^1$H NMR (400 MHz, DMSO-$d_6$) δ 0.76 (9H, s), 2.51 (2H, t, J=8.0 Hz), 2.60-2.72 (2H, m), 2.75 (2H, t, J=8.0 Hz), 3.71 (3H, s), 3.76 (3H, s), 5.18 (2H, s), 6.41-6.45 (2H, m), 6.53 (1H, s), 6.89-6.91 (1H, m), 6.99-7.03 (1H, m), 7.25 (1H, t, J=9.2 Hz), 7.43 (1H, d, J=7.6 Hz), 7.65 (1H, d, J=7.6 Hz), 12.11 (1H, brs).

MS (ESI+): [M+H]$^+$ 482.2

Example 16

3-(3-((6-(2,2-dimethylpropyl)-5-(2-fluoro-5-methoxyphenyl)pyridin-2-yl)methoxy)-5-fluorophenyl)propanoic acid A) 1-(benzyloxy)-3-bromo-5-fluorobenzene To a solution of benzyl alcohol (1.10 g) in THF (90 mL) was added 60% sodium hydride (2.50 g) at 0° C., and the mixture was stirred for 1 hr. A solution of 1-bromo-3,5-difluorobenzene (1.00 g) in THF (10 mL) was added dropwise to the reaction mixture at 0° C. over 1 hr, and the mixture was stirred for 15 hr. Water was added to the reaction mixture, and the mixture was extracted with ethyl acetate. The extract was washed with saturated brine, and dried over anhydrous sodium sulfate. The solvent was evaporated under reduced pressure to give the title compound (2.00 g) as a yellow oil. This compound was used for the next step without further purification.

$^1$H NMR (400 MHz, CDCl$_3$) δ 5.01 (2H, s), 6.62 (1H, dd, J=10.4, 1.2 Hz), 6.85 (1H, dd, J=8.0, 1.2 Hz), 6.93-6.95 (1H, m), 7.33-7.39 (5H, m).

B) methyl 3-(3-(benzyloxy)-5-fluorophenyl)acrylate

To a solution of 1-(benzyloxy)-3-bromo-5-fluorobenzene (6.60 g) in acetonitrile (130 mL) were added methyl acrylate (13.7 g), triphenylphosphine (3.36 g) and triethylamine (14.5 g), and toluene (2.0 mL) and palladium acetate (480 mg) were further added. The reaction mixture was stirred at 100° C. for 96 hr, and the solvent was evaporated under reduced pressure. The residue was purified by silica gel column chromatography (ethyl acetate/hexane) to give the title compound (2.70 g) as a white solid.

MS (ESI+): [M+H]$^+$ 286.9

C) methyl 3-(3-fluoro-5-hydroxyphenyl)propanoate

To a solution of methyl 3-(3-(benzyloxy)-5-fluorophenyl)acrylate (2.60 g) in methanol (15 mL) was added 10% palladium-activated carbon (2.20 g), and the mixture was stirred for 1 hr under a hydrogen atmosphere. The reaction mixture was filtered, and the filtrate was concentrated under reduced pressure. The residue was purified by silica gel column chromatography (ethyl acetate/hexane) to give the title compound (710 mg) as a white solid.

MS (ESI+): [M+H]$^+$ 199.9

D) methyl 3-(3-((6-(2,2-dimethylpropyl)-5-(2-fluoro-5-methoxyphenyl)pyridin-2-yl)methoxy)-5-fluorophenyl)propanoate To a solution of 6-(chloromethyl)-2-(2,2-dimethylpropyl)-3-(2-fluoro-5-methoxyphenyl)pyridine (350 mg) in acetonitrile (25 mL) were added methyl 3-(3-fluoro-5-hydroxyphenyl)propanoate (208 mg) and cesium carbonate (1.41 g), and the mixture was heated under reflux for 15 hr. Ethyl acetate was added to the reaction mixture, and the insoluble material was filtered off. The solvent in the filtrate was evaporated under reduced pressure, and the residue was purified by silica gel column chromatography (ethyl acetate/hexane) to give the title compound (390 mg) as a white solid.

MS (ESI+): [M+H]$^+$ 484.2

E) 3-(3-((6-(2,2-dimethylpropyl)-5-(2-fluoro-5-methoxyphenyl)pyridin-2-yl)methoxy)-5-fluorophenyl)propanoic acid To a solution of methyl 3-(3-((6-(2,2-dimethylpropyl)-5-(2-fluoro-5-methoxyphenyl)pyridin-2-yl)methoxy)-5-fluorophenyl)propanoate (380 mg) in methanol (4.0 mL) and THF (3.0 mL) was added a solution of sodium hydroxide (183 mg) in water (4.0 mL), and the mixture was stirred at room temperature for 15 hr. 2N Hydrochloric acid was added to the reaction to mixture to adjust to pH<2, and the mixture was extracted with ethyl acetate. The extract was washed with saturated brine, and dried over anhydrous sodium sulfate. The solvent was evaporated under reduced pressure to give the title compound (290 mg) as a white solid.

MS (ESI+): [M+H]$^+$ 468.1

$^1$H NMR (400 MHz, DMSO-d$_6$) δ 0.75 (9H, s), 2.50-2.55 (2H, m), 2.64-2.69 (2H, m), 2.79 (2H, t, J=7.2 Hz), 3.76 (3H, s), 5.21 (2H, s), 6.68 (1H, d, J=9.2 Hz), 6.75-6.80 (2H, m), 6.89-6.91 (1H, m), 6.99-7.03 (1H, m), 7.25 (1H, t, J=9.2 Hz), 7.44 (1H, d, J=8.4 Hz), 7.66 (1H, d, J=8.4 Hz).

Example 17

3-(5-((6-(2,2-dimethylpropyl)-5-(2-fluoro-5-methoxyphenyl)pyridin-2-yl)methoxy)-2-methylphenyl)propanoic acid A) benzyl 5-(benzyloxy)-2-methylbenzoate To a solution of 5-hydroxy-2-methylbenzoic acid (1.52 g) in DMF (25 mL) were added benzyl bromide (3.40 g) and potassium carbonate (4.14 g), and the mixture was stirred at room temperature for 3 hr. Water was added to the reaction mixture, and the precipitated crystals were collected by filtration, and dried to give the title compound (2.80 g) as a white solid. This compound was used for the next step without further purification.

MS (ESI+): [M+H]$^+$ 333.0

B) 5-(benzyloxy)-2-methylbenzoic acid

To a solution of benzyl 5-(benzyloxy)-2-methylbenzoate (2.80 g) in methanol (50 mL) and THF (50 mL) was added a solution of sodium hydroxide (3.30 g) in water (50 mL), and the mixture was stirred at room temperature for 3 hr. Water was added to the reaction mixture and the mixture was concentrated. Water (30 mL) was added to the residue, and the mixture was adjusted with 2N hydrochloric acid to pH<2. The precipitated crystals were collected by filtration, and dried to give the title compound (1.70 g) as a white solid. This compound was used for the next step without further purification.

C) (5-(benzyloxy)-2-methylphenyl)methanol

To a solution of 3-(benzyloxy)-2-methylbenzoic acid (300 mg) in THF (10 mL) was added a 1.0 M solution of borane-THF complex in THF (1.85 mL) over 30 min. After stirring for 2 hr, methanol (20 mL) was added dropwise to the reaction mixture over 20 min. Methanol (10 mL) was added to the reaction mixture, and the solvent was evaporated under reduced pressure to give the title compound (280 mg) as a white solid. This compound was used for the next step without further purification.

MS (ESI+): [M+H]$^+$ 246.0

D) 5-(benzyloxy)-2-methylbenzaldehyde

To a solution of (5-(benzyloxy)-2-methylphenyl)methanol (280 mg) in DMSO (5.0 ml) was added 2-iodoxybenzoic acid (343 mg), and the mixture was stirred at room temperature for 2 hr. Water was added to the reaction mixture, and the mixture was extracted with ethyl acetate. The extract was washed with saturated brine, and dried over anhydrous sodium sulfate. The solvent was evaporated under reduced pressure to give the title compound (250 mg) as a pale-yellow oil. This compound was used for the next step without further purification.

MS (ESI+): [M+H]+ 227.0.

E) ethyl 3-(5-(benzyloxy)-2-methylphenyl)acrylate

To a solution of 5-(benzyloxy)-2-methylbenzaldehyde (250 mg) in toluene (20 mL) was added ethyl (triphenylphosphoranylidene)acetate (379 mg), and the mixture was stirred at 60° C. for 15 hr. The reaction mixture was concentrated, diethyl ether was added, and the insoluble material was filtered off. The filtrate was concentrated, and the residue was purified by silica gel column chromatography (ethyl acetate/hexane) to give the title compound (200 mg) as a yellow oil.
MS (ESI+): [M+H]+ 297.1

F) ethyl 3-(5-hydroxy-2-methylphenyl)propanoate

To a solution of ethyl 3-(5-(benzyloxy)-2-methylphenyl)acrylate (1.00 g) in methanol (50 mL) was added 10% palladium-activated carbon (150 mg), and the mixture was stirred for 15 hr under a hydrogen atmosphere. The reaction mixture was filtered, and the filtrate was concentrated under reduced pressure. The residue was purified by silica gel column chromatography (ethyl acetate/hexane) to give the title compound (500 mg) as a yellow oil.
$^1$H NMR (400 MHz, CDCl$_3$) δ 1.28 (3H, t, J=6.8 Hz), 2.26 (3H, s), 2.58 (2H, t, J=7.6 Hz), 2.90 (2H, t, J=7.6 Hz), 4.16 (2H, q, J=6.8 Hz), 6.62 (1H, dd, J=2.8, 8.0 Hz), 6.67 (1H, d, J=2.8 Hz), 7.02 (1H, d, J=8.0 Hz).

G) ethyl 3-(5-((6-(2,2-dimethylpropyl)-5-(2-fluoro-5-methoxyphenyl)pyridin-2-yl)methoxy)-2-methylphenyl)propanoate To a solution of 6-(chloromethyl)-2-(2,2-dimethylpropyl)-3-(2-fluoro-5-methoxyphenyl)pyridine (320 mg) in acetonitrile (10 mL) were added ethyl 3-(5-hydroxy-2-methylphenyl)propanoate (230 mg) and cesium carbonate (546 mg), and the mixture was heated under reflux for 15 hr. Ethyl acetate was added to the reaction mixture, and the insoluble material was filtered off. The solvent in the filtrate was evaporated under reduced pressure, and the residue was purified by silica gel column chromatography (ethyl acetate/hexane) to give the title compound (427 mg) as a colorless oil.
MS (ESI+): [M+H]+ 494.2

H) 3-(5-((6-(2,2-dimethylpropyl)-5-(2-fluoro-5-methoxyphenyl)pyridin-2-yl)methoxy)-2-methylphenyl)propanoic acid To a solution of ethyl 3-(5-((6-(2,2-dimethylpropyl)-5-(2-fluoro-5-methoxyphenyl)pyridin-2-yl)methoxy)-2-methylphenyl)propanoate (427 mg) in methanol (4.0 mL) was added 1N aqueous sodium hydroxide solution (8.6 mL), and the mixture was stirred at room temperature for 15 hr. 1N Hydrochloric acid was added to the reaction mixture to adjust to pH<4, and the mixture was extracted with ethyl acetate. The extract was washed with saturated brine, and dried over anhydrous sodium sulfate. The solvent was evaporated under reduced pressure to give the title compound (275 mg) as a white solid.
MS (ESI+): [M+H]+ 466.1
$^1$H NMR (400 MHz, DMSO-d$_6$) δ 0.76 (9H, s), 2.19 (3H, s), 2.51 (2H, t, J=8.0 Hz), 2.60-2.74 (2H, m), 2.76 (2H, t, J=8.0 Hz), 3.76 (3H, s), 5.16 (2H, s), 6.77-6.79 (1H, m), 6.86-6.91 (2H, m), 6.99-7.06 (2H, m), 7.25 (1H, t, J=9.2 Hz), 7.41 (1H, d, J=7.6 Hz), 7.65 (1H, d, J=7.6 Hz), 12.17 (1H, s).

Example 18

3-(5-((6-(2,2-dimethylpropyl)-5-(2-fluoro-5-methoxyphenyl)pyridin-2-yl)methoxy)-2-methoxyphenyl) propanoic acid A) 4-methoxyphenyl methyl carbonate To a mixture of 4-hydroxyanisole (12.4 g), pyridine (8.5 mL) and dichloromethane (75 mL) was added methyl chloroformate (8.1 mL), and the mixture was stirred for 4 hr. The reaction mixture was concentrated, ethyl acetate was added to the residue, and the mixture was washed with saturated brine. The organic layer was dried over anhydrous sodium sulfate. The solvent was evaporated under reduced pressure to give the title compound (18.0 g) as a colorless oil. This compound was used for the next step without further purification.
MS (ESI+): [M+H]+ 183.0

B) 3-formyl-4-methoxyphenyl methyl carbonate

Under an argon atmosphere, to a solution of 4-methoxyphenyl methyl carbonate (10.0 g) in dichloromethane (125 mL) was added a solution of titanium (IV) chloride (14.3 mL) in dichloromethane (25 mL) at 0° C., and then dichloro(methoxy)methane (5.8 mL) was added dropwise over 30 min. The reaction mixture was warmed to room temperature, and stirred for 30 min. Dichloromethane (about 70 mL) was evaporated, and ice (120 g) and 12N hydrochloric acid were added. The mixture was extracted with ethyl acetate, and the extract was washed with saturated brine. The organic layer was dried over anhydrous sodium sulfate. The solvent was evaporated under reduced pressure to give the title compound (10.5 g) as a yellow oil. This compound was used for the next step without further purification.
MS (ESI+): [M+H]+ 211.0

C) ethyl 3-(2-methoxy-5-(methoxycarbonyloxy)phenyl)acrylate

To a solution of 3-formyl-4-methoxyphenyl methyl carbonate (10.0 g) in toluene (10 mL) was added ethyl (triphenylphosphoranylidene)acetate (21.5 g), and the mixture was stirred at 80° C. for 15 hr. The reaction mixture was concentrated, and the residue was purified by silica gel column chromatography (ethyl acetate/hexane) to give the title compound (12.0 g) as a yellow oil.
MS (ESI+): [M+H]+ 281.0

D) ethyl 3-(2-methoxy-5-(methoxycarbonyloxy) phenyl)propanoate

To a solution of ethyl 3-(2-methoxy-5-(methoxycarbonyloxy)phenyl)acrylate (1.00 g) in methanol (3.0 mL) was added 10% palladium-activated carbon (100 mg), and the mixture was stirred for 1 hr under a hydrogen atmosphere. The reaction mixture was filtered, and the filtrate was concentrated under reduced pressure to give the title compound (800 mg) as a yellow oil. This compound was used for the next step without further purification.
MS (ESI+): [M+H]+ 283.0

E) ethyl 3-(5-hydroxy-2-methoxyphenyl)propanoate

To a solution of sodium methoxide (227 mg) in methanol (10 ml) was added ethyl 3-(2-methoxy-5-(methoxycarbonyloxy)phenyl)propanoate (1.00 g), and the mixture was stirred for 1 hr. The reaction mixture was concentrated, and the residue was extracted with ethyl acetate. The extract was washed with saturated brine, and the organic layer was dried over anhydrous sodium sulfate. The solvent was evaporated under reduced pressure to give the title compound (730 mg) as a yellow oil. This compound was used for the next step without further purification.

MS (ESI+): [M+H]$^+$ 225.1

F) ethyl 3-(5-((6-(2,2-dimethylpropyl)-5-(2-fluoro-5-methoxyphenyl)pyridin-2-yl)methoxy)-2-methoxyphenyl)propanoate To a solution of 6-(chloromethyl)-2-(2,2-dimethylpropyl)-3-(2-fluoro-5-methoxyphenyl)pyridine (330 mg) in acetonitrile (8.0 mL) were added ethyl 3-(5-hydroxy-2-methoxyphenyl)propanoate (216 mg) and cesium carbonate (647 mg), and the mixture was heated under reflux for 15 hr. Ethyl acetate was added to the reaction mixture, and the insoluble material was filtered off. The solvent in the filtrate was evaporated under reduced pressure, and the residue was purified by silica gel column chromatography (ethyl acetate/hexane) to give the title compound (290 mg) as a white solid.

MS (ESI+): [M+H]$^+$ 510.7

G) 3-(5-((6-(2,2-dimethylpropyl)-5-(2-fluoro-5-methoxyphenyl)pyridin-2-yl)methoxy)-2-methoxyphenyl)propanoic acid To a solution of ethyl 3-(5-((6-(2,2-dimethylpropyl)-5-(2-fluoro-5-methoxyphenyl)pyridin-2-yl)methoxy)-2-methoxyphenyl)propanoate (200 mg) in methanol (3.0 mL) was added a solution of sodium hydroxide (100 mg) in water (3.0 mL), and the mixture was stirred at room temperature for 15 hr. 2N Hydrochloric acid was added to the reaction mixture to adjust to pH<2, and the mixture was extracted with ethyl acetate. The extract was washed with saturated brine, and dried over anhydrous sodium sulfate. The solvent was evaporated under reduced pressure to give the title compound (143 mg) as a white solid.

MS (ESI+): [M+H]$^+$ 482.2
$^1$H NMR (400 MHz, DMSO-d$_6$) δ 0.76 (9H, s), 2.45 (2H, t, J=8.0 Hz), 2.64-2.68 (2H, m), 2.75 (2H, t, J=8.0 Hz), 3.74 (3H, s), 3.76 (3H, s), 5.13 (2H, s), 6.86-6.90 (1H, m), 6.99-7.03 (1H, m), 7.25 (1H, t, J=8.8 Hz), 7.42 (1H, d, J=8.0 Hz), 7.64 (1H, d, J=8.0 Hz), 12.12 (1H, s).

Example 19

3-(5-((6-(2,2-dimethylpropyl)-5-(2-fluoro-5-methoxyphenyl)pyridin-2-yl)methoxy)-2-fluorophenyl)propanoic acid A) ethyl 3-(2-fluoro-5-methoxyphenyl)acrylate To a solution of 2-fluoro-5-methoxybenzaldehyde (1.54 g) in toluene (50 mL) was added ethyl (triphenylphosphoranylidene)acetate (3.83 g), and the mixture was stirred at 70° C. for 15 hr. The reaction mixture was concentrated, and diethyl ether was added. The insoluble material was filtered off, and the filtrate was concentrated. The residue was purified by silica gel column chromatography (ethyl acetate/hexane) to give the title compound (862 mg) as a colorless oil.

MS (ESI+): [M+H]$^+$ 225.0

B) ethyl 3-(2-fluoro-5-methoxyphenyl)propanoate

To a solution of ethyl 3-(2-fluoro-5-methoxyphenyl)acrylate (224 mg) in ethanol (50 mL) was added 10% palladium-activated carbon (24 mg), and the mixture was stirred for 15 hr under a hydrogen atmosphere. The reaction mixture was filtered, and the filtrate was concentrated under reduced pressure to give the title compound (208 mg) as a colorless oil. This compound was used for the next step without further purification.

MS (ESI+): [M+H]$^+$ 227.0

C) ethyl 3-(2-fluoro-5-hydroxyphenyl)propanoate

To a solution of ethyl 3-(2-fluoro-5-methoxyphenyl)propanoate (100 mg) in dichloromethane (3.0 mL) was added dropwise a 1.0 M solution of boron tribromide in dichloromethane (0.15 mL) at −15° C., and the mixture was stirred at −15° C. for 5 hr. Water (20 ml) was added dropwise to the reaction mixture, and the mixture was extracted with dichloromethane. The extract was washed with saturated brine, and dried over anhydrous sodium sulfate. The solvent was evaporated under reduced pressure to give the title compound (60 mg) as a colorless oil. This compound was used for the next step without further purification.

$^1$H NMR (400 MHz, CDCl$_3$) δ 1.23-1.30 (3H, m), 2.63 (2H, t, J=8.0 Hz), 2.92 (2H, t, J=8.0 Hz), 4.12-4.18 (2H, m), 6.15-6.42 (1H, m), 6.63-6.71 (2H, m), 6.84-6.89 (1H, m).

D) ethyl 3-(5-((6-(2,2-dimethylpropyl)-5-(2-fluoro-5-methoxyphenyl)pyridin-2-yl)methoxy)-2-fluorophenyl)propanoate To a solution of 6-(chloromethyl)-2-(2,2-dimethylpropyl)-3-(2-fluoro-5-methoxyphenyl)pyridine (380 mg) in acetonitrile (10 mL) were added ethyl 3-(2-fluoro-5-hydroxyphenyl)propanoate (300 mg) and cesium carbonate (650 mg), and the mixture was heated under reflux for 15 hr. Ethyl acetate was added to the reaction mixture, and the insoluble material was filtered off. The solvent in the filtrate was evaporated under reduced pressure, and the residue was purified by silica gel column chromatography (ethyl acetate/hexane) to give the title compound (480 mg) as a colorless oil.

MS (ESI+): [M+H]$^+$ 498.2

E) 3-(5-((6-(2,2-dimethylpropyl)-5-(2-fluoro-5-methoxyphenyl)pyridin-2-yl)methoxy)-2-fluorophenyl)propanoic acid To a solution of ethyl 3-(5-((6-(2,2-dimethylpropyl)-5-(2-fluoro-5-methoxyphenyl)pyridin-2-yl)methoxy)-2-fluorophenyl)propanoate (480 mg) in methanol (4.0 mL) and THF (8.0 mL) was added 1N aqueous sodium hydroxide solution (8.7 mL), and the mixture was stirred at room temperature for 15 hr.

1N Hydrochloric acid was added to the reaction mixture to adjust to pH<4, and the mixture was extracted with ethyl acetate. The extract was washed with saturated brine, and dried over anhydrous sodium sulfate. The solvent was evaporated under reduced pressure to give the title compound (388 mg) as a white solid.

MS (ESI+): [M+H]$^+$ 470.1
$^1$H NMR (400 MHz, DMSO-d$_6$) δ 0.75 (9H, s), 2.52 (2H, t, J=8.0 Hz), 2.58-2.77 (2H, m), 2.81 (2H, t, J=8.0 Hz), 3.76 (3H, s), 5.17 (2H, s), 6.88-6.93 (2H, m), 6.99-7.10 (3H, m), 7.25 (1H, t, J=9.2 Hz), 7.44 (1H, d, J=8.0 Hz), 7.66 (1H, d, J=8.0 Hz), 12.22 (1H, brs).

Example 20

3-(3-((6-(2,2-dimethylpropyl)-5-(2-fluoro-5-methoxyphenyl)pyridin-2-yl)methoxy)-2-methylphenyl)propanoic acid

A) benzyl 3-(benzyloxy)-2-methylbenzoate

To a solution of 3-hydroxy-2-methylbenzoic acid (1.52 g) in DMF (25 mL) were added benzyl bromide (3.40 g) and potassium carbonate (4.14 g), and the mixture was stirred at room temperature for 3 hr. Water was added to the reaction mixture, and the precipitated crystals were collected by filtration, and dried to give the title compound (2.90 g) as a white solid. This compound was used for the next step without further purification.
MS (ESI+): [M+H]$^+$ 333.0

B) 3-(benzyloxy)-2-methylbenzoic acid

To a solution of benzyl 3-(benzyloxy)-2-methylbenzoate (2.90 g) in methanol (50 ml) and THF (50 mL) was added a solution of sodium hydroxide (3.40 g) in water (50 mL), and the mixture was stirred at room temperature for 3 hr. Water was added to the reaction mixture and the mixture was concentrated. Water (30 ml) was added to the residue, and the mixture was adjusted with 2N hydrochloric acid to pH<2. The precipitated crystals were collected by filtration, and dried to give the title compound (2.00 g) as a white solid. This compound was used for the next step without further purification.
MS (ESI+): [M+H]$^+$ 243.0

C) (3-(benzyloxy)-2-methylphenyl)methanol

To a solution of 3-(benzyloxy)-2-methylbenzoic acid (800 mg) in THF (10 mL) was added dropwise a 1.0 M solution of borane-THF complex in THF (6.6 mL) at room temperature over 30 min, and the mixture was stirred at room temperature for 2 hr. Methanol (10 mL) was added to the reaction mixture under ice-cooling, and the solvent was evaporated under reduced pressure. The residue was purified by silica gel column chromatography (ethyl acetate/hexane) to give the title compound (480 mg) as a white solid.
MS (ESI+): [M+H]$^+$ 229.0

D) 3-(benzyloxy)-2-methylbenzaldehyde

To a solution of (3-(benzyloxy)-2-methylphenyl)methanol (228 mg) in DMSO (5.0 mL) was added 2-iodoxybenzoic acid (280 mg), and the mixture was stirred at room temperature for 2 hr. Water was added to the reaction mixture, and the mixture was extracted with ethyl acetate. The extract was washed with saturated brine, and dried over anhydrous sodium sulfate. The solvent was evaporated under reduced pressure to give the title compound (200 mg) as a yellow oil. This compound was used for the next step without further purification.
MS (ESI+): [M+H]$^+$ 227.0

E) ethyl 3-(3-(benzyloxy)-2-methylphenyl)acrylate

To a solution of 3-(benzyloxy)-2-methylbenzaldehyde (200 mg) in toluene (20 mL) was added ethyl (triphenylphosphoranylidene)acetate (303 mg), and the mixture was stirred at 60° C. for 15 hr. The reaction mixture was concentrated, and diethyl ether was added. The insoluble material was filtered off, and the filtrate was concentrated. The residue was purified by silica gel column chromatography (ethyl acetate/hexane) to give the title compound (120 mg) as a yellow oil.
$^1$H NMR (400 MHz, CDCl$_3$) δ 1.38 (3H, t, J=6.8 Hz), 2.40 (3H, s), 4.30 (2H, q, J=6.8 Hz), 5.11 (2H, s), 6.38 (1H, d, J=16.0 Hz), 6.96 (1H, d, J=7.6 Hz), 7.16-7.22 (2H, m), 7.36-7.48 (5H, m), 8.07 (1H, d, J=16.0 Hz).

F) ethyl 3-(3-hydroxy-2-methylphenyl)propanoate

To a solution of ethyl 3-(3-(benzyloxy)-2-methylphenyl)acrylate (5.00 g) in methanol (100 mL) was added 10% palladium-activated carbon (500 mg), and the mixture was stirred for 15 hr under a hydrogen atmosphere. The reaction mixture was filtered, and the filtrate was concentrated under reduced pressure. The residue was purified by silica gel column chromatography (ethyl acetate/hexane) to give the title compound (2.50 g) as a yellow oil.
MS (ESI+): [M+H]$^+$ 209.1

G) ethyl 3-(3-((6-(2,2-dimethylpropyl)-5-(2-fluoro-5-methoxyphenyl)pyridin-2-yl)methoxy)-2-methylphenyl)propanoate To a solution of 6-(chloromethyl)-2-(2,2-dimethylpropyl)-3-(2-fluoro-5-methoxyphenyl)pyridine (300 mg) in acetonitrile (20 mL) were added ethyl 3-(3-hydroxy-2-methylphenyl)propanoate (197 mg) and cesium carbonate (511 mg), and the mixture was heated under reflux for 15 hr. Ethyl acetate was added to the reaction mixture, and the insoluble material was filtered off. The solvent in the filtrate was evaporated under reduced pressure, and the residue was purified by silica gel column chromatography (ethyl acetate/hexane) to give the title compound (400 mg) as a yellow solid.
MS (ESI+): [M+H]$^+$ 494.1

H) 3-(3-((6-(2,2-dimethylpropyl)-5-(2-fluoro-5-methoxyphenyl)pyridin-2-yl)methoxy)-2-methylphenyl)propanoic acid To a solution of ethyl 3-(3-((6-(2,2-dimethylpropyl)-5-(2-fluoro-5-methoxyphenyl)pyridin-2-yl)methoxy)-2-methylphenyl)propanoate (400 mg) in methanol (5.0 mL) and THF (10 ml) was added a solution of sodium hydroxide (336 mg) in water (10 mL), and the mixture was stirred at room temperature for 15 hr. 1N Hydrochloric acid was added to the reaction mixture to adjust to pH<4, and the mixture was extracted with ethyl acetate. The extract was washed with saturated brine, and dried over anhydrous sodium sulfate. The solvent was evaporated under reduced pressure to give the title compound (210 mg) as a yellow solid.
MS (ESI+): [M+H]$^+$ 466.2
$^1$H NMR (400 MHz, CDCl$_3$) δ 0.82 (9H, s), 2.35 (3H, s), 2.68 (2H, t, J=8.0 Hz), 2.70-2.95 (2H, m), 3.03 (2H, t, J=8.0 Hz), 3.83 (3H, s), 5.26 (2H, s), 6.77-6.80 (1H, m), 6.84-6.93 (3H, m), 7.07-7.14 (2H, m), 7.49 (1H, d, J=7.2 Hz), 7.58 (1H, d, J=7.2 Hz).

Example 21

3-(3-((6-(2,2-dimethylpropyl)-5-(2-fluoro-5-methoxyphenyl)pyridin-2-yl)methoxy)-2-methoxyphenyl)propanoic acid

A) 5-(3-hydroxy-2-methoxybenzylidene)-2,2-dimethyl-1,3-dioxane-4,6-dione

To a solution of titanium (IV) chloride (11.1 g) in THF (50 mL) was added dropwise under ice-cooling a solution of 2,2-dimethyl-1,3-dioxane-4,6-dione (4.26 g) and 3-hydroxy-2-methoxybenzaldehyde (3.0 g) in THF (50 mL) at 0° C., and then a solution of pyridine (4.00 g) in THF (20 mL) was added dropwise. The reaction mixture was stirred at 0° C. for 1 hr, and water was added. The mixture was extracted with ethyl acetate, and the extract was washed with 1N hydrochloric acid and saturated brine, and dried over anhydrous sodium sulfate, and the solvent was evaporated under reduced pressure. The residue was purified by silica gel column chromatography (ethyl acetate/hexane) to give the title compound (3.50 g) as a yellow solid. This compound was used for the next step without further purification.

B) 5-(3-hydroxy-2-methoxybenzyl)-2,2-dimethyl-1,3-dioxane-4,6-dione

To a solution of 5-(3-hydroxy-2-methoxybenzylidene)-2,2-dimethyl-1,3-dioxane-4,6-dione (entire amount) in methanol (100 mL) was added 10% palladium-activated carbon (62 mg), and the mixture was stirred for 1.5 hr under a hydrogen atmosphere.

The reaction mixture was filtered, and the filtrate was concentrated under reduced pressure to give the title compound (510 mg) as a pale-yellow oil. This compound was used for the next step without further purification.
MS (ESI+): [M+H]$^+$ 281.0

C) 3-(3-hydroxy-2-methoxyphenyl)propanoic acid

To a solution of 5-(3-hydroxy-2-methoxybenzyl)-2,2-dimethyl-1,3-dioxane-4,6-dione (100 mg) in DMF (10 mL) was added water (1.0 mL), and the mixture was stirred at 90° C. for 15 hr. The reaction mixture was cooled to room temperature, and ethyl acetate was added. The mixture was washed with 1N hydrochloric acid and saturated brine, and dried over anhydrous sodium sulfate. The solvent was evaporated under reduced pressure to give the title compound (50 mg) as a yellow oil. This compound was used for the next step without further purification.
MS (ESI+): [M+H]$^+$ 179.0

D) methyl 3-(3-hydroxy-2-methoxyphenyl)propanoate

To a solution of 3-(3-hydroxy-2-methoxyphenyl)propanoic acid (50 mg) in methanol (10 mL) was added dropwise thionyl chloride (2.0 mL) at 0° C. The reaction mixture was heated under reflux for 3 hr. The reaction mixture was concentrated, and ethyl acetate was added. The reaction mixture was washed with saturated brine, and dried over anhydrous sodium sulfate. The solvent was evaporated under reduced pressure to give the title compound (45 mg) as a yellow oil. This compound was used for the next step without further purification.
MS (ESI+): [M+H]$^+$ 211.1

E) ethyl 3-(3-((6-(2,2-dimethylpropyl)-5-(2-fluoro-5-methoxyphenyl)pyridin-2-yl)methoxy)-2-methoxyphenyl)propanoate To a solution of 6-(chloromethyl)-2-(2,2-dimethylpropyl)-3-(2-fluoro-5-methoxyphenyl)pyridine (300 mg) in acetonitrile (10 mL) were added methyl 3-(3-hydroxy-2-methoxyphenyl)propanoate (210 mg) and cesium carbonate (512 mg), and the mixture was heated under reflux for 15 hr. Ethyl acetate was added to the reaction mixture, and the insoluble material was filtered off. The solvent in the filtrate was evaporated under reduced pressure. The residue was purified by silica gel column chromatography (ethyl acetate/hexane) to give the title compound (450 mg) as a colorless oil.
MS (ESI+): [M+H]$^+$ 496.1

F) 3-(3-((6-(2,2-dimethylpropyl)-5-(2-fluoro-5-methoxyphenyl)pyridin-2-yl)methoxy)-2-methoxyphenyl) propanoic acid To a solution of ethyl 3-(3-((6-(2,2-dimethylpropyl)-5-(2-fluoro-5-methoxyphenyl)pyridin-2-yl)methoxy)-2-methoxyphenyl)propanoate (450 mg) in methanol (4.0 mL) and THF (8.0 mL) was added 1N aqueous sodium hydroxide solution (8.0 mL), and the mixture was stirred at room temperature 15 hr. The reaction mixture was concentrated under reduced pressure, and 1N hydrochloric acid was added to the residue to adjust to pH<4. The reaction mixture was extracted with ethyl acetate, and the extract was washed with saturated brine, and dried over anhydrous sodium sulfate. The solvent was evaporated under reduced pressure to give the title compound (275 mg) as a white solid.
MS (ESI+): [M+H]$^+$ 482.2
$^1$H NMR (400 MHz, DMSO-d$_6$) δ 0.75 (9H, s), 2.49 (2H, t, J=7.6 Hz), 2.60-2.75 (2H, m), 2.82 (2H, t, J=7.6 Hz), 3.76 (3H, s), 3.83 (3H, s), 5.23 (2H, s), 6.80-6.83 (1H, m), 6.89-7.03 (4H, m), 7.25 (1H, t, J=8.8 Hz), 7.49 (1H, d, J=8.0 Hz), 7.68 (1H, d, J=8.0 Hz), 12.15 (1H, s).

Example 22

3-(3-((6-(2,2-dimethylpropyl)-5-(2-fluoro-5-methoxyphenyl)pyridin-2-yl)methoxy)-2-fluorophenyl)propanoic acid A) ethyl (2-fluoro-3-methoxyphenyl)acrylate To a solution of 2-fluoro-3-methoxybenzaldehyde (2.00 g) in toluene (50 mL) was added ethyl (triphenylphosphoranylidene)acetate (4.50 g), and the mixture was stirred at 110° C. for 4 hr. The reaction mixture was concentrated, and the residue was purified by silica gel column chromatography (ethyl acetate/hexane) to give the title compound (2.50 g) as a colorless oil.
MS (ESI+): [M+H]$^+$ 225.1

B) ethyl 3-(2-fluoro-3-methoxyphenyl)propanoate

To a solution of ethyl (2-fluoro-3-methoxyphenyl)acrylate (2.50 g) in methanol (50 mL) was added 10% palladium-activated carbon (200 mg), and the mixture was stirred for 15 hr under a hydrogen atmosphere. The reaction mixture was filtered, and the filtrate was concentrated under reduced pressure to give the title compound (2.50 g) as a colorless oil. This compound was used for the next step without further purification.
MS (ESI+): [M+H]$^+$ 227.1

C) ethyl 3-(2-fluoro-3-hydroxyphenyl)propanoate

To a solution of ethyl 3-(2-fluoro-3-methoxyphenyl)propanoate (2.50 g) in dichloromethane (50 mL) was added a 3.0 M solution of boron tribromide in dichloromethane (11 mL) at 0° C., and the mixture was stirred at room temperature for 15 hr. Ice water (100 mL) was added to the reaction mixture, and the mixture was extracted with ethyl acetate. The extract was washed with saturated brine, and dried over anhydrous sodium sulfate. The solvent was evaporated under reduced D) ethyl 3-(3-((6-(2,2-dimethylpropyl)-5-(2-fluoro-5-methoxyphenyl)pyridin-2-yl)methoxy)-2-fluorophenyl)propanoate To a solution of 6-(chloromethyl)-2-(2,2-dimethylpropyl)-3-(2-fluoro-5-methoxyphenyl)pyridine (321 mg) in acetonitrile (10 mL) were added ethyl 3-(2-fluoro-3-hydroxyphenyl)propanoate (430 mg) and cesium carbonate (980 mg), and the mixture was heated under reflux for 15 hr. Ethyl acetate was added to the reaction mixture, and the insoluble material was filtered off. The solvent in the filtrate was evaporated under reduced pressure. The residue was purified by silica gel column chromatography (ethyl acetate/hexane) to give the title compound (350 mg) as a white solid.
MS (ESI+): [M+H]+ 498.2

E) 3-(3-((6-(2,2-dimethylpropyl)-5-(2-fluoro-5-methoxyphenyl)pyridin-2-yl)methoxy)-2-fluorophenyl)propanoic acid To a solution of ethyl 3-(3-((6-(2,2-dimethylpropyl)-5-(2-fluoro-5-methoxyphenyl)pyridin-2-yl)methoxy)-2-fluorophenyl)propanoate (400 mg) in methanol (4.0 mL) was added 1N aqueous sodium hydroxide solution (4.0 mL), and the mixture was stirred at room temperature for 15 hr. 1N Hydrochloric acid was added to the reaction mixture to adjust to pH<4, and the mixture was extracted with ethyl acetate. The extract was washed with saturated brine, and dried over anhydrous sodium sulfate. The solvent was evaporated under reduced pressure to give the title compound (170 mg) as a white solid.
$^1$H NMR (400 MHz, DMSO-$d_6$) δ 0.74 (9H, s), 2.49-2.51 (2H, m), 2.52-2.57 (2H, m), 2.82-2.87 (2H, m), 3.76 (3H, s), 5.27 (2H, s), 6.87-6.91 (2H, m), 6.99-7.03 (2H, m), 7.11 (1H, t, J=7.6 Hz), 7.24 (1H, t, J=8.8 Hz), 7.44 (1H, d, J=8.0 Hz), 7.67 (1H, d, J=8.0 Hz), 12.21 (1H, brs).
MS (ESI+): [M+H]+ 470.0

Example 23

Sodium 3-(3-((6-(2,2-dimethylpropyl)-5-(2-fluoro-5-methoxyphenyl)pyridin-2-yl)methoxy)-5-methylphenyl)propanoate A) (3-methoxy-5-methylphenyl)methanol To a solution of 1-(bromomethyl)-3-methoxy-5-methylbenzene (2.14 g) in acetone (80 mL) were added sodium hydrogen carbonate (1.05 g) and water (50 mL), and the mixture was heated under reflux for 18 hr. The reaction mixture was extracted with ethyl acetate, and the extract was washed with saturated brine. The organic layer was dried over anhydrous sodium sulfate, and the solvent was evaporated under reduced pressure. The residue was purified by silica gel column chromatography (ethyl acetate/hexane) to give the title compound (1.22 g) as a yellow oil.
$^1$H NMR (400 MHz, CDCl$_3$) δ 2.35 (3H, s), 3.82 (3H, s), 4.64 (2H, s), 6.68 (1H, s), 6.75 (1H, s), 6.79 (1H, s).

B) 3-methoxy-5-methylbenzaldehyde

To a solution of (3-methoxy-5-methylphenyl)methanol (2.20 g) in DMSO (15 mL) was added 2-iodoxybenzoic acid (4.00 g), and the mixture was stirred at room temperature for 2 hr. Ethyl acetate (50 ml) and water (10 mL) were added to the reaction mixture, and the insoluble material was filtered off. The filtrate was washed with saturated brine, and dried over anhydrous sodium sulfate. The solvent was evaporated under reduced pressure to give the title compound (2.00 g) as a yellow oil. This compound was used for the next step without further purification.

C) ethyl 3-(3-methoxy-5-methylphenyl)acrylate

To a solution of 3-methoxy-5-methylbenzaldehyde (entire amount) obtained in Example 23, step C, in toluene (30 mL) was added ethyl (triphenylphosphoranylidene)acetate (4.60 g), and the mixture was stirred at 70° C. for 15 hr. The reaction mixture was concentrated, and diethyl ether (50 mL) was added. The insoluble material was filtered off, and the filtrate was concentrated under reduced pressure. The residue was purified by silica gel column chromatography (ethyl acetate/hexane) to give the title compound (2.00 g) as a yellow oil.
MS (ESI+): [M+H]+ 221.0

D) ethyl 3-(3-methoxy-5-methylphenyl)propanoate

To a solution of ethyl 3-(3-methoxy-5-methylphenyl)acrylate (2.00 g) in methanol (50 mL) was added 10% palladium-activated carbon (300 mg), and the mixture was stirred for 15 hr under a hydrogen atmosphere. The reaction mixture was filtered, and the filtrate was concentrated under reduced pressure. The residue was purified by silica gel column chromatography (ethyl acetate/hexane) to give the title compound (2.00 g) as a yellow oil.
MS (ESI+): [M+H]+ 223.1

E) ethyl 3-(3-hydroxy-5-methylphenyl)propanoate

To a solution of ethyl 3-(3-methoxy-5-methylphenyl)propanoate (2.00 g) in dichloromethane (30 mL) was added a 1.0 M solution (13.5 mL) of boron tribromide in dichloromethane at −5° C., and the mixture was stirred at −5° C. for 2 hr. Water (20 mL) was added dropwise to the reaction mixture over 30 min, and the mixture was extracted with dichloromethane. The extract was washed with saturated brine, and dried over anhydrous sodium sulfate. The solvent was evaporated under reduced pressure, and the residue was purified by silica gel column chromatography (ethyl acetate/hexane) to give the title compound (1.00 g) as a yellow oil.
MS (ESI+): [M+H]+ 209.2

F) ethyl 3-(3-((6-(2,2-dimethylpropyl)-5-(2-fluoro-5-methoxyphenyl)pyridin-2-yl)methoxy)-5-methylphenyl)propanoate To a solution of 6-(chloromethyl)-2-(2,2-dimethylpropyl)-3-(2-fluoro-5-methoxyphenyl)pyridine (320 mg) in acetonitrile (10 mL) were added ethyl 3-(3-hydroxy-5-methylphenyl)propanoate (260 mg) and cesium carbonate (546 mg), and the mixture was heated under reflux for 15 hr. The reaction mixture was concentrated, and water was added to the residue. The reaction mixture was extracted with ethyl acetate, and the extract was washed with saturated brine, and dried over anhydrous sodium sulfate, and the solvent was evaporated under reduced pressure. The residue was purified by silica gel column chromatography (ethyl acetate/hexane) to give the title compound (400 mg) as a colorless oil.

MS (ESI+): [M+H]+ 494.1

G) 3-(3-((6-(2,2-dimethylpropyl)-5-(2-fluoro-5-methoxyphenyl)pyridin-2-yl)methoxy)-5-methylphenyl)propanoic acid To a solution of ethyl 3-(3-((6-(2,2-dimethylpropyl)-5-(2-fluoro-5-methoxyphenyl)pyridin-2-yl)methoxy)-5-methylphenyl)propanoate (400 mg) in methanol (4.0 ml) and THF (8.0 mL) was added 1N aqueous sodium hydroxide solution (8.0 mL), and the mixture was stirred at room temperature for 15 hr. The reaction mixture was concentrated under reduced pressure, and 1N hydrochloric acid was added to the residue to adjust to pH<4. The reaction mixture was extracted with ethyl acetate, and the extract was washed with saturated brine. The organic layer was dried over anhydrous sodium sulfate. The solvent was evaporated under reduced pressure to give the title compound (249 mg) as a pale-yellow oil.
MS (ESI+): [M+H]+ 465.9

H) sodium 3-(3-((6-(2,2-dimethylpropyl)-5-(2-fluoro-5-methoxyphenyl)pyridin-2-yl)methoxy)-5-methylphenyl)propanoate To a solution of 3-(3-((6-(2,2-dimethylpropyl)-5-(2-fluoro-5-methoxyphenyl)pyridin-2-yl)methoxy)-5-methylphenyl)propanoic acid (259 mg) in methanol (5.0 mL) was added sodium methoxide (29 mg) at room temperature, and the mixture was stirred for 1 hr. The reaction mixture was concentrated under reduced pressure. The residue was washed with hexane, and dried to give the title compound (147 mg) as a white solid.
MS (ESI+): [M+H]+ 464.1
$^1$H NMR (400 MHz, MeOD-d$_4$) δ 0.79 (9H, s), 2.28 (3H, s), 2.48 (2H, t, J=8.0 Hz), 2.77-2.80 (2H, m), 2.85 (2H, t, J=8.0% Hz), 3.82 (3H, s), 5.20 (2H, s), 6.66-6.73 (3H, m), 6.85-6.87 (1H, m), 6.97-7.01 (1H, m), 7.13 (1H, t, J=9.2 Hz), 7.49 (1H, d, J=8.0 Hz), 7.65 (1H, d, J=8.0 Hz).

Example 24

3-(6-((6-(2,2-dimethylpropyl)-5-(2-fluoro-5-methoxyphenyl)pyridin-2-yl)methoxy)-2-methylpyrimidin-4-yl)propanoic acid A) methyl 3-(6-chloro-2-methylpyrimidin-4-yl)acrylate To a solution of 4,6-dichloro-2-methylpyrimidine (2.45 g) and methyl acrylate (3.87 g) in DMF (20 mL) were added tris(dibenzylideneacetone)dipalladium (680 mg), N-ethyldiisopropylamine (3.90 g) and tetrabutylammonium chloride (82 mg) under a nitrogen atmosphere, and the mixture was stirred at 90° C. for 15 hr. Water was added to the reaction mixture, and the mixture was extracted with ethyl acetate. The organic layer was washed with saturated brine, and dried over anhydrous sodium sulfate. The residue was purified by silica gel column chromatography (ethyl acetate/hexane) to give the title compound (1.20 g) as a white solid.
MS (ESI+): [M+H]+ 212.9

B) 3-(6-((6-(2,2-dimethylpropyl)-5-(2-fluoro-5-methoxyphenyl)pyridin-2-yl)methoxy)-2-methylpyrimidin-4-yl)acrylic acid To a solution of (6-(2,2-dimethylpropyl)-5-(2-fluoro-5-methoxyphenyl)pyridin-2-yl)methanol (606 mg) and methyl 3-(6-chloro-2-methylpyrimidin-4-yl)acrylate (424 mg) in THF (10 mL) was added 60% sodium hydride (120 mg) at 0° C., and the mixture was stirred at 50° C. for 2 hr. The reaction mixture was neutralized with 1N hydrochloric acid, and extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (450 mg) as a white solid.
MS (ESI+): [M+H]+ 465.9

C) 3-(6-((6-(2,2-dimethylpropyl)-5-(2-fluoro-5-methoxyphenyl)pyridin-2-yl)methoxy)-2-methylpyrimidin-4-yl)propanoic acid To a solution of 3-(6-((6-(2,2-dimethylpropyl)-5-(2-fluoro-5-methoxyphenyl)pyridin-2-yl)methoxy)-2-methylpyrimidin-4-yl)acrylic acid (330 mg) in THF (5.0 mL) and ethyl acetate (5.0 mL) was added 10% palladium-activated carbon (30 mg), and the mixture was stirred under a hydrogen atmosphere at room temperature for 2 hr. The reaction mixture was filtered, and the filtrate was concentrated under reduced pressure. The residue was purified by preparative HPLC to give the title compound (153 mg) as a white solid.
MS (ESI+): [M+H]+ 468.2
$^1$H NMR (400 MHz, DMSO-d$_6$) δ 0.71 (9H, s), 2.45 (3H, s), 2.57-2.61 (4H, m), 2.83 (2H, t, J=7.2 Hz), 3.76 (3H, s), 5.49 (2H, s), 6.72 (1H, s), 6.87-6.90 (1H, m), 6.98-7.02 (1H, m), 7.24 (1H, t, J=8.8 Hz), 7.37 (1H, d, J=8.0 Hz), 7.63 (1H, d, J=8.0 Hz).

Example 25

3-(6-((6-(2,2-dimethylpropyl)-5-(2-fluoro-5-methoxyphenyl)pyridin-2-yl)methoxy)-2-methoxypyrimidin-4-yl)propanoic acid A) methyl 3-(6-chloro-2-methoxypyrimidin-4-yl)acrylate To a solution of 4,6-dichloro-2-methoxypyrimidine (780 mg) in DMF (10 mL) were added methyl acrylate (760 mg), tris(dibenzylideneacetone)dipalladium (200 mg), N-ethyldiisopropylamine (1.14 g) and tetrabutylammonium chloride (61 mg), and the mixture was stirred at 90° C. for 15 hr. Water was added to the reaction mixture, and the mixture was extracted with ethyl acetate. The organic layer was washed with saturated brine, and dried over anhydrous sodium sulfate. The residue was purified by silica gel column chromatography (ethyl acetate/hexane) to give the title compound (330 mg) as a white solid.
MS (ESI+): [M+H]+ 229.0

B) 3-(6-((6-(2,2-dimethylpropyl)-5-(2-fluoro-5-methoxyphenyl)pyridin-2-yl)methoxy)-2-methoxypyrimidin-4-yl)acrylic acid To a solution of (6-(2,2-dimethylpropyl)-5-(2-fluoro-5-methoxyphenyl)pyridin-2-yl)methanol (480 mg) and methyl 3-(6-chloro-2-methoxypyrimidin-4-yl)acrylate (360 mg) in THF (8.0 mL) was added 60% sodium hydride (128 mg) at 0° C., and the mixture was stirred at 50° C. for 2 hr. 1N Hydrochloric acid was added to the reaction mixture, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (520 mg) as a white solid.

MS (ESI+): [M+H]$^+$ 482.0

C) 3-(6-((6-(2,2-dimethylpropyl)-5-(2-fluoro-5-methoxyphenyl)pyridin-2-yl)methoxy)-2-methoxypyrimidin-4-yl)propanoic acid To a solution of 3-(6-((6-(2,2-dimethylpropyl)-5-(2-fluoro-5-methoxyphenyl)pyridin-2-yl)methoxy)-2-methoxypyrimidin-4-yl)acrylic acid (530 mg) in THF (5.0 ml) and ethyl acetate (5.0 mL) was added 10% palladium-activated carbon (53 mg) and, under a hydrogen atmosphere, the mixture was stirred at room temperature for 2 hr. The reaction mixture was filtered, and the filtrate was concentrated under reduced pressure. The residue was purified by preparative HPLC to give the title compound (135 mg) as a white solid.

MS (ESI+): [M+H]$^+$ 484.0

$^1$H NMR (400 MHz, DMSO-d$_6$) δ 0.70 (9H, s), 2.61-2.65 (4H, m), 2.84 (2H, t, J=7.2 Hz), 3.76 (3H, s), 3.82 (3H, s), 5.49 (2H, s), 6.57 (1H, s), 6.87-6.89 (1H, m), 6.98-7.02 (1H, m), 7.24 (1H, t, J=9.2 Hz), 7.35 (1H, d, J=7.6 Hz), 7.63 (1H, d, J=8.0 Hz).

Example 26

3-(6-((6-(2,2-dimethylpropyl)-5-(2-fluoro-5-methoxyphenyl)pyridin-2-yl)methoxy)-5-methylpyrimidin-4-yl)propanoic acid A) 4-chloro-6-((6-(2,2-dimethylpropyl)-5-(2-fluoro-5-methoxyphenyl)pyridin-2-yl)methoxy)-5-methylpyrimidine To a solution of 4,6-dichloro-5-methylpyrimidine (160 mg) and (6-(2,2-dimethylpropyl)-5-(2-fluoro-5-methoxyphenyl)pyridin-2-yl)methanol (300 mg) in THF (8.0 mL) was added 60% sodium hydride (60 mg) at 0° C., and the mixture was stirred at 50° C. for 2 hr. The reaction mixture was neutralized with 1N hydrochloric acid, and extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (340 mg) as a white solid.

MS (ESI+): [M+H]$^+$ 429.9

B) ethyl (2E)-3-(6-((6-(2,2-dimethylpropyl)-5-(2-fluoro-5-methoxyphenyl)pyridin-2-yl)methoxy)-5-methylpyrimidin-4-yl)acrylate To a solution of 4-chloro-6-((6-(2,2-dimethylpropyl)-5-(2-fluoro-5-methoxyphenyl)pyridin-2-yl)methoxy)-5-methylpyrimidine (200 mg) in DMF (5.0 mL) were added ethyl 3-(4,4,5,5-tetramethyl-1,3,2-dioxaborolan-2-yl)acrylate (212 mg), tris(dibenzylideneacetone)dipalladium (50 mg), cesium carbonate (230 mg) and dicyclohexyl(2',6'-dimethoxy-[1,1'-biphenyl]-2-yl)phosphine (45 mg), and the mixture was stirred at 90° C. for 6 hr. Water was added to the reaction mixture, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (180 mg) as a white solid.

MS (ESI+): [M+H]$^+$ 494.2

C) ethyl 3-(6-((6-(2,2-dimethylpropyl)-5-(2-fluoro-5-methoxyphenyl)pyridin-2-yl)methoxy)-5-methylpyrimidin-4-yl)propanoate To a solution of ethyl (2E)-3-(6-((6-(2,2-dimethylpropyl)-5-(2-fluoro-5-methoxyphenyl)pyridin-2-yl)methoxy)-5-methylpyrimidin-4-yl)acrylate (180 mg) in THF (2.0 ml) and ethyl acetate (2.0 mL) was added 10% palladium-activated carbon (18 mg), and the mixture was stirred for 2 hr under a hydrogen atmosphere. The reaction mixture was filtered, and the filtrate was concentrated under reduced pressure to give the title compound (180 mg) as a pale-yellow solid. This compound was used for the next step without further purification.

MS (ESI+): [M+H]$^+$ 495.9

D) 3-(6-((6-(2,2-dimethylpropyl)-5-(2-fluoro-5-methoxyphenyl)pyridin-2-yl)methoxy)-5-methylpyrimidin-4-yl)propanoic acid To a solution of ethyl 3-(6-((6-(2,2-dimethylpropyl)-5-(2-fluoro-5-methoxyphenyl)pyridin-2-yl)methoxy)-5-methylpyrimidin-4-yl)propanoate (180 mg) in methanol (2.0 mL) and THF (2.0 mL) were added water (2.0 mL) and lithium hydroxide monohydrate (75 mg), and the mixture was stirred at room temperature for 2 hr. Water was added to the reaction mixture, and the mixture was extracted with ethyl acetate. The extract was washed with saturated brine, and dried over anhydrous sodium sulfate. The solvent was evaporated under reduced pressure, and the residue was purified by preparative HPLC to give the title compound (88 mg) as a white solid.

MS (ESI+): [M+H]$^+$ 468.0

$^1$H NMR (400 MHz, DMSO-d$_6$) δ 0.70 (9H, s), 2.20 (3H, s), 2.62-2.67 (4H, m), 2.90-2.93 (2H, m), 3.75 (3H, s), 5.53 (2H, s), 6.87-6.89 (1H, m), 6.98-7.01 (1H, m), 7.21-7.26 (1H, m), 7.35-7.38 (1H, m), 7.62-7.64 (1H, m), 8.52 (1H, s).

Example 27

3-(6-((6-(2,2-dimethylpropyl)-5-(2-fluoro-5-methoxyphenyl)pyridin-2-yl)methoxy)-5-methoxypyrimidin-4-yl)propanoic acid A) 4-chloro-6-((6-(2,2-dimethylpropyl)-5-(2-fluoro-5-methoxyphenyl)pyridin-2-yl)methoxy)-5-methoxypyrimidine To a solution of 4,6-dichloro-5-methoxypyrimidine (450 mg) and (6-(2,2-dimethylpropyl)-5-(2-fluoro-5-methoxyphenyl)pyridin-2-yl)methanol (760 mg) in THF (8.0 mL) was added 60% sodium hydride (200 mg) at 0° C., and the mixture was stirred at 50° C. for 2 hr. The reaction mixture was neutralized with 1N hydrochloric acid, and extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (1.05 g) as a white solid.

MS (ESI+): [M+H]$^+$ 445.9

B) ethyl (2E)-3-(6-((6-(2,2-dimethylpropyl)-5-(2-fluoro-5-methoxyphenyl)pyridin-2-yl)methoxy)-5-methoxypyrimidin-4-yl)acrylate To a solution of 4-chloro-6-((6-(2,2-dimethylpropyl)-5-(2-fluoro-5-methoxyphenyl)pyridin-2-yl)methoxy)-5-methoxypyrimidine (1.20 g) in DMF (10 mL) were added ethyl 3-(4,4,5,5-tetramethyl-1,3,2-dioxaborolan-2-yl)acrylate (1.22 g), tris(dibenzylideneacetone)dipalladium (310 mg), cesium carbonate (1.30 g) and dicyclohexyl(2',6'-dimethoxy-[1,1'-biphenyl]-2-yl)phosphine (257 mg), and the mixture was stirred at 90° C. for 6 hr. Water was added to the reaction mixture, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (1.09 g) as a white solid.

MS (ESI+): [M+H]$^+$ 510.0

C) ethyl 3-(6-((6-(2,2-dimethylpropyl)-5-(2-fluoro-5-methoxyphenyl)pyridin-2-yl)methoxy)-5-methoxypyrimidin-4-yl)propanoate To a solution of ethyl (2E)-3-(6-((6-(2,2-dimethylpropyl)-5-(2-fluoro-5-methoxyphenyl)pyridin-2-yl)methoxy)-5-methoxypyrimidin-4-yl)acrylate (1.13 g) in THF (10 mL) and ethyl acetate (10 mL) was added 10% palladium-activated carbon (113 mg) and, under a hydrogen atmosphere, the mixture was stirred at room temperature for 2 hr. The reaction mixture was filtered, and the filtrate was concentrated under reduced pressure to give the title compound (1.13 g) as a pale-yellow solid. This compound was used for the next step without further purification.

MS (ESI+): [M+H]$^+$ 512.1

D) 3-(6-((6-(2,2-dimethylpropyl)-5-(2-fluoro-5-methoxyphenyl)pyridin-2-yl)methoxy)-5-methoxypyrimidin-4-yl)propanoic acid To a solution of ethyl 3-(6-((6-(2,2-dimethylpropyl)-5-(2-fluoro-5-methoxyphenyl)pyridin-2-yl)methoxy)-5-methoxypyrimidin-4-yl)propanoate (1.13 g) in methanol (5.0 mL) and THF (10 mL) were added water (5.0 mL) and lithium hydroxide monohydrate (450 mg), and the mixture was stirred at room temperature for 2 hr. Water was added to the reaction mixture, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (330 mg) as a pale-yellow solid.

MS (ESI+): [M+H]$^+$ 484.0
$^1$H NMR (400 MHz, DMSO-d$_6$) δ 0.68 (9H, s), 2.62-2.69 (4H, m), 2.97 (2H, t, J=7.2 Hz), 3.76 (3H, s), 3.89 (3H, s), 5.60 (2H, s), 6.88-6.90 (1H, m), 6.99-7.03 (1H, m), 7.24 (1H, t, J=9.2 Hz), 7.39 (1H, d, J=8.0 Hz), 7.65 (1H, d, J=8.0 Hz), 8.41 (1H, s), 12.15 (1H, brs).

Example 28

3-(6-((6-(2,2-dimethylpropyl)-5-(2-fluoro-5-methoxyphenyl)pyridin-2-yl)methoxy)-5-fluoropyrimidin-4-yl)propanoic acid A) 4-chloro-6-((6-(2,2-dimethylpropyl)-5-(2-fluoro-5-methoxyphenyl)pyridin-2-yl)methoxy)-5-fluoropyrimidine To a solution of 4,6-dichloro-5-methoxypyrimidine (420 mg) and (6-(2,2-dimethylpropyl)-5-(2-fluoro-5-methoxyphenyl)pyridin-2-yl)methanol (760 mg) in THF (10 mL) was added 60% sodium hydride (200 mg) at 0° C., and the mixture was stirred at 50° C. for 2 hr. The reaction mixture was neutralized with 1N hydrochloric acid, and extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (1.00 g) as a white solid.

MS (ESI+): [M+H]$^+$ 433.8

B) ethyl (2E)-3-(6-((6-(2,2-dimethylpropyl)-5-(2-fluoro-5-methoxyphenyl)pyridin-2-yl)methoxy)-5-fluoropyrimidin-4-yl)acrylate To a solution of 4-chloro-6-((6-(2,2-dimethylpropyl)-5-(2-fluoro-5-methoxyphenyl)pyridin-2-yl)methoxy)-5-fluoropyrimidine (930 mg) in DMF (10 mL) were added ethyl 3-(4,4,5,5-tetramethyl-1,3,2-dioxaborolan-2-yl)acrylate (970 mg), tris(dibenzylideneacetone)dipalladium (250 mg), cesium carbonate (1.00 g) and dicyclohexyl(2',6'-dimethoxy-[1,1'-biphenyl]-2-yl)phosphine (205 mg), and the mixture was stirred at 90° C. for 6 hr. Water was added to the reaction mixture, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (285 mg) as a white solid.

MS (ESI+): [M+H]$^+$ 498.1

C) ethyl 3-(6-((6-(2,2-dimethylpropyl)-5-(2-fluoro-5-methoxyphenyl)pyridin-2-yl)methoxy)-5-fluoropyrimidin-4-yl)propanoate To a solution of ethyl (2E)-3-(6-((6-(2,2-dimethylpropyl)-5-(2-fluoro-5-methoxyphenyl)pyridin-2-yl)methoxy)-5-fluoropyrimidin-4-yl)acrylate (300 mg) in THF (2.0 mL) and ethyl acetate (2.0 mL) was added 10% palladium-activated carbon (30 mg) and, under a hydrogen atmosphere, the mixture was stirred at room temperature for 2 hr. The reaction mixture was filtered, and the filtrate was concentrated under reduced pressure to give the title compound (300 mg) as a pale-yellow solid.

MS (ESI+): [M+H]$^+$ 500.0

D) 3-(6-((6-(2,2-dimethylpropyl)-5-(2-fluoro-5-methoxyphenyl)pyridin-2-yl)methoxy)-5-fluoropyrimidin-4-yl)propanoic acid To a solution of ethyl 3-(6-((6-(2,2-dimethylpropyl)-5-(2-fluoro-5-methoxyphenyl)pyridin-2-yl)methoxy)-5-fluoropyrimidin-4-yl)propanoate (300 mg) in methanol (2.0 mL) and THF (4.0 mL) were added water (2.0 mL) and lithium hydroxide monohydrate (123 mg), and the mixture was stirred at room temperature for 2 hr. Water was added to the reaction mixture, and the mixture was extracted with ethyl acetate. The extract was washed with saturated brine, and dried over anhydrous sodium sulfate. The solvent was evaporated under reduced pressure, and the residue was purified by preparative HPLC to give the title compound (30 mg) as a pale-yellow solid.

MS (ESI+): [M+H]$^+$ 472.0
$^1$H NMR (400 MHz, DMSO-d$_6$) δ 0.68 (9H, s), 2.58-2.69 (4H, m), 2.93-2.97 (2H, m), 3.76 (3H, s), 5.63 (2H, s), 6.87-6.90 (1H, m), 6.99-7.02 (1H, m), 7.24 (1H, t, J=9.2 Hz), 7.39 (1H, d, J=8.0 Hz), 7.64 (1H, d, J=8.0 Hz), 8.47 (1H, s).

Example 29

3-(3-((6-(2,2-dimethylpropyl)-5-(2-fluoro-5-methoxyphenyl)pyridin-2-yl)methoxy)phenyl)propanoic acid

A) (E)-methyl 3-(3-hydroxyphenyl)acrylate

To a solution of (E)-3-(3-hydroxyphenyl)acrylic acid (15.0 g) in methanol (100 mL) was added sulfuric acid (2.0 mL), and the mixture was stirred at 70° C. for 15 hr. Water was added to the reaction mixture, and the mixture was extracted with ethyl acetate. The extract was washed with saturated brine, and dried over anhydrous magnesium sulfate. The solvent was evaporated under reduced pressure to give the title compound (15.8 g) as white crystals. This compound was used for the next step without further purification.

$^1$H NMR (300 MHz, CDCl$_3$) δ 3.81 (3H, s), 5.18 (1H, s), 6.41 (1H, d, J=16.2 Hz), 6.87 (1H, dd, J=7.9, 2.6 Hz), 6.96-7.04 (1H, m), 7.10 (1H, d, J=7.5 Hz), 7.21-7.30 (1H, m), 7.64 (1H, d, J=16.2 Hz).

B) methyl 3-(3-hydroxyphenyl)propanoate

To a solution of (E)-methyl 3-(3-hydroxyphenyl)acrylate (15.8 g) in methanol (150 mL) was added 10% palladium-activated carbon (1.50 g) and, under a hydrogen atmosphere, the mixture was stirred at room temperature for 5 hr. The reaction mixture was filtered to remove palladium carbon, and the filtrate was evaporated under reduced pressure to give the title compound (16.0 g) as a colorless oil. This compound was used for the next step without further purification.

$^1$H NMR (300 MHz, CDCl$_3$) δ 2.57-2.68 (2H, m), 2.83-2.95 (2H, m), 3.68 (3H, s), 6.63-6.72 (2H, m), 6.75 (1H, d, J=7.6 Hz), 7.04-7.19 (1H, m).

C) methyl 3-(3-((5-(2-fluoro-5-methoxyphenyl)-6-neopentylpyridin-2-yl)methoxy)phenyl)propanoate Under an argon atmosphere, to a solution of methyl 3-(3-hydroxyphenyl)propanoate (131 mg), (5-(2-fluoro-5-methoxyphenyl)-6-neopentylpyridin-2-yl)methanol (200 mg) and triphenylphosphine (259 mg) in THF (3.0 mL) was added a about 2.2 M solution of diethyl azodicarboxylate in toluene (450 µL), and the mixture was stirred for 30 min. The reaction mixture was concentrated under reduced pressure, and the residue was purified by silica gel column chromatography (ethyl acetate/hexane) to give the title compound (249 mg) as a colorless oil.

$^1$H NMR (300 MHz, CDCl$_3$) δ 0.80 (9H, s), 2.63 (2H, t, J=7.8 Hz), 2.93 (2H, t, J=7.8 Hz), 3.67 (3H, s), 3.80 (3H, s), 5.23 (2H, s), 6.75 (1H, dd, J=5.5, 3.2 Hz), 6.81 (1H, d, J=7.5 Hz), 6.84-6.91 (3H, m), 7.05 (1H, t, J=9.0 Hz), 7.21 (1H, t, J=8.1 Hz), 7.42 (1H, d, J=7.9 Hz), 7.52 (1H, d, J=7.8 Hz).

D) 3-(3-((6-(2,2-dimethylpropyl)-5-(2-fluoro-5-methoxyphenyl)pyridin-2-yl)methoxy)phenyl)propanoic acid To a solution of methyl 3-(3-((5-(2-fluoro-5-methoxyphenyl)-6-neopentylpyridin-2-yl)methoxy)phenyl)propanoate (240 mg) in methanol (2.0 mL) was added 1N aqueous sodium hydroxide solution (1.0 mL), and the mixture was stirred at room temperature for 1 hr. 1N Hydrochloric acid (1.0 mL) was added to the reaction mixture, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (181 mg) as white crystals.

MS (ESI+): [M+H]$^+$ 452.4

$^1$H NMR (300 MHz, DMSO-d$_6$) δ 0.76 (9H, s), 2.50 (2H, t, J=7.6 Hz), 2.79 (2H, t, J=7.6 Hz), 5.19 (2H, s), 6.82 (1H, d, J=7.4 Hz), 6.88 (2H, t, J=8.2 Hz), 6.93 (1H, s), 6.97-7.06 (1H, m), 7.14-7.28 (2H, m), 7.43 (1H, d, J=8.0 Hz), 7.65 (1H, d, J=7.9 Hz), 12.11 (1H, brs).

Example 30

3-cyclopropyl-3-(2-((6-(2,2-dimethylpropyl)-5-(2-fluoro-5-methoxyphenyl)pyridin-2-yl)methoxy)pyridin-4-yl)propanoic acid

A) methyl 2-methoxyisonicotinate

Under a nitrogen atmosphere, to a solution of 2-chloroisonicotinic acid (10.0 g) in DMF (150 mL) was added a 28% solution of sodium methoxide in methanol (38.6 mL), and the mixture was stirred at 130° C. for 14 hr. Iodomethane (15.9 mL) was added to the reaction mixture at 80° C., and the mixture was stirred at 80° C. for 5 min. Water was added at 0° C., and the mixture was extracted with ethyl acetate. The extract was washed with saturated aqueous sodium hydrogen carbonate solution, water and saturated brine, and dried over anhydrous magnesium sulfate. After silica gel filtration, the solvent was evaporated under reduced pressure to give a crude product of the title compound (8.57 g) as a pale-yellow oil. This compound was used for the next step without further purification.

$^1$H NMR (400 MHz, DMSO-d$_6$) δ 3.88 (3H, s), 3.90 (3H, s), 7.22 (1H, s), 7.41 (1H, d, J=5.1 Hz), 8.37 (1H, d, J=5.3 Hz).

B) (2-methoxypyridin-4-yl)methanol

To a suspension of lithium aluminum hydride (2.92 g) in diethyl ether (200 ml) and THF (50 mL) was added dropwise a solution of methyl 2-methoxyisonicotinate (8.57 g) in diethyl ether (50 mL) at 0° C., and the reaction mixture was stirred at 0° C. for 20 min. Water (3.0 mL), 4N aqueous sodium hydroxide solution (3.0 mL) and water (9.0 mL) were successively added to the reaction mixture at 0° C., and the mixture was stirred at room temperature for 15 min. The resulting white precipitate was filtered off, and the solvent in the filtrate was evaporated under reduced pressure to give a crude product of the title compound (6.74 g) as a pale-yellow oil. This compound was used for the next step without further purification.

$^1$H NMR (400 MHz, DMSO-d$_6$) δ 3.83 (3H, s), 4.48 (2H, d, J=5.5 Hz), 5.37 (1H, t, J=5.6 Hz), 6.73 (1H, s), 6.90 (1H, d, J=5.3 Hz), 8.07 (1H, d, J=5.1 Hz).

C) 2-methoxyisonicotinaldehyde

To a solution of (2-methoxypyridin-4-yl)methanol (6.74 g) and triethylamine (67.5 mL) in DMSO (200 mL) was added sulfur trioxide pyridine complex (30.8 g), and the mixture was stirred at room temperature for 30 min. Water was added to the reaction mixture at room temperature, and the mixture was extracted with ethyl acetate. The extract was washed with water and saturated brine, and dried over anhydrous magnesium sulfate. After silica gel filtration, the solvent was evaporated under reduced pressure to give a crude product of the title compound (4.33 g) as a brown oil. This compound was used for the next step without further purification.

$^1$H NMR (300 MHz, DMSO-$d_6$) δ 3.92 (3H, s), 7.24-7.32 (1H, m), 7.37 (1H, dd, J=5.1, 1.3 Hz), 8.42 (1H, d, J=5.2 Hz), 10.03 (1H, d, J=0.3 Hz).

D) cyclopropyl(2-methoxypyridin-4-yl)methanol

Under a nitrogen atmosphere, to a solution of 2-methoxy-isonicotinaldehyde (4.33 g) in THF (100 mL) was added 0.60 M cyclopropylmagnesium bromide (63.1 mL) at 0° C., and the mixture was stirred at 0° C. for 10 min. Saturated aqueous ammonium chloride solution was added to the reaction mixture at 0° C., and the mixture was extracted with ethyl acetate. The extract was washed with water and saturated brine, and dried over anhydrous magnesium sulfate. After silica gel filtration, the solvent was evaporated under reduced pressure to give a crude product of the title compound (5.30 g) as a brown oil. This compound was used for the next step without further purification.

$^1$H NMR (400 MHz, DMSO-$d_6$) δ 0.34-0.50 (4H, m), 0.90-1.04 (1H, m), 3.83 (3H, s), 3.95 (1H, dd, J=7.2, 4.6 Hz), 5.35 (1H, d, J=4.6 Hz), 6.77 (1H, s), 6.99 (1H, d, J=5.3 Hz), 8.07 (1H, d, J=5.3 Hz).

E) cyclopropyl(2-methoxypyridin-4-yl)methanone

To a solution of cyclopropyl(2-methoxypyridin-4-yl) methanol (5.30 g) and triethylamine (41.2 mL) in DMSO (120 mL) was added sulfur trioxide pyridine complex (18.8 g), and the mixture was stirred at room temperature for 30 min. Water was added to the reaction mixture at room temperature, and the mixture was extracted with ethyl acetate. The extract was washed with water and saturated brine, and dried over anhydrous magnesium sulfate. After silica gel filtration, the solvent was evaporated under reduced pressure to give a crude product of the title compound (4.42 g) as a brown oil. This compound was used for the next step without further purification.

$^1$H NMR (400 MHz, DMSO-$d_6$) δ 1.00-1.19 (4H, m), 2.82-2.95 (1H, m), 3.92 (3H, s), 7.34 (1H, s), 7.45 (1H, d, J=5.3 Hz), 8.37 (1H, d, J=5.3 Hz).

F) ethyl 3-cyclopropyl-3-(2-methoxypyridin-4-yl)acrylate

Under a nitrogen atmosphere, to a suspension of 60% sodium hydride (2.99 g) in THF (200 ml) was added ethyl diethylphosphonoacetate (29.7 mL) at 0° C., and the mixture was stirred at 0° C. for 5 min. To the obtained colorless solution was added cyclopropyl(2-methoxypyridin-4-yl) methanone (4.42 g) at 0° C., and the mixture was heated under reflux for 1 hr. Water was added to the reaction mixture at room temperature, and the mixture was extracted with ethyl acetate. The extract was washed with water and saturated brine, and dried over anhydrous magnesium sulfate. The solvent was evaporated under reduced pressure to give a crude product of the title compound. This compound was used for the next step without further purification.

G) ethyl 3-cyclopropyl-3-(2-methoxypyridin-4-yl)propanoate

To a solution of ethyl 3-cyclopropyl-3-(2-methoxypyridin-4-yl)acrylate in acetic acid (100 mL) was added a zinc powder (16.3 g), and the mixture was stirred at room temperature for 5 min. The reaction mixture was filtered, and the solvent in the filtrate was evaporated under reduced pressure. The residue was purified by silica gel column chromatography (NH, ethyl acetate/hexane) to give the title compound (4.17 g) as a pale-yellow oil.

$^1$H NMR (400 MHz, DMSO-$d_6$) δ 0.09-0.20 (1H, m), 0.20-0.29 (1H, m), 0.29-0.38 (1H, m), 0.44-0.57 (1H, m), 0.94-1.05 (1H, m), 1.08 (3H, t, J=7.1 Hz), 2.19-2.30 (1H, m), 2.75 (2H, d, J=7.5 Hz), 3.82 (3H, s), 3.90-4.02 (2H, m), 6.71 (1H, s), 6.92 (1H, d, J=5.1 Hz), 8.05 (1H, d, J=5.1 Hz).

H) ethyl 3-cyclopropyl-3-(2-hydroxypyridin-4-yl)propanoate

Under a nitrogen atmosphere, to a solution of ethyl 3-cyclopropyl-3-(2-methoxypyridin-4-yl)propanoate (4.17 g) in DMF (10 mL) was added pyridinium chloride (19.3 g), and the mixture was stirred at 130° C. for 15 min. Ethyl acetate was added to the reaction mixture at 0° C., and the resulting white precipitate was filtered off. The solvent in the filtrate was evaporated under reduced pressure, and the residue was purified by silica gel column chromatography (methanol/ethyl acetate) to give the title compound (3.61 g) as a yellow oil.

$^1$H NMR (300 MHz, DMSO-$d_6$) δ 0.10-0.28 (2H, m), 0.29-0.43 (1H, m), 0.43-0.58 (1H, m), 0.86-1.03 (1H, m), 1.11 (3H, t, J=7.1 Hz), 2.07 (1H, dt, J=9.7, 7.6 Hz), 2.68 (2H, d, J=7.5 Hz), 3.91-4.07 (2H, m), 6.19 (1H, s), 6.20-6.25 (1H, m), 7.30 (1H, d, J=6.7 Hz), 11.48 (1H, brs).

I) ethyl 3-cyclopropyl-3-(2-((5-(2-fluoro-5-methoxyphenyl)-6-neopentylpyridin-2-yl)methoxy)pyridin-4-yl)propanoate Under a nitrogen atmosphere, to a solution of 6-(bromomethyl)-3-(2-fluoro-5-methoxyphenyl)-2-neopentylpyridine (200 mg) in toluene (3.0 mL) were added ethyl 3-cyclopropyl-3-(2-hydroxypyridin-4-yl)propanoate (141 mg) and silver carbonate (166 mg), and the mixture was heated under reflux for 3 hr. The reaction mixture was cooled to room temperature, and filtered. The solvent in the filtrate was evaporated under reduced pressure, and the residue was purified by silica gel column chromatography (ethyl acetate/hexane) to give the title compound (218 mg) as a pale-yellow oil.

$^1$H NMR (400 MHz, DMSO-$d_6$) δ 0.12-0.22 (1H, m), 0.22-0.30 (1H, m), 0.30-0.40 (1H, m), 0.46-0.58 (1H, m), 0.73 (9H, s), 0.97-1.07 (1H, m), 1.09 (3H, t, J=7.1 Hz), 2.22-2.34 (1H, m), 2.64 (2H, brs), 2.77 (2H, d, J=7.5 Hz), 3.76 (3H, s), 3.92-4.02 (2H, m), 5.44 (2H, s), 6.84-6.92 (2H, m), 6.96 (1H, d, J=5.3 Hz), 6.98-7.04 (1H, m), 7.24 (1H, t, J=9.2 Hz), 7.35 (1H, d, J=8.0 Hz), 7.62 (1H, d, J=7.9 Hz), 8.04 (1H, d, J=5.1 Hz).

J) 3-cyclopropyl-3-(2-((6-(2,2-dimethylpropyl)-5-(2-fluoro-5-methoxyphenyl)pyridin-2-yl)methoxy)pyridin-4-yl)propanoic acid To a solution of ethyl 3-cyclopropyl-3-(2-((5-(2-fluoro-5-methoxyphenyl)-6-neopentylpyridin-2-yl)methoxy)pyridin-4-yl)propanoate (218 mg) in THF (3.0 mL) and methanol (1.5 mL) was added 1N aqueous sodium hydroxide solution (3.0 mL), and the mixture was stirred at room temperature for 1 hr. 1N Hydrochloric acid (3.0 mL) was added to the reaction mixture, and the mixture was extracted with ethyl acetate. The extract was washed with water and saturated brine, and dried over anhydrous magnesium sulfate. After silica gel filtration, the solvent was evaporated under reduced pressure to give the title compound (175 mg) as a white amorphous solid.

MS (ESI+): [M+H]$^+$ 493.2

$^1$H NMR (400 MHz, DMSO-d$_6$) δ 0.13-0.23 (1H, m), 0.24-0.41 (2H, m), 0.46-0.58 (1H, m), 0.73 (9H, s), 0.95-1.05 (1H, m), 2.20-2.32 (1H, m), 2.65 (2H, brs), 2.70 (2H, d, J=7.4 Hz), 3.76 (3H, s), 5.43 (2H, s), 6.86 (1H, s), 6.88 (1H, dd, J=6.0, 3.1 Hz), 6.96 (1H, d, J=5.4 Hz), 6.98-7.03 (1H, m), 7.24 (1H, t, J=9.2 Hz), 7.36 (1H, d, J=7.9 Hz), 7.62 (1H, d, J=7.9 Hz), 8.04 (1H, d, J=5.3 Hz), 12.13 (1H, brs).

Example 31

3-cyclopropyl-3-(3-((6-(2-fluoro-5-methoxyphenyl)-5-isobutoxypyridin-3-yl)methoxy)phenyl)propanoic acid A) methyl 5-isobutoxynicotinate Under a nitrogen atmosphere, to a solution of methyl 5-hydroxynicotinate (5.00 g) in DMF (50 mL) were added isobutyl bromide (5.33 mL) and potassium carbonate (9.04 g), and the mixture was stirred at 80° C. for 2 hr. Water was added to the reaction mixture at room temperature, and the mixture was extracted with ethyl acetate. The extract was washed with water and saturated brine, and dried over anhydrous magnesium sulfate. After silica gel filtration, the solvent was evaporated under reduced pressure to give a crude product of the title compound (5.13 g) as a pale-brown oil. The obtained crude product was directly used for the next step.

$^1$H NMR (300 MHz, DMSO-d$_6$) δ 0.99 (6H, d, J=6.8 Hz), 1.99-2.13 (1H, m), 3.86-3.94 (5H, m), 7.74 (1H, dd, J=2.8, 1.7 Hz), 8.53 (1H, d, J=3.0 Hz), 8.68 (1H, d, J=1.9 Hz).

B) 3-isobutoxy-5-(methoxycarbonyl)pyridine 1-oxide

Under a nitrogen atmosphere, to a mixture of methyl 5-isobutoxynicotinate (5.13 g), urea-hydrogen peroxide adduct (4.84 g) and acetonitrile (82 mL) was added trifluoroacetic anhydride (8.25 mL) at 0° C., and the mixture was stirred at 0° C. for 2 hr. Saturated aqueous sodium hydrogen carbonate solution was added to the reaction mixture, and the solvent was evaporated under reduced pressure. The residue was filtered, and washed with acetonitrile. The solvent in the filtrate was evaporated under reduced pressure, and the residue was purified by silica gel column chromatography (NH, ethyl acetate/hexane) and silica gel column chromatography (ethyl acetate/hexane) to give a crude product of the title compound (7.04 g) as a white amorphous solid. This compound was used for the next step without further purification.

$^1$H NMR (300 MHz, DMSO-d$_6$) δ 0.97 (6H, d, J=6.4 Hz), 1.79-2.11 (1H, m), 3.85-3.93 (5H, m), 7.37 (1H, dd, J=2.1, 1.3 Hz), 8.19 (1H, t, J=1.5 Hz), 8.25-8.35 (1H, m).

C) methyl 6-chloro-5-isobutoxynicotinate

To 3-isobutoxy-5-(methoxycarbonyl)pyridine 1-oxide (7.04 g) was added phosphoryl chloride (25 mL), and the mixture was heated under reflux for 30 min. The solvent in the reaction mixture was evaporated under reduced pressure, and saturated aqueous sodium hydrogen carbonate solution was added at 0° C. The reaction mixture was extracted with ethyl acetate, and the extract was washed with water and saturated brine, and dried over anhydrous magnesium sulfate. The solvent was evaporated under reduced pressure, and the obtained residue was purified by silica gel column chromatography (ethyl acetate/hexane) to give a crude product of the title compound (3.18 g) as a white amorphous solid. This compound was used for the next step without further purification.

$^1$H NMR (300 MHz, DMSO-d$_6$) δ 1.00 (6H, s), 2.00-2.16 (1H, m), 3.90 (3H, s), 3.99 (2H, d, J=6.4 Hz), 7.81 (1H, d, J=3.0 Hz), 7.87 (1H, d, J=1.9 Hz), 8.49 (1H, d, J=1.9 Hz).

D) methyl 6-(2-fluoro-5-methoxyphenyl)-5-isobutoxynicotinate

Under an argon atmosphere, to a solution of methyl 6-chloro-5-isobutoxynicotinate (1.84 g) in toluene (25 mL) were added 2-fluoro-5-methoxyphenylboronic acid (2.21 g), tris(dibenzylideneacetone)dipalladium(0) (318 mg), 2-dicyclohexylphosphino-2',6'-dimethoxybiphenyl (570 mg) and 2.0 M aqueous sodium carbonate solution (13.0 mL), and the mixture was stirred at 100° C. for 1 hr. The reaction mixture was filtered through celite, and water was added at room temperature. The reaction mixture was extracted with ethyl acetate, and the extract was washed with water and saturated brine. The organic layer was dried over anhydrous magnesium sulfate, and the solvent was evaporated under reduced pressure. The residue was purified by silica gel column chromatography (ethyl acetate/hexane) to give the title compound (1.82 g) as a yellow oil.

$^1$H NMR (300 MHz, DMSO-d$_6$) δ 0.88 (6H, d, J=6.8 Hz), 1.79-1.97 (1H, m), 3.77 (3H, s), 3.89 (2H, d, J=6.4 Hz), 3.93 (3H, s), 6.58-7.09 (2H, m), 7.15-7.31 (1H, m), 7.88 (1H, d, J=1.5 Hz), 8.76 (1H, d, J=1.9 Hz).

E) (6-(2-fluoro-5-methoxyphenyl)-5-isobutoxypyridin-3-yl)methanol

To a suspension of lithium aluminum hydride (622 mg) in diethyl ether (20 mL) was added a solution of methyl 6-(2-fluoro-5-methoxyphenyl)-5-isobutoxynicotinate (1.82 g) in diethyl ether (5.0 mL) at 0° C., and the mixture was stirred for 30 min. Water and aqueous sodium hydroxide solution were added to the reaction mixture, and the resulting precipitate was filtered off. The solvent in the filtrate was concentrated, and the residue was recrystallized (ethyl acetate/hexane) to give the title compound (1.30 g) as a white solid.

$^1$H NMR (300 MHz, DMSO-d$_6$) δ 0.87 (6H, d, J=6.8 Hz), 1.83-1.97 (1H, m), 3.76 (3H, s), 3.79 (2H, d, J=6.4 Hz), 4.58 (2H, d, J=5.7 Hz), 5.35 (1H, t, J=5.7 Hz), 6.78-7.03 (2H, m), 7.06-7.26 (1H, m), 7.45 (1H, d, J=1.5 Hz), 8.18 (1H, d, J=1.5 Hz).

F) methyl 3-cyclopropyl-3-(3-((6-(2-fluoro-5-methoxyphenyl)-5-isobutoxypyridin-3-yl)methoxy)phenyl)propanoate Under a nitrogen atmosphere, to a solution of (6-(2-fluoro-5-methoxyphenyl)-5-isobutoxypyridin-3-yl)methanol (100 mg) and methyl 3-cyclopropyl-3-(3-hydroxyphenyl)propanoate (72 mg) in toluene (4.7 mL) were added 1,1'-(azodicarbonyl)dipiperidine (132 mg) and tributylphosphine (131 μL), and the mixture was stirred at room temperature for 14 hr. Hexane/ethyl acetate (1:1) was added to the reaction mixture, and the resulting precipitate was filtered off. The solvent in the filtrate was evaporated under reduced pressure, and the residue was purified by silica gel column chromatography (ethyl acetate/hexane) to give the title compound (132 mg) as a colorless oil.

$^1$H NMR (300 MHz, DMSO-d$_6$) δ 0.04-0.39 (3H, m), 0.43-0.57 (1H, m), 0.87 (6H, d, J=6.4 Hz), 0.94-1.11 (1H, m), 1.83-1.96 (1H, m), 2.17-2.33 (1H, m), 2.75 (2H, dd, J=7.6, 3.4 Hz), 3.51 (3H, s), 3.76 (3H, s), 3.81 (2H, d, J=6.4 Hz), 5.18 (2H, s), 6.80-6.93 (2H, m), 6.93-7.04 (3H, m), 7.11-7.28 (2H, m), 7.64 (1H, d, J=1.5 Hz), 8.33 (1H, d, J=1.5 Hz).

G) 3-cyclopropyl-3-(3-((6-(2-fluoro-5-methoxyphenyl)-5-isobutoxypyridin-3-yl)methoxy)phenyl)propanoic acid To a solution of methyl 3-cyclopropyl-3-(3-((6-(2-fluoro-5-methoxyphenyl)-5-isobutoxypyridin-3-yl)methoxy)phenyl)propanoate (132 mg) in THF (2.0 mL) and methanol (1.0 mL) was added 1N aqueous sodium hydroxide solution (2.0 mL), and the mixture was stirred at room temperature for 4 hr. 1N Hydrochloric acid (2.0 mL) was added to the reaction mixture at room temperature, and the mixture was extracted with ethyl acetate. The extract was washed with water and saturated brine, and dried over anhydrous magnesium sulfate. After silica gel filtration, the solvent was evaporated under reduced pressure to give the title compound (114 mg) as a white amorphous solid.

MS (ESI+): [M+H]$^+$ 494.2

$^1$H NMR (300 MHz, DMSO-d$_6$) δ 0.05-0.18 (1H, m), 0.18-0.38 (2H, m), 0.43-0.56 (1H, m), 0.87 (6H, d, J=6.8 Hz), 0.92-1.10 (1H, m), 1.81-1.98 (1H, m), 2.17-2.37 (1H, m), 2.65 (2H, dd, J=7.3, 4.0 Hz), 3.76 (3H, s), 3.81 (2H, d, J=6.4 Hz), 5.17 (2H, s), 6.79-7.07 (5H, m), 7.11-7.30 (2H, m), 7.65 (1H, d, J=1.5 Hz), 8.33 (1H, d, J=1.5 Hz), 12.02 (1H, brs).

Example 32

3-cyclopropyl-3-(6-((6-(2-fluoro-5-methoxyphenyl)-5-isobutoxypyridin-3-yl)methoxy)pyrimidin-4-yl)propanoic acid A) ethyl 3-cyclopropyl-3-(6-((6-(2-fluoro-5-methoxyphenyl)-5-isobutoxypyridin-3-yl)methoxy)pyrimidin-4-yl)propanoate Under an argon atmosphere, to a solution of (6-(2-fluoro-5-methoxyphenyl)-5-isobutoxypyridin-3-yl)methanol (587 mg) and ethyl 3-(6-chloropyrimidin-4-yl)-3-cyclopropylpropanoate (587 mg) in THF (9.6 mL) was added 60% sodium hydride (100 mg) at 0° C., and the mixture was stirred at room temperature for 4 hr. 1N Hydrochloric acid was added to the reaction mixture at 0° C., and the mixture was neutralized with saturated aqueous sodium hydrogen carbonate solution. The reaction mixture was extracted with ethyl acetate, and the extract was washed with water and saturated brine. The organic layer was dried over anhydrous magnesium sulfate. The solvent was evaporated under reduced pressure, and the obtained residue was purified by silica gel column chromatography (ethyl acetate/hexane) to give the title compound (890 mg) as a colorless oil.

$^1$H NMR (400 MHz, DMSO-d$_6$) δ 0.22-0.43 (3H, m), 0.48-0.58 (1H, m), 0.87 (6H, d, J=6.8 Hz), 0.92-1.05 (1H, m), 1.08 (3H, t, J=7.2 Hz), 1.91 (1H, dt, J=13.3, 6.6 Hz), 2.36 (1H, td, J=9.3, 5.9 Hz), 2.74 (1H, dd, J=15.7, 5.8 Hz), 2.94 (1H, dd, J=15.6, 8.8 Hz), 3.76 (3H, s), 3.81 (2H, d, J=6.4 Hz), 3.90-4.01 (2H, m), 5.49 (2H, s), 6.92-7.03 (3H, m), 7.18 (1H, t, J=9.2 Hz), 7.67 (1H, d, J=1.4 Hz), 8.34 (1H, d, J=1.4 Hz), 8.76 (1H, s).

B) 3-cyclopropyl-3-(6-((6-(2-fluoro-5-methoxyphenyl)-5-isobutoxypyridin-3-yl)methoxy)pyrimidin-4-yl)propanoic acid To a solution of ethyl 3-cyclopropyl-3-(6-((6-(2-fluoro-5-methoxyphenyl)-5-isobutoxypyridin-3-yl)methoxy)pyrimidin-4-yl)propanoate (890 mg) in THF (5.0 mL) and methanol (2.5 mL) was added 1N aqueous sodium hydroxide solution (5.0 mL), and the mixture was stirred at room temperature for 1 hr. 1N Hydrochloric acid (5.0 mL) was added to the reaction mixture at room temperature, and the mixture was extracted with ethyl acetate. The extract was washed with water and saturated brine, and dried over anhydrous magnesium sulfate. After silica gel filtration, the solvent was evaporated under reduced pressure, and the obtained crude crystals were recrystallized (ethyl acetate/hexane) to give the title compound (688 mg) as a white solid.

MS (ESI+): [M+H]$^+$ 496.2

$^1$H NMR (400 MHz, DMSO-d$_6$) δ 0.21-0.43 (3H, m), 0.44-0.59 (1H, m), 0.87 (6H, d, J=6.8 Hz), 0.91-1.05 (1H, m), 1.91 (1H, dt, J=13.1, 6.5 Hz), 2.34 (1H, td, J=9.3, 5.5 Hz), 2.67 (1H, dd, J=16.0, 5.5 Hz), 2.90 (1H, dd, J=16.0, 9.0 Hz), 3.76 (3H, s), 3.81 (2H, d, J=6.3 Hz), 5.48 (2H, s), 6.89-7.05 (3H, m), 7.18 (1H, t, J=9.1 Hz), 7.68 (1H, d, J=1.1 Hz), 8.35 (1H, d, J=1.1 Hz), 8.76 (1H, s), 12.05 (1H, brs).

Example 33

3-cyclopropyl-3-(3-((6-(2-fluoro-5-methoxyphenyl)-5-isobutoxy-2-methoxypyridin-3-yl)methoxy)phenyl)propanoic acid A) 2-(2-fluoro-5-methoxyphenyl)-3-isobutoxy-5-(methoxycarbonyl)pyridine 1-oxide Under a nitrogen atmosphere, to a solution of methyl 6-(2-fluoro-5-methoxyphenyl)-5-isobutoxynicotinate (758 mg) in acetonitrile (9.4 mL) were added urea-hydrogen peroxide adduct (555 mg) and trifluoroacetic anhydride (793 μL) at 0° C., and the mixture was gradually warmed to room temperature and stirred overnight. Saturated aqueous sodium hydrogen carbonate solution was added to the reaction mixture, and the solvent was evaporated under reduced pressure. The residue was filtered, and the solvent in the filtrate was evaporated under reduced pressure. The residue was purified by silica gel column chromatography (ethyl acetate/hexane) to give the title compound (631 mg) as a pale-yellow oil.

$^1$H NMR (300 MHz, DMSO-d$_6$) δ 0.80 (6H, d, J=6.8 Hz), 1.71-1.94 (1H, m), 3.74 (3H, s), 3.85-3.96 (5H, m), 6.99 (1H, dd, J=5.3, 3.0 Hz), 7.03-7.11 (1H, m), 7.24 (1H, t, J=9.1 Hz), 7.51 (1H, d, J=1.5 Hz), 8.37 (1H, d, J=1.1 Hz).

B) methyl 2-chloro-6-(2-fluoro-5-methoxyphenyl)-5-isobutoxynicotinate

A mixture of 2-(2-fluoro-5-methoxyphenyl)-3-isobutoxy-5-(methoxycarbonyl)pyridine 1-oxide (600 mg) and phosphoryl chloride (5.0 mL) was heated under reflux for 1 hr. The solvent was evaporated under reduced pressure, and the residue was purified by silica gel column chromatography (ethyl acetate/hexane) to give the title compound (315 mg) as a pale-yellow oil.

$^1$H NMR (300 MHz, DMSO-d$_6$) δ 0.86 (6H, d, J=6.8 Hz), 1.84-1.97 (1H, m), 3.77 (3H, s), 3.88 (2H, d, J=6.1 Hz), 3.92 (3H, s), 6.90-7.12 (2H, m), 7.16-7.30 (1H, m), 7.96 (1H, s).

C) methyl 6-(2-fluoro-5-methoxyphenyl)-5-isobutoxy-2-methoxynicotinate

Under a nitrogen atmosphere, to a solution of methyl 2-chloro-6-(2-fluoro-5-methoxyphenyl)-5-isobutoxynicotinate (248 mg) in THF (5.0 mL) was added a 28% solution of sodium methoxide in methanol (3.42 mL). The reaction mixture was stirred at room temperature for 1 hr and further at 60° C. for 48 hr. 6N Hydrochloric acid (0.44 mL) was added to the reaction mixture, and the resulting sodium chloride was filtered off. The solvent in the filtrate was evaporated under reduced pressure, and the residue was heated with conc. sulfuric acid (108 μL) and methanol (10 mL) under reflux for 3 hr. The reaction mixture was neutralized with sodium hydrogen carbonate, and the solvent in the reaction mixture was evaporated under reduced pressure and the residue was filtered. The solvent in the filtrate was evaporated under reduced pressure to give a crude product of the title compound (213 mg) as a yellow oil. This compound was used for the next step without further purification.

$^1$H NMR (300 MHz, DMSO-d$_6$) δ 0.85 (6H, d, J=6.8 Hz), 1.81-1.94 (1H, m), 3.77 (5H, s), 3.84 (3H, s), 3.88 (3H, s), 6.97-7.09 (2H, m), 7.13-7.28 (1H, m), 7.89 (1H, s).

D) (6-(2-fluoro-5-methoxyphenyl)-5-isobutoxy-2-methoxypyridin-3-yl)methanol

To a suspension of lithium aluminum hydride (67 mg) in diethyl ether (2.0 mL) was added a solution of methyl 6-(2-fluoro-5-methoxyphenyl)-5-isobutoxy-2-methoxynicotinate (213 mg) in diethyl ether (1.0 mL) at 0° C., and the mixture was stirred for 20 min. Water and aqueous sodium hydroxide solution were added to the reaction mixture, and the resulting precipitate was filtered off. The solvent in the filtrate was evaporated to give a crude product of the title compound (1.30 g) as an orange oil. This compound was used for the next step without further purification.

$^1$H NMR (300 MHz, DMSO-d$_6$) δ 0.85 (6H, d, J=6.4 Hz), 1.78-1.95 (1H, m), 3.71 (2H, d, J=6.4 Hz), 3.76 (3H, s), 3.82 (3H, s), 4.49 (2H, d, J=5.3 Hz), 5.30 (1H, t, J=5.5 Hz), 6.92-7.04 (2H, m), 7.07-7.23 (1H, m), 7.58 (1H, s).

E) methyl 3-cyclopropyl-3-(3-((6-(2-fluoro-5-methoxyphenyl)-5-isobutoxy-2-methoxypyridin-3-yl)methoxy)phenyl)propanoate Under a nitrogen atmosphere, to a solution of (6-(2-fluoro-5-methoxyphenyl)-5-isobutoxy-2-methoxypyridin-3-yl)methanol (94 mg) and methyl 3-cyclopropyl-3-(3-hydroxyphenyl)propanoate (62 mg) in toluene (4.0 mL) were added 1,1'-(azodicarbonyl)dipiperidine (113 mg) and tributylphosphine (112 μL), and the mixture was stirred at room temperature for 14 hr. Hexane/ethyl acetate (1:1) was added to the reaction mixture, and the resulting precipitate was filtered off. The solvent in the filtrate was evaporated under reduced pressure, and the residue was purified by silica gel column chromatography (ethyl acetate/hexane) to give the title compound (120 mg) as a colorless oil.

$^1$H NMR (300 MHz, DMSO-d$_6$) δ 0.04-0.38 (3H, m), 0.43-0.57 (1H, m), 0.83 (6H, d, J=6.8 Hz), 0.93-1.12 (1H, m), 1.73-1.93 (1H, m), 2.18-2.34 (1H, m), 2.75 (2H, dd, J=7.7, 3.2 Hz), 3.51 (3H, s), 3.72 (2H, d, J=6.4 Hz), 3.77 (3H, s), 3.88 (3H, s), 5.06 (2H, s), 6.77-6.92 (2H, m), 6.93-7.06 (3H, m), 7.10-7.30 (2H, m), 7.71 (1H, s).

F) 3-cyclopropyl-3-(3-((6-(2-fluoro-5-methoxyphenyl)-5-isobutoxy-2-methoxypyridin-3-yl)methoxy)phenyl)propanoic acid To a solution of methyl 3-cyclopropyl-3-(3-((6-(2-fluoro-5-methoxyphenyl)-5-isobutoxy-2-methoxypyridin-3-yl)methoxy)phenyl)propanoate (120 mg) in THF (2.0 mL) and methanol (1.0 mL) was added 1N aqueous sodium hydroxide solution (2.0 mL), and the mixture was stirred at 50° C. for 1 hr. 1N Hydrochloric acid (2.0 mL) was added to the reaction mixture at 0° C., and the mixture was extracted with ethyl acetate. The extract was washed with water and saturated brine, and dried over anhydrous magnesium sulfate. After silica gel filtration, the solvent was evaporated under reduced pressure. The crude crystals were recrystallized (ethyl acetate/hexane) to give the title compound (98 mg) as a colorless amorphous solid.

MS (ESI+): [M+H]$^+$ 524.1

$^1$H NMR (300 MHz, DMSO-d$_6$) δ 0.05-0.38 (3H, m), 0.43-0.58 (1H, m), 0.83 (6H, d, J=6.8 Hz), 0.94-1.08 (1H, m), 1.78-1.91 (1H, m), 2.20-2.34 (1H, m), 2.65 (2H, dd, J=7.4, 4.0 Hz), 3.72 (2H, d, J=6.4 Hz), 3.77 (3H, s), 3.88 (3H, s), 5.06 (2H, s), 6.78-6.92 (2H, m), 6.93-7.08 (3H, m), 7.11-7.29 (2H, m), 7.72 (1H, s), 12.01 (1H, brs).

Example 34

3-cyclopropyl-3-(3-((5-(2,2-dimethylpropyl)-6-(2-fluoro-5-methoxyphenyl)pyridin-3-yl)methoxy)phenyl)propanoic acid A) methyl 6-chloro-5-hydroxynicotinate To a mixture of methyl 5-hydroxynicotinate (10.0 g) and water (2.0 mL) was added dropwise 5% aqueous sodium hypochlorite solution (69.2 mL) at 0° C., and the mixture was stirred for 2 hr. 2N Hydrochloric acid (50 mL) was added to the reaction mixture at 0° C., and the resulting white precipitate was collected by filtration. The crude crystals were washed with water, and the obtained solid was dissolved in acetonitrile. The solvent was evaporated under reduced pressure to give a crude product of the title compound (3.71 g) as a pale-yellow solid. This compound was used for the next step without further purification.

$^1$H NMR (300 MHz, DMSO-d$_6$) δ 3.87 (3H, s), 7.76 (1H, d, J=1.9 Hz), 8.37 (1H, d, J=1.9 Hz), 11.29 (1H, s).

B) methyl 5-(benzyloxy)-6-chloronicotinate

To a solution of methyl 6-chloro-5-hydroxynicotinate (3.71 g) in DMF (30 mL) were added potassium carbonate (5.47 g) and benzyl bromide (2.59 mL), and the mixture was stirred at room temperature for 30 min. Water was added to the reaction mixture at 0° C., and the resulting precipitate was collected by filtration. The obtained crude crystals were washed with water and hexane, and dried at 50° C. for 15 min under reduced pressure to give a crude product of the title compound (4.57 g) as a pale-yellow solid. This compound was used for the next step without further purification.

$^1$H NMR (300 MHz, DMSO-d$_6$) δ 3.90 (3H, s), 5.37 (2H, s), 7.31-7.56 (5H, m), 8.01 (1H, d, J=1.9 Hz), 8.52 (1H, d, J=1.9 Hz).

C) (5-(benzyloxy)-6-chloropyridin-3-yl)methanol

To a suspension of methyl 5-(benzyloxy)-6-chloronicotinate (3.00 g) in ethanol (40 mL) was added sodium tetrahydroborate (1.02 g), and the mixture was stirred at 60° C. for 3 hr. Water was added to the reaction mixture at 0° C., and the mixture was extracted with ethyl acetate. The extract was washed with water and saturated brine, and dried over anhydrous magnesium sulfate. The solvent was evaporated under reduced pressure, and the residue was purified by silica gel column chromatography (ethyl acetate/hexane) to give the title compound (1.76 g) as a colorless solid.

¹H NMR (300 MHz, DMSO-d$_6$) δ 4.52 (2H, d, J=5.7 Hz), 5.25 (2H, s), 5.42 (1H, t, J=5.7 Hz), 7.24-7.53 (5H, m), 7.61 (1H, d, J=1.9 Hz), 7.94 (1H, d, J=1.5 Hz).

D) 3-(benzyloxy)-5-(((tert-butyldimethylsilyl)oxy)methyl)-2-chloropyridine

To a solution of (5-(benzyloxy)-6-chloropyridin-3-yl)methanol (1.76 g) and tert-butyldimethylchlorosilane (1.59 g) in DMF (10 mL) was added imidazole (960 mg), and the mixture was stirred at room temperature for 14 hr. Water was added to the reaction mixture at room temperature, and the mixture was extracted with ethyl acetate. The extract was washed with water and saturated brine, and dried over anhydrous magnesium sulfate. The solvent was evaporated under reduced pressure, and the residue was purified by silica gel column chromatography (ethyl acetate/hexane) to give the title compound (2.64 g) as a colorless oil.

¹H NMR (300 MHz, DMSO-d$_6$) δ 0.06 (6H, s), 0.88 (9H, s), 4.73 (2H, s), 5.27 (2H, s), 7.18-7.51 (5H, m), 7.53 (1H, d, J=1.5 Hz), 7.93 (1H, d, J=1.5 Hz).

E) 3-(benzyloxy)-5-(((tert-butyldimethylsilyl)oxy)methyl)-2-(2-fluoro-5-methoxyphenyl)pyridine Under an argon atmosphere, to a solution of 3-(benzyloxy)-5-(((tert-butyldimethylsilyl)oxy)methyl)-2-chloropyridine (2.53 g) in toluene (20 mL) were added 2-fluoro-5-methoxyphenylboronic acid (1.77 g), tris(dibenzylideneacetone)dipalladium(0) (255 mg), 2-dicyclohexylphosphino-2',6'-dimethoxybiphenyl (457 mg) and 2.0 M aqueous sodium carbonate solution (10.4 ml), and the mixture was stirred at 90° C. for 3 hr. The reaction mixture was filtered through celite, and water was added at room temperature. The reaction mixture was extracted with ethyl acetate, and the extract was washed with water and saturated brine, and dried over anhydrous magnesium sulfate, and the solvent was evaporated under reduced pressure. The residue was purified by silica gel column chromatography (ethyl acetate/hexane) to give the title compound (2.81 g) as a pale-yellow oil.

¹H NMR (300 MHz, DMSO-d$_6$) δ 0.09 (6H, s), 0.90 (9H, s), 3.75 (3H, s), 4.78 (2H, s), 5.17 (2H, s), 6.86-7.05 (2H, m), 7.10-7.23 (1H, m), 7.24-7.41 (5H, m), 7.48 (1H, s), 8.21 (1H, s).

F) 5-(((tert-butyldimethylsilyl)oxy)methyl)-2-(2-fluoro-5-methoxyphenyl)pyridin-3-ol Under a hydrogen atmosphere, a mixture of 3-(benzyloxy)-5-(((tert-butyldimethylsilyl)oxy)methyl)-2-(2-fluoro-5-methoxyphenyl)pyridine (2.81 g), 10% palladium-activated carbon (280 mg) and ethyl acetate (30 mL) was stirred at room temperature for 30 min. The catalyst was filtered off, and the solvent in the filtrate was evaporated under reduced pressure to give the title compound (2.33 g) as a pale-yellow solid.

This compound was used for the next step without further purification.

¹H NMR (300 MHz, DMSO-d$_6$) δ 0.12 (6H, s), 0.93 (9H, s), 3.75 (3H, s), 4.74 (2H, s), 6.73-7.01 (2H, m), 7.08-7.19 (1H, m), 7.27 (1H, d, J=1.5 Hz), 8.05 (1H, d, J=1.5 Hz), 10.01 (1H, s).

G) 5-(((tert-butyldimethylsilyl)oxy)methyl)-2-(2-fluoro-5-methoxyphenyl)pyridin-3-yl trifluoromethanesulfonate Under a nitrogen atmosphere, to a mixture of 5-(((tert-butyldimethylsilyl)oxy)methyl)-2-(2-fluoro-5-methoxyphenyl)pyridin-3-ol (2.33 g) and pyridine (20 mL) was added trifluoromethanesulfonic anhydride (2.17 mL) at 0° C., and the mixture was stirred for 10 min. Water was added to the reaction mixture at 0° C., and the mixture was extracted with ethyl acetate. The extract was washed with 1N hydrochloric acid and saturated brine, and dried over anhydrous magnesium sulfate. The solvent was evaporated under reduced pressure, and the residue was purified by silica gel column chromatography (ethyl acetate/hexane) to give the title compound (2.72 g) as a pale-yellow oil.

¹H NMR (300 MHz, DMSO-d$_6$) δ 0.13 (6H, s), 0.93 (9H, s), 3.79 (3H, s), 4.93 (2H, s), 6.98-7.19 (2H, m), 7.23-7.39 (1H, m), 7.97 (1H, d, J=1.5 Hz), 8.75 (1H, d, J=1.5 Hz).

H) 5-(((tert-butyldimethylsilyl)oxy)methyl)-2-(2-fluoro-5-methoxyphenyl)-3-neopentylpyridine Under an argon atmosphere, to a solution of 5-(((tert-butyldimethylsilyl)oxy)methyl)-2-(2-fluoro-5-methoxyphenyl)pyridin-3-yl trifluoromethanesulfonate (2.72 g) and PEPPSI-SIPr (trade name) (374 mg) in THF (25 mL) was added dropwise a 1.0 M solution (24 mL) of neopentylmagnesium chloride in diethyl ether, and the mixture was stirred at room temperature for 10 min. 1N Hydrochloric acid was added at room temperature, and the mixture was extracted with ethyl acetate. The extract was washed with water and saturated brine, and dried over anhydrous magnesium sulfate. The solvent was evaporated under reduced pressure to give a crude product of the title compound. This compound was used for the next step without further purification.

I) (6-(2-fluoro-5-methoxyphenyl)-5-neopentylpyridin-3-yl)methanol

To a solution of 5-(((tert-butyldimethylsilyl)oxy)methyl)-2-(2-fluoro-5-methoxyphenyl)-3-neopentylpyridine in THF (25 mL) was added a 1 M solution of tetrabutylammonium fluoride in THF (10 mL), and the mixture was stirred at room temperature for 5 min. Water was added to the reaction mixture at room temperature, and the mixture was extracted with ethyl acetate. The extract was washed with water and saturated brine, and dried over anhydrous magnesium sulfate. The solvent was evaporated under reduced pressure, and the residue was purified by silica gel column chromatography (ethyl acetate/hexane) to give the title compound (1.50 g) as a pale-yellow oil.

¹H NMR (300 MHz, DMSO-d$_6$) δ 0.67 (9H, s), 2.54 (2H, s), 3.75 (3H, s), 4.58 (2H, d, J=5.7 Hz), 5.33 (1H, t, J=5.7 Hz), 6.88 (1H, dd, J=5.9, 3.2 Hz), 6.96-7.05 (1H, m), 7.20 (1H, t, J=9.3 Hz), 7.62 (1H, d, J=2.3 Hz), 8.45 (1H, d, J=2.3 Hz).

J) methyl 3-cyclopropyl-3-(3-((6-(2-fluoro-5-methoxyphenyl)-5-neopentylpyridin-3-yl)methoxy)phenyl)propanoate Under a nitrogen atmosphere, to a solution of (6-(2-fluoro-5-methoxyphenyl)-5-neopentylpyridin-3-yl)methanol (100 mg) and methyl 3-cyclopropyl-3-(3-hydroxyphenyl)propanoate (73 mg) in toluene (4.7 mL) were added 1,1'-(azodicarbonyl)dipiperidine (133 mg) and tributylphosphine (130 μL), and the mixture was stirred at room temperature for 60 hr. Hexane/ethyl acetate (1:1) was added to the reaction mixture, and the resulting precipitate was filtered off. The solvent in the filtrate was evaporated under reduced pressure, and the residue was purified by silica gel column chromatography (ethyl acetate/hexane) to give the title compound (144 mg) as a colorless oil.

¹H NMR (300 MHz, DMSO-d₆) δ 0.04-0.38 (3H, m), 0.41-0.55 (1H, m), 0.65 (9H, s), 0.92-1.10 (1H, m), 2.20-2.32 (1H, m), 2.56 (2H, s), 2.73 (2H, dd, J=7.5, 4.1 Hz), 3.51 (3H, s), 3.75 (3H, s), 5.20 (2H, s), 6.80-6.98 (4H, m), 7.02 (1H, dt, J=8.9, 3.6 Hz), 7.14-7.26 (2H, m), 7.76 (1H, d, J=1.9 Hz), 8.61 (1H, d, J=1.9 Hz).

K) 3-cyclopropyl-3-(3-((5-(2,2-dimethylpropyl)-6-(2-fluoro-5-methoxyphenyl)pyridin-3-yl)methoxy)phenyl)propanoic acid To a solution of methyl 3-cyclopropyl-3-(3-((6-(2-fluoro-5-methoxyphenyl)-5-neopentylpyridin-3-yl)methoxy)phenyl)propanoate (143 mg) in THF (2.0 mL) and methanol (1.0 mL) was added 1N aqueous sodium hydroxide solution (2.0 mL), and the mixture was stirred at room temperature for 4 hr. 1N Hydrochloric acid (2.0 mL) was added to the reaction mixture at room temperature, and the mixture was extracted with ethyl acetate. The extract was washed with water and saturated brine, and dried over anhydrous magnesium sulfate. After silica gel filtration, the solvent was evaporated under reduced pressure to give the title compound (129 mg) as a white amorphous solid.

MS (ESI+): [M+H]⁺ 492.2
¹H NMR (300 MHz, DMSO-d₆) δ 0.04-0.16 (1H, m), 0.17-0.38 (2H, m), 0.41-0.57 (1H, m), 0.65 (9H, s), 0.91-1.09 (1H, m), 2.18-2.34 (1H, m), 2.56 (2H, s), 2.64 (2H, dd, J=7.5, 4.9 Hz), 3.75 (3H, s), 5.19 (2H, s), 6.79-6.96 (4H, m), 6.97-7.07 (1H, m), 7.14-7.28 (2H, m), 7.77 (1H, d, J=1.9 Hz), 8.61 (1H, d, J=1.9 Hz), 11.98 (1H, brs).

Example 35

3-cyclopropyl-3-(6-((5-(2,2-dimethylpropyl)-6-(2-fluoro-5-methoxyphenyl)pyridin-3-yl)methoxy)pyrimidin-4-yl)propanoic acid A) ethyl 3-cyclopropyl-3-(6-((6-(2-fluoro-5-methoxyphenyl)-5-neopentylpyridin-3-yl)methoxy)pyrimidin-4-yl)propanoate Under a nitrogen atmosphere, to a solution of (6-(2-fluoro-5-methoxyphenyl)-5-neopentylpyridin-3-yl)methanol (379 mg) and ethyl 3-(6-chloropyrimidin-4-yl)-3-cyclopropylpropanoate (382 mg) in THF (5.0 mL) was added 60% sodium hydride (65 mg) at 0° C., and the mixture was stirred at room temperature for 5 hr. 1N Hydrochloric acid was added to the reaction mixture at 0° C., and the mixture was extracted with ethyl acetate. The extract was washed with water and saturated brine, and dried over anhydrous magnesium sulfate. The solvent was evaporated under reduced pressure, and the residue was purified by silica gel column chromatography (ethyl acetate/hexane) to give the title compound (489 mg) as a colorless oil.

¹H NMR (400 MHz, DMSO-d₆) δ 0.21-0.30 (2H, m), 0.31-0.41 (1H, m), 0.47-0.57 (1H, m), 0.64 (9H, s), 0.92-1.04 (1H, m), 1.08 (3H, t, J=7.1 Hz), 2.29-2.41 (1H, m), 2.55 (2H, brs), 2.74 (1H, dd, J=15.8, 5.9 Hz), 2.93 (1H, dd, J=15.6, 8.9 Hz), 3.75 (3H, s), 3.89-4.00 (2H, m), 5.52 (2H, s), 6.88-6.94 (1H, m), 6.97 (1H, s), 6.99-7.06 (1H, m), 7.21 (1H, t, J=9.2 Hz), 7.79 (1H, s), 8.63 (1H, s), 8.74 (1H, s).

B) 3-cyclopropyl-3-(6-C(5-(2,2-dimethylpropyl)-6-(2-fluoro-5-methoxyphenyl)pyridin-3-yl)methoxy)pyrimidin-4-yl)propanoic acid To a solution of ethyl 3-cyclopropyl-3-(6-((6-(2-fluoro-5-methoxyphenyl)-5-neopentylpyridin-3-yl)methoxy)pyrimidin-4-yl)propanoate (489 mg) in THF (5.0 mL) and methanol (2.5 ml) was added 1N aqueous sodium hydroxide solution (5.0 mL), and the mixture was stirred at room temperature for 1 hr. 1N Hydrochloric acid (5.0 mL) was added to the reaction mixture at room temperature, and the mixture was extracted with ethyl acetate. The extract was washed with water and saturated brine, and dried over anhydrous magnesium sulfate. After silica gel filtration, the solvent was evaporated under reduced pressure, and the obtained solid was washed with diisopropyl ether to give the title compound (336 mg) as a white solid.

MS (ESI+): [M+H]⁺ 494.3
¹H NMR (400 MHz, DMSO-d₆) δ 0.19-0.39 (3H, m), 0.52 (1H, t, J=8.7 Hz), 0.64 (9H, s), 0.89-1.02 (1H, m), 2.25-2.40 (1H, m), 2.56 (2H, brs), 2.66 (1H, dd, J=16.0, 5.3 Hz), 2.90 (1H, dd, J=16.0, 9.1 Hz), 3.75 (3H, s), 5.51 (2H, s), 6.88-6.98 (2H, m), 6.99-7.07 (1H, m), 7.21 (1H, t, J=9.2 Hz), 7.80 (1H, s), 8.63 (1H, s), 8.74 (1H, s), 12.06 (1H, brs).

Example 36

3-cyclopropyl-3-(6-((5-(2,2-dimethylpropoxy)-6-(2-fluoro-5-methoxyphenyl)pyridin-3-yl)methoxy)pyrimidin-4-yl)propanoic acid A) methyl 6-chloro-5-((tetrahydro-2H-pyran-2-yl)oxy)nicotinate Under a nitrogen atmosphere, to a solution of methyl 6-chloro-5-hydroxynicotinate (703 mg) in toluene (15 mL) were added 3,4-dihydro-2H-pyran (685 μL) and pyridinium p-toluenesulfonate (94 mg), and the mixture was stirred at room temperature for 2 hr and further at 60° C. for 1.5 hr. The reaction mixture was poured into water at room temperature, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (546 mg) as a white solid.

¹H NMR (300 MHz, CDCl₃) δ 1.60-1.83 (3H, m), 1.84-2.21 (3H, m), 3.59-3.71 (1H, m), 3.80 (1H, td, J=11.1, 3.2 Hz), 3.94 (3H, s), 5.62 (1H, t, J=2.7 Hz), 8.02 (1H, d, J=1.9 Hz), 8.63 (1H, d, J=2.3 Hz).

B) methyl 6-(2-fluoro-5-methoxyphenyl)-5-((tetrahydro-2H-pyran-2-yl)oxy)nicotinate Under a nitrogen atmosphere, to a solution of methyl 6-chloro-5-((tetrahydro-2H-pyran-2-yl)oxy)nicotinate (546 mg) in toluene (6.7 mL) were added 2-fluoro-5-methoxyphenylboronic acid (512 mg), 2-dicyclohexylphosphino-2',6'-dimethoxybiphenyl (132 mg), tris(dibenzylideneacetone)dipalladium(0) (74 mg) and 2.0 M aqueous sodium carbonate (3.0 mL) solution, and the mixture was stirred at 100° C. for 20 hr. The reaction mixture was poured into water, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (466 mg) as a yellow oil.

¹H NMR (300 MHz, CDCl₃) δ 1.57-1.85 (6H, m), 3.57-3.70 (1H, m), 3.75-3.88 (4H, m), 3.93-4.01 (3H, m), 5.54 (1H, s), 6.89-6.99 (1H, m), 7.01-7.11 (2H, m), 8.14 (1H, d, J=1.5 Hz), 8.94 (1H, d, J=1.9 Hz).

C) (6-(2-fluoro-5-methoxyphenyl)-5-((tetrahydro-2H-pyran-2-yl)oxy)pyridin-3-yl)methanol Under a nitrogen atmosphere, to a suspension of lithium aluminum hydride (74 mg) in THF (9.7 mL) was added dropwise a solution of methyl 6-(2-fluoro-5-methoxyphenyl)-5-((tetrahydro-2H-pyran-2-yl)oxy)nicotinate (466 mg) in THF (3.2 ml) at 0° C., and the mixture was stirred for 1 hr. Sodium sulfate decahydrate was added by small portions, and the mixture was further stirred at room temperature for 1 hr. The reaction mixture was filtered, and the solvent was evaporated under reduced pressure. The residue was purified by silica gel column chromatography (ethyl acetate/hexane) to give the title compound (193 mg) as a colorless gummy substance.

$^1$H NMR (300 MHz, CDCl$_3$) δ 1.55-1.86 (7H, m), 3.56-3.66 (1H, m), 3.77-3.89 (4H, m), 4.78 (2H, d, J=5.7 Hz), 5.48 (1H, s), 6.86-6.94 (1H, m), 6.98-7.09 (2H, m), 7.62 (1H, d, J=1.9 Hz), 8.33 (1H, d, J=1.9 Hz).

D) ethyl 3-cyclopropyl-3-(6-((6-(2-fluoro-5methoxyphenyl)-5-((tetrahydro-2H-pyran-2-yl) oxy)pyridin-3-yl)methoxy)pyrimidin-4-yl)propanoate Under a nitrogen atmosphere, to a solution of (6-(2-fluoro-5-methoxyphenyl)-5-((tetrahydro-2H-pyran-2-yl)oxy)pyridin-3-yl)methanol (189 mg) and ethyl 3-(6-chloropyrimidin-4-yl)-3-cyclopropylpropanoate (174 mg) in THF (2.8 mL) was added 60% sodium hydride (25 mg) at 0° C., and the mixture was stirred at room temperature for 2 hr. The reaction mixture was cooled to 0° C., and neutralized with 1N hydrochloric acid. The reaction mixture was extracted with ethyl acetate, and the extract was washed with saturated brine, and dried over anhydrous sodium sulfate. The solvent was evaporated under reduced pressure and the residue was purified by silica gel column chromatography (ethyl acetate/hexane and then methanol/ethyl acetate) to give the title compound (164 mg) as a colorless oil.

$^1$H NMR (300 MHz, CDCl$_3$) δ 0.20-0.38 (2H, m), 0.45-0.57 (1H, m), 0.57-0.70 (1H, m), 0.98-1.14 (1H, m), 1.19 (3H, t, J=7.2 Hz), 1.56-1.83 (6H, m), 2.30-2.43 (1H, m), 2.72-2.86 (1H, m), 2.96-3.09 (1H, m), 3.57-3.66 (1H, m), 3.78-3.84 (4H, m), 4.01-4.18 (2H, m), 5.45-5.51 (3H, m), 6.74 (1H, s), 6.87-6.95 (1H, m), 6.99-7.10 (2H, m), 7.67-7.72 (1H, m), 8.43 (1H, d, J=1.5 Hz), 8.74 (1H, s).

E) ethyl 3-cyclopropyl-3-(6-((6-(2-fluoro-5-methoxyphenyl)-5-hydroxypyridin-3-yl)methoxy)pyrimidin-4-yl)propanoate Under a nitrogen atmosphere, to a solution of ethyl 3-cyclopropyl-3-(6-((6-(2-fluoro-5-methoxyphenyl)-5-((tetrahydro-2H-pyran-2-yl)oxy)pyridin-3-yl)methoxy)pyrimidin-4-yl)propanoate (163 mg) in methanol (1.5 mL) was added pyridinium p-toluenesulfonate (7.5 mg), and the mixture was stirred at 50° C. for 20 hr. The reaction mixture was poured into water at room temperature, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (119 mg) as a white amorphous solid.

$^1$H NMR (300 MHz, CDCl$_3$) δ 0.18-0.37 (2H, m), 0.45-0.56 (1H, m), 0.57-0.69 (1H, m), 1.01-1.14 (1H, m), 1.19 (3H, t, J=7.2 Hz), 2.34 (1H, td, J=9.2, 5.7 Hz), 2.79 (1H, dd, J=15.8, 5.7 Hz), 3.03 (1H, dd, J=15.8, 8.7 Hz), 3.83 (3H, s), 4.00-4.13 (2H, m), 5.45-5.53 (3H, m), 6.75 (1H, s), 6.93-7.02 (1H, m), 7.08 (1H, dt, J=5.7, 2.8 Hz), 7.11-7.19 (1H, m), 7.44 (1H, d, J=1.9 Hz), 8.42 (1H, d, J=1.5 Hz), 8.73 (1H, s).

F) ethyl 3-cyclopropyl-3-(6-((6-(2-fluoro-5methoxyphenyl)-5-(neopentyloxy)pyridin-3-yl) methoxy)pyrimidin-4-yl)propanoate Under a nitrogen atmosphere, to a solution of ethyl 3-cyclopropyl-3-(6-((6-(2-fluoro-5-methoxyphenyl)-5-hydroxypyridin-3-yl)methoxy)pyrimidin-4-yl)propanoate (60 mg) in DMF (1.3 mL) were added 1-bromo-2,2-dimethylpropane (80 μL) and cesium carbonate (83 mg), and the mixture was stirred at 80° C. for 20 hr. The reaction mixture was poured into water at room temperature, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (20 mg) as a colorless amorphous solid.

$^1$H NMR (300 MHz, CDCl$_3$) δ 0.13-0.37 (2H, m), 0.43-0.56 (1H, m), 0.56-0.73 (1H, m), 0.91 (9H, s), 1.02-1.16 (1H, m), 1.16-1.24 (3H, m), 2.30-2.42 (1H, m), 2.79 (1H, dd, J=15.6, 5.8 Hz), 3.04 (1H, dd, J=15.6, 8.9 Hz), 3.64 (2H, s), 3.77-3.86 (3H, m), 3.99-4.16 (2H, m), 5.47 (2H, s), 6.75 (1H, s), 6.85-6.95 (1H, m), 6.96-7.05 (2H, m), 7.35 (1H, s), 8.37 (1H, s), 8.75 (1H, s).

G) 3-cyclopropyl-3-(6-((5-(2,2-dimethylpropoxy)-6-(2-fluoro-5-methoxyphenyl)pyridin-3-yl) methoxy) pyrimidin-4-yl)propanoic acid To a solution of ethyl 3-cyclopropyl-3-(6-((6-(2-fluoro-5-methoxyphenyl)-5-(neopentyloxy)pyridin-3-yl)methoxy)pyrimidin-4-yl)propanoate (20 mg) in methanol (1.0 mL) was added 2N aqueous sodium hydroxide (91 μL) solution, and the mixture was stirred at room temperature for 20 hr. The reaction mixture was cooled to 0° C. and neutralized with 1N hydrochloric acid, and extracted with ethyl acetate. The extract was washed with saturated brine, and dried over anhydrous sodium sulfate. The solvent was evaporated under reduced pressure, and the residue was fractionated by HPLC (C18, mobile phase: water/acetonitrile (10 mM NH$_4$HCO$_3$-containing system)). The obtained fraction was evaporated under reduced pressure to give the title compound (4.4 mg) as a colorless oil.

$^1$H NMR (300 MHz, DMSO-d$_6$) δ 0.02-0.15 (1H, m), 0.17-0.41 (2H, m), 0.85 (10H, s), 0.94-1.05 (1H, m), 2.29-2.37 (1H, m), 3.40 (2H, s), 3.69 (2H, s), 3.76 (3H, s), 5.47 (2H, s), 6.86-7.07 (3H, m), 7.13-7.24 (1H, m), 7.67 (1H, s), 8.35 (1H, s), 8.75 (1H, s).

Example 37

3-cyclopropyl-3-(6-((6-(2-fluoro-5-methoxyphenyl)-5-(3,3,3-trifluoropropoxy)pyridin-3-yl)methoxy) pyrimidin-4-yl)propanoic acid

A) ethyl 3-cyclopropyl-3-(6-((6-(2-fluoro-5-methoxyphenyl)-5-(3,3,3-trifluoropropoxy)pyridin-3-yl) methoxy)pyrimidin-4-yl)propanoate Under a nitrogen atmosphere, to a solution of ethyl 3-cyclopropyl-3-(6-((6-(2-fluoro-5-methoxyphenyl)-5-hydroxypyridin-3-yl)methoxy)pyrimidin-4-yl)propanoate (57 mg) in toluene (1.2 mL) were added 3,3,3-trifluoro-1-propanol (21 μL) and cyanomethylenetributylphosphorane (64 uL), and the mixture was stirred at 100° C. for 4 hr. After allowing to cool to room temperature, the reaction mixture was poured into water, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (53 mg) as a pale-yellow amorphous solid.

$^1$H NMR (300 MHz, CDCl$_3$) δ 0.17-0.39 (2H, m), 0.42-0.57 (1H, m), 0.58-0.73 (1H, m), 1.00-1.15 (1H, m), 1.19 (3H, t, J=7.2 Hz), 2.28-2.44 (1H, m), 2.50-2.70 (2H, m), 2.75-2.85 (1H, m), 2.98-3.11 (1H, m), 3.81 (3H, s), 4.01-4.13 (2H, m), 4.26 (2H, t, J=6.8 Hz), 5.49 (2H, s), 6.76 (1H, s), 6.87-6.96 (1H, m), 6.98-7.06 (2H, m), 7.41 (1H, d, J=1.5 Hz), 8.44 (1H, d, J=1.5 Hz), 8.74 (1H, s).

B) 3-cyclopropyl-3-(6-((6-(2-fluoro-5-methoxyphenyl)-5-(3,3,3-trifluoropropoxy)pyridin-3-yl) methoxy)pyrimidin-4-yl)propanoic acid To a solution of ethyl 3-cyclopropyl-3-(6-((6-(2-fluoro-5-methoxyphenyl)-5-(3,3,3-trifluoropropoxy) pyridin-3-yl) methoxy)pyrimidin-4-yl)propanoate (53 mg) in methanol (1.0 mL) was added 2N aqueous sodium hydroxide (235 μL) solution at room temperature, and the mixture was stirred for 20 hr. The reaction mixture was cooled to 0° C., neutralized with 1N hydrochloric acid and extracted with ethyl acetate. The extract was washed with saturated brine. The organic layer was dried over anhydrous sodium sulfate, and the solvent was evaporated under reduced pressure. The residue was purified by preparative HPLC (C18, mobile phase: water/acetonitrile (10 mM NH$_4$HCO$_3$-containing system)), and the obtained fraction was evaporated under reduced pressure to give the title compound (32 mg) as a colorless oil.

$^1$H NMR (300 MHz, DMSO-d$_6$) δ 0.22-0.41 (3H, m), 0.46-0.60 (1H, m), 0.90-1.06 (1H, m), 2.28-2.40 (1H, m), 2.61-2.80 (3H, m), 2.82-2.97 (1H, m), 3.75 (3H, s), 4.28 (2H, t, J=5.9 Hz), 5.49 (2H, s), 6.91-7.04 (3H, m), 7.11-7.21 (1H, m), 7.78 (1H, d, J=1.5 Hz), 8.40 (1H, d, J=1.5 Hz), 8.76 (1H, d, J=0.8 Hz), 12.06 (1H, s).

Example 38

3-cyclopropyl-3-(6-((5-((5,5-dimethyltetrahydrofuran-3-yl)methoxy)-6-(2-fluoro-5-methoxyphenyl) pyridin-3-yl)methoxy)pyrimidin-4-yl)propanoic acid A) methyl 5-(benzyloxy)-6-chloronicotinate To a solution of methyl 6-chloro-5-hydroxynicotinate (10.5 g) in DMF (80 mL) was added 60% sodium hydride (2.80 g) at 0° C., and the mixture was stirred at 0° C. for 0.5 hr. Benzyl bromide (10.5 g) was added, and the mixture was stirred at room temperature for 20 hr. The reaction mixture was poured into water, and the precipitate was collected by filtration. The crude crystals were purified by silica gel column chromatography (petroleum ether/THF) to give the title compound (6.00 g) as a white solid.

MS (ESI+): [M+H]$^+$ 278.0

B) methyl 5-(benzyloxy)-6-(2-fluoro-5-methoxyphenyl)nicotinate

Under a nitrogen atmosphere, to a solution of methyl 5-(benzyloxy)-6chloronicotinate (2.77 g) in 1,4-dioxane (100 mL) were added 2-fluoro-5methoxyphenylboronic acid (2.00 g), potassium carbonate (2.76 g), [1,1-bis(diphenylphosphino)ferrocene]dichloropalladium(II) (36 mg) and water (10 mL), and the mixture was stirred at 80° C. for 20 hr. The reaction mixture was concentrated, and the residue was extracted with ethyl acetate. The extract was washed with saturated brine, and dried over anhydrous sodium sulfate. The solvent was evaporated under reduced pressure, and the residue was purified by silica gel column chromatography (petroleum ether/ethyl acetate) to give the title compound (3.50 g) as a colorless oil.

$^1$H NMR (400 MHz, CDCl$_3$) δ 3.82 (3H, s), 4.00 (3H, s), 5.21 (2H, s), 6.95-6.98 (1H, m), 7.06-7.11 (2H, m), 7.29-7.38 (5H, m), 7.95 (1H, d, J=1.6 Hz), 8.94 (1H, d, J=1.6 Hz).

C) methyl 6-(2-fluoro-5-methoxyphenyl)-5-hydroxynicotinate

Under a nitrogen atmosphere, to a solution of methyl 5-(benzyloxy)-6-(2-fluoro-5-methoxyphenyl)nicotinate (1.50 g) in ethyl acetate (20 mL) was added 10% palladium-activated carbon (433 mg) and the mixture was stirred under a hydrogen atmosphere at room temperature for 20 hr. The reaction mixture was filtered through celite, and the filtrate was concentrated under reduced pressure to give the title compound (1.00 g) as a yellow solid. This compound was used for the next step without further purification.

$^1$H NMR (400 MHz, DMSO-d$_6$) δ 3.81 (3H, s), 3.90 (3H, s), 6.99-/o 7.05 (2H, m), 7.20 (1H, t, J=8.8 Hz), 7.79 (1H, d, J=1.6 Hz), 8.65 (1H, d, J=2.0 Hz), 10.60 (1H, s).

D) dimethyl 2-(2-methylallyl)malonate

To a solution of diethyl malonate (2.30 g) in THF (20 mL) was added 60% sodium hydride (592 mg) at 0° C., and the mixture was stirred for 1 hr. 3Bromo-2-methylpropene (2.00 g) was added to the reaction mixture, and the mixture was stirred at room temperature for 20 hr. Aqueous ammonium chloride solution was added to the reaction mixture, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/petroleum ether) to give the title compound (2.60 g) as a colorless oil.

$^1$H NMR (400 MHz, CDCl$_3$) δ 1.26-1.30 (6H, m), 1.77 (3H, s), 2.63 (2H, d, J=7.6 Hz), 3.59 (1H, t, J=8.0 Hz), 4.18-4.21 (4H, m), 4.75 (1H, s), 4.80 (1H, s).

E) 2-(2-methylallyl)propane-1,3-diol

To a solution of lithium aluminum hydride (9.20 g) in THF (250 mL) was slowly added a solution of dimethyl 2-(2-methylallyl)malonate (13.0 g) in THF (20 mL) at 0° C. The reaction mixture was heated under reflux for 2 hr. Water (60 mL) and 15% aqueous sodium hydroxide solution (72 mL) were added to the reaction mixture, and the mixture was filtered and extracted with ethyl acetate. The extract was dried over anhydrous sodium sulfate, and the solvent was evaporated under reduced pressure. The residue was purified by silica gel column chromatography (ethyl acetate/petroleum ether) to give the title compound (4.80 g) as a yellow oil.

$^1$H NMR (400 MHz, CDCl$_3$) δ 1.76 (3H, s), 2.01 (3H, s), 2.49 (2H, s), 3.64-3.68 (2H, m), 3.78-3.82 (2H, m), 4.74 (1H, m), 4.81 (1H, m).

F) (5,5-dimethyltetrahydrofuran-3-yl)methanol

Under a nitrogen atmosphere, a solution of 2-(2-methylallyl)propane-1,3-diol (2.00 g) and silver trifluoromethanesulfonate (197 mg) in dichloromethane (40 mL) was stirred at 80° C. for 2 days. The reaction mixture was filtered through celite, and the filtrate was evaporated under reduced pressure to give the title compound (2.00 g) as a brown oil. This compound was used for the next step without further purification.

$^1$H NMR (400 MHz, CDCl$_3$) δ 1.23 (3H, s), 1.32 (3H, s), 1.43-1.48 (1H, m), 1.90-1.95 (1H, m), 2.39 (1H, s), 2.60-2.62 (1H, m), 3.60-3.70 (3H, m), 3.97-4.02 (1H, m).

G) 4-(bromomethyl)-2,2-dimethyltetrahydrofuran

To a solution of (5,5-dimethyltetrahydrofuran-3-yl)methanol (2.00 g) in dichloromethane (30 ml) were added carbon tetrabromide (6.10 g) and triphenylphosphine (4.80 g) at room temperature. The reaction mixture was stirred at room temperature for 20 hr, and extracted with diethyl ether. The extract was dried over anhydrous sodium sulfate, and the solvent was evaporated under reduced pressure. The residue was purified by silica gel column chromatography (ethyl acetate/petroleum ether) to give the title compound (2.40 g) as a colorless oil.

$^1$H-NMR (400 MHz, CDCl$_3$) δ 1.22 (3H, s), 1.31 (3H, s), 1.47-1.52 (1H, m), 1.98-2.03 (1H, m), 2.78-2.82 (1H, m), 3.39-3.42 (2H, m), 3.60-3.65 (1H, m), 4.00-4.04 (1H, m).

H) methyl 5-((5,5-dimethyltetrahydrofuran-3-yl) methoxy)-6-(2-fluoro-5-methoxyphenyl)nicotinate A solution of methyl 6-(2-fluoro-5-methoxyphenyl)-5-hydroxynicotinate (700 mg), potassium carbonate (1.10 g) and 4-(bromomethyl)-2,2-dimethyltetrahydrofuran (730 mg) in DMF (5.0 mL) was stirred at 80° C. for 4 hr. Water was added to the reaction mixture, and the mixture was extracted with ethyl acetate and the extract was dried over anhydrous sodium sulfate. The solvent was evaporated under reduced pressure to give the title compound (980 mg) as a pale-yellow oil. This compound was used for the next step without further purification.

$^1$H NMR (400 MHz, DMSO-d$_6$) δ 1.13 (3H, s), 1.16 (3H, s), 1.45-1.49 (1H, m), 1.76-1.79 (1H, m), 2.47-2.51 (1H, m), 3.47-3.56 (2H, m), 3.77 (3H, s), 3.93 (3H, s), 4.04-4.08 (1H, m), 4.12-4.14 (1H, m), 6.99-7.06 (2H, m), 7.22 (1H, t, J=9.2 Hz), 7.92 (1H, s), 8.77 (1H, s).

I) (5-((5,5-dimethyltetrahydrofuran-3-yl)methoxy)-6-(2-fluoro-5-methoxyphenyl)pyridin-3-yl)methanol A solution of methyl 5-((5,5-dimethyltetrahydrofuran-3-yl)methoxy)-6-(2-fluoro-5-methoxyphenyl)nicotinate (700 mg) in methanol (10 mL) was cooled to 0° C., and sodium tetrahydroborate (342 mg) was slowly added by small portions. The reaction mixture was stirred at 60° C. for 4 hr. The solvent was evaporated under reduced pressure, saturated brine was added to the residue, and the mixture was extracted with ethyl acetate. The extract was dried over anhydrous sodium sulfate, and the solvent was evaporated under reduced pressure to give the title compound (700 mg) as a pale-yellow oil. This compound was used for the next step without further purification.

$^1$H NMR (400 MHz, DMSO-d$_6$) δ 1.15 (3H, s), 1.21 (3H, s), 1.41-1.46 (1H, m), 1.76-1.82 (1H, m), 2.62-2.65 (1H, m), 3.46-3.50 (1H, m), 3.72-3.79 (4H, m), 3.92-3.96 (1H, m), 4.00-4.06 (1H, m), 4.58-4.60 (1H, m), 5.36-5.39 (1H, m), 6.92-7.00 (2H, m), 7.17 (1H, t, J=9.2 Hz), 7.49 (1H, s), 8.20 (1H, s).

J) 3-cyclopropyl-3-(6-((5-((5,5-dimethyltetrahydrofuran-3-yl)methoxy)-6-(2-fluoro-5-methoxyphenyl) pyridin-3-yl)methoxy)pyrimidin-4-yl)propanoic acid To a solution of (5-((5,5-dimethyltetrahydrofuran-3-yl) methoxy)-6-(2-fluoro-5-methoxyphenyl)pyridin-3-yl) methanol (180 mg) and ethyl 3-(6-chloropyrimidin-4-yl)-3-cyclopropylpropanoate (140 mg) in THF (5.0 mL) was slowly added 60% sodium hydride (60 mg) at 0° C. by small portions, and the mixture was stirred at 50° C. for 3 hr. The mixture was acidified with 1N hydrochloric acid at 0° C. and extracted with ethyl acetate. The extract was dried over anhydrous sodium sulfate, and the solvent was evaporated under reduced pressure. The residue was purified by preparative HPLC (C18, mobile phase: water/acetonitrile (10 mM NH$_4$HCO$_3$-containing system)), and the obtained fraction was evaporated under reduced pressure to give the title compound (40 mg) as a white solid.

$^1$H NMR (400 MHz, DMSO-d$_6$) δ 0.27-0.36 (3H, m), 0.48-0.54 (1H, br), 0.94-1.00 (1H, m), 1.10 (3H, s), 1.14 (3H, s), 1.40-1.45 (1H, m), 1.75-1.82 (1H, m), 2.30-2.36 (1H, m), 2.60-2.67 (2H, m), 2.82-2.88 (1H, m), 3.46-3.50 (1H, m), 3.71-3.80 (4H, m), 3.95-4.07 (2H, m), 5.47 (1H, s), 6.92-7.01 (3H, m), 7.18 (1H, t, J=9.2 Hz), 7.71 (1H, s), 8.36 (1H, s), 8.76 (1H, s).

Example 39

3-cyclopropyl-3-(6-((5-((2,2-dimethyltetrahydro-2H-pyran-4-yl)methoxy)-6-(2-fluoro-5-methoxyphenyl) pyridin-3-yl)methoxy)pyrimidin-4-yl)propanoic acid A) 4-(methoxymethylene)-2,2-dimethyltetrahydro-2H-pyran Thereto was added (methoxymethyl)triphenylphosphonium chloride (17.0 g), and the mixture was dried under reduced pressure at 100° C. for 1 hr. Under a nitrogen atmosphere, dehydrated THF (80 mL) was added, and potassium tert-butoxide (5.40 g) was further added at −30° C. After 40 min, to the reaction mixture was added dropwise a solution of 2,2-dimethyltetrahydropyran-4-one (5.20 g) in dehydrated THF (5.0 mL) over 15 min, and the mixture was stirred at room temperature for 4 hr. To the reaction mixture was added aqueous ammonium chloride solution, and the mixture was extracted with diethyl ether. The extract was washed with saturated brine, and dried. The solvent was evaporated, and the residue was purified by silica gel column chromatography (ethyl acetate/petroleum ether) to give an isomer mixture (E:Z=1:1, 4.00 g) of the title compound as a colorless oil.

$^1$H NMR (400 MHz, CDCl$_3$) δ 1.18 (6H, s), 1.20 (6H, s), 1.92 (2H, d, J=1.2 Hz), 1.98-2.02 (2H, m), 2.17 (2H, d, J=0.8 Hz), 2.23-2.26 (2H, m), 3.54 (3H, s), 3.56 (3H, s), 3.64-3.70 (4H, m), 5.77-5.78 (1H, m), 5.92-5.93 (1H, m).

B) 2,2-dimethyltetrahydro-2H-pyran-4-carbaldehyde

To a solution of 4-(methoxymethylene)-2,2-dimethyltetrahydro-2H-pyran (4.00 g) in THF (20 mL) were added water (8.0 mL) and p-toluenesulfonic acid (4.90 g), and the mixture was stirred at room temperature for 20 hr. To the reaction mixture was added water, and the mixture was extracted with diethyl ether. The extract was dried over anhydrous sodium sulfate, and the solvent was evaporated under reduced pressure. The residue was purified by silica gel column chromatography (ethyl acetate/petroleum ether) to give the title compound (2.20 g) as a colorless oil.

¹H NMR (400 MHz, CDCl₃) δ 1.24 (3H, s), 1.27 (3H, s), 1.53-1.60 (2H, m), 1.74-1.81 (2H, m), 2.59-2.64 (1H, m), 3.66-3.73 (1H, m), 3.80-3.84 (1H, m), 9.61 (1H, s).

C) (2,2-dimethyltetrahydro-2H-pyran-4-yl)methanol

To a solution of 2,2-dimethyltetrahydro-2H-pyran-4-carbaldehyde (2.50 g) in methanol (15 mL) was slowly added at 0° C. sodium tetrahydroborate (3.30 g) by small portions, and the mixture was stirred at room temperature for 6 hr. The solvent was evaporated under reduced pressure, and saturated brine was added to the residue. The reaction mixture was extracted with dichloromethane, and the extract was dried over anhydrous sodium sulfate. The solvent was evaporated under reduced pressure to give the title compound (2.50 g) as a pale-yellow oil. This compound was used for the next step without further purification.
¹H NMR (400 MHz, CDCl₃) δ 1.23 (6H, s), 1.56-1.65 (4H, m), 1.90-1.94 (1H, m), 3.45-3.48 (2H, m), 3.67-3.71 (1H, m), 3.75-3.77 (1H, m).

D) 4-(bromomethyl)-2,2-dimethyltetrahydro-2H-pyran

To a solution of (2,2-dimethyltetrahydro-2H-pyran-4-yl)methanol (2.50 g) in dichloromethane (30 mL) were added carbon tetrabromide (6.80 g) and triphenylphosphine (5.40 g), and the mixture was stirred at room temperature for 20 hr. Water was added and the mixture was extracted with diethyl ether. The extract was dried over anhydrous sodium sulfate and the solvent was evaporated under reduced pressure. The residue was purified by silica gel column chromatography (petroleum ether) to give the title compound (1.10 g) as a colorless oil.
¹H NMR (400 MHz, CDCl₃) δ 1.08-1.27 (8H, m), 1.67-1.77 (2H, m), 1.98-2.08 (1H, m), 3.24 (2H, d, J=6.8 Hz), 3.62-3.69 (1H, m), 3.75-3.80 (1H, m).

E) methyl 5-((2,2-dimethyltetrahydro-2H-pyran-4-yl)methoxy)-6-(2-fluoro-5-methoxyphenyl)nicotinate To a solution of methyl 6-(2-fluoro-5-methoxyphenyl)-5-hydroxynicotinate (739 mg) and 4-(bromomethyl)-2,2-dimethyltetrahydro-2H-pyran (828 mg) in DMF (20 mL) was added potassium carbonate (736 mg), and the mixture was stirred at room temperature for 2 hr. The reaction mixture was poured into water (100 mL), and the mixture was extracted with ethyl acetate. The extract was dried over anhydrous sodium sulfate and the solvent was evaporated under reduced pressure. The residue was purified by silica gel column chromatography (ethyl acetate/petroleum ether) to give the title compound (950 mg) as a colorless oil.
¹H NMR (400 MHz, DMSO-d₆) δ 1.23 (3H, s), 1.26 (3H, s), 1.56-1.65 (4H, m), 2.17-2.20 (1H, m), 3.63-3.70 (1H, m), 3.75-3.80 (1H, m), 3.83 (3H, s), 3.89 (2H, m), 4.00 (3H, s), 6.94-6.98 (1H m), 7.03-7.08 (2H, m), 7.85 (1H, d, J=1.2 Hz), 8.92 (1H, d, J=2.0 Hz).

F) (5-((2,2-dimethyltetrahydro-2H-pyran-4-yl)methoxy)-6-(2-fluoro-5-methoxyphenyl)pyridin-3-yl)methanol To a solution of methyl 5-((2,2-dimethyltetrahydro-2H-pyran-4-yl)methoxy)-6-(2-fluoro-5-methoxyphenyl)nicotinate (950 mg) in methanol (20 mL) was added, at 0° C., sodium tetrahydroborate (1.16 g) by small portions, and the mixture was stirred at 60° C. for 4 hr. The solvent was evaporated under reduced pressure, and ethyl acetate was added to the residue. The organic layer was washed with saturated brine, and dried over anhydrous sodium sulfate. The solvent was evaporated under reduced pressure to give the title compound (930 mg) as a pale-yellow oil.
¹H NMR (400 MHz, CDCl₃) δ 1.13-1.31 (8H, m), 1.54-1.64 (2H, m), 2.13-2.18 (1H, m), 3.63-3.69 (1H, m), 3.74-3.77 (1H, m), 3.78-3.80 (5H, m), 4.80 (2H, s), 6.90-6.94 (1H, m), 7.01-7.07 (2H, m), 7.37 (1H, s), 8.27 (1H, s).

G) 3-cyclopropyl-3-(6-((5-((2,2-dimethyltetrahydro-2H-pyran-4-yl)methoxy)-6-(2-fluoro-5-methoxyphenyl)pyridin-3-yl)methoxy)pyrimidin-4-yl)propanoic acid To a solution of (5-((2,2-dimethyltetrahydro-2H-pyran-4-yl)methoxy)-6-(2-fluoro-5-methoxyphenyl)pyridin-3-yl)methanol (930 mg) and ethyl 3-(6-chloropyrimidin-4-yl)-3-cyclopropylpropanoate (945 mg) in THF (20 mL) was slowly added, at 0° C., 60% sodium hydride (300 mg) by small portions, and the mixture was stirred at 60° C. for 3 hr. After cooling to 0° C., water (1.0 mL) was added to the reaction mixture, and the mixture was further stirred at 60° C. for 1 hr. The mixture was acidified with 1N hydrochloric acid at 0° C., and the mixture was extracted with ethyl acetate. The extract was washed with saturated brine, and dried over anhydrous sodium sulfate. The solvent was evaporated under reduced pressure, and the residue was purified by preparative HPLC (C18, mobile phase: water/acetonitrile (0.1% TFA-containing system)), and saturated aqueous sodium carbonate solution was added to the obtained fraction. The mixture was extracted with ethyl acetate, and the extract was dried over anhydrous sodium sulfate and evaporated under reduced pressure to give the title compound (192 mg) as a white solid.
¹H NMR (400 MHz, DMSO-d₆) δ 0.28-0.38 (3H, m), 0.50-0.55 (1H, m), 0.94-1.16 (9H, m), 1.47-1.50 (2H, m), 2.01-2.04 (1H, m), 2.33-2.37 (1H, m), 2.63-2.69 (1H, m), 2.86-2.93 (1H, m), 3.47-3.60 (2H, m), 3.77 (3H, s), 3.86 (2H, d. J=6.4 Hz), 5.49 (2H, s), 6.75-7.02 (3H, m), 7.18 (1H, t, J=9.2 Hz), 7.70 (1H, s), 8.36 (1H, s), 8.77 (1H, s).

Example 40

3-cyclopropyl-3-(2-((5-(2,2-dimethylpropyl)-6-(2-fluoro-5-methoxyphenyl)pyridin-3-yl)methoxy)pyridin-4-yl)propanoic acid A) 5-(bromomethyl)-2-(2-fluoro-5-methoxyphenyl)-3-neopentylpyridine Under a nitrogen atmosphere, phosphorus tribromide (37 µL) was added to DMF (1.0 mL) at 0° C. and the mixture was stirred at 0° C. for 5 min. To the obtained white suspension was added (6-(2-fluoro-5-methoxyphenyl)-5-neopentylpyridin-3-yl)methanol (100 mg), and the mixture was stirred at room temperature for 30 min. A saturated aqueous sodium hydrogen carbonate solution was added to the reaction solution at 0° C., and the mixture was extracted with ethyl acetate. The extract was washed with water and saturated brine, and dried over anhydrous magnesium sulfate. The solvent was evaporated under reduced pressure to give a crude product of the title compound (88 mg) as a pale-yellow oil. This compound was used for the next step without further purification.
¹H NMR (400 MHz, DMSO-d₆) δ 0.67 (9H, s), 2.55 (2H, brs), 3.75 (3H, s), 4.80 (2H, s), 6.93 (1H, dd, J=5.6, 3.1 Hz), 6.98-7.07 (1H, m), 7.12-7.29 (1H, m), 7.78 (1H, s), 8.59 (1H, d, J=1.8 Hz).

B) ethyl 3-cyclopropyl-3-(2-((6-(2-fluoro-5-methoxyphenyl)-5-neopentylpyridin-3-yl)methoxy)pyridin-4-yl)propanoate A mixture of 5-(bromomethyl)-2-(2-fluoro-5-methoxyphenyl)-3-neopentylpyridine (88 mg), ethyl 3-cyclopropyl-3-(2-hydroxypyridin-4-yl)propanoate (62 mg), silver carbonate (72.6 mg) and toluene (2.0 mL) was heated under reflux for 3 hr. The reaction mixture was cooled to room temperature and filtered. The solvent in the filtrate was evaporated under reduced pressure, and the residue was purified by silica gel column chromatography (ethyl acetate/hexane) to give the title compound (28 mg) as an orange oil.

$^1$H NMR (400 MHz, DMSO-$d_6$) δ 0.12-0.20 (1H, m), 0.21-0.29 (1H, m), 0.29-0.38 (1H, m), 0.45-0.57 (1H, m), 0.64 (9H, s), 0.96-1.05 (1H, m), 1.07 (3H, t, J=7.2 Hz), 2.21-2.30 (1H, m), 2.54 (2H, brs), 2.76 (2H, d, J=7.5 Hz), 3.75 (3H, s), 3.92-4.01 (2H, m), 5.43 (2H, s), 6.82 (1H, s), 6.91 (1H, dd, J=5.6, 3.2 Hz), 6.96 (1H, d, J=5.3 Hz), 6.98-7.05 (1H, m), 7.21 (1H, t, J=9.2 Hz), 7.76 (1H, s), 8.07 (1H, d, J=5.1 Hz), 8.60 (1H, s).

C) 3-cyclopropyl-3-(2-((5-(2,2-dimethylpropyl)-6-(2-fluoro-5-methoxyphenyl)pyridin-3-yl)methoxy)pyridin-4-yl)propanoic acid To a solution of ethyl 3-cyclopropyl-3-(2-((6-(2-fluoro-5-methoxyphenyl)-5-neopentylpyridin-3-yl)methoxy)pyridin-4-yl)propanoate (28 mg) in THF (1.0 mL) and methanol (0.50 ml) was added 1N aqueous sodium hydroxide solution (1.0 mL), and the mixture was stirred at room temperature for 1 hr. The solvent in the reaction mixture was evaporated under reduced pressure, and the residue was purified by silica gel column chromatography (ethyl acetate/hexane) to give the title compound (21 mg) as a yellow amorphous solid.

MS (ESI+): [M+H]$^+$ 493.2

$^1$H NMR (400 MHz, DMSO-$d_6$) δ 0.11-0.20 (1H, m), 0.23-0.38 (2H, m), 0.44-0.56 (1H, m), 0.64 (9H, s), 0.93-1.05 (1H, m), 2.20-2.31 (1H, m), 2.55 (2H, brs), 2.66 (2H, d, J=7.2 Hz), 3.75 (3H, s), 5.42 (2H, s), 6.80 (1H, s), 6.92 (1H, dd, J=5.5, 3.1 Hz), 6.96 (1H, d, J=5.0 Hz), 6.98-7.07 (1H, m), 7.21 (1H, t, J=9.2 Hz), 7.77 (1H, s), 8.07 (1H, d, J=5.3 Hz), 8.60 (1H, s), 12.20 (1H, brs).

Example 41

3-cyclopropyl-3-(6-((5-(2-fluoro-5-methoxyphenyl)-4-isobutoxypyrimidin-2-yl)methoxy)pyrimidin-4-yl)propanoic acid

A) 5-bromo-2-chloro-4-isobutoxypyrimidine

Under a nitrogen atmosphere, to a solution of 5-bromo-2,4-dichloropyrimidine (2.56 mL) and 2-methyl-1-propanol (1.85 mL) in THF (80 mL) was added 60% sodium hydride (960 mg) at 0° C., and the mixture was stirred at 0° C. for 1 hr. To the reaction mixture was added water at 0° C., and the mixture was extracted with ethyl acetate. The extract was washed with water and saturated brine, and dried over anhydrous magnesium sulfate. The solvent was evaporated under reduced pressure, and the residue was purified by silica gel column chromatography (NH, ethyl acetate/hexane) to give a crude product of the title compound (4.15 g) as a colorless oil. This compound was used for the next step without further purification.

$^1$H NMR (300 MHz, DMSO-$d_6$) δ 0.99 (6H, d, J=6.8 Hz), 2.01-2.15 (1H, m), 4.20 (2H, d, J=6.8 Hz), 8.72 (1H, s).

B) 5-bromo-4-isobutoxypyrimidine-2-carbonitrile

To a solution of 5-bromo-2-chloro-4-isobutoxypyrimidine (2.16 g) and 1,4-diazabicyclo[2.2.2]octane (1.83 g) in acetonitrile (30 mL) was added tetraethylammonium cyanide (1.40 g), and the mixture was stirred at room temperature for 30 min. To the reaction mixture was added water at room temperature, and the mixture was extracted with ethyl acetate. The extract was washed with water and saturated brine, and dried over anhydrous magnesium sulfate. The solvent was evaporated under reduced pressure, and the residue was purified by silica gel column chromatography (ethyl acetate/hexane) to give the title compound (1.71 g) as a colorless oil.

$^1$H NMR (300 MHz, DMSO-$d_6$) δ 1.00 (6H, d, J=6.4 Hz), 2.04-2.22 (1H, m), 4.24 (3H, d, J=6.8 Hz), 8.98 (1H, s).

C) 5-(2-fluoro-5-methoxyphenyl)-4-isobutoxypyrimidine-2-carbonitrile

Under an argon atmosphere, to a solution of methyl 5-bromo-4-isobutoxypyrimidine-2-carbonitrile (1.71 g) in toluene (20 mL) were added 2-fluoro-5-methoxyphenylboronic acid (1.70 g), tris(dibenzylideneacetone)dipalladium(0) (245 mg), 2-dicyclohexylphosphino-2',6'-dimethoxybiphenyl (439 mg) and 2.0 M aqueous sodium carbonate solution (10.0 mL), and the mixture was stirred at 80° C. for 1 hr. The reaction mixture was filtered through celite, and water was added at room temperature. The reaction mixture was extracted with ethyl acetate, and the extract was washed with water and saturated brine. The organic layer was dried over anhydrous magnesium sulfate, and the solvent was evaporated under reduced pressure. The residue was purified by silica gel column chromatography (ethyl acetate/hexane) to give the title compound (1.78 g) as a yellow oil.

$^1$H NMR (300 MHz, DMSO-$d_6$) δ 0.90 (6H, d, J=6.8 Hz), 1.87-2.08 (1H, m), 3.78 (3H, s), 4.21 (2H, d, J=6.4 Hz), 7.00-7.16 (2H, m), 7.20-7.36 (1H, m), 8.76 (1H, s).

D) ethyl 5-(2-fluoro-5-methoxyphenyl)-4-isobutoxypyrimidine-2-carboxylate

To a solution of 5-(2-fluoro-5-methoxyphenyl)-4-isobutoxypyrimidine-2-carbonitrile (1.00 g) in ethanol (25 mL) and water (8.3 mL) was added conc. sulfuric acid (25 mL) at 0° C., and the mixture was stirred at 120° C. for 1 hr. To the reaction mixture was added water at 0° C., and the mixture was extracted with ethyl acetate. The extract was washed with water, saturated aqueous sodium hydrogen carbonate solution and saturated brine, and dried over anhydrous magnesium sulfate. The solvent was evaporated under reduced pressure, and the residue was purified by silica gel column chromatography (ethyl acetate/hexane) to give the title compound (284 mg) as a pale-yellow oil.

$^1$H NMR (300 MHz, DMSO-$d_6$) δ 0.91 (6H, d, J=6.4 Hz), 1.34 (3H, t, J=7.0 Hz), 1.90-2.07 (1H, m), 3.78 (3H, s), 4.21 (2H, d, J=6.4 Hz), 4.38 (2H, q, J=7.2 Hz), 6.99-7.14 (2H, m), 7.28 (1H, t, J=9.2 Hz), 8.69 (1H, s).

E) (5-(2-fluoro-5-methoxyphenyl)-4-isobutoxypyrimidin-2-yl)methanol

To a suspension of lithium aluminum hydride (93 mg) in diethyl ether (5.0 mL) was added a solution of ethyl 5-(2-fluoro-5-methoxyphenyl)-4-isobutoxypyrimidine-2-carboxylate (284 mg) in diethyl ether (2.0 mL) at 0° C., and the mixture was stirred for 10 min. To the reaction mixture were added water and aqueous sodium hydroxide solution, and the resulting white precipitate was filtered off. The solvent in the filtrate was evaporated under reduced pressure, and the residue was dissolved in toluene (2.0 mL) and THF (1.0 mL). To the obtained solution was added 2,3-dichloro-5,6-dicyano-p-benzoquinone (277 mg), and the mixture was stirred at room temperature for 20 min. The solvent in the reaction mixture was evaporated under reduced pressure, and the residue was purified by silica gel column chromatography (NH, ethyl acetate/hexane) to give the title compound (111 mg) as a colorless solid.

$^1$H NMR (300 MHz, DMSO-d$_6$) δ 0.90 (6H, d, J=6.8 Hz), 1.72-2.05 (1H, m), 3.77 (3H, s), 4.17 (2H, d, J=6.8 Hz), 4.55 (2H, d, J=6.1 Hz), 5.24 (1H, t, J=6.1 Hz), 6.71-7.08 (2H, m), 7.15-7.34 (1H, m), 8.50 (1H, s).

F) ethyl 3-cyclopropyl-3-(6-((5-(2-fluoro-5-methoxyphenyl)-4-isobutoxypyrimidin-2-yl)methoxy)pyrimidin-4-yl)propanoate Under a nitrogen atmosphere, to a solution of (5-(2-fluoro-5-methoxyphenyl)-4-isobutoxypyrimidin-2-yl)methanol (111 mg) and ethyl 3-(6-chloropyrimidin-4-yl)-3-cyclopropylpropanoate (92 mg) in THF (2.0 mL) was added 60% sodium hydride (17 mg) at room temperature, and the mixture was stirred at 50° C. for 2 hr. To the reaction mixture was added 1N hydrochloric acid at 0° C., and the mixture was extracted with ethyl acetate. The extract was washed with water and saturated brine, and dried over anhydrous magnesium sulfate. The solvent was evaporated under reduced pressure, and the residue was purified by silica gel column chromatography (NH, ethyl acetate/hexane) to give the title compound (111 mg) as a colorless oil.

$^1$H NMR (300 MHz, DMSO-d$_6$) δ 0.22-0.44 (3H, m), 0.48-0.61 (1H, m), 0.81 (6H, d, J=6.8 Hz), 0.91-1.05 (1H, m), 1.10 (3H, t, J=7.0 Hz), 1.69-1.95 (1H, m), 2.27-2.46 (1H, m), 2.62-2.82 (1H, m), 2.84-3.03 (1H, m), 3.76 (3H, s), 3.91-4.07 (4H, m), 5.56 (2H, s), 6.88-7.07 (3H, m), 7.13-7.31 (1H, m), 8.49 (1H, s), 8.63 (1H, d, J=1.1 Hz).

G) 3-cyclopropyl-3-(6-((5-(2-fluoro-5-methoxyphenyl)-4-isobutoxypyrimidin-2-yl)methoxy)pyrimidin-4-yl)propanoic acid To a solution of ethyl 3-cyclopropyl-3-(6-((5-(2-fluoro-5-methoxyphenyl)-4-isobutoxypyrimidin-2-yl)methoxy)pyrimidin-4-yl)propanoate (111 mg) in THF (2.0 mL) and methanol (1.0 ml) was added 1N aqueous sodium hydroxide solution (2.0 mL), and the mixture was stirred at room temperature for 30 min. To the reaction mixture was added 1N hydrochloric acid (2.0 mL) at 0° C., and the mixture was extracted with ethyl acetate. The extract was washed with water and saturated brine, and dried over anhydrous magnesium sulfate. After silica gel filtration, the solvent was evaporated under reduced pressure to give the title compound (105 mg) as a white amorphous solid.

MS (ESI+): [M+H]$^+$ 497.1

$^1$H NMR (300 MHz, DMSO-d$_6$) δ 0.19-0.45 (3H, m), 0.47-0.60 (1H, m), 0.81 (6H, d, J=6.8 Hz), 0.90-1.08 (1H, m), 1.75-1.93 (1H, m), 2.29-2.43 (1H, m), 2.59-2.75 (1H, m), 2.79-2.97 (1H, m), 3.76 (3H, s), 4.03 (2H, d, J=6.4 Hz), 5.55 (2H, s), 6.91-7.09 (3H, m), 7.16-7.30 (1H, m), 8.49 (1H, s), 8.64 (1H, d, J=0.8 Hz), 12.05 (1H, brs).

Example 42

3-cyclopropyl-3-(5-fluoro-2-((5-(2-fluoro-5-methoxyphenyl)-6-neopentylpyridin-2-yl)methoxy)pyridin-4-yl)propanoic acid Step A) cyclopropyl(5-fluoro-2-methoxypyridin-4-yl)methanol Under a nitrogen atmosphere, a hexane solution (1.6 M, 29.5 mL) of n-butyllithium was added to a solution of diisopropylamine (6.60 mL) in THF (80 mL) at −15° C., and the mixture was stirred at −15° C. for 5 min. A solution of 5-fluoro-2-methoxypyridine (5.00 g) in THF (30 mL) was added dropwise to the reaction mixture at −78° C. over 15 min, and the mixture was stirred at −78° C. for 1.5 hr. A solution of cyclopropanecarbaldehyde (3.53 mL) in THF (15 mL) was added dropwise to the reaction mixture at −78° C. over 20 min, and the mixture was stirred at −78° C. for 30 min. To the reaction mixture was added saturated aqueous ammonium chloride solution at 0° C., and the mixture was extracted with ethyl acetate. The extract was washed with water and saturated brine, and dried over anhydrous magnesium sulfate. The solvent was evaporated under reduced pressure to give a crude product (8.87 g) of the title compound as a pale-yellow oil. This compound was used for the next step without further purification.

$^1$H NMR (300 MHz, DMSO-d$_6$) δ 0.25-0.52 (4H, m), 0.94-1.14 (1H, m), 3.82 (3H, s), 4.30 (1H, dd, J=6.9, 5.0 Hz), 5.52 (1H, d, J=4.9 Hz), 6.88 (1H, d, J=4.8 Hz), 8.05 (1H, d, J=1.8 Hz).

Step B) cyclopropyl(5-fluoro-2-methoxypyridin-4-yl)methanone

To a solution of cyclopropyl(5-fluoro-2-methoxypyridin-4-yl)methanol (entire amount) obtained in Example 42, step A, and triethylamine (55.2 mL) in DMSO (200 mL) was added sulfur trioxide pyridine complex (31.5 g), and the mixture was stirred at room temperature for 30 min. To the reaction mixture was added water at room temperature, and the mixture was extracted with ethyl acetate. The extract was washed with water and saturated brine, and dried over anhydrous magnesium sulfate. The solvent was evaporated under reduced pressure to give a crude product (7.49 g) of the title compound as a brown oil. This compound was used for the next step without further purification.

$^1$H NMR (300 MHz, DMSO-d$_6$) δ 1.07-1.22 (4H, m), 2.56-2.67 (1H, m), 3.88 (3H, s), 7.06 (1H, d, J=4.7 Hz), 8.34 (1H, d, J=1.9 Hz).

Step C) ethyl 3-cyclopropyl-3-(5-fluoro-2-methoxypyridin-4-yl)acrylate

Under a nitrogen atmosphere, to a suspension of 60% sodium hydride (2.76 g) in THF (100 mL) was added ethyl diethylphosphonoacetate (15.2 mL) at 0° C., and the mixture was stirred at 0° C. for 5 min. To the obtained colorless solution was added cyclopropyl(5-fluoro-2-methoxypyridin-4-yl)methanone (entire amount) obtained in Example 42, step B, at 0° C., and the mixture was stirred at room temperature for 30 min. To the reaction mixture was added water at room temperature, and the mixture was extracted with ethyl acetate. The extract was washed with water and saturated brine, and dried over anhydrous magnesium sulfate. The solvent was evaporated under reduced pressure to give a crude product of the title compound as a brown oil. This compound was used for the next step without further purification.

Step D) ethyl 3-cyclopropyl-3-(5-fluoro-2-methoxy-pyridin-4-yl)propanoate

To a solution of ethyl 3-cyclopropyl-3-(5-fluoro-2-methoxypyridin-4-yl)acrylate (entire amount) in acetic acid (100 mL) was added a zinc powder (50.2 g), and the mixture was stirred at room temperature for 30 min. The reaction mixture was filtered, and the solvent in the filtrate was evaporated under reduced pressure. The residue was purified by silica gel column chromatography (ethyl acetate/hexane) to give the title compound (5.72 g) as a colorless oil.
$^1$H NMR (400 MHz, DMSO-$d_6$) δ 0.05-0.16 (1H, m), 0.23-0.41 (2H, m), 0.47-0.58 (1H, m), 0.99-1.08 (1H, m), 1.08 (3H, t, J=7.1 Hz), 2.51-2.59 (1H, m), 2.73-2.90 (2H, m), 3.81 (3H, s), 3.90-4.07 (2H, m), 6.91 (1H, d, J=4.9 Hz), 8.05 (1H, s).

Step E) ethyl 3-cyclopropyl-3-(5-fluoro-2-hydroxy-pyridin-4-yl)propanoate

Under a nitrogen atmosphere, to a solution of ethyl 3-cyclopropyl-3-(5-fluoro-2-methoxypyridin-4-yl)propanoate (5.72 g) in DMF (10 ml) was added pyridinium chloride (24.7 g), and the mixture was stirred at 130° C. for 1 hr. To the reaction mixture was added ethyl acetate at 0° C., and the resulting precipitate was removed by filtration. The solvent in the filtrate was evaporated under reduced pressure, and the residue was purified by silica gel column chromatography (methanol/ethyl acetate) to give the title compound (4.29 g) as a colorless oil.
$^1$H NMR (400 MHz, DMSO-$d_6$) δ 0.07-0.18 (1H, m), 0.21-0.31 (1H, m), 0.35-0.44 (1H, m), 0.47-0.60 (1H, m), 0.93-1.05 (1H, m), 1.10 (3H, t, J=7.0 Hz), 2.35-2.46 (1H, m), 2.66-2.86 (2H, m), 3.90-4.09 (2H, m), 6.43 (1H, d, J=5.9 Hz), 7.60 (1H, d, J=4.0 Hz), 11.14 (1H, brs).

Step F) ethyl 3-cyclopropyl-3-(5-fluoro-2-((5-(2-fluoro-5-methoxyphenyl)-6-neopentylpyridin-2-yl)methoxy)pyridin-4-yl)propanoate Silver oxide (327 mg) was added to a solution of (6-(2,2-dimethylpropyl)-5-(2-fluoro-5-methoxyphenyl)pyridin-2-yl)methanol (415 mg) and ethyl 3-cyclopropyl-3-(5-fluoro-2-hydroxypyridin-4-yl)propanoate (300 mg) in toluene (5 mL) at room temperature, and the mixture was heated under reflux for 2 hr. The reaction mixture was filtered, and the solvent in the filtrate was evaporated under reduced pressure. The residue was purified by silica gel column chromatography (ethyl acetate/hexane) to give the title compound (379 mg) as a pale-yellow oil.
$^1$H NMR (400 MHz, DMSO-$d_6$) δ 0.09-0.18 (1H, m), 0.24-0.43 (2H, m), 0.55 (1H, d, J=4.0 Hz), 0.71 (9H, s), 0.99-1.13 (1H, m), 1.08 (3H, t, J=7.0 Hz), 2.48-2.74 (3H, m), 2.76-2.95 (2H, m), 3.76 (3H, s), 3.91-4.03 (2H, m), 5.41 (2H, s), 6.80-6.91 (1H, m), 6.96-7.03 (1H, m), 7.07 (1H, d, J=4.6 Hz), 7.24 (1H, t, J=9.0 Hz), 7.36 (1H, d, J=7.8 Hz), 7.62 (1H, d, J=7.9 Hz), 8.05 (1H, s).

Step G) 3-cyclopropyl-3-(5-fluoro-2-((5-(2-fluoro-5-methoxyphenyl)-6-neopentylpyridin-2-yl)methoxy)pyridin-4-yl)propanoic acid To a solution of ethyl 3-cyclopropyl-3-(5-fluoro-2-((5-(2-fluoro-5-methoxyphenyl)-6-neopentylpyridin-2-yl)methoxy)pyridin-4-yl)propanoate (379 mg) in THF (2.0 mL) and methanol (1.0 mL) was added 1N aqueous sodium hydroxide solution (2.0 mL), and the mixture was stirred at 50° C. for 20 min. To the reaction mixture was added 1N hydrochloric acid (2.0 mL) at room temperature, and the mixture was extracted with ethyl acetate. The extract was washed with water and saturated brine, and dried over anhydrous magnesium sulfate. After silica gel filtration, the solvent was evaporated under reduced pressure to give the title compound (330 mg) as a white amorphous solid.
$^1$H NMR (400 MHz, DMSO-$d_6$) δ 0.14 (1H, d, J=4.4 Hz), 0.26-0.43 (2H, m), 0.48-0.61 (1H, m), 0.72 (9H, s), 1.00-1.13 (1H, m), 2.52-2.70 (3H, m), 2.71-2.87 (2H, m), 3.76 (3H, s), 5.41 (2H, s), 6.82-6.93 (1H, m), 6.96-7.03 (1H, m), 7.05 (1H, d, J=4.6 Hz), 7.24 (1H, t, J=9.1 Hz), 7.37 (1H, d, J=7.9 Hz), 7.63 (1H, d, J=7.9 Hz), 8.05 (1H, s), 12.17 (1H, brs).
MS (ESI+): [M+H]$^+$ 511.5

Example 43

3-(2-((5-((1-cyanocyclopentyl)methyl)-6-(2-fluoro-5-methoxyphenyl)pyridin-3-yl)methoxy)-5-fluoropyridin-4-yl)-3-cyclopropylpropanoic acid Step A) methyl 5-bromo-6-methoxynicotinate Bromine (0.60 ml) was added to a solution of 6-hydroxynicotinic acid (1.02 g) in acetic acid (5 mL) and the mixture was stirred at 60° C. for 16 hr. The solvent was evaporated under reduced pressure and the residue was dissolved in phosphorus oxychloride (5 mL). Phosphorus pentachloride (3.05 g) was added and the mixture was stirred at 100° C. for 2 hr. The solvent was evaporated under reduced pressure, and the residue was dissolved in methanol (5 mL), and the mixture was refluxed for 2 hr. To the reaction mixture was added saturated aqueous sodium hydrogen carbonate solution, and the mixture was extracted with ethyl acetate. The extract was washed with saturated brine, and dried over anhydrous sodium sulfate. The solvent was evaporated under reduced pressure and the residue was dissolved in methanol (10 mL). A methanol solution (28%, 2.2 mL) of sodium methoxide was added and the mixture was stirred at room temperature for 2 hr. To the reaction mixture was added saturated aqueous ammonium chloride solution, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (1.18 g) as white crystals.
$^1$H NMR (400 MHz, CDCl$_3$) δ 3.92 (3H, s), 4.08 (3H, s), 8.40 (1H, d, J=1.8 Hz), 8.75 (1H, d, J=1.6 Hz).

Step B) methyl 5-(2-cyanovinyl)-6-methoxynicotinate

Under a nitrogen atmosphere, to a mixture of methyl 5-bromo-6-methoxynicotinate (2.37 g), palladium acetate (430 mg), tri(o-tolyl)phosphine (1.17 g), triethylamine (4.0 mL) and DMF (20 mL) was added acrylonitrile (6.4 mL), and the mixture was stirred under microwave irradiation at 120° C. for 10 hr. To the reaction mixture was added saturated aqueous ammonium chloride solution, and the mixture was extracted with ethyl acetate and THF. The extract was washed with saturated brine, and dried over anhydrous sodium sulfate. The solvent was evaporated under reduced pressure and the residue was purified by silica gel column chromatography (ethyl acetate/hexane) to give the title compound (552 mg) as pale-yellow crystals. This compound was used for the next step without further purification.

Step C) methyl 5-(2-cyanoethyl)-6-methoxynicotinate

To a mixture of methyl 5-(2-cyanovinyl)-6-methoxynicotinate (1.02 g), acetic acid (20 ml) and methanol (20 mL) was added 10% palladium-carbon (504 mg), and the mixture was stirred under a hydrogen atmosphere at 70° C. for 40 hr. The reaction mixture was filtered, and the filtrate was diluted with THF and ethyl acetate. The diluted solution was washed with saturated aqueous sodium hydrogen carbonate solution and saturated brine, and dried over anhydrous sodium sulfate. The solvent was evaporated under reduced pressure and the residue was purified by silica gel column chromatography (ethyl acetate/hexane) to give the title compound (589 mg) as white crystals.
$^1$H NMR (300 MHz, DMSO-$d_6$) δ 2.79-2.95 (4H, m), 3.85 (3H, s), 3.98 (3H, s), 8.14 (1H, d, J=2.3 Hz), 8.68 (1H, d, J=2.3 Hz).

Step D) methyl 5-(2-cyanoethyl)-6-hydroxynicotinate

Under a nitrogen atmosphere, to a solution of methyl 5-(2-cyanoethyl)-6-methoxynicotinate (589 mg) in DMF (10 mL) was added pyridinium chloride (3.01 g), and the mixture was stirred at 100° C. for 4 hr. To the reaction mixture was added THF at 0° C., and the resulting precipitate was removed by filtration. The solvent in the filtrate was evaporated under reduced pressure, and the residue was purified by silica gel column chromatography (ethyl acetate/hexane) to give the title compound (479 mg) as white crystals.
$^1$H NMR (400 MHz, DMSO-$d_6$) δ2.67-2.74 (2H, m), 2.75-2.82 (2H, m), 3.78 (3H, s), 7.81 (1H, d, J=2.0 Hz), 8.01 (1H, d, J=2.1 Hz), 12.23 (1H, brs).

Step E) methyl 5-(2-cyanoethyl)-6-(((trifluoromethyl)sulfonyl)oxy)nicotinate To a solution of methyl 5-(2-cyanoethyl)-6-hydroxynicotinate (479 mg) in pyridine (10 mL) was added trifluoromethanesulfonic anhydride (0.79 mL), and the mixture was stirred at room temperature for 1 hr. To the reaction mixture was added saturated aqueous ammonium chloride solution, and the mixture was extracted with ethyl acetate. The extract was washed with saturated brine, and dried over anhydrous sodium sulfate. The solvent was evaporated under reduced pressure and the residue was purified by silica gel column chromatography (ethyl acetate/hexane) to give the title compound (701 mg) as a pale-yellow oil.
$^1$H NMR (400 MHz, DMSO-$d_6$) δ 2.96 (2H, t, J=6.8 Hz), 3.06 (2H, t, J=7.1 Hz), 3.92 (3H, s), 8.63 (1H, d, J=1.9 Hz), 8.86 (1H, d, J=2.0 Hz).

Step F) methyl 5-(2-cyanoethyl)-6-(2-fluoro-5-methoxyphenyl)nicotinate

Under a nitrogen atmosphere, to a mixture of methyl 5-(2-cyanoethyl)-6-(((trifluoromethyl)sulfonyl)oxy)nicotinate (700 mg), 2-fluoro-5-methoxyphenylboronic acid (700 mg), tetrakis(triphenylphosphine)palladium (237 mg) and toluene (10 mL) was added 2 M aqueous sodium carbonate solution (3.1 mL), and the mixture was stirred at 90° C. for 1 hr. The reaction mixture was filtered, and the filtrate was diluted with ethyl acetate and THF. The diluted solution was washed with water and saturated brine, and dried over anhydrous sodium sulfate. The solvent was evaporated under reduced pressure and the residue was purified by silica gel column chromatography (ethyl acetate/hexane) to give the title compound (635 mg) as a colorless oil.
$^1$H NMR (400 MHz, DMSO-$d_6$) δ2.77 (2H, t, J=7.0 Hz), 2.89 (2H, t, J=7.0 Hz), 3.78 (3H, s), 3.94 (3H, s), 7.00 (1H, dd, J=5.8, 3.1 Hz), 7.06-7.14 (1H, m), 7.30 (1H, t, J=9.2 Hz), 8.44 (1H, d, J=1.8 Hz), 9.07 (1H, d, J=1.8 Hz).

Step G) 3-(2-(2-fluoro-5-methoxyphenyl)-5-(hydroxymethyl)pyridin-3-yl)propanenitrile To a mixture of methyl 5-(2-cyanoethyl)-6-(2-fluoro-5-methoxyphenyl)nicotinate (548 mg), methanol (2 mL) and THF (10 mL) was added sodium borohydride (208 mg), and the mixture was refluxed for 1 hr. To the reaction mixture was added saturated aqueous ammonium chloride solution, and the mixture was extracted with ethyl acetate. The extract was washed with saturated brine, and dried over anhydrous sodium sulfate. The solvent was evaporated under reduced pressure and the residue was purified by silica gel column chromatography (ethyl acetate/hexane) to give the title compound (425 mg) as a colorless oil.
$^1$H NMR (400 MHz, DMSO-$d_6$) δ2.71 (2H, t, J=6.6 Hz), 2.79 (2H, t, J=6.5 Hz), 3.77 (3H, s), 4.60 (2H, d, J=5.6 Hz), 5.40 (1H, t, J=5.6 Hz), 6.93 (1H, dd, J=5.8, 3.1 Hz), 7.01-7.09 (1H, m), 7.25 (1H, t, J=9.2 Hz), 7.82 (1H, s), 8.51 (1H, s).

Step H) 3-(5-(((tert-butyl(dimethyl)silyl)oxy)methyl)-2-(2-fluoro-5-methoxyphenyl)pyridin-3-yl)propanenitrile To a solution of 3-(2-(2-fluoro-5-methoxyphenyl)-5-(hydroxymethyl)pyridin-3-yl)propanenitrile (424 mg) and imidazole (155 mg) in DMF (10 mL) was added tert-butyldimethylchlorosilane (265 mg), and the mixture was stirred at room temperature for 30 min. To the reaction mixture was added saturated aqueous ammonium chloride solution, and the mixture was extracted with ethyl acetate. The extract was washed with saturated brine, and dried over anhydrous sodium sulfate. The solvent was evaporated under reduced pressure and the residue was purified by silica gel column chromatography (ethyl acetate/hexane) to give the title compound (524 mg) as a colorless oil.
$^1$H NMR (400 MHz, DMSO-$d_6$) δ0.13 (6H, s), 0.93 (9H, s), 2.66-2.74 (2H, m), 2.76-2.84 (2H, m), 3.77 (3H, s), 4.82 (2H, s), 6.94 (1H, dd, J=5.8, 3.1 Hz), 7.01-7.08 (1H, m), 7.25 (1H, t, J=9.2 Hz), 7.81 (1H, s), 8.51 (1H, s).

Step I) 1-((5-(((tert-butyl(dimethyl)silyl)oxy)methyl)-2-(2-fluoro-5-methoxyphenyl)pyridin-3-yl)methyl)cyclopentanecarbonitrile To a solution of 3-(5-(((tert-butyl(dimethyl)silyl)oxy)methyl)-2-(2-fluoro-5-methoxyphenyl)pyridin-3-yl)propanenitrile (514 mg) and 1,4-dibromobutane (0.30 mL) in THF (10 mL) was added a THF solution (1 M, 3.9 mL) of lithium bis(trimethylsilyl)amide, and the mixture was stirred at room temperature for 1 hr. To the reaction mixture was added saturated aqueous ammonium chloride solution, and the mixture was extracted with ethyl acetate. The extract was washed with saturated brine, and dried over anhydrous sodium sulfate. The solvent was evaporated under reduced pressure and the residue was purified by silica gel column chromatography (ethyl acetate/hexane) to give the title compound (514 mg) as a colorless oil.

$^1$H NMR (400 MHz, DMSO-$d_6$) δ 0.13 (6H, s), 0.93 (9H, s), 1.35-1.48 (2H, m), 1.49-1.64 (4H, m), 1.75-1.91 (2H, m), 2.92 (2H, s), 3.76 (3H, s), 4.83 (2H, s), 6.97 (1H, dd, J=5.5, 2.9 Hz), 7.00-7.07 (1H, m), 7.22 (1H, t, J=9.0 Hz), 7.90 (1H, s), 8.53 (1H, s).

Step J) 1-((2-(2-fluoro-5-methoxyphenyl)-5-(hydroxymethyl)pyridin-3-yl)methyl)cyclopentanecarbonitrile To a solution of 1-((5-(((tert-butyl(dimethyl)silyl)oxy)methyl)-2-(2-fluoro-5-methoxyphenyl)pyridin-3-yl)methyl)cyclopentanecarbonitrile (514 mg) in THF (10 mL) was added a THF solution (1 M, 2.2 mL) of tetrabutylammonium fluoride, and the mixture was stirred at room temperature for 20 min. To the reaction mixture was added saturated aqueous ammonium chloride solution, and the mixture was extracted with ethyl acetate. The extract was washed with water and saturated brine, and dried over anhydrous sodium sulfate. The solvent was evaporated under reduced pressure and the residue was purified by silica gel column chromatography (ethyl acetate/hexane) to give the title compound (355 mg) as white crystals.

$^1$H NMR (400 MHz, DMSO-$d_6$) δ1.37-1.48 (2H, m), 1.49-1.66 (4H, m), 1.77-1.90 (2H, m), 2.92 (2H, s), 3.76 (3H, s), 4.61 (2H, d, J=5.5 Hz), 5.41 (1H, t, J=5.6 Hz), 6.97 (1H, dd, J=5.6, 3.1 Hz), 7.00-7.06 (1H, m), 7.22 (1H, t, J=9.2 Hz), 7.88 (1H, s), 8.53 (1H, s).

Step K) 1-((5-(bromomethyl)-2-(2-fluoro-5-methoxyphenyl)pyridin-3-yl)methyl)cyclopentanecarbonitrile To a solution of 1-((2-(2-fluoro-5-methoxyphenyl)-5-(hydroxymethyl)pyridin-3-yl)methyl)cyclopentanecarbonitrile (353 mg) and triphenylphosphine (410 mg) in toluene (10 mL) was added carbon tetrabromide (512 mg), and the mixture was stirred at room temperature for 3 hr. To the reaction mixture was added water, and the mixture was extracted with ethyl acetate. The extract was washed with saturated brine, and dried over anhydrous sodium sulfate. The solvent was evaporated under reduced pressure and the residue was purified by silica gel column chromatography (ethyl acetate/hexane) to give the title compound (339 mg) as white crystals.

$^1$H NMR (400 MHz, DMSO-$d_6$) δ 1.38-1.49 (2H, m), 1.49-1.66 (4H, m), 1.77-1.90 (2H, m), 2.94 (2H, s), 3.76 (3H, s), 4.82 (2H, s), 6.98-7.08 (2H, m), 7.24 (1H, t, J=9.2 Hz), 8.02 (1H, d, J=201.9 Hz), 8.68 (1H, d, J=1.6 Hz).

Step L) ethyl 3-(2-((5-(((1-cyanocyclopentyl)methyl)-6-(2-fluoro-5-methoxyphenyl)pyridin-3-yl)methoxy)-5-fluoropyridin-4-yl)-3-cyclopropylpropanoate Under a nitrogen atmosphere, to a solution of 1-((5-(bromomethyl)-2-(2-fluoro-5-methoxyphenyl)pyridin-3-yl)methyl)cyclopentanecarbonitrile (48 mg) and ethyl 3-cyclopropyl-3-(5-fluoro-2-hydroxypyridin-4-yl)propanoate (40 mg) obtained in Example 42, step E, in toluene (1 mL) was added silver carbonate (48 mg), and the mixture was refluxed for 2 hr. The reaction mixture was filtered, and the solvent in the filtrate was evaporated under reduced pressure and the residue was purified by preparative HPLC (water/acetonitrile, TFA added) to give the title compound (11 mg) as a yellow oil.

$^1$H NMR (400 MHz, DMSO-$d_6$) δ0.07-0.18 (1H, m), 0.24-0.42 (2H, m), 0.48-0.59 (1H, m), 1.01-1.12 (4H, m), 1.37-1.48 (2H, m), 1.48-1.65 (4H, m), 1.74-1.87 (2H, m), 2.53-2.61 (1H, m), 2.74-2.88 (2H, m), 2.94 (2H, s), 3.76 (3H, s), 3.90-4.05 (2H, m), 5.42 (2H, s), 6.95-7.09 (3H, m), 7.23 (1H, t, J=8.9 Hz), 8.02 (1H, s), 8.10 (1H, s), 8.69 (1H, s).

Step M) 3-(2-((5-(((1-cyanocyclopentyl)methyl)-6-(2-fluoro-5-methoxyphenyl)pyridin-3-yl)methoxy)-5-fluoropyridin-4-yl)-3-cyclopropylpropanoic acid In the same manner as in Example 42, step G, the title compound (6 mg) was obtained as a yellow oil.

$^1$H NMR (400 MHz, CDCl$_3$) δ0.15-0.26 (1H, m), 0.28-0.39 (1H, m), 0.42-0.53 (1H, m), 0.57-0.68 (1H, m), 1.06-1.15 (1H, m), 1.38-1.55 (4H, m), 1.63-1.79 (2H, m), 1.83-2.02 (2H, m), 2.49-2.61 (1H, m), 2.83 (2H, d, J=7.4 Hz), 2.95 (2H, s), 3.81 (3H, s), 5.44 (2H, s), 6.75 (1H, d, J=4.5 Hz), 6.89-6.98 (2H, m), 7.05 (1H, t, J=8.7 Hz), 7.93 (1H, s), 8.06 (1H, s), 8.70 (1H, s).

MS (ESI-): [M−H]$^-$ 546.4

Example 44

3-(2-((5-(((1-cyanocyclopentyl)methyl)-6-(2-fluoro-5-methoxyphenyl)pyridin-3-yl)methoxy)-5-fluoropyridin-4-yl)-3-cyclopropylpropanoic acid step A) ethyl 3-cyclopropyl-3-(5-fluoro-2-methoxypyridin-4-yl)propanoate Chiral separation of the racemate (3.09 g) of ethyl 3-cyclopropyl-3-(5-fluoro-2-methoxypyridin-4-yl)propanoate was conducted by preparative HPLC (column: CHIRALPAK AS (CC001), 50 mmID×500 mmL, manufactured by DAICEL CHEMICAL INDUSTRIES, LTD., mobile phase: hexane/2-propanol =950/50), and the title compound (1.38 g) with a longer retention time was obtained.

Step B) ethyl 3-cyclopropyl-3-(5-fluoro-2-hydroxypyridin-4-yl)propanoate

Under a nitrogen atmosphere, to a solution of ethyl 3-cyclopropyl-3-(5-fluoro-2-methoxypyridin-4-yl)propanoate (1.38 g) obtained in step A in DMF (2.5 mL) was added pyridinium chloride (5.97 g), and the mixture was stirred at 130° C. for 2 hr. To the reaction mixture was added ethyl acetate at 0° C., and the resulting precipitate was removed by filtration. The solvent in the filtrate was evaporated under reduced pressure, and the residue was purified by silica gel column chromatography (methanol/ethyl acetate) to give the title compound (1.65 g) as a pale-yellow oil.

Step C)

Using ethyl 3-cyclopropyl-3-(5-fluoro-2-hydroxypyridin-4-yl)propanoate obtained in step B, and in the same manner as in Example 43, the title compound (47 mg) was obtained as a white amorphous solid.

$^1$H NMR (400 MHz, DMSO-$d_6$) δ0.07-0.19 (1H, m), 0.25-0.41 (2H, m), 0.46-0.59 (1H, m), 0.97-1.13 (1H, m), 1.37-1.48 (2H, m), 1.48-1.64 (4H, m), 1.74-1.88 (2H, m), 2.53-2.62 (1H, m), 2.66-2.84 (2H, m), 2.94 (2H, s), 3.76 (3H, s), 5.42 (2H, s), 6.96-7.08 (3H, m), 7.23 (1H, t, J=9.2 Hz), 8.03 (1H, s), 8.09 (1H, s), 8.69 (1H, s), 12.14 (1H, brs).

MS (ESI-): [M-H]⁻ 546.3

Reference Example 1

3-cyclopropyl-3-(3-((5-(2-fluoro-5-methoxyphenyl)-4-(4-(trifluoromethyl)phenyl)-1,3-thiazol-2-yl)methoxy)phenyl)propanoic acid A) (4-bromothiazol-2-yl)methanol To a solution of 4-bromothiazole-2-carbaldehyde (1.20 g) in THF (10 mL) were successively added sodium borohydride (236 mg) and methanol (1.0 mL) at 0° C., and the mixture was stirred at room temperature for 1 hr. 1N Hydrochloric acid was added, and the reaction mixture was extracted with ethyl acetate. The extract was washed with saturated brine, and dried over anhydrous sodium sulfate. The solvent was evaporated under reduced pressure, and the residue was purified by silica gel column chromatography (NH, ethyl acetate/hexane) to give the title compound (865 mg) as a colorless oil.

$^1$H NMR (300 MHz, DMSO-$d_6$) δ 4.72 (2H, d, J=6.0 Hz), 6.19 (1H, t, J=5.9 Hz), 7.75 (1H, s).

B) 4-bromo-2-((tert-butyldimethylsilyloxy)methyl)thiazole

To a solution of (4-bromothiazol-2-yl)methanol (1.30 g) and imidazole (600 mg) in THF (10 mL) was added dropwise tert-butyldimethylchlorosilane (1.60 mL), and the mixture was stirred at room temperature for 1 hr. 1N Hydrochloric acid was added, and the reaction mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (1.90 g) as a colorless oil.

$^1$H NMR (300 MHz, DMSO-$d_6$) δ 0.12 (6H, s), 0.92 (9H, s), 4.95 (2H, s), 7.77 (1H, s).

C) 2-((tert-butyldimethylsilyloxy)methyl)-4-(4-(trifluoromethyl)phenyl)thiazole

To a solution of 4-bromo-2-((tert-butyldimethylsilyloxy)methyl)thiazole (900 mg) in toluene (50 mL) were added 4-trifluorophenylboronic acid (998 mg), 2-dicyclohexylphosphino-2',6'-dimethoxybiphenyl (192 mg), tris(dibenzylideneacetone)dipalladium(0) (134 mg) and 2.0 M aqueous sodium carbonate solution (4.4 mL), and the mixture was stirred at 100° C. for 1 hr. The mixture was allowed to cool to room temperature, and water was added. The reaction mixture was extracted with ethyl acetate, and the extract was washed with saturated brine. The organic layer was dried over anhydrous sodium sulfate, and the solvent was evaporated under reduced pressure. The residue was purified by silica gel column chromatography (ethyl acetate/hexane) to give the title compound (1.10 g) as white crystals.

$^1$H NMR (400 MHz, DMSO-$d_6$) δ 0.15 (6H, s), 0.94 (9H, s), 5.03 (2H, s), 7.80 (2H, d, J=8.3 Hz), 8.16 (2H, d, J=8.3 Hz), 8.29 (1H, s).

D) 5-bromo-2-((tert-butyldimethylsilyloxy)methyl)-4-(4-(trifluoromethyl)phenyl)thiazole To a solution of 2-((tert-butyldimethylsilyloxy)methyl)-4-(4-(trifluoromethyl)phenyl)thiazole (500 mg) in ethyl acetate (10 mL) was added bromine (428 mg), and the mixture was stirred at room temperature 12 hr, and further at 60° C. for 2 hr. To the reaction mixture was added aqueous sodium thiosulfate solution, and the reaction mixture was extracted with ethyl acetate. The extract was washed with saturated brine, and dried over anhydrous sodium sulfate. The solvent was evaporated under reduced pressure to give a crude product of the title compound. This compound was used for the next step without further purification.

E) (5-bromo-4-(4-(trifluoromethyl)phenyl)thiazol-2-yl)methanol

To a solution of 5-bromo-2-((tert-butyldimethylsilyloxy)methyl)-4-(4-(trifluoromethyl)phenyl)thiazole (entire amount) obtained in Reference Example 1, step D, in THF (10 mL) was added a 1.0 M solution of tetrabutylammonium fluoride in THF (1.6 mL), and the mixture was stirred at room temperature for 10 min. Water was added, and the reaction mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (310 mg) as pale-yellow crystals.

$^1$H NMR (400 MHz, DMSO-$d_6$) δ 4.77 (2H, d, J=4.9 Hz), 6.24-6.37 (1H, m), 7.87 (2H, d, J=8.3 Hz), 8.11 (2H, d, J=8.3 Hz).

F) methyl 3-(3-((5-bromo-4-(4-(trifluoromethyl)phenyl)thiazol-2-yl)methoxy)phenyl)-3-cyclopropylpropanoate To a solution of (5-bromo-4-(4-(trifluoromethyl)phenyl)thiazol-2-yl)methanol (300 mg) in THF (15 ml) were added triphenylphosphine (349 mg), methyl 3-cyclopropyl-3-(3-hydroxyphenyl)propanoate (293 mg), and a 40% solution of diethyl azodicarboxylate in toluene (520 μL), and the mixture was stirred at room temperature for 30 min. The reaction mixture was concentrated under reduced pressure, and the residue was purified by silica gel column chromatography (ethyl acetate/hexane) to give the title compound (110 mg) as a colorless oil.

MS (ESI+): [M+H]⁺ 541.9

G) methyl 3-cyclopropyl-3-(3-((5-(2-fluoro-5-methoxyphenyl)-4-(4-(trifluoromethyl)phenyl)thiazol-2-yl)methoxy)phenyl)propanoate To methyl 3-(3-((5-bromo-4-(4-(trifluoromethyl)phenyl)thiazol-2-yl)methoxy)phenyl)-3-cyclopropylpropanoate (115 mg) in toluene (10 mL) were added (2-fluoro-5-methoxyphenyl)boronic acid (108 mg), 2-dicyclohexylphosphino-2',6'-dimethoxybiphenyl (26 mg), tris(dibenzylideneacetone)dipalladium(0) (20 mg) and 2.0 M aqueous sodium carbonate solution (0.32 mL), and the mixture was stirred at 100° C. for 1 hr. The mixture was allowed to cool to room temperature, and water was added. The reaction mixture was extracted with ethyl acetate, and the extract was washed with saturated brine. The organic layer was dried over anhydrous sodium sulfate, and the solvent was evaporated under reduced pressure. The residue was purified by silica gel column chromatography (ethyl acetate/hexane) to give the title compound (120 mg) as orange crystals.

MS (ESI+): [M+H]⁺ 586.1

H) 3-cyclopropyl-3-(3-((5-(2-fluoro-5-methoxyphenyl)-4-(4-(trifluoromethyl)phenyl)-1,3-thiazol-2-yl)methoxy)phenyl)propanoic acid To a solution of methyl 3-cyclopropyl-3-(3-((5-(2-fluoro-5-methoxyphenyl)-4-(4-(trifluoromethyl)phenyl)thiazol-2-yl)methoxy)phenyl)propanoate (120 mg) in THF (3.0 mL) and methanol (3.0 mL) was added 1N aqueous sodium hydroxide solution (3.0 mL), and the mixture was stirred at 50° C. for 1 hr. 1N Hydrochloric acid was added, and the reaction mixture was extracted with ethyl acetate. The extract was washed with saturated brine and dried over anhydrous sodium sulfate. The solvent was evaporated under reduced pressure, and the residue was purified by silica gel column chromatography (ethyl acetate/hexane) to give the title compound (100 mg) as pale-yellow crystals.

MS (ESI+): [M+H]$^+$ 572.2

$^1$H NMR (300 MHz, DMSO-$d_6$) δ 0.06-0.17 (1H, m), 0.19-0.35 (2H, m), 0.49 (1H, dt, J=7.8, 5.1 Hz), 0.93-1.08 (1H, m), 2.23-2.35 (1H, m), 2.66 (2H, dd, J=7.5, 2.6 Hz), 3.72 (3H, s), 5.52 (2H, s), 6.87-6.99 (2H, m), 7.00-7.11 (3H, m), 7.20-7.33 (2H, m), 7.61-7.79 (4H, m), 12.01 (1H, brs).

The structural formulas of the compounds obtained in Examples 1-44 are shown in the following Tables 1-8.

TABLE 1

| Ex. No. | compound name | structural formula | salt | MS |
|---|---|---|---|---|
| 1 | 3-cyclopropyl-3-(3-((5-(2-fluoro-5-methoxyphenyl)-6-isobutoxypyridin-2-yl)methoxy)phenyl)propanoic acid | | — | 494.2 |
| 2 | 3-cyclopropyl-3-(6-((5-(2-fluoro-5-methoxyphenyl)-6-isobutoxypyridin-2-yl)methoxy)pyrimidin-4-yl)propanoic acid | | — | 496.3 |
| 3 | 3-cyclopropyl-3-(6-(((5-(2-fluoro-5-methoxyphenyl)-6-isobutoxypyridin-2-yl)methyl)amino)pyrimidin-4-yl)propanoic acid | | — | 495.2 |
| 4 | 3-cyclopropyl-3-(6-(((5-(2-fluoro-5-methoxyphenyl)-6-isobutoxypyridin-2-yl)methyl)(methyl)amino)pyrimidin-4-yl)propanoic acid | | — | 509.2 |

TABLE 1-continued

| Ex. No. | compound name | structural formula | salt | MS |
|---|---|---|---|---|
| 5 | 3-cyclopropyl-3-(3-((5-(2-fluoro-5-methoxyphenyl)-4-isobutoxypyridin-2-yl)methoxy)phenyl)-propanoic acid | | — | 494.2 |
| 6 | 3-cyclopropyl-3-(6-((5-(2-fluoro-5-methoxyphenyl)-4-isobutoxypyridin-2-yl)methoxy)pyrimidin-4-yl)propanoic acid | | — | 496.3 |

TABLE 2

| Ex. No. | compound name | structural formula | salt | MS |
|---|---|---|---|---|
| 7 | 3-cyclopropyl-3-(3-((6-(2,2-dimethylpropyl)-5-(2-fluoro-5-methoxyphenyl)pyridin-2-yl)methoxy)phenyl)-propanoic acid | | — | 492.2 |
| 8 | 3-cyclopropyl-3-(6-((6-(2,2-dimethylpropyl)-5-(2-fluoro-5-methoxyphenyl)pyridin-2-yl)methoxy)pyrimidin-4-yl)propanoic acid | | — | 492.2 |
| 9 | 3-cyclopropyl-3-(3-((6-(2,2-dimethylpropyl)-5-(2-fluoro-5-methoxyphenyl)pyridin-2-yl)methoxy)phenyl)-propanoic acid | | — | 492.2 |

TABLE 2-continued

| Ex. No. | compound name | structural formula | salt | MS |
|---|---|---|---|---|
| 10 | N-(3-((6-(2,2-dimethylpropyl)-5-(2-fluoro-5-methoxyphenyl)pyridin-2-yl)methoxy)phenyl)-N-ethylglycine | 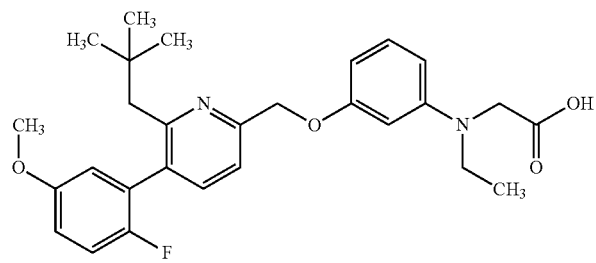 [SMILES: CCN(CC(=O)O)c1cccc(OCc2ccc(-c3cc(OC)ccc3F)c(CC(C)(C)C)n2)c1] | — | 481.3 |
| 11 | 3-cyclopropyl-3-(3-((6-(2,2-dimethylpropyl)-5-(2-fluoro-5-methoxyphenyl)pyridin-2-yl)methoxy)phenyl)propanoic acid | 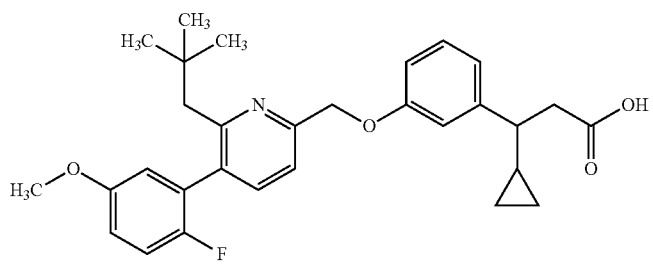 [SMILES: COc1ccc(F)c(-c2ccc(COc3cccc(C(CC(=O)O)C4CC4)c3)nc2CC(C)(C)C)c1] | — | 492.2 |
| 12 | 3-cyclopropyl-3-(3-((6-(2,2-dimethylpropyl)-5-(2-fluoro-5-methoxyphenyl)pyridin-2-yl)methoxy)-4-methoxyphenyl)propanoic acid | 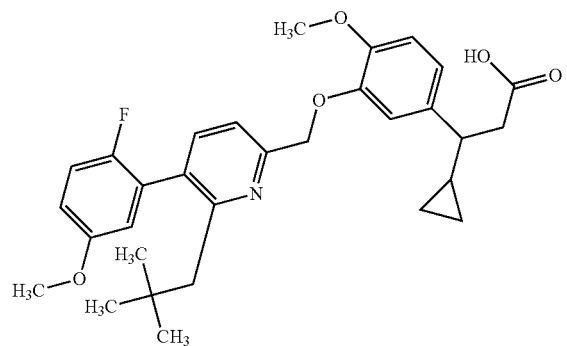 [SMILES: COc1ccc(F)c(-c2ccc(COc3cc(C(CC(=O)O)C4CC4)ccc3OC)nc2CC(C)(C)C)c1] | — | 522.2 |

TABLE 3

| Ex. No. | compound name | structural formula | salt | MS |
|---|---|---|---|---|
| 13 | 3-(3-((6-(2,2-dimethylpropyl)-5-(2-fluoro-5-methoxyphenyl)pyridin-2-yl)methoxy)-4-methylphenyl)propanoic acid | 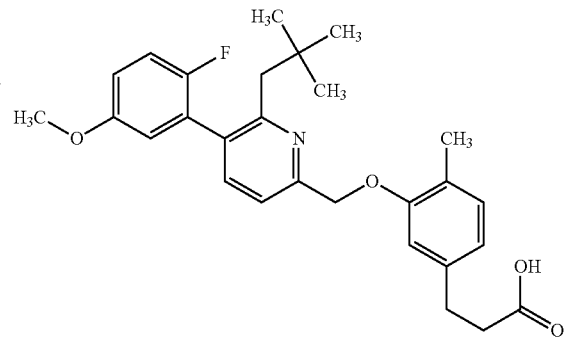 [SMILES: COc1ccc(F)c(-c2ccc(COc3cc(CCC(=O)O)ccc3C)nc2CC(C)(C)C)c1] | — | 466.1 |

TABLE 3-continued

| Ex. No. | compound name | structural formula | salt | MS |
|---|---|---|---|---|
| 14 | 3-cyclopropyl-3-(3-((6-(2,2-dimethylpropyl)-5-(2-fluoro-5-methoxyphenyl)pyridin-2-yl)methoxy)-4-fluorophenyl)propanoic acid | 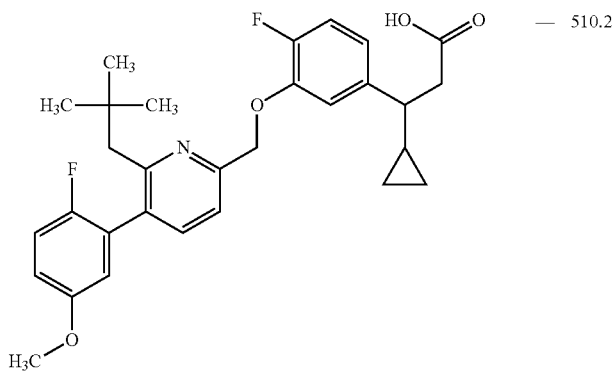 | — | 510.2 |
| 15 | 3-(3-((6-(2,2-dimethylpropyl)-5-(2-fluoro-5-methoxyphenyl)pyridin-2-yl)methoxy)-5-methoxyphenyl)propanoic acid | 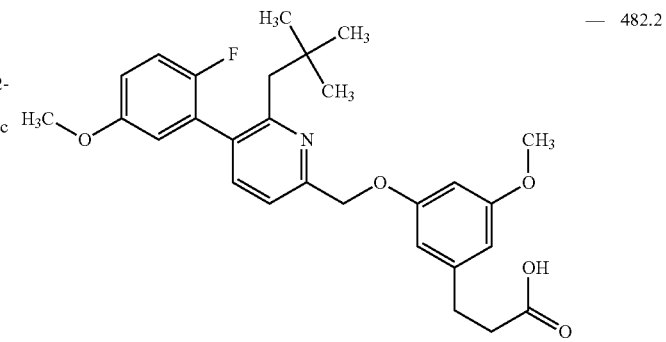 | — | 482.2 |
| 16 | 3-(3-((6-(2,2-dimethylpropyl)-5-(2-fluoro-5-methoxyphenyl)pyridin-2-yl)methoxy)-5-fluorophenyl)propanoic acid | 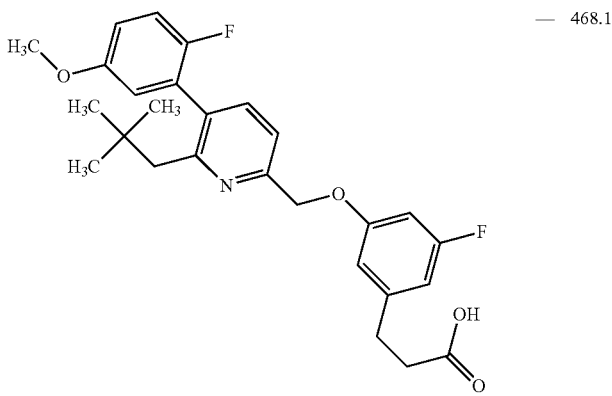 | — | 468.1 |
| 17 | 3-(5-((6-(2,2-dimethylpropyl)-5-(2-fluoro-5-methoxyphenyl)pyridin-2-yl)methoxy)-2-methylphenyl)propanoic acid | 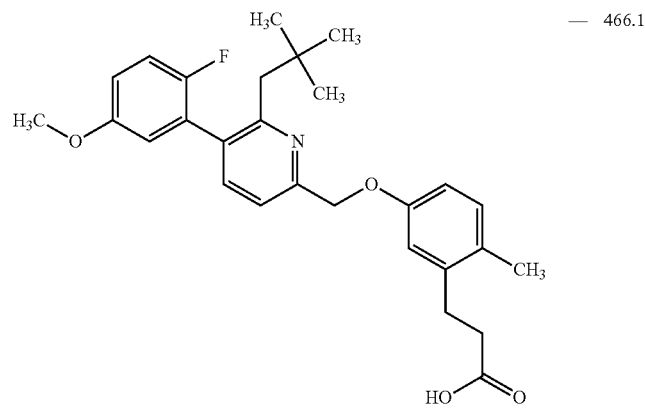 | — | 466.1 |

TABLE 3-continued

| Ex. No. | compound name | structural formula | salt | MS |
|---|---|---|---|---|
| 18 | 3-(5-((6-(2,2-dimethylpropyl)-5-(2-fluoro-5-methoxyphenyl)pyridin-2-yl)methoxy)-2-methoxyphenyl)propanoic acid | | — | 482.2 |

TABLE 4

| Ex. No. | compound name | structural formula | salt | MS |
|---|---|---|---|---|
| 19 | 3-(5-((6-(2,2-dimethylpropyl)-5-(2-fluoro-5-methoxyphenyl)pyridin-2-yl)methoxy)-2-fluorophenyl)propanoic acid | | — | 470.1 |
| 20 | 3-(3-((6-(2,2-dimethylpropyl)-5-(2-fluoro-5-methoxyphenyl)pyridin-2-yl)methoxy)-2-methylphenyl)propanoic acid | | — | 466.2 |

TABLE 4-continued

| Ex. No. | compound name | structural formula | salt | MS |
|---|---|---|---|---|
| 21 | 3-(3-((6-(2,2-dimethylpropyl)-5-(2-fluoro-5-methoxyphenyl)pyridin-2-yl)methoxy)-2-methoxyphenyl)propanoic acid | | — | 482.2 |
| 22 | 3-(3-((6-(2,2-dimethylpropyl)-5-(2-fluoro-5-methoxyphenyl)pyridin-2-yl)methoxy)-2-fluorophenyl)propanoic acid | | — | 470.0 |
| 23 | 3-(3-((6-(2,2-dimethylpropyl)-5-(2-fluoro-5-methoxyphenyl)pyridin-2-yl)methoxy)-5-methylphenyl)propanoic acid | | Na+ | 464.1 |
| 24 | 3-(6-((6-(2,2-dimethylpropyl)-5-(2-fluoro-5-methoxyphenyl)pyridin-2-yl)methoxy)-2-methylpyrimidin-4-yl)propanoic acid | | — | 468.2 |

TABLE 5

| Ex. No. | compound name | structural formula | salt | MS |
|---|---|---|---|---|
| 25 | 3-(6-((6-(2,2-dimethylpropyl)-5-(2-fluoro-5-methoxyphenyl)pyridin-2-yl)methoxy)-2-methoxypyrimidin-4-yl)propanoic acid | | — | 484.0 |
| 26 | 3-(6-((6-(2,2-dimethylpropyl)-5-(2-fluoro-5-methoxyphenyl)pyridin-2-yl)methoxy)-5-methylpyrimidin-4-yl)propanoic acid | | — | 468.0 |
| 27 | 3-(6-((6-(2,2-dimethylpropyl)-5-(2-fluoro-5-methoxyphenyl)pyridin-2-yl)methoxy)-5-methoxypyrimidin-4-yl)propanoic acid | | — | 484.0 |
| 28 | 3-(6-((6-(2,2-dimethylpropyl)-5-(2-fluoro-5-methoxyphenyl)pyridin-2-yl)methoxy)-5-fluoropyrimidin-4-yl)propanoic acid | | — | 472.0 |

TABLE 5-continued

| Ex. No. | compound name | structural formula | salt | MS |
|---|---|---|---|---|
| 29 | 3-(3-((6-(2,2-dimethylpropyl)-5-(2-fluoro-5-methoxyphenyl)-pyridin-2-yl)methoxy)-phenyl)propanoic acid | | — | 452.2 |
| 30 | 3-cyclopropyl-3-(2-((6-(2,2-dimethylpropyl)-5-(2-fluoro-5-methoxyphenyl)pyridin-2-yl)methoxy)pyridin-4-yl)propanoic acid | | — | 492.2 |

TABLE 6

| Ex. No. | compound name | structural formula | salt | MS |
|---|---|---|---|---|
| 31 | 3-cyclopropyl-3-(3-((6-(2-fluoro-5-methoxyphenyl)-5-isobutoxypyridin-3-yl)-methoxy)phenyl)propanoic acid | | — | 494.2 |
| 32 | 3-cyclopropyl-3-(6-((6-(2-fluoro-5-methoxyphenyl)-5-isobutoxypyridin-3-yl)methoxy)pyrimidin-4-yl)propanoic acid | | — | 496.2 |
| 33 | 3-cyclopropyl-3-(3-((6-(2-fluoro-5-methoxyphenyl)-5-isobutoxy-2-methoxypyridin-3-yl)-methoxy)phenyl)propanoic acid | | — | 524.1 |

TABLE 6-continued

| Ex. No. | compound name | structural formula | salt | MS |
|---|---|---|---|---|
| 34 | 3-cyclopropyl-3-(3-((5-(2,2-dimethylpropyl)-6-(2-fluoro-5-methoxyphenyl)pyridin-3-yl)methoxy)phenyl)-propanoic acid | | — | 492.2 |
| 35 | 3-cyclopropyl-3-(6-((5-(2,2-dimethylpropyl)-6-(2-fluoro-5-methoxyphenyl)-pyridin-3-yl)methoxy)-pyrimidin-4-yl)propanoic acid | | — | 494.2 |
| 36 | 3-cyclopropyl-3-(6-((5-(2,2-dimethylpropoxy)-6-(2-fluoro-5-methoxyphenyl)pyridin-3-yl)methoxy)pyrimidin-4-yl)propanoic acid | | — | 510.3 |

TABLE 7

| Ex. No. | compound name | structural formula | salt | MS |
|---|---|---|---|---|
| 37 | 3-cyclopropyl-3-(6-((6-(2-fluoro-5-methoxyphenyl)-5-(3,3,3-trifluoropropoxy)pyridin-3-yl)methoxy)pyrimidin-4-yl)propanoic acid | | — | 536.3 |

TABLE 7-continued

| Ex. No. | compound name | structural formula | salt | MS |
|---|---|---|---|---|
| 38 | 3-cyclopropyl-3-(6-((5-((5,5-dimethyltetrahydrofuran-3-yl)methoxy)-6-(2-fluoro-5-methoxyphenyl)pyridin-3-yl)methoxy)pyrimidin-4-yl)propanoic acid | 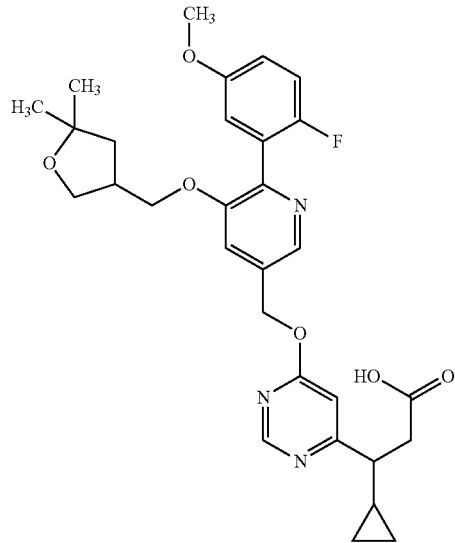 [SMILES: COc1ccc(F)c(-c2ncc(COc3cc(C(CC(=O)O)C4CC4)ncn3)cc2OCC2COC(C)(C)C2)c1] | — | 552.0 |
| 39 | 3-cyclopropyl-3-(6-((5-((2,2-dimethyltetrahydro-2H-pyran-4-yl)methoxy)-6-(2-fluoro-5-methoxyphenyl)pyridin-3-yl)methoxy)pyrimidin-4-yl)propanoic acid | 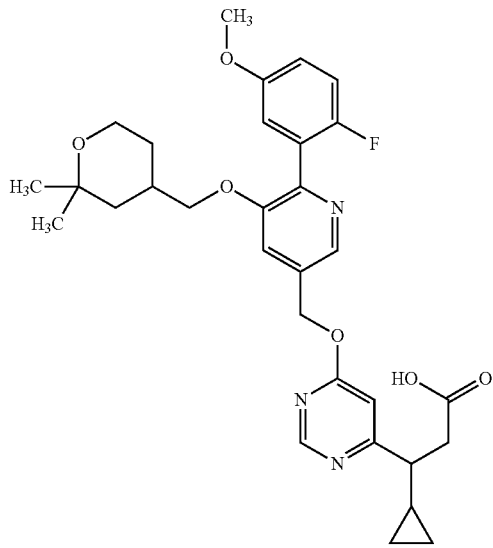 [SMILES: COc1ccc(F)c(-c2ncc(COc3cc(C(CC(=O)O)C4CC4)ncn3)cc2OCC2CCOC(C)(C)C2)c1] | — | 566.1 |
| 40 | 3-cyclopropyl-3-(2-((5-(2,2-dimethylpropyl)-6-(2-fluoro-5-methoxyphenyl)pyridin-3-yl)methoxy)pyridin-4-yl)propanoic acid | 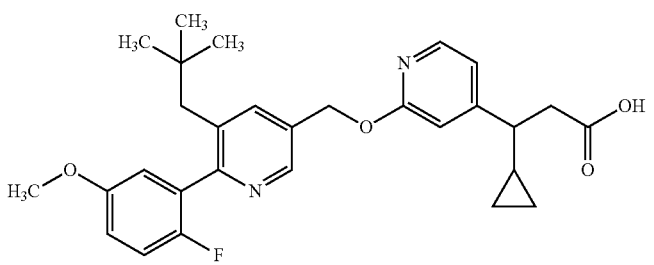 [SMILES: COc1ccc(F)c(-c2ncc(COc3cc(C(CC(=O)O)C4CC4)ccn3)cc2CC(C)(C)C)c1] | — | 493.2 |

TABLE 7-continued

| Ex. No. | compound name | structural formula | salt | MS |
|---|---|---|---|---|
| 41 | 3-cyclopropyl-3-(6-((5-(2-fluoro-5-methoxyphenyl)-4-isobutoxypyrimidin-2-yl)methoxy)pyrimidin-4-yl)propanoic acid | | — | 497.1 |

TABLE 8

| Ex. No. | compound name | structural formula | salt | MS |
|---|---|---|---|---|
| 42 | 3-cyclopropyl-3-(5-fluoro-2-((5-(2-fluoro-5-methoxyphenyl)-6-neopentylpyridin-2-yl)methoxy)pyridin-4-yl)propanoic acid | | — | 511.5 |
| 43 | 3-(2-((5-((1-cyanocyclopentyl)methyl)-6-(2-fluoro-5-methoxyphenyl)-pyridin-3-yl)methoxy)-5-fluoropyridin-4-yl)-3-cyclopropylpropanoic acid | | — | 546.4 |
| 44 | 3-(2-((5-((1-cyanocyclopentyl)methyl)-6-(2-fluoro-5-methoxyphenyl)-pyridin-3-yl)methoxy)-5-fluoropyridin-4-yl)-3-cyclopropylpropanoic acid | | — | 546.3 |

Experimental Example 1

Evaluation of Human GPR40 Agonist Activity with Increase in Intracellular $Ca^{2+}$ Concentration as an Index CHO(dhfr−) cells that stably expressed human GPR40 were suspended in MEMα (Nikken Bio Medical Laboratory) containing 10% dialysis serum (GEMINI BIO-PRODUCTS), 10 mM HEPES (Invitrogen), 100 U/mL penicillin, 100 μg/mL streptomycin (Invitrogen), and plated on a 384 well black/clear cell culture plate at 10,000 cells/well. After culture overnight in a $CO_2$ incubator at 37° C., the culture supernatant was removed, and a loading buffer [dye attached to Calcium 5 Assay Kit (Molecular Devices) was dissolved in an assay buffer (20 mM HEPES, 0.2% fatty acid-free BSA (Sigma-Aldrich), 2.5 mM probenecid (DOJINDO)-containing HBSS (Invitrogen)) added with 0.025% Cremophor EL (DOJINDO)] was added at 37.5 μL/well. After incubation in a $CO_2$ incubator at 37° C. for 1 hr, the cells were stood at room temperature for 15 min, an assay buffer containing the test compound at a final concentration of 1 μM was added at 12.5 μL/well in FLIPR Tetra (Molecular Devices), and the fluorescence amount was successively measured. Human GPR40 agonist activity calculated using an increase in the intracellular $Ca^{2+}$ concentration as an index, wherein the activity of 1

μM of the compound described in WO 2009/048527 (WO2009/048527 Example 99.2) was 100%, and the activity when DMSO was added instead of the test compound was 0%. The results are shown in Table 9.

TABLE 9

| Example | 1 μM |
|---|---|
| 1 | 100 |
| 2 | 107 |
| 6 | 98 |
| 7 | 106 |
| 8 | 106 |
| 9 | 1007 |
| 11 | 100 |
| 12 | 112 |
| 13 | 110 |
| 15 | 103 |
| 16 | 109 |
| 17 | 109 |
| 18 | 109 |
| 19 | 109 |
| 22 | 103 |
| 23 | 99 |
| 29 | 103 |
| 30 | 112 |
| 31 | 104 |
| 32 | 104 |
| 34 | 118 |
| 35 | 101 |
| 36 | 106 |
| 37 | 101 |
| 40 | 113 |
| 41 | 110 |
| 42 | 115 |
| 43 | 115 |
| 44 | 107 |

Formulation Example 1 (Production of Capsule)

| 1) compound of Example 1 | 30 mg |
|---|---|
| 2) finely divided powder cellulose | 10 mg |
| 3) lactose | 19 mg |
| 4) magnesium stearate | 1 mg |
| | total 60 mg |

1), 2), 3) and 4) are mixed and filled in a gelatin capsule.

Formulation Example 2 (Production of Tablets)

| 1) compound of Example 1 | 30 g |
|---|---|
| 2) lactose | 50 g |
| 3) cornstarch | 15 g |
| 4) calcium carboxymethylcellulose | 44 g |
| 5) magnesium stearate | 1 g |
| 1000 tablets | total 140 g |

The entire amount of 1), 2) and 3) and 4) (30 g) is kneaded with water, vacuum dried, and sieved. The sieved powder is mixed with 4) (14 g) and 5) (1 g), and the mixture is punched by a tableting machine, whereby 1000 tablets containing 30 mg of the compound of Ex. 1 per tablet are obtained.

Industrial Applicability

The compound of the present invention has a superior GPR40 agonist activity, and is useful as an agent for the prophylaxis or treatment of diabetes and the like.

This application is based on patent application No. 2012-028943 filed in Japan, the contents of which are encompassed in full herein.

The invention claimed is:

1. A compound represented by the formula (I):

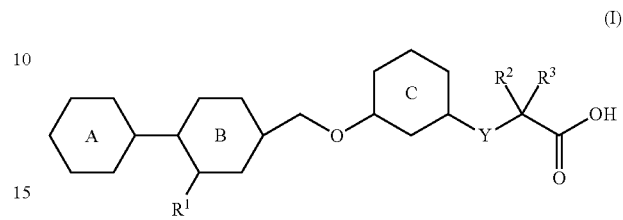

(I)

wherein ring A is an optionally further substituted 6-membered aromatic ring;
ring B is an optionally further substituted 6-membered aromatic heterocycle;
ring C is an optionally further substituted 6-membered aromatic ring;
Y is —$NR^{4A}$—, —$CR^{4B}R^{4C}$— or —O—;
$R^1$ is a substituent;
$R^2$ and $R^3$ are each independently a hydrogen atom or a substituent; and
$R^{4A}$, $R^{4B}$ and $R^{4C}$ are each independently a hydrogen atom, an optionally substituted $C_{1-6}$ alkyl group, an optionally substituted $C_{2-6}$ alkenyl group, an optionally substituted $C_{2-6}$ alkynyl group, or an optionally substituted $C_{3-7}$ cycloalkyl group,
or a salt thereof.

2. The compound according to claim 1, wherein ring A is a benzene ring further substituted by one halogen atom and one $C_{1-6}$ alkoxy group, or a salt thereof.

3. The compound according to claim 1, wherein ring B is (1) a pyridine ring optionally further substituted by 1 to 3 $C_{1-6}$ alkoxy groups, or (2) a pyrimidine ring, or a salt thereof.

4. The compound according to claim 1, wherein ring C is (1) a benzene ring optionally further substituted by 1 to 3 substituents selected from a halogen atom, a $C_{1-6}$ alkyl group and a $C_{1-6}$ alkoxy group, (2) a pyridine ring, or (3) a pyrimidine ring optionally further substituted by 1 to 3 substituents selected from a halogen atom, a $C_{1-6}$ alkyl group and a $C_{1-6}$ alkoxy group, or a salt thereof.

5. The compound according to claim 1, wherein Y is —N(ethyl)-, —$CH_2$— or —CH(cyclopropyl)-, or a salt thereof.

6. The compound according to claim 1, wherein $R^1$ is (1) a $C_{1-8}$ alkyl group optionally substituted by 1 to 3 substituents selected from (i) a $C_{3-7}$ cycloalkyl group and cyano, or (2) a $C_{1-6}$ alkoxy group optionally substituted by 1 to 3 substituents selected from (i) a halogen atom and (ii) a non-aromatic heterocyclic group optionally substituted by 1 or 2 $C_{1-6}$ alkyl groups, or a salt thereof.

7. The compound according to claim 1, wherein both $R^2$ and $R^3$ are hydrogen atoms, or a salt thereof.

8. 3-Cyclopropyl-3-(6-((5-(2,2-dimethylpropyl)-6-(2-fluoro-5-methoxyphenyl)pyridin-3-yl)methoxy)pyrimidin-4-yl)propanoic acid or a salt thereof.

9. 3-Cyclopropyl-3-(6-((6-(2,2-dimethylpropyl)-5-(2-fluoro-5-methoxyphenyl)pyridin-2-yl)methoxy)pyrimidin-4-yl)propanoic acid or a salt thereof.

10. 3-Cyclopropyl-3-(3-((5-(2,2-dimethylpropyl)-6-(2-fluoro-5-methoxyphenyl)pyridin-3-yl)methoxy)phenyl)propanoic acid or a salt thereof.

11. A medicament comprising the compound according to claim 1 or a salt thereof.

12. A method for the treatment of diabetes in a human, comprising administering an effective amount of the compound according to claim 1 or a salt thereof to the human.

* * * * *